(12) United States Patent
Lillard, Jr.

(10) Patent No.: US 8,541,564 B2
(45) Date of Patent: Sep. 24, 2013

(54) CHEMOKINE-IMMUNOGLOBULIN FUSION POLYPEPTIDES, COMPOSITIONS, METHOD OF MAKING AND USE THEREOF

(75) Inventor: James W. Lillard, Jr., Smyrna, GA (US)

(73) Assignee: Morehouse School of Medicine, Atlanta, GA (US)

( * ) Notice: Subject to any disclaimer, the term of this patent is extended or adjusted under 35 U.S.C. 154(b) by 0 days.

(21) Appl. No.: 13/480,526

(22) Filed: May 25, 2012

(65) Prior Publication Data

US 2012/0308565 A1 Dec. 6, 2012

Related U.S. Application Data

(60) Provisional application No. 61/492,260, filed on Jun. 1, 2011.

(51) Int. Cl.
| | |
|---|---|
| *C07H 21/04* | (2006.01) |
| *C12P 21/04* | (2006.01) |
| *C12P 21/06* | (2006.01) |
| *C12P 21/08* | (2006.01) |
| *C07K 1/00* | (2006.01) |

(52) U.S. Cl.
USPC ..... 536/23.4; 536/23.5; 536/23.53; 435/69.7; 435/69.1; 530/387.3; 530/402; 530/350

(58) Field of Classification Search
None
See application file for complete search history.

(56) References Cited

U.S. PATENT DOCUMENTS

| 5,766,897 A * | 6/1998 | Braxton | 435/463 |
| 2005/0053579 A1 | 3/2005 | Galipeau et al. | |
| 2007/0116669 A1 * | 5/2007 | Merzouk et al. | 424/85.1 |
| 2009/0098101 A1 * | 4/2009 | Raines et al. | 424/94.6 |
| 2010/0196406 A1 * | 8/2010 | Karin et al. | 424/184.1 |

OTHER PUBLICATIONS

Proost et al. 2007. Blood. 110:37-44).*
The International Search Report and the Written Opinion of the International Searching Authority (Application No. PCT/US2012/039550, International Filing Date: May 25, 2012), Mailed Dec. 18, 2012.
Biragyn, A., et al., "Mediators of Innate Immunity That Target Immature, But Not Mature, Dendritic Cells Induce Antitumor Immunity When Genetically Fused with Nonimmunogenic Tumor Antigens", The Journal of Immunology, Dec. 1, 2001, vol. 167, No. 11, pp. 6644-6653.
Fagète, S., et al., "Specificity tuning of antibody fragments to neutralize two human chemokines with a single agent", MAbs, May-Jun. 2009, vol. 1, No. 3, pp. 288-296.
Van Heeke, G. et al., "Expression of Human Asparagine Synthetase in *Escherichia coli*," The Journal of Biological Chemistry, vol. 264, No. 10, Apr. 5, 1989, pp. 5503-5509.
Allen, S.J., et al. "Chemokine: Receptor Structure, Interactions, and Antagonism," Annu. Rev. Immunol., 2007, 25:787-820.

* cited by examiner

*Primary Examiner* — Shulamith H Shafer
(74) *Attorney, Agent, or Firm* — Ping Wang; Andrews Kurth LLP

(57) ABSTRACT

This application is directed to chemokine-immunoglobulin fusion polypeptides and chemokine-polymer conjugates. The fusion polypeptides and conjugates can be used for treating chemokine receptor-mediated disorders and modulating inflammation, inflammatory cell motility, cancer cell motility, or cancer cell survival.

13 Claims, 70 Drawing Sheets

FIG.1C

IL2ss.CCL2.hIgG1Fc GAGless plasmid sequence

```
   1 GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101 GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCT
 201 GTGAACGTTC TTTTTCGCAA CGGGTTTGCC CCAGAACACT TCGAGGAAGCT TCGACGGGGC CCATCCGCG CCCCGCGCCT ACCTGAGGCC
 301 GCCATCCACG CCGGTTGAGT CCGGTTCTGC CCGCTCCCGC CTGTGGTGCG CTCTGAACTG CGTCCGCCGT CTAGGTAAGT GGTCGAGACC
 401 GGGCCTTTGT CCGGCGCTCC CTTGGAGCCT AGCCGGTCT ACCTAGACTC AGCCGGGTCC CCTGACCCTG CTTGCTCAAC TCTACGTCTT TGTTTCGTTT

KasI
                                                                                       NarI
                                                                                       SfoI
                                                                                       BbeI
                                                                                       ---------
                                                                                         IL-2 secretion signal (SEQ ID NO:106)
                                                                                         MetTyrArg MetGlnLeu LeuSerCysIle
 501 TCTGTTCTGC GCCGTTACAG ATCCAAGCTG TGACCGGCGC CTACCTGAGA TCACCGGCGA AGGAGGCCA CCATGTACAG GATGCAACTC CTGTCTTGCA
                                            EcoRI
                                        ~~~~~~ CCL2 (1-76)
                                        -------
     AlaLeuSer LeuAlaLeu ValThrAsnAsp GlnProAsp AlaIleAsn AlaProValThr CysCysTyr AsnPheThr AsnArgLysIle SerValGln
 601 TTGCACTAAG TCTTGCACTT GTCACGAATT CGCAGCCAGA TGCAATCAAT GCCCCAGTCA CCTGCTGCTA TAACTTCACC AATAGGAAGA TCTCAGTGCA
     ArgLeuAla SerTyrArgArg IleThrSer SerLysCys ProLysGluAla ValIlePhe LysThrIle ValAlaLysGlu IleCysAla AspProLys
 701 GAGGCTCGCG AGCTATAGAA GAATCACCAG CAGCAAGTGT CCCAAAGAAG CTGTGATCTT CAAGACCATT GTGGCCAAGG AGATCTGTGC TGACCCCAAG
                                                                                                    human IgG1 Fc (constant region)
                                                                                                    -----------
     GlnLysTrpVal GlnAspSer MetAspHis LeuAspLysGln ThrGlnThr AsnPheThr AspLysThrHis ThrCysPro ProCysPro AlaProGluLeu
 801 CAGAAGTGGG TTCAGGATTC CATGGACCAT CTGGACAAGC AAACCCAAAC CTGGAAGACT GACAAAACTC ACACATGCCC ACCGTGCCCA GCACCTGAAC
     LeuGlyGly ProSerVal PheLeuPhePro ProLysPro LysAspThr LeuMetIleSer ArgThrPro GluValThr CysValValVal AspValSer
 901 TCCTGGGGGG ACCGTCAGTC TTCCTCTTCC CCCCAAAACC CAAGGACACC CTCATGATCT CCCGGACCCC TGAGGTCACA TGCGTGGTGG TGGACGTGAG
     HisGluAsp ProGluValLys PheAsnTrp TyrValAsp GlyValGluVal HisAsnAla LysThrLys ProArgGluGlu GlnTyrAsn SerThrTyr
1001 CCACGAAGAC CCTGAGGTCA AGTTCAACTG GTACGTGGAC GGCGTGGAGG TGCATAATGC CAAGACAAAG CCGCGGGAGG AGCAGTACAA CAGCACGTAC
     ArgValValSer ValLeuThr ValLeuHis GlnAspTrpLeu AsnGlyLys GluTyrLys CysLysValSer AsnLysAla LeuProAla ProIleGluLysTyr
1101 CGTGTGGTCA GCGTCCTCAC CGTCCTGCAC CAGGACTGGC TGAATGGCAA GGAGTACAAG TGCAAGGTCT CCAACAAAGC CCTCCCAGCC CCCATCGAGA
     ThrIleSer LysAlaLys GlyGlnProArg GluProGln ValTyrThr LeuProProSer ArgGluGlu MetThrLys AsnGlnValSer LeuThrCys
1201 AAACCATCTC CAAGGCCAAA GGGCAGCCCC GAGAACCACA GGTGTACACC CTGCCCCCAT CCCGGGAGGA GATGACCAAG AACCAGGTCA GCCTGACCTG
     LeuValLys GlyPheTyrPro SerAspIle AlaValGlu TrpGluSerAsn GlyGlnPro GluAsnAsn TyrLysThrThr ProProVal LeuAspSer
1301 CCTGGTCAAA GGCTTCTATC CCAGCGACAT CGCCGTGGAG TGGGAGAGCA ATGGGCAGCC GGAGAACAAC TACAAGACCA CGCCTCCCGT GCTGGACTCC
     AspGlySerPhe PheLeuTyr SerLysLeu ThrValAspLys SerArgTrp GlnGlnGly AsnValPheSer CysSerVal MetHisGlu AlaLeuHisAsn
1401 GACGGCTCCT TCTTCCTCTA CAGCAAGCTC ACCGTGGACA AGAGCAGGTG GCAGCAGGGG AACGTCTTCT CATGCTCCGT GATGCAGCAG GCTCTGCACA
                                                                                                     BmtI
                                                                                                     NheI
     HisTyrThr GlnLysSer LeuSerLeuSer ProGlyLys ***(SEQ ID NO: 52)
1501 ACCACTACAC GCAGAAGAGC CTCTCCCTGT CTCCGGGTAA ATGAGTGCTA GCTGGCCAGA CATGATAAGA TACATTGATG ACTTTGCACA AACCACAACT
1601 ACAATGCAGT GAAAAAAATG CTTTATTTGT GAAATTTGTG ATGCTATTGC TTTATTTGTA ACCATTATAA GCTGCAATAA ACAAGTTAAC AACAACAATT
                                                                                                     AseI
1701 GCATTCATTT TATGTTTCAG GTTCAGGGGG AGGTGTGGAA GGTTTTTTAA AGCAAGTAAA ACCTCTACAA ATGTGGTATG GAATTAATTC TAAAATACAG
1801 CATAGCAAAA CTTTAACCTC CAAATCAGC CTTACTTGA AICCTTTCT GAGGGATGAA TAAGGCATAG CATCAGGGGG CTGTTGCCAA TGTGCATTAG
```

```
1901  CTGTTTGCAG CCTCACCTTC TTTCATGGAG AGTGTATTTT CCCAAGGTTT GAACTAGCTC TTCATTTCTT TATGTTTTAA ATGCACTGAC
2001  CTCCCACATT CCCTTTTTAG TAAAATATTC AGAAATATTC ATTGCAATGA TAAATACATC TAAATAAATGT TTTTTATTAG GCAGAATCCA GATGCTCAAG
2101  GCCCTTCATA ATATCCCCCA GTTTAGTAGT TGGACTTAGG GAACAAAGGA ACCTTTAATA GAAATTGGAC AGCAAGAAAG CGAGCTTCTA GCTTATCCTC
2201  AGTCCTGCTC CCTGCCACCA AAGTGCACGC AGTTGCCGGC CGGGTCGCGC AGGGCGAACT CCCGCCCCA CGGCTGCTCG CCGATCTCGG TCATGGCCGG
2301  CCCGGAGGCG TCCCGGAAGT TCGTGGACAC GACCTCGTC ACAGCTCGTC CAGCCGCGT ACAGCTCGTC CACCACCACC AGGCCAGGGT GTTGTCCGGC
2401  ACCACCTGGT CCTGGACCGC GCTGATGAAC AGGGTCACGT CGTCCCGGAC CACACCGGCG AAGTCGTCCT CCACGAAGTC CCGGAGAAC CCGAGCCGGT
2501  CGGTCCAGAA CTCGACCGCT CCGGCGACGT CGCGCGCGGT GAGCACCGGA ACGCACTGG TCAACTTGGC CATGATGGCT CCTCCTGTCA GGAGAGAAA
                                                                        AseI

2601  GAGAAGAAGG TTAGTACAAT TGCTATAGTG AGTTGTATTA TACTATGCAG ATATACTATG CCAATGATTA ATTGTCAAAC TAGGGCTGCA GGGTTCATAG
2701  TGCCACTTTT CCTGCACTGC CCCATCTCCT GCCCACCCTT TCCCAGGCAT AGACAGTCAG TGACTTACCA AACTCACAGG AGGGAGAAGG CAGAAGCTTG
2801  AGACAGACCC GCGGGACCGC CGAACTGCGA GGGACGTGG CTAGGGCGGC TTCTTTTATG GTGCGCCGGC CCTCGGAGGC AGGGCGCTCG GGGAGGCCTA
2901  GCGGCCAATC TGCCGGTGGCA TAGCGCCAGC GGAGGCGGGG CCGAAGGCCG TGCCTGACCA CATAGGAGTC TCAGCCCCCC GCCCAAAAGC AAGGGAAGT
3001  CACGCGCCTG TAGCGCCAGC GTGTTGTGAA ATGGGGGGCTT TGATGTACTG GGGCCCTGAC TAGTCAAAAC AAACTCCCAT TGACGTCAAT GGGGTGAGA
3101  CTTGGAAATC CCCGTGAGTC AAACCGCTAT CCAGCCCCAT CTGATGTACT GGGCCATTAC CCAAAACCGC ATCATCATGG TAATAGCGAT TAGATGTACT
3201  GCCAAGTAGG AAAGTCCCAT ACTGCCAAGT GGGCAGTTTA ATGCCAGGCG TCCACCCATT GACGTCAATG CGTCATTTAC ATTGGCGTTA GCATATGATA
3301  CACTTGATGT ACTGCCAAGT GGGCAGTTTA CCGTAAATAC GGTCAGCCAG GGGCGCCATT TACCGTAAGT GAAAGTCCCT TATGGCGTTA CTATGGAAAC ATACGTCATT
3401  ATTGACGTCA ATGGGCGGGG TCGTTGGGC ACCGGTAAAA GGCCGCCGTTG CTGGCGTTTT TCCATAGGCT CCGCCCCCCT CTGCAGGCATC CTGGTAACGC TGTGAGCAAA
3501  AGGCCAGCAA AAGGCCAGGA AAGGCCAGGA ACCGTAAAAA AGATACCAGG CGTTTCCCCC TGGAAGCTCC CTCGTGCGCT CTCCTGTTCC GACCCTGCCG ACGCTCAAGT
3601  CAGAGGTGGC GAAACCCGAC AGGACTATAA AGATACCAGG CGTTTCCCCC TCATAGCTCA CGCTGTAGGT ATCTCAGTTC GGTGTAGGTC GTTCGCTCCA AGCTGGGCTG
3701  ACCTGTCCGC CTTTCTCCCT TCGGGAAGCG TGGCGCTTTC TCATAGCTCA CGCTGTAACT ATCGTCTTGA GTCCAACCCG GTAAGACACG ACTTATCGCC ACTGGCAGCA
3801  TGTGCACGAA CCCCCCGTTC AGCCCGACCG CTGCGCCTTA TCCGGTAACT ATCGTCTTGA GTCCAACCCG GTAAGACACG ACTTATCGCC ACTGGCAGCA
3901  GCCACTGGTA ACAGGATTAG CAGAGCGAGG TATGTAGGCG GTGCTACAGA GTTCTTGAAG TGGTGGCCTA ACTACGGCTA CACCGCTGGT AGCGGTGGTT TTTTTGTTTG
4001  GTATCTGCGC TCTGCTGAAG CCAGTTACCT TCGGAAAAAG AGTTGGTAGC TCTTGATCCG GCAAACAAAC CACCGCTGGT AGCGGTGGTT TTTTTGTTTG
4101  CAAGCAGCAG ATTACGCGCA GAAAAAAAGG ATCTCAAGAA GATCCTTTGA TCTTTTCTAC GGGGTCTGAC GCTCAGTGGA ACGAAAACTC ACGTTAAGGG
4201  ATTTTGGTCA TGAGATTATC AAAAAGGATC TTCACCTAGA TCCTTTTAAA TTAAAAATGA AGTTTTAAAT CAATCTAAAG TATATATGAG TAAACTTGGT CTGACAGTTA
4301  ACTAACATAC GCTCTCCATC AAAACAAAAC GAAACAAAAC AATAGGCTGT CCCAGTGCA AGTGCAGGTG CCAGTGCAGG GTCAGTGCAGG GTTTTTTTGT GTGAATCGTA TCTCTATCGA
4401  A (SEQ ID NO: 79)
```

IL2ss.CCL2(5-76).hIgG1Fc GAGless plasmid sequence

```
   1  GGATCTGCGA TCGCTCCGGT GCCCGTCAGT GGGCAGAGCG CACATGCGCC ACAGTCCCCG AGAAGTTGGG GGGAGGGGTC GGCAATTGAA CGGGTGCCTA
 101  GAGAAGGTGG CGGGGGTAA ACTGGGAAAG TGATGTCGTG TACTGGCTCC GCCTTTTTCC CGAGGGTGGG GGAGAAACGT CTTCACGCGG CCTGCCCCT AGTAGTCGCC
 201  GTGAACGTTC TTTTTCGCAA CGGGTTTGCC GCCAGAACAC AGCTGAAGCT TCTGAGGGCT GCATCCTCT CGCATCCGGG CTTCACGCGG CCTGCCCCT ACCTGAGCC
 301  GCCATCCACG CCGGTTGAGT GCGGTTCTGC CGCCTCCCGC CTGTGGTGCC CTGTGAACTG CGTCGCCGT CTAGTAAGT TTAAGCCA GGTCGAGACC
 401  GGGCCTTTGT CCGGGCTCC CTTGGAGCCT ACCTAGACTC AGCCGGCTCT CCTGACCCTG CTTGCTCAAC TCTACTGTCTT TGTTTCGTT

KasI
                                NarI
                                SfoI
                                BbeI                                                    IL-2 secretion signal
                                                                                        MetTyrArg MetGlnLeu LeuSerCysIle
 501  TCTGTTCTGC GCCGTTACAG ATCCAAGCTG TGACCGGCGC CTACCTGAGA TCACCGGCGA AGGAGGGGCCA CCATGTACAG GATGCAACTC CTGTCTTGCA
                                       EcoRI                   ~~~~~~ CCL2(5-76)
      AlaLeuSer LeuAlaLeu ValThrAsnSer IleAsnAla ProValThr CysCysTyrAsn PheThrAsn ArgLysIle SerValGlnArg LeuAlaSer
 601  TTGCACTAAG TCTTGCACTT GTCACGAATT CGATCAATGC CCCAGTCACC TGCTGTTATA ACTTCACCAA TAGGAAGATC TCAGTGCAGA GGCTCGCGAG
      TyrArgArg IleThrSerSer LysCysCysPro LysValAla ValIlePheLys ThrIleVal AlaLysGlu IleCysAlaAsp ProLysGln LysTrpVal
 701  CTATAGAAGA ATCACCAGCA GCAAGTGTTG CAAAGAAGCT GTGATCTTCA AGACCATTGT GGCCAAGGAG ATCTGTGCTG ACCCCAAGCA GAAGTGGGTT
                                                                                              human IgG1 Fc (constant region)
      GlnAspSerMet AspHisLeu ThrGlnThrPro LysThrAsp LysThrHis ThrCysProPro CysProAla ProGluLeu LeuGlyGlyPro
 801  CAGGATTCCA TGGACCACCT GGACAAGCAA ACCCAAACTG CGAAGACTGA CAAAACTCAC ACATGCCCAC CGTGCCCAGC ACTTGAACTC CTGGGGGGAC
      SerValPhe LeuPhePro ProLysProLys AspThrLeu MetIleSer ArgThrProGlu ValThrCys ValValVal AspValSerHis GluAspPro
 901  CGTCAGTCTT CCTCTTCCCC CCAAAACCCA AGGACACCCT CATGATCTCC CGGACCCCTG AGGTCACATG CGTGGTGGTG GACGTGAGCC ACGAAGACCC
      GluValLys PheAsnTrpTyr ValAspGly ValGluVal HisAsnAlaLys ThrLysPro ArgGluGlu GlnTyrAsnSer ThrTyrArg ValValSer
1001  TGAGGTCAAG TTCAACTGT ACGTGGACGG CGTGGAGGTG CATAATGCCA AGACAAAGCC GCGGGAGGAG CAGTACAACA GCACGTACCG TGTGGTCAGC
      ValLeuThrVal LeuHisGln AspTrpLeu AsnGlyLysGlu TyrLysCys LysValSer AsnLysAlaLeu ProAlaPro IleGluLys ThrIleSerLys
1101  GTCCTCACCG TCCTGCACCA GGACTGGCTG AATGGCAAGG AGTACAAGTG CAAGGTCTCC AACAAAGCC TCCCAGCCCC CATCGAGAAA ACCATCTCCA
      AlaLysGly GlnProArg GluProGlnVal TyrThrLeu ProProSer ArgGluGluMet ThrLysAsn GlnValSer LeuThrCysLeu ValLysGly
1201  AAGCCAAAGG GCAGCCCCGA GAACCACAGG TGTACACCC TGCCCCCATCC CGGGAGGAG ATGACCAAGAA CCAGGTCAGC CTGACCTGCC TGGTCAAAGG
      PheTyrPro SerAspIleAla ValGluTrp GluSerAsn GlyGlnProGlu AsnAsnTyr LysThrThr ProProVelLeu AspSerAsp GlySerPhe
1301  CTTCTATCCC AGCGACATCG CCGTGGAGTG GGAGAGCAAT GGGCAGCCGG AGAACAACTA CAAGACCACG CCTCCCGTGC TGGACTCCGA CGGCTCCTTC
      PheLeuTyrSer LysLeuThr ValAspLys SerArgTrpGln GlnGlyAsn ValPheSer CysSerValMet HisGluAla LeuHisAsn HisTyrThrGln
1401  TTCCTCTACA GCAAGCTCAC CGTGGACAAG AGCAGGTGGC AGCAGGGGAA CGTCTTCTCA TGCTCCGTGA TGCACGAGGC TCTGCACAAC CACTACACGC
                                                                                 BmtI
                                                                                 NheI
      LysSerLeu SerLeuSer ProGlyLys***(SEQ ID NO: 53)
1501  AGAAGAGCCT CTCCCTGTCT CCGGGTAAAT GAGTGCTAGC TGGCCAGACA TGATAAGATA CATTGATGAG TTTGGACAAA CCACAACTAG AATGCAGTGA
1601  AAAAAATGCT TTATTTGTGA AATTTGTGAT GCTATTGCTT TATTTGTAAC CATTATAAGC TGCAATAAAC AAGTTAACAA CAACAATTGC ATTCATTTTA
                                                                                                     AseI
1701  TGTTTCAGGT TCAGGGGGAG GTGTGGGAGG TTTTTTAAAG CAAGTAAAAC CTCTACAAAT GTGGTATGGA ATTAATTCTA AAATACAGCA TAGCAAAACT
1801  TTAACCTCCA AATCAAGCCT CTACTTGAAT CCTTTCTGA GGGATGAATA AGGCATAGGC ATCAGGGGCT GTTGCCAATG TGCATTAGCT GTTTGCAGCC
```

IL2ss.CCL2(5-76).hIgG1Fc sequence [Alanine substitutions for removal of GAG binding sites – Lys & His]

```
   1 GGATCTGCGA TCGCTCCGGT GCCCGTCAGT GGGCAGAGCG CACATCGCCC ACAGTCCCCG AGAAGTTGGG GGAGGGGTC GGCAATTGAA CGGGTGCCTA
 101 GAGAAGTTGG CGCGGGGTAA ACTGGGAAAG TGATGTCCTG GCCAGAACAC CGGGTTTG

```
1901  TCACCTTCTT TCATGAGAGTT TAAGATATAG TGTATTTTCC CAAGGTTTGA ACTAGCTCTT CATTTCTTTA TGTTTTAAAT GCACTGACCT CCCACATTCC
2001  CTTTTTAGTA AAATATTCAG AAATAATTTA AATACATCAT TGCAATGAAA ATAAATGTTT TTTATTAGGC AGAATCCAGA TGCTCAAGGC CCTTCATAAT
2101  ATCCCCCAGT TTAGTAGTTG GACTTAGGGA ACAAAGGAAC CTTTAATAGA AATTGACAG CAAGAAAGCG AGCTTCTAGC TTATCCTCAG TCCTGTCCT
2201  CTGCCACAGT GTGCACGCAG TTGCCGGCCG GGTCGCGCAG GGCGAACTCC GCTCGCTCGC GATCTCGGTC GCCAGGGCC ATGGCCGGCC CGGAGGCGTC
2301  CCGGAAGTTC GTGGACACGA CCTCCGACCA CTCGGCGTAC AGCTCGTTCA GGCCGCGCAC CCACACCCAG GCCAGGGTGT TGTCCGGCAC CACCTGGTCC
2401  TGGACCGCGC TGATGAACAG GGTCACGTCG TCCCGGACCA CACCGGCGAA GTCGTCCTCC ACGAAGTCCC GGGAGAACCC GAGCCGGTCG GTCCAGAACT
2501  CGACCGCTCC GGCGACGTCG CGCGCGGTGA GCACCGGAAC GGCACTGGTC AACTTGGCCA TGATGGCTCC TCCTGTCAGG AGAGGAAAGA GAAGAAGGTT
                                                                   AseI
2601  AGTACACATTG CTATAGTGAG TTGTATTATA CTATGCAGAT ATACTATAAT TGTCAAACTA GGGCTGCAGG GTTCATAGTG CCACTTTTCC
2701  TGCACTGCCC CATCTCCTGC CCACCCTTTC CCAGGCATAG ACAGTCAGTG ACTTACCAAA CTCACAGGAG GGAGAAGGCA GAAGCTTGAG ACAGACCCGC
2801  GGGACCGCCG AACTGCGAGG GGACGTGGCT AGGGCGGCTT CTTTTATGGT GCGCCGGCCC TCGGAGGCAG GCGCTCGGG GAGGCCTAGC GGCCAATCTG
2901  CGGTGGCAGG AGGCGGGGCC GAAGGCCGTG CCTGACCAAT CGGAGCACA TAGGAGTCTC AGCCCCCGC CCAAAGCAA GGGGAAGTCA CGGGCCTGTA
3001  GCGCCAGCGT GTTGTGAAAT GGGGGCTTGG GGGGTTTACTGCT ACTCCCATTG AGTGAGACT TGAAATCCC
3101  CGTGAGTCAA ACCGCTATCC ACGCCATTG ATGTACTGCC AAAACCGCAT GTCAAAACAA CATCATGGTA ATAGCGATGA CAAGTAGGCT CAAGTAGGAA
3201  AGTCCCATAA GGTCATGTAC TGGGCATAAT GCCAGGCGGG CCATTACCG TCATTACCG CAATAGGGGG CGTACTTGGC ATATGATAC CTTGATGATGTAC
3301  TGCCAAGTGG GCAGTTTACC GTAAATACTC GGTAAGTTGA AAGTCCCTAT TGGCGTTACT ATGGAACAT ACGTCATTAT TGACGTCAAT
3401  GGGCGGGGGT CGTTGGGCGG TCAGCCAGG CGTAAGCCT GGGCCATTTA CGTAAGTTA AAGTCCCTAT GGCGCTATCG GCGTTAGACT TGACGTCAAT
3501  GGCCAGGAAC CGTAAAAGG CCGGTTTGCT CGGCCATTT GTCGTTTTT GCCCCCCTGA CGTAAACGCT CCCTGCGCT TACCGATAC TGTCCGCCT
3601  AACCCGACAG GACTATAAAG ATACCAGGCG TTTCCCTTG GAAGCTCCT CGTGTTCCGA CCTGTCGT TCGGCTATGT CTGCACGAGAC
3701  TTCTCCCTTC GGGAAGCGTG GCGCTTTCTC ATAGCTCACG CTGTAGGTAT CTCAGTTCGG TGTAGGTCGT TCGCTCCAAG CTGGGCTGTG TGCACGAACC
3801  CCCCGTTCAG CCCGACCGCT GCGCCTTATC CGGTAACTAT CGTCTTGAGT CCAACCCGGT AAGACACGAC TTATGCCAC TGGCCAGCAG CCACTGGTAAC
3901  AGGATTAGCA GAGCGAGGTA TGTAGGCGGT GCTACAGAGT TCTTGAAGTG GTGGCCTCA AAGACAGAAC TACGCGTAG CGCTGGTAG ATCTCGCTC
4001  TGCTGAAGCC AGTTACCTTC GGAAAAAGAG TTGGTAGCTC TTGATCCGGC AAACAACCA CGCTACAG CGGTGGTTT TTTGTTTGCA ATCTCGCTC
4101  TACGCGCAGA AAAAAGGAT CTCAAGAAGA TCCTTTGATC TTTTCTACGG GGTCTGACGC TCAGTGGAAC GAAACTCAC GTTAAGGGAT TTTGGTCATG
4201  GCTAGTTAAT TAACATTAA ATCAGCGCCG CAATAAAAT ATCTTTATTT TCATTACATC TGTGTGTTGG TTTTTTGTGT GAATCGTAAC TAACATACGC
4301  TCTCCATCAA AACAAAACGA AACAAAACAA ACTAGCAAAA TAGGCTGTCC CCAGTGCAAG TGCAGGTGCC AGAACATTTC TCTATCGAA (SEQ ID NO: 81)
```

IL2ss.CCL7.hIgG1Fc sequence

```
   1  GGATCTCCGA TCGCTCCGGT GCCGTCAGT GGGCAGAGCG CACATGCCCC ACAGTCCCCG AGAAGTTGGG GGGAGGGGTC GGCAATTGAA CGGGTGCCTA
 101  GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201  GTGAACGTTC TTTTTCGCAA CGGGTTTGCC GCCAGAACAC AGCTGAAGCT TCCAGGGGCT CCGATCTCTC CTTCACGCGC CCGCCGCCCT ACCTGAGGCC
 301  GCCATCCACG CCGGTTGAGT CGCGTTCTGC CGCCTCCGC CTGTGTGCC CGCGCCCCGT CCTGAACTG CGTCCGCCGT CTAGGTAAGT TTAAAGCTCA GGTCGAGACC
 401  GGGCCTTTGT CCGGCGCTCC CTTGGAGCCT ACCTAGACTC AGCCGGCTCT CAAGCGGCTT CCACGCCTCT CCCTGACCCTG CTTGCTCAAC TCTACGTCTT TGTTTCGTTT
                                       KasI
                                       NarI
                                       SfoI
                                       BbeI
                                                                                                                IL-2 secretion signal
                                                                                                                MetTyrArg MetGlnLeu LeuSerCysIle
 501  TCTGTTCTGC GCCGTTACAG ATCCAAGCTG TGACCGGCGC CTACCTGAGA AGGAGGGCCA CCATGTACAG GATGCAACTC CTGTCTTGCA
        EcoRI
         ~~~~~~~ CCL7 (1-76)
        AlaLeuSer LeuAlaLeu ValThrAsnSer CysCysTyr ArgPheIle AsnLysLysIle ProLysGln ArgLeuGlu SerTyrArgArg ThrThrSer
 601  TTGCACTAAG TCTTGCACTT GTCACGAATT CGTGCTGCTA CAGATTATC AATAAGAAAA TCCCTAAGCA GAGGCTGGAG AGCTACAGAA GGACCACCAG
        SerHisCys ProArgGluAla ValIlePhe LysThrLys LeuAspLysGlu IleCysAla AspProThr GlnLysTrpVal GlnAspPhe MetLysHis
 701  TAGCCACTGT CCCCGGGAAG CTGTAATCTT CAAGACCAAA CTGGACAAGG AGATCTGTGC TGACCCCACA CAGAAGTGGG TCCAGGACTT TATGAAGCAC
                                                         human IgG1 Fc (constant region)
        LeuAspLysLys ThrGlnThr ProLysLeu AspLysThrHis ThrCysPro ProCysPro AlaProGluGlu LeuGlyGly ProSerVal PheLeuPhePro
 801  CTGGACAAGA AAACCAAAC TCCAAAGCTT GACAAAACTC ACACATGCCC ACCGTGCCCA GCACCTGAAC TCCTGGGGGG ACCGTCAGTC TTCCTCTTCC
        ProLysPro LysAspThr LeuMetIleSer ArgThrPro GluValThr CysValValVal AspValSer HisGluAsp ProGluValLys PheAsnTrp
 901  CCCCAAAACC CAAGGACACC CTCATGATCT CCCGGACCCC TGAGGTCACA TGCGTGGTGG TGGACGTGAG CCACGAAGAC CCTGAGGTCA AGTTCAACTG
        TyrValAsp GlyValGluVal HisAsnAla LysThrLys ProArgGluGlu ValGlnTyr AsnSerThr TyrArgValVal SerValLeuThr ValLeuHis
1001  GTACGTGGAC GGCGTGGAGG TGCATAATGC CAAGACAAAG CCGCGGGAGG AGCAGTACAA CAGCACGTAC CGTGTGGTCA GCGTCCTCAC CGTCCTGCAC
        GlnAspTrpLeu AsnGlyLys GluTyrLys CysLysValSer AsnLysAla LeuProAla ProIleGluLys ThrIleSer LysAlaLys GlyGlnProArg
1101  CAGGACTGGC TGAATGGCAA GGAGTACAAG TGCAAGGTCT CCAACAAAGC CCTCCCAGCC CCCATCGAGA AAACCATCTC CAAAGCCAAA GGGCAGCCCC
        GluProGln ValTyrThr LeuProProSer ArgGluGlu LeuThrLys AsnGlnValSer LeuThrCys LeuValLys GlyPheTyrPro SerAspIle
1201  GAGAACCACA GGTGTACACC CTGCCCCCAT CCCGGGAGGA GATGACCAAG AACCAGGTCA GCCTGACCTG CCTGGTCAAA GGCTTCTATC CCAGCGACAT
        AlaValGlu TrpGluSerAsn GlyGlnPro GluAsnAsn TyrLysThrThr ProProVal LeuAspSer AspGlySerPhe PheLeuTyr SerLysLeu
1301  CGCCGTGGAG TGGGAGAGCA ATGGGCAGCC GGAGAACAAC TACAAGACCA CGCCTCCCGT GCTGGACTCC GACGGCTCCT TCTTCCTCTA CAGCAAGCTC
                                                                                                               AseI
        ThrValAspLys SerArgTrp GlnGlnGly AsnValPheSer CysSerVal MetHisGlu AlaLeuHisAsn HisTyrThr GlnLysSer LeuSerLeuSer
1401  ACCGTGGACA AGAGCAGGTG GCAGCAGGGG AACGTCTTCT CATGCTCCGT GATGCACGAG GCTCTGCACA ACCACTACAC GCAGAAGAGC CTCTCCCTGT
        ProGlyLys ***(SEQ ID NO: 55)
1501  CTCCGGGTAA ATGAGTGCTA GCTGCCCACA CATGATAAGA TACATTGATG AGTTTGGACA AACCACAACT AGAATGCAGT GAAAAAAATG CTTTATTTGT
1601  GAAATTTGTG ATGCTATTGC TTTATTTGTA ACCATTATAA GCTGCAATAA ACAAGTAAC ACAACAATT GCATTCATTT TATGTTTCAG GTTCAGGGGG
1701  AGGTGTGGGA GGTTTTTTAA AGCAAGTAAA ACCTCTACAA ATGTGGTATG GAATTAATTC TAAAATACAG CATAGCAAAA CTTTAACCTC CAAATCAAGC
1801  CTCTACTTGA ATCCTTTCT GAGGGATGAA GAGGAAGGAA GCATCAGGGG GCATCAGGG CTGTTGCCAA ACCTCTACAA TGTGCATTAG CTGTTTGCAG CCTCACCTTC TTTCATGGAG
```

```
1901 TTTAAGATAT AGTGTATTTT CCCAAGGTTT GAACTAGCTC TTCATTTCTT TATGTTTTAA ATGCACTGAC CTCCCACATT CCCTTTTTAG TAAAATATTC
2001 AGAAATAATT TAAATACATC ATTGCAATGA ACTTTAATA TTTTTATTAG GCAGAATCCA GATGCTCAAG GCCCTTCATA ATATCCCCA GTTTAGTAGT
2101 TGGACTTAGG GAACAAAGA ACCTTTAATA GAAATTGGAC AGCAAGAAAG CGAGCTTCTA GCTTATCCTC AGTCCTGCTC CTCTGCCACA AAGTGCACGC
2201 AGTTGCCGGC CGGGTCGCGC AGGGCGAACT CCCGCCCCA CGGCTGCTCG CCGATCTCGG TCATGGCCGG CCCGGAGGCG TCCGGAAGT TCGTGGACAC
2301 GACCTCCGAC CACTCGGCGT ACAGCTCGTC CAGGCCGCGC ACCCACACCC AGGCCAGGGT GTTGTCCGGC ACCAACTGGT CCTGACCGC GCTGATGAAC
2401 AGGGTCACGT CGTCCCGGAC CACACCGGCG AAGTCGTCCT CCACGAAGTC CCGAAGTC CCGGAGAAC CCGAGCCGGT CGTCAGAA CTCGACCGCT CGGGCGACGT
2501 CGGCGCGCGT GAGCACCGGA ACGGCACTGG TCAACTTGGC CATGATGGCT CCTCCTGTCA GGAAGGAAA GAGAGAAGG TTAGTACAAT TGCTATAGTG
                          AseI
2601 AGTTGTATTA TACTATGCAG ATATACTATG CCAATGATTA ATTGTCAAAC TAGGGCTGCA GGGTTCATAG TGCCACTTTT CCTGCACTGC CCCATCTCCT
2701 GCCCACCCTT TCCCAGCCAT AGACAGTCAG TGACTTACCA AACTCACAGG AGGGAGAAGG CAGAAGCTTG AGACAGACCC GGGGACCGC CGAACTGCGA
2801 GGGGACGTGG CTAGGCGCG TTCTTTTATG GTGCGCCAGC CCTCGGAGGC AGGGCGCTCA GGGAGGCCTA GGGGCCAATC TGCGGTGGCA GGAGGCGGGG
2901 CCGAAGGCCG TGCCTGACCA CATAGGAGTC TCAGCCCCCC GCCCAAAGC AAGGGGAAGT CACGGCCTG TAGCGCCAGC GTGTTGTGAA
3001 ATGGGGGCTT GGGGGGTTG GGGCCCTGAC TAGTCAAAAT TGACGTCAAT GGGGTGGAGA CTTGAAATC CCCGTGAGTC AAAGTCCCAT AAACCGCTAT
3101 CCACGCCCAT TGATGTACTG CCAAAACCGC GGCCATTTAC ATCATCATGG TAATAGCGAT GACTATACG GCCAAGTAGG AAAGTCCCAT AAGGTCATGT
3201 ACTGGGCATA ATGCCAGGCG GGCCATTTAC CGTCATTGAC GTCAATAGGG GGCGTACTTG GCATATGATA CACTTGATGT ACTGCCAAGT GGGCAGTTTA
3301 CCGTAAATAC TCCACCCATT GACGTCAATG GAAAGTCCCT ATTGGCGTTA CTATGGGAAC ATACGTCATT ATTGACGTCA ATGGGGGGG GTCGTTGGGC
3401 GGTCAGCCAG GCGGGCCATT TACCGTAAGT TATGTAACGC CTGCAGGTTA ATTAAGAACA TGTGAGCAAA AGGCCAGCAA ACCGTAAAAA
3501 GGCCGCGTTG CTGGCGTTTT TCCATAGGCT CCGCCCCCCT GACGAGCATC ACAAAAATCG ACGCTCAAGT CAGAGGTGGC GAAACCGAC AGGACTATAA
3601 AGATACCAGG CGTTTCCCCC TGGAAGCTCC CTCGTGCGCT CTCCTGTTCC GACCCTGCCG CTTACCGGAT ACCTGTCCGC CTTTCTCCCT TCGGGAAGCG
3701 TGGCGCTTTC TCATAGCTCA CGCTGTAGGT ATCTCAGTTC GGTGTAGGTC GTTCGCTCCA AGCTGGGCTG TGTGCACGAA CCCCCCGTTC AGCCCGACCG
3801 CTGCGCCTTA TCCGGTAACT ATCGTCTTGA GTCCAACCCG GTAAGACACG ACTTATCGCC ACTGGCAGCA ACAGTATTTG GTATCTGCGC TCTGCTGAAG CCAGTTACCT
3901 TATGTAGGCG GTGCTACAGA GTTCTTGAAG TGGTGGCCTA ACTACGGCTA CACCGCTGGT AGCGGTGGTT TTTTTGTTTG CAAGCAGCAG ATTACGCGCA GAAAAAAGG
4001 TCGGAAAAAG AGTTGGTAGC TCTTGATCCG GCAAACAAAC GGGGTCTGAC GCTCAGTGGA ACGAAAACTC ACGTTAAGGG ATTTTGGTCA TGGCTAGTTA ATTAACATTT
4101 ATCTCAAGAA GATCCTTTGA TCTTTTCTAC CCGAATAAA ATATCTTTAT TTTCATTACA TCTGTGTGTT GGTTTTTTGT GTGAATCGTA ACTAACATAC GCTCTCCATC AAAACAAAC
4201 AAATCAGCGG CCGCAATAAA AATATCTTTAT TTTCATTACA TCTGTGTGTT GGTTTTTTGT GTGAATCGTA ACTAACATAC GCTCTCCATC AAAACAAAC
4301 GAAACAAAAC AAACTAGCAA AATAGGCTGT CCCCAGTGCA AGTGCAGGTG CCAGAACATT TCTCTATCGA TA (SEQ ID NO: 82)
```

IL2ss.CCL7(5-76).hIgG1Fc sequence

```
   1  GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101  GAGAAGGTGG CGCGGGGTAA ACTGGGAAAG TGATGTCGTG TACTGGCTCC GCCTTTTTCC CAAGGGTGGG GAGAAACCGT ATATAAGTGC AGTAGTCGCG
 201  GTGAACGTTC TTTTTCGCAA CGGGTTTGCC GCCAGAACAC AGCTGAAGCT TCGAGGGGCT CGCATCTCTC CTTCACGCGC CGCCGCCCT  ACCTGAGGCC
 301  GCCATCCACG CCGGTTGAGT CCGTTCTGC  CTGGTGTGCC TCCTGAACTG CGTCCGCCGT CTAGGTAAGT CTAGGGAAGA CTAGTAAGCTCA GGTCGAGACC
 401  GGGCCTTTGT CCGGCGTCC  CTTGGAGCCT AGCCGGCTCT ACCTAGACTC AGCGCCAAAT GGACAGAGAG CCTGACCCTG CTTGCTCAAC TCTACGTCTT TGTTTCGTTT
                             KasI
                             NarI
                             SfoI
                             BbeI                                                                  IL-2 secretion signal
                                                                                                   MetTyrArg MetGlnLeu LeuSerCysIle
 501  TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                          EcoRI
                                                   ------ CCL7 (5-76)
                                          AlaLeuSer LeuAlaLeu ValThrAsnSer PheIleAsn LysLysIle ProLysGlnArg LeuGluSer TyrArgArg ThrThrSerSer HisCysPro
 601  TTGCACTAAG TCTTGCACTT GTCACGAATT CGTTTATCAA CAAGAAAATC CCTAAGCAGA GGCTGGAGAG CTACAGAAGG ACCACCAGTA GCCACTGTCC
      ArgGluAla ValIlePheLys ThrLysLeu AspLysGlu IleCysAlaGlu AspThrGln LysTrpVal GlnAspPheMet LysHisLeu AspLysLys
 701  CCGGGAAGCT GTAATCTCA  AGACCAAACT GGACAAGGAG ATCTGTGCTG AGGACACACA GAAGTGGGTC CAGGACTTTA TGAAGCACCT GGACAAGAAA
                                        ------ CCL7 (5-76) ------
                                        human IgG1 Fc (constant region)
      ThrGlnThrPro LysLeuAsp LysThrHis ThrCysProPro CysProAla ProGluLeu LeuGlyGlyPro SerValPhe LeuPhePro ProLysProLys
 801  ACCCAAACTC CAAAGCTTGA CAAAACTCAC ACATGCCCAC CGTGCCCAGC ACCTGAACTC CTGGGGGGAC CGTCAGTCTT CCTCTTCCCC CCAAAACCCA
      AspThrLeu MetIleSer ArgThrProGlu ValThrCys ValValVal AspValSerHis GluAspPro GluValLys PheAsnTrpTyr ValAspGly
 901  AGGACACCCT CATGATCTCC CGGACCCCTG AGGTCACATG CGTGGTGGTG GACGTGAGCC ACGAAGACCC TGAGGTCAAG TTCAACTGGT ACGTGGACGG
      ValGluVal HisAsnAlaLys ThrLysPro ArgGluGlu GlnTyrAsnSer ThrTyrArg ValValSer ValLeuThrVal LeuHisGln AspTrpLeu
1001  CGTGGAGGTG CATAATGCCA AGACAAAGCC GCGGGAGGAG CAGTACAACA GCACGTACCG TGTGGTCAGC GTCCTCACCG TCCTGCACCA GGACTGGCTG
      AsnGlyLysGlu TyrLysCys LysValSer AsnLysAlaLeu ProAlaPro IleGluLys ThrIleSerLys AlaLysGly GlnProArg GluProGlnVal
1101  AATGGCAAGG AGTACAAGTG CAAGGTCTCC AACAAAGCCC TCCCAGCCCC CATCGAGAAA ACCATCTCCA AAGCCAAAGG GCAGCCCCGA GAACCACAGG
      TyrThrLeu ProProSer ArgGluGluMet ThrLysAsn GlnValSer LeuThrCysLeu ValLysGly PheTyrPro SerAspIleAla ValGluTrp
1201  TGTACACCCT GCCCCCATCC CGGGAGGAGA TGACCAAGAA CCAGGTCAGC CTGACCTGCC TGGTCAAAGG CTTCTATCCC AGCGACATCG CCGTGGAGTG
      GluSerAsn GlyGlnProGlu AsnAsnTyr LysThrThr ProProValLeu AspSerAsp GlySerPhe PheLeuTyrSer LysLeuThr ValAspLys
1301  GGAGAGCAAT GGGCAGCCGG AGAACAACTA CAAGACCACG CCTCCCGTGC TGGACTCCGA CGGCTCCTTC TTCCTCTACA GCAAGCTCAC CGTGGACAAG
      SerArgTrpGln GlnGlyAsn ValPheSer CysSerValMet HisGluAla LeuHisAsn HisTyrThrGln LysSerLeu SerLeuSer ProGlyLys***
                                                                                                                  (SEQ ID NO: 56)
1401  AGCAGGTGGC AGCAGGGGAA CGTCTTCTCA TGCTCCGTGA TGCACGAGGC TCTGCACAAC CACTACACGC AGAAGAGCCT CTCCCTGTCT CCGGGTAAAT
            BmtI
            ** NheI
1501  GAGTGCTAGC TGGCCAGACA TGATAAGATA CATTGATGAG TTTGGACAAA CCACAACTAG AATGCAGTGA AAAAAATGCT TTATTTGTGA AATTTGTGAT
1601  GCTATTGCTT TATTTGTAAC CATTATAAGC TGCAATAAAC AAGTTAACAA CAACAATTGC ATTCATTTTA TGTTTCAGGT TCAGGGGGAG GTGTGGGAGG
1701  TTTTTTAAAG CAAGTAAAAC CTCTACAAAT GTGGTATGGA ATTAATTCTA AAATACAGCA TAGCAAAACT TAACCTTCCA AATCAAGCCT CTACTTGAAT
```

```
1801  CCTTTTCTGA GGGATGAATA AGGCATAGCC ATCAGGGGCT GTTGCCAATG TGCATTAGCT GTTTGCAGCC TCACCTTCTT TCATGGAGTT TAAGATATAG
1901  TGTATTTTCC CAAGGTTTGA ACTAGCTCTT CATTTCTTTA TGTTTTAAAT GCACTGACCT CCCACATTCC CTTTTTAGTA AAATATTCAG AAATAATTTA
2001  AATACATCAT TGCAATGAAA ATAAATGTTT TTTATTAGGC AGAATCCAGA AGCTTCTAGC TGCTCAAGGC CCTTCATAAT ATCCCCCAGT TTAGTAGTTG GACTTAGGGA
2101  ACAAAGGAAC CTTTAATAGA AATTGGACAG CAAGAAAGCG AGCTTCTAGC TTATCCTCAG TCCTGCTCCT CTGCCACAAA GTGCACGCAG TTGCCGGCCG
2201  GGTCGCGCAG GGCGAACTCC CGCCCCACG  GCTGCTCGCC GATCTCGGTC ATGGCCGGCC CGGAGGCGTC CCGGAAGTTC CCGGACACGA CCTCCGACCA
2301  CTCGGGCTAC AGCTCGTCCA GGCCGCGCAC GCCAGGGTGT GCCAGGGCAC TGTCCGGCAC CACCTGGTCC TGGACCGCGC TGATGAACAG GGTCACGTCG
2401  TCCCGGACCA CACCGGCGAA GTCGTCCTCC ACGAAGTCCC GGGAGAACCC GAGCCGTCG  GTCCAGAACT GACCGCTCC  CGGCGACGTCG CGCGGGTGA
2501  GCACCGGAAC GGCACTGGTC AACTTGGCCA TGATGGCTCC TCCTGTCAGG AGAGGAAAGA GAAGAAGTT  AGTACAATTG CTATAGTGAG TTGTATTATA
                                              AseI
2601  CTATGCAGAT ATACTATGCC AATGATTAAT TGTCAAACTA GGGCTGCAGG GTTCATAGTG CCACTTTTCC TGCACTGCCC CATCTCCTGC CCACCCTTTC
2701  CCAGGCATAG ACAGTCAGTG ACTTACCAAA CTCACAGGAG GGAGAAGGCA GAAGCTTGAG ACAGACCGGC GGGACCGCGG AACTGCGAGG GGACGTGGCT
2801  AGGGCGGCTT CTTTTATGGT GCGCCGGCGC TCGGAGGCAG GGCGCTCGGG CCCAAAGCAA GGCCAATCTG CGGCCCAGGG CGTGGCCAGG AGGCGGGGCC GAAGGCCGTG
2901  CCTGACCAAT CCGGAGCACA TAGGAGTCTC AGCCCCCCGC ACTCCCCATT ACGTCAATGG GGTGGAGACT CGGCCAGCGT GCGCCAGCGT ACCGCTATCC GGGGGCTTGG
3001  GGGGGTTGGG GCCCTGACTA GTCAAAACAA ACTCCCCATT ACGTCAATGG GGTGGAGACT CGTGAGTCAA ACCGCTATCC ACGGGCATTG
3101  ATGTACTGCC AAAACCGCAT CATCATGGTA ATAGCGATGA CGTACTTGGC GATGTACTGC CAAGTAGGAA AGTCCCATAA GGTCATGTAC TGGGCATAAT
3201  GCCAGGCGGG CCATTTACCG TCATTGACGT CAATGGGAGT TTGTTTTGGC ACCCAATTGA CGTCAATGGG GCGGTAACTG TGCCAAGTGG GCAGTTTACC GTAAATACTC
3301  CACCCATTGA CGTCAATGGA AAGTCCCTAT TGGCGTTACT ATGGGAACAT ACGTCATTAT TGACGTCAAT GGGCGGGGGT CGTTGGGCGG TCAGCCAGGC
3401  GGGCCATTTA CCGTAAGTTA TGTAACGCCT GCAGTTAAT CGAGCATTCAC TAAGAACATG GCTCAAGTCA GAGGTGGCGA GGCCAGGAAC AACCCGACAG CCGCGTTGCT
3501  GGCGTTTTTC CATAGGCTCC GCCCCCCTGA CGAGCATCAC CCTGCCCGCT TACCCGGATAC CTGGGCCGCT CTGTCCGCCT TTCTCCCTTC GGGAAGCGTG ATACCAGGCG
3601  TTTCCCCCTG GAAGCTCCCT CGTGCGCTCT CCTGTTCCGA CCTGCGCTCT TGCTCCAAG  CCCGTTCAG  CCCGACCGCT GCGCCTATC  GCGCTTCTC
3701  ATAGCTCACG CTGTAGGTAT CTCAGTTCGG TGTAGGTCGT TCGCTCCAAG CTGGGCTGTG TGCACGAACC AGGATTAGCA GAGCGAGGTA TGTAGGCGGT GCGCCTATC
3801  CGGTAACTAT CGTCTTGAGT TTCAGTTCGG AAGACACGAC TTATCGCCAC TGGCAGCAGC CACTGGTAAC AGGATTAGCA AGTTACCTTC GGAAAAAGAG
3901  GCTACAGAGT TCTTGAAGTG GTGGCCTAACA TACGGCTACA CTAGAAGAAC AGTATTTGGT ATCTGCGCTC TGCTGAAGCC TACGCGCAGA AAAAAGGAT CTCAAGAAGA
4001  TTGGTAGCTC TTGATCCGGC AAACAACCA  CCGCTGGTAG CGGTGGTTTT TTTGTTTGCA AGCAGCAGAT TACGCGCAGA AAAAAGGAT  CTCAAGAAGA
4101  TCCTTTGATC TTTTCTACGG GTCTGACGC  TCAGTGGAAC GAAAACTCAC GTTAAGGGAT TTTGGTCATG AGATTATCAA AAAGGATCTT CACCTAGATC
4201  GCAATAAAAT ATCTTTATTT TCATTACATC TGTGTGTTGG TTTTTGTGT  GAATCGTAAC CTCCATCAA  TAACATACG  GCTAGTTAAT AACAAAACGA
4301  ACTAGCACAAA TAGGCTGTCC CCAGTGCAAG TGCAGGTGCC AGAACATTTC TCTATCGAA  (SEQ ID NO:83)
```

FIG. 2E

IL2ss.CCL7(5-76).hIgG1Fc sequence
[Alanine substitutions for removal of GAG binding sites – Lys & His]

```
   1  GGATCTGCGA TCGCTCCGGT GCCCTCCAGT GGGCAGAGCG CACATCGCCC ACAGTCCCCG AGAAGTTGGG GGGAGGGGTC GGCAATTGAA CGGGTGCCTA
 101  GAGAAGGTGG CGCGGGGTAA ACTGGGAAAG TGATGTCGTG GCCAGAACAC AGCTGAAGCT TCGAGGGCT  TCCTGAAGCA CGTCAGCGCT CGAGGGGGAC CGAGGGTGGG GGAGAACCGT CCGCCGCGC ACTAGTCGCC
 201  GTGAACGTTC TTTTTGCAA  CGGGTTCGCC CCCAGAACAC AGCTGAAGCT TCGAGGGGCT TGAGGGGCT TCGATCTCT CGTCAGCGCT CTTCAGCGCT CCGCCGCGC ACTAGTCGCC
 301  GCCATCCACG CCGGTTCGT  CCGGTTCGCC CGCCTCCGC  TGTGGCTGCA AGCTGAAGCT TCCTGAAGCA CGTCCGCCGT CTAGGTAAGT TTAAAGCTCA GGTGAGACC
 401  GGGCCTTTGT CCGGCGCTCC CTTGGAGCCT ACCTAGAGCT AGCCGGCTCT CCACGGCTTT GGACCCCTG  CTTGCTCAAC TCTACGTCTT TGTTTCGTTT
```

IL-2 secretion signal
                                                                                MetTyrArg MetGlnLeu LeuSerCysIle
                                                       CCATGTACAG GATGCAACTC CTGTCTTGCA

```
 501  TCTGTTCTGC GCCGTTACAG ATCCAAGCTG TGACCGGCGC CTACCTGAGA TCACCGGCGA AGGAGGGCCA
                 EcoRI                                                                  ~~~~ CCL7 (5-76)
```

AlaLeuSer LeuAlaLeu ValThrPro AsnSer PheIleAsn LysThrHis ThrCysProCys SerValPhe LeuPhePro ProLysProLys
```
 601  TTGCACTAAG TCTTGCACTT GTCACGAATT CGTTTATCAA TAAGAAAATC CCTAAGCAGA GGCTGGAGAG CTACACAGG ACCACCAGTA GCCACTGTCC
```
                 ArgGluAla ValIlePheAla ThrAlaLeu AspIleAsp IleCysAlaGlu ProThrGln AlaTrpVal GlnAspPheMet AlaAlaLeu AspAlaAla
```
 701  CGGGGAAGCT GTAATCTTCg cCACCgCtgCT GGACgCtGAG ATCTGCGTG ACCCACACA GCCTGGGTC CAGGACTTTA TGgCtgCCCT GGACgCgGCt
                                                                               human IgG1 Fc (constant region)
```
                ThrGlnThrPro AlaLeuAsp LysThrHis ThrCysProPro CysProAla ProGluLeu LeuGlyGlyPro SerValPhe LeuPhePro ProLysProLys
```
 801  ACCCAAACTC CAGCGCTTGA CAAAACTCAC ACATGCCCAC CGTGCCCAGC ACCTGAACTC CTGGGGGGAC CGTCAGTCTT CCTCTTCCCC CCAAAACCA
```
                AspThrLeu MetIleSer ArgThrProGlu ValThrCys ValValVal AspValSerHis GluAspPro GluValLys PheAsnTrpTyr ValAspGly
```
 901  AGGACACCCT CATGATCTCC CGGACCCCTG AGGTCACATG CGTGGTGGTG GACGTGAGCC ACGAAGACCC TGAGGTCAAG TTCAACTGGT ACGTGGACGG
```
                ValGluVal HisAsnAlaLys ThrLysPro ArgGluGlu GlnTyrAsnSer ArgGluGlu GluGlnTyrAsnSer GluValHisGlu ValValSer ValLeuThrVal LeuHisGln AspTrpLeu
```
1001  CGTGGAGGTG CATAATGCCA AGACAAAGCC GCGGGAGGAG CAGTACAACA GCACGTACCG TGTGGTCAGC GTCCTCACCG TCCTGCACCA GGACTGGCTG
```
                AsnGlyLysGlu TyrLysCys LysValSer AsnLysAlaLeu ProAlaPro IleGluLys ThrIleSerLys AlaLysGly GlnProArg GluProGlnVal
```
1101  AATGGCAAGG AGTACAAGTG CAAGGTCTCC AACAAAGCC  TCCCAGCCC  CATCGAGAAA ACCATCTCCA AAGCCAAAGG GCAGCCCCGA GAACCACAGG
```
                TyrThrLeu ProProSer ArgGluGluMet ThrLysAsn GlnValSer LeuThrCysLeu ValLysGly PheTyrPro SerAspIleAla ValGluTrp
```
1201  TGTACACCCT GCCCCCATCC CGGGAGGAGA TGACCAAGAA CCAGGTCAGC CTGACCTGCC TGGTCAAAGG CTTCTATCCC AGCGACATCG CCGTGGAGTG
                GluSerAsn GlyGlnProGlu AsnAsnTyr LysThrThr ProProValLeu AspSerAsp GlySerPhe PheLeuTyrSer LysLeuThr ValAspLys
1301  GGAGAGCAAT GGGCAGCCGG AGAACAACTA CAAGACCACG CCTCCCGTGC TGGACTCCGA CGGCTCCTTC TTCCTCTACA GCAAGCTCAC CGTGGACAAG
                SerArgTrpGln GlnGlyAsn ValPheSer CysSerValMet HisGluAla LeuHisAsn HisTyrThrGln LysSerLeu SerLeuSer ProGlyLys***
1401  AGCAGGTGGC AGCAGGGGAA CGTCTTCTCA TGCTCCGTGA TGCACGAGGC TCTGCACAAC CACTACACGC AGAAGAGCCT CTCCCTGTCT CCGGGTAAAT
                                                                                                                (SEQ ID NO: 57)
                Bmti
                ** NheI
1501  CAGTGCTAGC TGCCCAGACA TGATAAGATA CATTGATGAG TTTGGACAAA CCACAACTAG AATGCAGTGA AAAAAATGCT TAATTGTGAA
1601  GCTATTGCTT TATTTGTAAC CATTATAAGC TGCAATAAAC AAGTTAACAA CAACAATTGC ATTCATTTTA TGTTTCAGGT TCAGGGGGAG GTGTGGGAG
                                                                  AseI
```

```
1701  TTTTTTAAAG CAAGTAAAAC CTCTACAAAT GTGGTATGGA ATTAATTCTA AAATACAGCA TAGCAAAACT TTAACCTCCA AATCAAGCCT CTACTTGAAT
1801  CCTTTTCTGA GGGATGAATA AGGCATAGGC ACTAGCTCTT GTTGCCAATG ATCAGGGGCT GTTGCAGCCT TGTTTGCAGC TCACCTTCTT TCATGGAGTT TAAGATATAG
1901  TGTATTTTCC CAAGGTTTGA ACTAGCTCTT CATTTCTTTA TGTTTTAAAT GCACTGACCT CCCACATTCC CTTTTTAGTA AATATTCAG AAATAATTTA
2001  AATACATCAT TGCAATGAAA ATAAATGTTT TTTATTAGGC AGAATCCAGA TGCTCAAGGC CCTTCATAT ATCCCCCAGT TTAGTAGTTG GACTAGGGA
2101  ACAAAGGAAC CTTTAATAGA CAAGAAAGCG AGCTTCTAGC CAAGAAAGCG TCCTGCTCCT CTGCCACAAA GTGCACGCAG TTGCCGGCCG
2201  GGTCGCGCAG GGCGAACTCC CGCGCCCACG GCTGCTCGCC GATCTCGGTC ATGGCCGGCC CGGAGGCGTC CCGGAAGTTC GTGGACACGA CCTCCGACCA
2301  CTCGGCGTAC AGTCGTCCA GGCCGCGCAC CCAACCCAG GCCAGGGTGT TGTCCGGCAC CACCTGGTC TGGACCGCGC TGATGAACAG GGTCACGTCG
2401  TCCCGGACCA CACCGGCGAA GTCGTCCTCC ACGAAGTCCC GGGAGAACCC GAGCCCGTCG GTCCAGAACT CGACCGCTCC GGCGACGTCG CGCGGGTGA
2501  GCACCGGAAC GGCACTGGTC AACTTGGCCA TGATGGCTCC TCCTGTCAGG AGAGGAAAGA GAAGAAGGTT AGTACAATTG CTATAGTGAG TTGTATTATA
      AseI
2601  CTATGCAGAT ATACTATGCC AATGATTAAT TGTCAAACTA GGGCTGCAGG GTTCATAGTG CCACTTTTCC TGCACTGCCC CATCTCCTGC CCACCCTTTC
2701  CCAGGCATAG ACAGTCAGTG ACTTACCAAA CTCACAGGAG GGAGAAGGCA GAAGCTTGAA ACAGACCGCG GGGACCGCCG AACTGCGAGG GGACGTGGCT
2801  AGGGCGGCTT CTTTTATGGT CGCCCGGCCC TCGGAGGCAG GGCGCTCGGG AGGCCTAGC CGGTGGCAGG AGGCGGGGGC CGGCCATCTG GAAGGCCCTG
2901  CCTGACCAAT CGGAGCACA TAGGAGTCTC AGCCCCCGC CCCAAAGCAA CGCGCCCTGTA GCGCCAGCGT GTTGTGAAAT GACTATAAAG ATACCAGGCG
3001  GGGGGTTGGG GCCCTGACTA GTCAAAACAA ACTCCCATTG ACGTCAATGG GGTGGAGACT CGTGAGTCAA ACCGCTATCC GGGGCTTGG ACGCCCATTG
3101  ATGTACTGCC AAAACCGCAT CATCATGTA ATAGCGATGA CTAATACGTA CGTACTTGGC AGTCCCATAA AGTCCCATAA GCAGTTTACC TGGGCATAAT
3201  GCCAAGTACG CCATTACCG TCATTACCG AAGTCCCTAT ATGGGAACAT ACGTCATTAT TGACGTCAAT GGGCGGGGGT CGTTGGGCGG TCAGCCAGGC
3301  CACCCATTGA CGTCAATGGA AGTCCCTAT GCCAATACGCC GCAGCAAAG GCCAGCAAG AACCCGACAG CGTAAAAAGG CCGCGTTGCT
3401  GGGCCATTTA CCGTAAGTTA TGTAACGCT GCCCCCCTGA AAAAATCGAC GCTCAAGTCA GAGGTGGCGA AACCCGACAG TTTCCCCCT GGAAGCGTG GCGCTTTCTC
3501  GGCGTTTTC CATAGGCTCC GCCCCCCTGA CGTGCGCTCT CCTGTTCCGA CCCTGCCGCT TACCGGATAC CCCGACCGCT GCGCTTATC
3601  TTTCCCCCTG GAAGCTCCT CGTGCGCTCT CCTGTTCCGA CCCTGCCGCT TCGCTCCAAG CTGGGCTGTG TGCACGAACC CCCGTTCAG
3701  ATAGCTCACG CTGTAGGTAT CTCAGTTCGG TGTAGGTCGT TCGCTCCAAG CTGGGCTGTG CACTGGCAGC AGCCACTGGT AACAGGATTA GCAGAGCGAG GTATGTAGGCGGT
3801  CGGTAACTAT CGTCTTGAGT CCAACCCGGT AAGACACGAC CGCCTACACA CTAGAAGAAC AGTATTTGGT ATCTGCGCTC TGCTGAAGCC
3901  GCTACAGAGT TCTTGAAGTG GTGGCCTAAC CGCTGGTAG GGGGGTTTT TTTGTTGCA GCAGCAGAT TACGCGCAGA AAAAAAGGAT CTCAAGAAGA
4001  TTGGTAGCTC TTGATCCGGG CAAACAAACCA CGGTCGACGC GAAAACTCAC GTTAAGGGAT TTTGGTCATG AGCATTTAA ATCAGCGCC
4101  TCCTTTGATC TTTTCTACGG GTCTGACGC TCATTACATC TTTTTGTGT GAATCGTAAC TCTCCATCAA AACAAAACGA AACAAAACAA
4201  GCAATAAAAT ATCTTATTT CCAGTGCAAG TGCAGGTGCC AGAACATTTC TCTATCGAA (SEQ ID NO: 84)
4301  ACTAGCAAAA TAGGCTGTCC CCAGTGCAAG
```

FIG. 2E (CONT)

FIG.3A
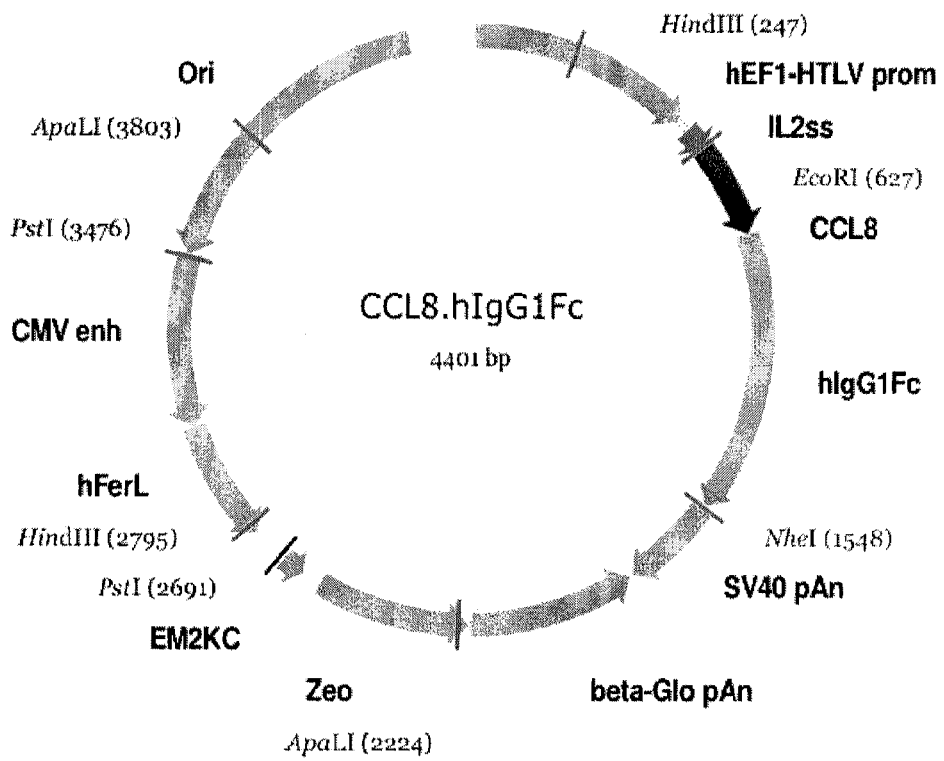
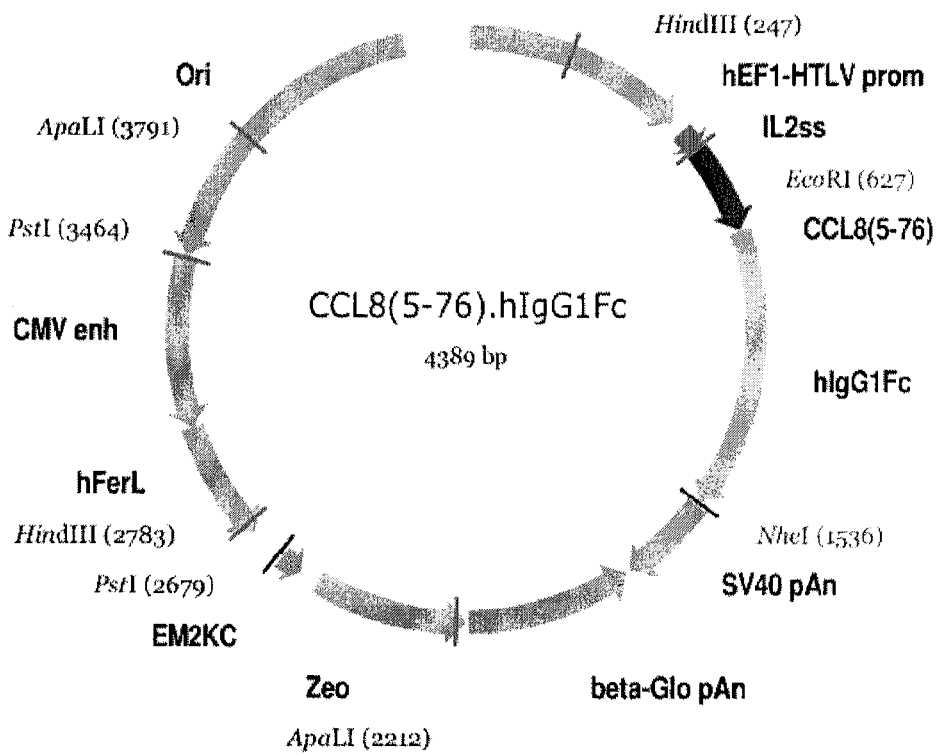
FIG.3B

FIG. 3C

IL2ss.CCL8.hIgG1Fc sequence

```
   1  GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101  GAGAAGGTGG CGCGGGGTAA ACTGGGAAAG TGATGTCGTG TACTGGCTCC GCCTTTTTCC CGAGGGGCT TCGAGGGGCT CTTCACGCGC CTTCACGCGC AGTAGTGCC
 201  GTGACGTTC TTTTTCGCAA CGGGTTTGCC GCCAGAACAC AGCTGAAGCT TCGAGGGGCT TCGCACGCGC CTTCACGCGC CTAGGTAAGT TAAAGCTCA ACCTGAGCC
 301  GCCATCCACG CCGGTTGAGT CGCGTTCTGC CGGCGTGCGC CTGGTGTGCG CTCCTGAACTG CGTCCGCGT CGTGCGCGC CTAGTAAGT TAAAGCTCA GGTCGAGACC
 401  GGGCCTTTGT CCGGCGCTCC CTTGGAGCCT ACCTAGACTC AGCCGGCTCC CCACCCTTTG CCTGACCCTG CTTGCTCAAC CTTGCTGTGT CTACGTCTT TGTTTCGTTT

IL-2 secretion signal
                                                                                                         MetTyrArg MetGlnLeu LeuSerCysIle
 501  TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                                              EcoRI
                                                                        ━━━━━ CCL8 (1-76)
         AlaLeuSer LeuAlaLeu ValThrAsnSer GlnProAsp SerValSer IleProIleThr CysCysPhe AsnValIle AsnArgLysIle ProIleGln
 601  TTGCACTAAG TCTTGCACTT GTCACGAATT CGATACGAGA TTCAGTTTCC ATTCCAATCA CCTGCTGCTT TAACGTGATC AATAGGAAAA TTCCTATCCA
         ArgLeuGlu SerTyrThrArg IleThrAsn IleGlnCys ProLysGluAla ValIlePhe LysThrLys ArgGlyLysGlu ValCysAla AspProLys
 701  GAGGCTGGAG AGCTACACAA GAATCACCAA CATCCAATGT CCCAAAGAAG CTGTGATCTT CAAGACCAAA CGGGGCAAGG AGTCTGTGC TGACCCCAAG
                                                                                          human IgG1 Fc (constant region)
         GluArgTrpVal ArgAspSer MetLysHis LeuAspGlnAsn LeuIlePhe GlnLysAsn ThrCysPro AspLysThrHis ThrCysPro AlaProGluLeu
 801  GAGAGATGGG TCAGGGATTC CATGAAGCAT CTGGACCAAA TATTTCAAAA TCTGAAGCCA GACAAAACTC ACACATGCCC ACCGTGCCCA GCACCTGAAC
         LeuGlyGly ProSerVal PheLeuPhePro ProLysProLys AspThrLeu MetIleSer ArgThrPro GluValThr CysValValVal AspValSer
 901  TCCTGGGGGG ACCGTCAGTC TTCCTCTTCC CCCCAAAACC CAAGGACACC CTCATGATCT CCCGGACCCC TGAGGTCACA TGCGTGGTGG TGGACGTGAG
         HisGluAsp ProGluValLys PheAsnTrp TyrValAsp GlyValGluVal HisAsnAla LysThrLys ProArgGluGlu GlnTyrAsn SerThrTyr
1001  CCACGAAGAC CCTGAGGTCA AGTTCAACTG GTACGTGGAC GGCGTGGAGG TGCATAATGC CAAGACAAAG CCGCGGGAGG AGCAGTACAA CAGCACGTAC
         ArgValValSer ValLeuThr ValLeuHis GlnAspTrpLeu AsnGlyLys GluTyrLys CysLysValSer AsnLysAla LeuProAla ProIleGluLys
1101  CGTGTGGTCA GCGTCCTCAC CGTCCTGCAC CAGGACTGGC TGAATGGCAA GGAGTACAAG TGCAAGGTCT CCAACAAAGC CCTCCCAGCC CCCATCGAGA
         ThrIleSer LysAlaLys GlyGlnProArg GluProGln ValTyrThr LeuProProSer ArgGluGlu MetThrLys AsnGlnValSer LeuThrCys
1201  AAACCATCTC CAAAGCCAAA GGGCAGCCCC GAGAACCACA GGTCTACACC CTGCCCCCAT CCCGGGAGGA GATGACCAAG AACCAGGTCA GCCTGACCTG
         LeuValLys GlyPheTyrPro SerAspIle AlaValGlu TrpGluSerAsn GlyGlnPro GluAsnAsn TyrLysThrThr ProProVal LeuAspSer
1301  CCTGGTCAAA GGCTTCTATC CCAGCGACAT CGCCGTGGAG TGGGAGAGCA ATGGGCAGCC GGAGAACAAC TACAAGACCA CGCCTCCCGT GCTGGACTCC
         AspGlySerPhe PheLeuTyr SerLysLeu ThrValAspLys SerArgTrp GlnGlnGly AsnValPheSer CysSerVal MetHisGlu AlaLeuHisAsn
1401  GACGGCTCCT TCTTCCTCTA CAGCAAGCTC ACCGTGGACA AGAGCAGGTG GCAGCAGGGG AACGTCTTCT CATGCTCCGT GATGCACGAG GCTCTGCACA
                                                                                                         BmtI
                                                                                                         NheI
         HisTyrThr GlnLysSer LeuSerLeuSer ProGlyLysLys ***(SEQ ID NO: 58)
1501  ACCACTACAC GCAGAAGAGC CTCTCCCTGT CTCCGGGTAA ATGAGTGCTA GCTGGCCAGA CATGATAAGA TACATTGATG AGTTTGGACA AACCACAACT
1601  AGAATGCAGT GAAAAAAATG CTTTATTTGT GAAATTTGTG ATGCTATTGC TTTATTTGTA ACCATTATAA GCTGCAATAA ACAAGTAAC AACAACAATT
                                                                                                         AseI
1701  GCATTCATTT TATGTTTCAG GTTCAGGGGG AGGTGTGGGA GGTTTTTTAA AGCAAGTAAA ACCTCTACAA ATGTGGTATG GAATTAATTC TAAAATACAG
1801  CATAGCAAAA CTTTAACCTC CAAATCAAGC CTCTACTTCA ATCCTTTTCT GAGGGATGAA TAAGGCATAG GCATCAGGGG CTGTTGCCAA TGTCATTAG
```

```
1901  CTGTTTGCAG CCTCACCTTC TTTCATGGAG TTTTAAGATAT AGTGTATTTT CCCAAGGTTT GAACTAGCTC TTCATTTCTT TATGTTTTAA ATGCACTGAC
2001  CTCCCACATT CCCTTTTTAG TATATCCCCA GTTTAGTAGT TAAATACATC ATTGCAATGA ACCTTTAATA GAACAAAGGA AAATAAATGT GCAGAATCCA GATGCTCAAG
2101  GCCCTTCATA ATATCCCCCA CTCTGCCACA AAGTGCACGC AGTTGCCGGC CGGGTCGCGC AGGGCGAACT CCCGCCCCCA GGCTGCTCG CGAGCTTCTA GCTTATCCTC
2201  AGTCCTGCTC TCCCGGAAGT TCGTGGACAC GACCTCCGAC CACTCGGCGT ACAGCTCGTC CAGGCCGCGC ACCCACACCC AGGCCAGGGT TCATGCCGG
2301  CCCGGAGGCG CCTGGACCGC CTGATGAAC AGGGTCACGT CGTCCCGGAC CACACCGGCG AAGTGTCCT CCACGAAGTC CGGGAGAAC GTGTCCGGC
2401  ACCACCTGGT CTCGACCGCT CCGGCGACGT CGCGCGCGGT GAGCACCGGA ACGGCACTGG TCAACTTGGC CATGATGGCT CCTCCCGTCA GGAGAGAAA
2501  CGGTCCAGAA

2601  GAGAGAAGG TTAGTACAAT TGCTATATAGTG AGTTGTATTA TACTATGCAG ATATACTATG CCAATGATTA ATTGTCAAAC TAGGGCTGCA GGTTCATAG
2701  TGCCACTTT CCTGCACTGC CCCATCTCCT GCCCACCCTT TCCCAGGCAT AGACAGTCAG TGACTTACCA AACTCACAGG AGGGAGAAGG CAGAAGCTTG
2801  AGACAGACCC GCGGGACCGC CGAACTGCGA GGGGACGTGG CTAGGGCGGC TTTCTTTTATG GTGCGCCGGC CCTCGGAGGC AGGGGGCTCG GGGAGGCCTA
2901  GCGCCAATC TGCGGGTGGCA AGGCCGGGG CCGAAGGCCG TGCCTGACCA CATAGGAGTC ATCCGGAGCA TCAGCCCCCC GCCCCAAAGC AAGGGAAGT
3001  CACGCGCCTG TAGGCCCAGC GTGTTGTGAA ATGGGGGCTT GGGAGGGTTG TGAGTACTG AATCCCCAT AGTCAAAAAC AAACTCCCAT TGACTCAAT GGGGTGAGA
3101  CTTGGAAATC CCCGTGAGTC AAACCGCTAT CCACGCCCAT CCAAAACCGC TGATGTACTG GGCCATTTAC CGTCATTGAC TAATAGCGAT GCCGTACTTG TAGATGTACT
3201  GCCAAGTAGG AAAGTCCCAT AAGGTCATGT ACTGGGCATA ATGCCAGGCG GGCCATTTAC GAAAGTCCT ATTGGCGTTA GTCAATAGGG GCCGTACTTG ATACGTCATT
3301  CACTTGATGT ACTGCCAAGT GGGCAGTTTA CCGTAAATAC CGGGCCAG GACGTAAGTG TATGTAAGCG CTGCAGGTTA ATTAAGAACA ATACGTCATT
3401  ATTGACGTCA ATGGCGGGG ACCGTAAAAA GGCCGCGTTG CTGGCGTTTT TCCATAGGCT CGGCCCCCC GACGAGCATC ACAAAATCG AGCTCAAGT
3501  AGGCCAGCAA GAAACCCGAC AGGACTATAA AGATACCAGG CGTTTCCCCC TGGAAGCTCC CTCGTGTTCC GACCCTGCGC CTTACCGGAT
3601  CAGAGGTGGC CTTTCTCCCT TCGGGAAGCG TGGCGCTTTC TCATAGCTCA CGCTGTAGGT ATCTCAGTTC GGTGTAGGTC GTTCGCTCCA AGCTGGGCTG
3701  ACCTGTCCGC CCCCCGTTC AGCCCGACCG CTGCGCCTTA TCCGGTAACT ATCGTCTTGA GTCCAACCCG GTAAGACACG ACTTATCGCC ACTGGCAGCA
3801  TGTGCACGAA ACAGGATTAG CAGAGCGAGG TATGTAGGCG GTGCTACAGA GTTCTTGAAG TGGTGGCCTA ACTACGGCTA CACTAGAAGA ACAGTATTTG
3901  GCCACTGGTA TCTGCTGAAG CCAGTTACCT TCGGAAAAAG AGTTGGTAGC TCTTTTCTAC CACCGCTGGT AGCGGTGGTT TTTTTGTTTG
4001  GTATCTGCGC ATTACGCCA GAAAAAAAGG ATCTCAAGAA GATCCTTTGA TCTTTTCTAC GGGGTCTGAC GCTCAGTGGA ACGAAAACTC ACGTTAAGGG
4101  CAAGCAGCAG ATTACGCGCA GAAAAAAAGG ATCTCAAGAA GATCCTTTGA TCTTTTCTAC GGGGTCTGAC GCTCAGTGGA ACGAAAACTC ACGTTAAGGG
4201  ATTTTGGTCA TGGCTAGTTA ATTAACATTT AAATCAGCGG CCGCAATAAA ATATCTTTAT TTTCATTACA TCTGTGTGTT GGTTTTTTGT GTGAATCGTA
4301  ACTAACATAC GCTCTCCATC AAAACAAAAC GAAACAAAAC AAACTAGCAA AAACTAGCAA CCCCAGTGCA AGTGCAGGTG CCAGAACATT TCTCTATCGA
4401  A (SEQ ID NO: 85)
```

IL2ss.CCL8(5-76).hIgG1Fc sequence

```
   1  GGATCTGCGA TCGCTCCGGT GCCCGTCAGT GGGCAGAGCG CACATGCGCC ACAGTCCCCG AGAAGTTGGG GGGAGGGGTC GGCAATTGAA CGGGTGCCTA
 101  GAGAAGGTGG CGCGGGGTAA ACTGGGAAAG TGATGTCGTG GCCAGAACAC CGGGTTTGCC GCCATCTCTC CGAGGGTGGG GGAGAACCGT ATATAAGTGC AGTAGTCGCT
 201  GTGAACGTTC TTTTTCGCAA CGGGTTTGCC GCCAGAACAC CGGGTTTGCC TCGAGGGCT CGCATCTCTC CTTCACGCGC CGGCCGCCCT ACCTGAGGCC
 301  GCCATCCACG CCGGTTGAGT CCGGTTCTGC CCGCTGGTGCC CCTGAACTG CGTCCGCCGT CTAGGTAAGT TTAAAGCTCA GGTCGAGACC
 401  GGGCCTTTGT CCGGGCGTCC CTTGGAGCCT AGCCGGCTCT CCAGCCCTTG CCTGACCCTG CTTGCTCAAC CTTCTAGGAGACCTA TGTTTCGTTT
                   KasI
                   NarI
                   SfoI
                   BbeI
                           EcoRI                                   ~~~~~~ CCL8 (5-76)
                                                                                                        IL-2 secretion signal
                                                                                                        MetTyrArg MetGlnLeu LeuSerCysIle
 501  TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
      AlaLeuSer LeuThrAsnLeu ValSerIle ProIleThr CysCysPheAsn ValIleAsn ArgLysIle ProIleGlnArg LeuGluSer
 601  TTGCACTAAG TCTTGCACTT GTCACGAATT CGGTTCCAT TCCAATCACC TGCTGCTTTA ACGTGCTTAA TAGGAAAATT CCTATCCAGA GGCTGGAGAG
      TyrThrArg IleThrAsnIle GlnCysProGly LysGluAla ValIlePheLys ThrLysArg GlyLysGlu ValCysAlaAsp ProLysGlu ArgTrpVal
 701  CTACACAAGA ATCACCAACA TCCAATGTCC CAAGGAAGCT GTGATCTTCA AGACCAAACG GGGCAAGGAG GTCTGTGCTG ACCCCAAGGA GAGATGGGTC
                                                         human IgG1 Fc (constant region)
      ArgAspSerMet LysHisLeu AspGlnIle PheGlnAsnLeu LysProAsp LysThrHis ThrCysProPro CysProAla ProGluLeu LeuGlyGlyPro
 801  AGGGATTCCA TGAAGCATCT GGACCAAATA TTTCAAAATC TGAAGCCAGA CAAAACTCAC ACATGCCCAC CGTGCCCAGC ACCTGAACTC CTGGGGGGAC
      SerValPhe LeuPhePro ProLysProLys AspThrLeu MetIleSer ArgThrProGlu ValThrCys ValValVal AspValSerHis GluAspPro
 901  CGTCAGTCTT CCTCTTCCCC CCAAAACCCA AGGACACCCT CATGATCTCC CGGACCCCTG AGGTCACATG CGTGGTGGTG GACGTGAGCC ACGAAGACCC
      GluValLys PheAsnTrpTyr ValAspGly ValGluVal HisAsnAlaLys ThrLysPro ArgGluGlu GlnTyrAsnSer ThrTyrArg ValValSer
1001  TGAGGTCAAG TTCAACTGGT ACGTGGACGG CGTGGAGGTG CATAATGCCA AGACAAAGCC CAGTAGAACA GCAGTACACA GCACGTACCG TGTGGTCAGC
      ValLeuThrVal LeuHisGln AspThrpLeu AsnGlyLysGlu TyrLysCys LysValSer AsnLysAlaLeu ProAlaPro IleGluLys ThrIleSerLys
1101  GTCCTCACCG TCCTGCACCA GGACTGGCTG AATGGCAAGG AGTACAAGTG CAAGGTCTCC AACAAAGCCC TCCCAGCCCC CATCGAGAAA ACCATCTCCA
      AlaLysGly GlnProArg GluProGlnVal TyrThrLeu ProProSer ArgGluGluMet ThrLysAsn GlnValSer LeuThrCysLeu ValLysGly
1201  AAGCCAAAGG GCAGCCCCGA GAACCACAGG TGTACACCCT GCCCCCATCC CGGGAGGAGA TGACCAAGAA CCAGGTCAGC CTGACCTGCC TGGTCAAAGG
      PheTyrPro SerAspIleAla ValGluTrp GluSerAsn GlyGlnProGlu AsnAsnTyr LysThrThr ProProValLeu AspSerAsp GlySerPhe
1301  CTTCTATCCC AGCGACATCG CCGTGGAGTG GGAGAGCAAT GGGCAGCCGG AGAACAACTA CAAGACCACG CCTCCCGTGC TGGACTCCGA CGGCTCCTTC
      PheLeuTyrSer LysLeuThr ValAspLys SerArgTrpGln GlnGlyAsn ValPheSer CysSerValMet HisGluAla LeuHisAsn HisTyrThrGln
1401  TTCCTCTACA GCAAGCTCAC CGTGGACAAG AGCAGGTGGC AGCAGGGGAA CGTCTTCTCA TGCTCCGTGA TGCACGAGGC TCTGCACAAC CACTACACGC
      LysSerLeu SerLeuSer ProGlyLys***(SEQ ID NO. 59)
1501  AGAAGAGCCT CTCCCTGTCT CCGGGTAAAT GAGTGCTAGC TGGCCAGACA TGATAAGATA CATTGATGAG TTTGGACAAA CCAACAACTAG AATGCAGTGA
1601  AAAAAATGCT TTATTTGTGA AATTTGTGAT GCTATTGCTT TATTTGTAAC CATTATAAGC TGCAATAAAC AAGTTAACAA TGCAATAAAC CTCTACAACT
                                                                                                                       AseI
1701  TGTTTCAGGT TCAGGGGGAG GTGTGGGAGG TTTTTTAAAG CAAGTAAAAC CTCTACAAAT GTGGTATGGA ATTAATTCTA AAATACAGCA TAGCAAAACT
1801  TTAACCTCCA AATCAAGGCT CTACTTGAAT CCTTTTCTGA GGGATGAATA AGGCATAGGC ATCAGGGGCT GTTGCCAATG TGCATTAGCT GTTTGCAGCC
```

```
1901 TCACCTTCTT TCATGGAGTT TAAGATATAG TGTATTTTCC CAAGGTTTGA ACTAGCTCTT CATTTCTTTA TGTTTTAAAT GCACTGACCT CCCACATTCC
2001 CTTTTTAGTA AAATATTCAG GACTTAGGGA AATACATCAT TGCAATGAAA ATAAATGTTT TTTATTAGGC AGAATCCAGA TGCTCAAGGC CCTTCATAAT
2101 ATCCCCCAGT TTAGTAGTTG GACTTAGGGA ACAAAGGAAC CTTTAATAGA AATTGGACAG CAAGAAAGCG AGCTTCTAGC TTATCCTTCAG TCCTGCTCCT
2201 CTGCCACAAA GTGCACGCAG TTGCCGGCCG GGCGAACTCC CGCGCTCGCC GCTGCTCGCC GATCTCGGTC ATGGCCGGCC CGGAGGCGTC
2301 CCGGAAGTTC GTGGACACGA CCTCCGACCA CTCGGCGTAC AGCTCGTCCA CCACACCCAC GCCAGGGTGT TCTCCCGGCAC CACCTGGTCC
2401 TGGACCGCGC TGATGAACAG GGTCACGTCG TCCCGGACCA CACCGGCGAA GTCGTCCTCC ACGAAGTCCC GGGAGAACCC GAGCCGGTCG GTCCAGAACT
2501 CGACCGCTCC GGCGACGTCG CGGCGGTGA GCACCGGAAC GGCACTGGTC AACTTGGCCA TGATGGCTCC TCCTGTCAGG AGAGAAAAGA GAAGAAGGTT

AseI
2601 AGTACAATTG CTATAGTGAG TTGTATTATA CTATGCAGAT ATACTATGCC AATGATTAAT TGTCAAACTA GGGCTGCAGG GTTCATAGTG CCACTTTTCC
2701 TGCACTGCCC CATCTCCTGC CCACCCTTTC CCAGGCATAG ACAGTCAGTG ACTTACCAAA CTCACAGGAG GGAGAAGGCA GAAGCTTGAG ACAGACCCGC
2801 GGGACCGCCG AACTGCGAGG GGACGTGGCT AGGGCGGCTT CTTTTATGGT GCGCCGGCCC TCGGAGCCAG TCGGAGGCAG GAGGCCTAGC GGCCAATCTG
2901 CGGTGGCAGG AGGCGGGGCC GAAGGCCGTG CCTGACCAAT CGGAGCACA TAGGAGTCTC AGCCCCCCGC CCCAAAGCAA GGGGAAGTCA CGCGCCTGTA
3001 GCGCCAGCGT GTTGTGAAAT GGGGGCTTGG GCCCTGACTA GTCAAAACAA ACTCCCATTG ACTGTCAATG GGTGGAGACT TGGAAATCCC
3101 CGTGAGTCAA ACCGCTATCC ACGCCCATTG ATGTACTGCC AAAACCGCAT CATCATGGTA ATAGCGATGA CTAATACGTA CAAGTAGGAA
3201 AGTCCCATAA GGTCATGTAC TGGGCATAAT GCCAGGCGGG CCATTTACCG TCATTGACGT CAATAGGGGG CGTACTTGGC ATATGATACA CTTGATGTAC
3301 TGCCAAGTCG GCAGTTTACC GTAAATACTC CACCCATTGA CGTCAATGGA AAGTCCCTAT TGGCCTTACT ATGGGAACAT ACGTCATTAT TGACGTCAAT
3401 GGGCGGGGGT CGTTGGGCGG TCAGCCAGGC GGGCCATTTA CCGTAAGTTA TGTAACGCCT GCAGGTTAAT TAAGAACATG TGAGCAAAAG GCCAGCAAAA
3501 GGCCAGGAAC CGTAAAAAGG CCGCGTTGCT GGCGTTTTTC CATAGGCTCC GCCCCCCTGA CGAGCATCAC AAAATCGAC GCTCAAGTCA GAGGTGGCGA
3601 AACCCGACAG GACTATAAAG ATACCAGGCG TTTCCCCCTG GAAGCTCCCT CGTGCGCTCT CCTGTTCCGA CCCTGCGCCT TACCGGATAC CTGTCCGCCT
3701 TTCTCCCTTC GGGAAGCGTG GCGCTTTCTC ATAGCTCACG CTGTAGGTAT CTCAGTTCGG TGTAGGTCGT TCGCTCCAAG CTGGGCTGTG TGCACGAACC
3801 CCCCGTTCAG CCCGACCGCT GCGCCTTATC CGGTAACTAT CGTCTTGAGT CCAACCCGGT AAGACACGAC TTATCGCCAC TGGCAGCAGC CACTGGTAAC
3901 AGGATTAGCA GAGCGAGGTA TGTAGGCGGT GCTACAGAGT TCTTGAAGTG GTGGCCTAAC TACGGCTACA CTAGAAGAAC AGTATTTGGT ATCTGCGCTC
4001 TGCTGAAGCC AGTTACCTTC GGAAAAAGAG TTGGTAGCTC TTGATCCGGC AAACAACCA GGTCTGACGC TCAGTGGAAC GAAAACTCAC CGGCTGGTAG
4101 TACGGCCAGA AAAAAGGAT CTCAAGAAGA TCCTTTGATC TTTTCTACGG GTCTGACGC TCAGTGGAAC CGGCTGGTAG TCAGTGGAAC CGGCTGGTAG
4201 GCTAGTTAAT TAACATTTAA ATCAGCGGCC GCAATAAAAT ATCTTTATTT TCATTACATC TGTGTGTTGG TTTTTTGTGT GAATCGTAAC TTTGGTCATG
4301 TCTCCATCAA AACAAAACGA AACAAAACAA ACTAGCAAAA TAGGCTGTCC CCAGTGCAAG TGCAGGTGCC AGAACATTTC TCTATCGAA (SEQ ID NO: 86)
```

IL2ss.CCL8(5-76).hIgG1Fc sequence
[Alanine substitutions for GAG binding sites – Lys, Arg & His]

```
   1  GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101  GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201  GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301  GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401  GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                         KasI
                                         NarI
                                         SfoI
                                         BbeI
                                        ~~~~~~~                                          IL-2 secretion signal
                                                                                         MetTyrArg MetGlnLeu LeuSerCysIle
 501  TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                              EcoRI
                              ~~~~~~~ CCL8 (5-76)
        AlaLeuSer LeuAlaLeu ValThrAsnSer ValSerIle ProIleThr CysCysPheAsn ValIleAsn ArgLysIle ProIleGlnArg LeuGluSer
 601  TTGCACTAAG TCTTGCACTT GTCACGAATT CGGTTTCCAT TCCAATCACC TGCTGCTTTA ACGTGATCAA TAGGAAAATT CCTATCCAGA GGCTGGAGAG
       TyrThrArg IleThrAsnIle GlnCysPro LysGluAla ValIlePheLys ThrAlaAla GlyAlaGlu ValCysAlaAsp ProAlaGlu AlaTrpVal
 701  CTACACAAGA ATCACCAACA TCCAATGTCC CAAGGAAGCT GTGATCTTCA AGACCgccgc gGGCgctGAG GTCTGTGCTG ACCCCgccGA GgcgTGGGTC
                                                          human IgG1 Fc (constant region)
      AlaAspSerMet AlaAlaLeu AspGlnIle PheGlnAsnLeu AlaProAsp LysThrHis ThrCysProPro CysProAla ProGluLeu LeuGlyGlyPro
 801  gctGATTCCA TGgccgccCT GGACCAAATA TTTCAAAATC TGgctCCAGA CAAAACTCAC ACATGCCCAC CGTGCCCAGC ACCTGAACTC CTGGGGGGAC
        SerValPhe LeuPhePro ProLysProLys AspThrLeu MetIleSer ArgThrProGlu ValThrCys ValValVal AspValSerHis GluAspPro
 901  CGTCAGTCTT CCTCTTCCCC CCAAAACCCA AGGACACCCT CATGATCTCC CGGACCCCTG AGGTCACATG CGTGGTGGTG GACGTGAGCC ACGAAGACCC
       GluValLys PheAsnTrpTyr ValAspGly ValGluVal HisAsnAlaLys ThrLysPro ArgGluGlu GlnTyrAsnSer ThrTyrArg ValValSer
1001  TGAGGTCAAG TTCAACTGGT ACGTGGACGG CGTGGAGGTG CATAATGCCA AGACAAAGCC GCGGGAGGAG CAGTACAACA GCACGTACCG TGTGGTCAGC
      ValLeuThrVal LeuHisGln AspTrpLeu AsnGlyLysGlu TyrLysCys LysValSer AsnLysAlaLeu ProAlaPro IleGluLys ThrIleSerLys
1101  GTCCTCACCG TCCTGCACCA GGACTGGCTG AATGGCAAGG AGTACAAGTG CAAGGTCTCC AACAAAGCCC TCCCAGCCCC CATCGAGAAA ACCATCTCCA
        AlaLysGly GlnProArg GluProGlnVal TyrThrLeu ProProSer ArgGluGluMet ThrLysAsn GlnValSer LeuThrCysLeu ValLysGly
1201  AAGCCAAAGG GCAGCCCCGA GAACCACAGG TGTACACCCT GCCCCCATCC CGGGAGGAGA TGACCAAGAA CCAGGTCAGC CTGACCTGCC TGGTCAAAGG
       PheTyrPro SerAspIleAla ValGluTrp GluSerAsn GlyGlnProGlu AsnAsnTyr LysThrThr ProProValLeu AspSerAsp GlySerPhe
1301  CTTCTATCCC AGCGACATCG CCGTGGAGTG GGAGAGCAAT GGGCAGCCGG AGAACAACTA CAAGACCACG CCTCCCGTGC TGGACTCCGA CGGCTCCTTC
      PheLeuTyrSer LysLeuThr ValAspLys SerArgTrpGln GlnGlyAsn ValPheSer CysSerValMet HisGluAla LeuHisAsn HisTyrThrGln
1401  TTCCTCTACA GCAAGCTCAC CGTGGACAAG AGCAGGTGGC AGCAGGGGAA CGTCTTCTCA TGCTCCGTGA TGCACGAGGC TCTGCACAAC CACTACACGC
                                         BmtI
                                         NheI
        LysSerLeu SerLeuSer ProGlyLys***(SEQ ID NO: 60)
1501  AGAAGAGCCT CTCCCTGTCT CCGGGTAAAT GAGTGCTAGC TGGCCAGACA TGATAAGATA CATTGATGAG TTTGGACAAA CCACAACTAG AATGCAGTGA
1601  AAAAAATGCT TTATTTGTGA AATTTGTGAT GCTATTGCTT TATTTGTAAC CATTATAAGC TGCAATAAAC AAGTTAACAA CAACAATTGC ATTCATTTTA
                                                                                 AseI
1701  TGTTTCAGGT TCAGGGGGAG GTGTGGGAGG TTTTTTAAAG CAAGTAAAAC CTCTACAAAT GTGGTATGGA ATTAATTCTA AAATACAGCA TAGCAAAACT
```

```
1801  TTAACCTCCA AATCAAGCCT CTACTTGAAT CCTTTTCTGA GGGATGAATA AGGCATAGGC ATCAGGGGCT GTTGCCAATG TGCATTAGCT GTTTGCAGCC
1901  TCACCTTCTT TCATGGAGTT TAAGATATAG TGTATTTTCC CAAGGTTTGA ACTAGCTCTT CATTTCTTTA TGTTTAAAT GCACTGACCT CCCACATTCC
2001  CTTTTAGTA AAATATTCAG AAATAATTTA GACTTAGTTG TGCAATGAAA ATAAATGTTT TTTATTAGGC AGAATCCAGA TGTCAAGGC CCTTCATAAT
2101  ATCCCCAGT TTAGTAGTTG GACTAGGGA ACAAAGGAAC CTTTAATAGA AATTGGACAG CAAGAAAGCG AGCTTCTAGC TTATCCTCAG TCCTGCTCCT
2201  CTGCCACAAA GTGCACGCAG TTGCCGGCCG GGCGAACTCC CGCCCCACCG GCTGCTCGCG GATCTCGGTC ATGGCCGGCC CGGAGGCGTC
2301  CCGGAAGTTC GTGGACACGA CCTCCGACCA CTCGGCGTAC AGCTCGTCCA GGCCGCGCAC CCACACCCAG GCCAGGGTGT TGTCCGGCAC CACCTGGTCC
2401  TGGACCGCGC TGATGAACAG GGTCACGTCG TCCCGGCGAA CACCGGCCA GTCGTCCTCC ACGAAGTCCC GGGAGAACCC GAGCCGGTCG GTCCAGAACT
2501  CGACCGCTCC GGCGACGTCG CGCGCGGTGA GCACCGGAAC AACTTGGCCA TGATGGCTCC TCCTGTCAGG AGAGGAAAGA GAAGAAGGTT
                                                          AseI
2601  AGTACAATTG CTATAGTGAG TTGTATTATA CTATGCAGAT AATGATTAAT TGTCAAACTA GGGCTGCAGG GTTCATAGTG CCACTTTTCC
2701  TGCACTGCCC CATCTCCTGC CCACCCTTTC CCAGGCATAG ACAGTCAGTG ACTTACCAAA CTCACAGGAG GGAGAAGGCA GAAGCTTGAG ACAGACCCGC
2801  GGGACCGCCG AACTGCGAGG GGACGTGGCT AGGGCGGCTT GCGCCGGCCC TCGGAGGCAG GGCGCTCGGG GAGGCCTAGC GGCCAATCTG
2901  CGGTGGCAGG AGGCGGGGCC GAAGGCCGTG CCTGACCAAT CCGGAGCACA TAGGAGCTCTC AGCCCCCCGC CCAAAGCAA GGGAAGTCA CGCGCCTGTA
3001  GCGCAGCGT GTTGTGAAAT GGGGGCTTGG TTTCCCCATG GCCCTGACTA GTCAAAACAA ACTCCCATTG AGTCAATGG GGTGGAGACT TGAAATCCC
3101  CGTGAGTCAA ACCGCTATCC ACGCCTATTG ATGTACTGCG CAAATCGCAT CATCATGGTA ATAGCGATGA CTAATACGTA GATGTACTGC CAAGTAGGAA
3201  AGTCCCATAA GGTCATGTAC TGGGCATAAT GCCAGGCGGG CCATTTACCG TCATTGACGT CAATAGGGGG CGTACTTGGC ATATGATACA CTTGATGTAC
3301  TGCCAAGTGG GCAGTTTACC GTAAATACTC CACCCATTGA CGTCAATGGA AAGTCCCTAT TGGCGTTACT ATGGGAACAT ACGTCATTAT TGACGTCAAT
3401  GGGCGGGGGT CGTTGGGCGG TCAGCCAGGC GGGCCATTTA CCGTAAGTTA TGTAACGCCT TAAGAACATG GCCAGCAAAA
3501  GGCCAGGAAC CGTAAAAAGG CCGCGTTGCT GGCGTTTTTC CATAGGCTCC GCCCCCCTGA CGAGCATCAC AAAAATCGAC GCTCAAGTCA GAGGTGGCGA
3601  AACCCGACAG GACTATAAAG ATACCAGGCG TTTCCCCCTG GAAGCTCCCT CGTGCGCTCT CCTGTTCCGA CCCTGCGCCT TACCGGATAC CTGTCCGCCT
3701  TTCTCCCCTTC GGGAAGCGTG GCGCTTTCTC ATAGCTCACG CTGTAGGTAT CTCAGTTCGG TGTAGGTCGT TCGCTCCAAG CTGGGCTGTG TGCACGAACC
3801  CCCCGTTCAG CCCGACCGCT GCGCCTTATC CGGTAACTAT CGTCTTGAGT CCAACCCGGT AAGACACGAC TTATCGCCAC TGGCAGCAGC CACTGGTAAC
3901  AGGATTAGCA GAGCGAGGTA TGTAGGCGGT GCTACAGAGT TCTTGAAGTG GTGGCCTAAC TACGGCTACA CTAGAAGAAC AGTATTTGGT ATCTGCGCTC
4001  TGCTGAAGCC AGTTACCTTC GGAAAAAGAG CTCAAGAAGA TTGGTAGCTC TTGATCCGGC AAACAACCA CCGCTGGTAG CGGTGGTTTT TTTGTTTGCA AGCAGCAGAT
4101  TACGCGCAGA AAAAAAGGAT CTCAAGAAGA TCCTTTGATC TTTTCTACGG GTCTGACGC TCAGTGAAC GAAAACTCAC GGTAGGTTTT GTTAAGGGAT TTTGGTCATG
4201  GCTAGTTTAAT TAACATTTAA ATCAGCGGCC GCAATAAAAT ATCTTTATTT TCATTACATC TGTGTGTTGG TTTTTTGTGT GAATCGTAAC TAACATACGC
4301  TCTCCATCAA AACAAAACGA AACAAAACAA ACTAGCAAAA TAGGCTGTCC CCAGTGCAAG TGCAGGTGCC AGAACATTTC TCTATCGAA  (SEQ ID NO:87)
```

IL2ss.CCL13.hIgG1Fc sequence

```
   1  GGATCTGCGA TCCCTCCGGT GCCCGTCAGT GGGCAGAGCG CACATCGCCC ACAGTCCCCG AGAAGTTGGG GGGAGGGGTC GGCAATTGAA CGGGTGCCTA
 101  GAGAAGGTGG CGCGGGGTAA ACTGGGAAAG TGATGTCGTG GCCAGAACCT GCCTTTTTCC CAGGGGTGGT CAAGGATCCT CTTCACGCGC AGTAGTGCAA
 201  GTGAACGTTC TTTTTCGCAA CGGGTTTGCC GCCAGAAGCT TCGACGAACG TCCATCTCTC CGCATCGCGC CGGCCGCGC CCGCCGCCT ACCTGAGGCC
 301  GCCATCCACG CCGGTTGAGT CCGGTTCTGC CGCCTCCCGC TCCTGAACTG CGTCCGCCGT CTAGGTAAGT CTAGGTAAGT TTAAAGCTCA GGTCGAGACC
 401  GGGCCTTTGT CCGGGCGCTCC CTTGGAGCCT ACCTAGACTC AGCCGGGTCT CCTGACCCTG CTTGCTCAAC CTTACGTCTT TGTTTCGTTT
                                       SfoI
                                       NarI
                                       KasI
                                       BbeI
                                                                                         IL-2 secretion signal
                                                                                         MetTyrArg MetGlnLeu LeuSerCysIle
 501  TCTGTTCTGC GCCGTTACAG ATCCAAGCTG TGACCGGCGC CTACCTGAGA TCACCGGGGA AGGAGGGCCA CCATGTACAG GATGCAACTC CTGTCTTGCA
                                        EcoRI
                                                 ~~~~~~~~ CCL13 (1-75)
      AlaLeuSer LeuAlaLeu ValThrAsnSer GlnProAsp AlaLeuAsn ValProSerThr CysCysPhe ThrPheSer SerLysLysIle SerLeuGln
 601  TTGCACTAAG TCTTGCACTT GTCACGACCA GAA CCAGCCAGA TGCACTCAAC GTCCACATCA CTTGCTGCTT CACATTAGC AGTAAGAAGA TCTCCTTGCA
      ArgLeuLys SerTyrValIle ThrThrSer ArgCysPro GlnLysAla ValProLys LeuPheArg ThrLysGlu GlyLysIle CysAlaAsp ProLysGlu
 701  GAGGCTGAAG AGCTATGTGA TCACCACCAG CAGGTGTCCC CAGAAGGCTG TCATCTTCAG AACCAAGCTG GGCAAGGAGA TCTGTGCTGA CCCAAAGGAG
      ~~~~~~~~ human IgG1 Fc (constant region)
      LysTrpValGln AsnTyrMet LysHisLeu GlyArgLysAla HisThrLeu LysThrAsp LysThrHisThr CysProPro CysProAla ProGluGluLeu
 801  AAGTGGGTCC AGAATTATAT GAAACACCTG GGCCGGAAAG CTCACACCCT GAAGACTGAC AAAACTCACA CATGCCCACC GTGCCCAGCA CCTGAACTCC
      GlyGlyPro SerValPhe LeuPheProPro LysProLys AspThrLeu MetIleSerArg ThrProGlu ValThrCys ValValValAsp ValSerHis
 901  TGGGGGACC GTCAGTCTTC CTCTTCCCCC CAAAACCCAA GGACACCCTC ATGATCTCCC GGACCCCTGA GGTCACATGC GTGGTGGTGG ACGTGAGCCA
      GluAspPro GluValLysPhe AsnTrpTyr ValAspGly ValGluValHis AsnAlaLys ThrLysPro ArgGluGluGln TyrAsnSer ThrTyrArg
1001  CGAAGACCCT GAGGTCAAGT TCAACTGGTA CGTGGACGGC GTGGAGGTGC ATAATGCCAA GACAAAGCCG CGGGAGGAGC AGTACAACAG CACGTACCGT
      ValValSerVal LeuThrVal LeuHisGln AspTrpLeuAsn GlyLysGlu TyrLysCys LysValSerAsn LysAlaLeu ProAlaPro IleGluLysThr
1101  GTGGTCAGCG TCCTCACCGT CCTGCACCAG GACTGGCTGA ATGGCAAGGA GTACAAGTGC AAGGTCTCCA ACAAAGCCCT CCCAGCCCCC ATCGAGAAAA
      IleSerLys AlaLysGly GlnProArgGlu ProGlnVal TyrThrLeu ProProSerArg GluGluMet ThrLysAsn GlnValSerLeu ThrCysLeu
1201  CCATCTCCAA AGCCAAAGGG CAGCCCCGAG AACCACAGGT GTACACCCTG CCCCCATCCC GGGAGGAGAT GACCAAGAAC CAGGTCAGCC TGACCTGCCT
      ValLysGly PheTyrProSer AspIleAla ValGluTrp GluSerAsnGly GlnProGlu AsnAsnTyr LysThrThrPro ProValLeu AspSerAsp
1301  GGTCAAAGGC TTCTATCCCA GCGACATCGC CGTGGAGTGG GAGAGCAATG GACAGCCGGA GAACAACTAC AAGACCACGC CTCCCGTGCT GGACTCCGAC
      GlySerPhePhe LeuTyrSer LysSerLysLeu ThrValAspLysSer ArgTrpGln GlnGlyAsn ValPheSerCys SerValMet HisGluAla LeuHisAsnHis
1401  GGCTCCTTCT TCCTCTACAG CAAGCTCACC GTGGACAAGA GCAGGTGGCA GCAGGGGAAC GTCTTCTCAT GCTCCGTGAT GCATGAGGCT CTGCACAACC
                                                                                                    BmtI
                                                                                                    NheI
      TyrThrGln LysSerLeu SerLeuSerPro GlyLysLys***(SEQ ID NO:61)
1501  ACTACACGCA GAAGAGCCTC TCCCTGTCTC CGGGTAAATG AGTGCTAGCC GGCCAGACAT GATAAGATAC ATTGATGAGT TTGGACAAAC CACAACTAGA
1601  ATGCCAGTGA AAAAATGCTT TATTTGTGAA ATTTGTGATG CTATTGCTTT TATTTGTAAC AAGTAAACAC GCAATAAACA ATTATAAGCT AACAATTGCA
                                                                                                      AseI
1701  TTCATTTTAT GTTTCAGGTT CAGGGGGAGG TGTGGGAGGT TTTTTAAAGC AAGTAAAACC TCTACAAATG TGGTATGAA TTAATTCTAA AATACAGCAT
1801  AGCAAAACTT TAACCTCCAA ATCAAGCCTC TACTTGAATC CTTTCTGAG GGCATAGGCA TCAGGGGCTG TTGCCAATGT CAGGAGCCT GCATTAGCTG
```

```
1901  TTTGCAGCCT CACCTTCTTT CATGGAGTTT AAGATATAGT GTATTTTCCC AAGGTTTGAA CTAGCTCTTC ATTTCTTTAT GTTTTAAATG CACTGACCTC
2001  CCACATTCCC TTTTTAGTAA AATATTCAGA AATAATTTAA ATACATCATT GCAATGAAAA TAAATGTTTT TTATTAGGCA GAATCCAGAT GCTCAAGGCC
2101  CTTCATAATA TCCCCCAGTT TAGTAGTTGG ACTTAGGGAA CAAAGGAACC TTTAATAGAA ATTGGACAGA AAGAAAGCGA GCTTCTAGCT TATCCTCAGT
2201  CCTGCTCCTC TGCCACAAAG TGCACGCAGT GTCCGGCCGG GTCGCCAGG CGGAACTCCC GCCCCCACGG CTGCTCGCCG ATCCGGTCA TGGCCGGCCC
2301  GGAGGCGTCC CGGAAGTTCG TGGACACGAC CTCCGACCAC TCGGCGTACA GCTCGTCCAG CACACCCAGG CACACCGCAC CCAGGGTGTT GTCCGCACC
2401  ACCTGGTCCT GGACCGCGCT GATGAACAGG GTCACGTCGT CCCGACCCAG TGTCCTCCA CGAAGTCCCG GGAGAACCCG AGCCGGTCGG
2501  TCCAGAACTC GACCGCTCCG GCGACGTCCG GCGCGGTGAG CACCGGAACG GCACTGGTCA ACTTGGCCAT GATGGCTCCT CCTGTCAGGA GAGGAAAGAG

AseI
2601  AAGAAGGTTA GTACAATTGC TATAGTGAGT TGTATTATAC ATGATTAATT TACTATGCCA GTCAAACTAG GGCTGCAGGG TTCATAGTGC
2701  CACTTTTCCT GCACTGCCCC ATCTCCTGCC CACCCTTTCC CAGGCATAGA CTTACCAAAC TCACAGGAGG GAGAAGGCAG AAGCTTGAGA
2801  CAGACCCGCG GGACCGCGGA ACTGCGAGGG GACGTGGCTA TTTTATGGTG CGCCGGCCCT CGGAGGCAGG GCGCTCGGGG AGGCCTAGCG
2901  GCCAATCTGC GGTGGCAGGA GGCGGGGCCG AAGGCCGTGC CTGACCAATC AGGAGTCTCA GCCCCCGCC CCAAAGCAAG GGGAAGTCAC
3001  GCGCCTGTAG CGCCAGCGTG TTGTGAAATG GGGGTTTGGG GGGGTTGGCA CCTGACTAG TCAAAACAAA CTCCCATTGA CGTCAATGAC GTGGAGACTT
3101  GGAAATCCCC GTGAGTCAAA CCGCTATCCA TGTACTGCCA AACCGCATC ATCATGGTAA TAGCGATGAC ATGTACTGCC
3201  AAGTAGGAAA GTCCATAAG GTCATGTACT CGGGCGGGC TAAATACTCC CAGGCGGGC CATTTACCGT CATTGACGTC AATAGGGGC GTACTTGGCA TATGATACAC
3301  TTGATGTACT GCCAAGTGGG CAGTTTACCG CAGTTTACC CCCATGCTG GTCAATGTTAT AGTCCCTATT GGGTTACTA TGGGAACATA CGTCATTATT
3401  GACGTCAATG GGCGGGGGTC GTTGGGCGGT CGCGTTGCTG CCCCCCTGAC CCCGCTCTC GTGCCGCTCC CTGTTCCGAC GAGCATCACA AAAATCGACG CTCAAGTCAG
3501  CCAGCAAAAG GCCAGGAACC GTAAAAAGGC CGCGTTGCTG TTCCCCCTGG AAGCTCCCTC GTGCGCTCTC CTGTTCCGAC CCTGCCGCTT ACCGGATACC
3601  AGGTGGCGAA ACCCGACAGG ACTATAAAGA TACCAGGCGT TTCCCCCTGG AAGCTCCCTC GTAGGTCGT TCAGTTCGGT GTAGGTCGTT GGGCTGTGT
3701  TGTCCGCCTT TCTCCCTTCG GGAAGCGTGG CGCTTTCTCA TAGCTCACGC GGTAACTATC GTCTTGAGTC CAACCCGGTA TGCCTAACT ACGGCTACAC GCTTCCAAGC TATCGCCACT
3801  GCACGAACCC CCCGTTCAGC CCGACCGCTG CGCCTTATCC GGTAACTATC GTCTTGAGTC CAACCCGGTA TGCCTAACT ACGGCTACAC TAGAAGAACA GGCAGCAGCC
3901  ACTGGTAACA GGATTAGCAG AGCGAGGTAT GTAGGCGGTG CTACAGAGT TGATCCGGCA ACCAAACCAC CGCTGGTAGC GGTGGTTTTT TTGTTTGCAA
4001  TCTGCGCTCT GCTGAAGCCA GTTACCTTCG GAAAAAGAGT TGGTAGCTCT CTTTGATCT TTTCTACGGG GTCTGACGCT CAGTGGAACG AAAACTCACG TTAAGGGATT
4101  GCAGCAGATT ACGCGCAGAA AAAAAGGATC TCAAGAAGAT CCTTTGATCT TTTCTATTT CAATAAAAT GTCTGACGCT CATTACATCT GTGTGTTGGT AATCGTAACT
4201  TTGGTCATGG CTAGTTAATT AACATTTAAA TCAGCGGCCG ACAAAACAAA CTAGCAAAAT AGGCTGTCCC CAGTGCAAGT GCAGTGCCA GAACATTTCT CTATCGAA
4301  AACATACGCT CTCCATCAAA ACAAAACGAA ACAAAACAAA CTAGCAAAAT AGGCTGTCCC CAGTGCAAGT GCAGTGCCA GAACATTTCT CTATCGAA
                                                                                                  (SEQ ID NO:88)
```

IL2ss.CCL13(5-75).hIgG1Fc sequence

```
   1  GGATCTGCGA TCGCTCCGGT GCCCCTCAGT GGGCAGAAGC CACATCGCCC ACAGTCCCCG AGAAGTTGGG GGGAGGGGTC GGCAATTGAA CGGGTGCCTA
 101  GAGAAGGTGG CGCGGGGTAA ACTGGGAAAG TGATGTCGTG TACTGGCTCC GCCTTTTTCC CGAGGGTGGG GGAGAACCGT CTTCACGCGC ATATAAGTGC AGTAGTCGCC
 201  GTGAACGTTC TTTTTGCAA  CGGGTTTGCC GCCAGAACAC AGCTGAAGCT TCGAGGGGCT CGCATCTCTC CGCATCGCGC CCGCCGCCT  ACCTGAGGCC
 301  GCCATCCACG CCGGTTGAGT CCGGTTCTGC CGTGGTGCC  CCTGAACTG  CGTCCGCCGT CGTCCGCCGT CTAGGTAAGT TTAAAGCTCA GGTCGAGACC
 401  GGGCTTTGT  CCGGCGTCC  CTTGGAGCCT ACCTAGACCT AGCCGGCTCT CCACGCTTTG CCTGACCCTG CTTGCTCAAC TCTACGTCTT TGTTTCGTTT
                                      SfoI
                                      NarI
                                      KasI
                                      BbeI
                                                                                                         IL-2 secretion signal
                                                                                                         MetTyrArg MetGlnLeu LeuSerCysIle
 501  TCTGTTCTGC GCCGTTACAG ATCCAAGCTG TGACCGGGCG CTACCTGAGA TCACCGGCGA AGGAGGGCCA CCATGTACAG GATGCAACTC CTGTCTTGCA
                           EcoRI                                             ~~~~~~ CCL13 (5-75)
           AlaLeuSer LeuAlaLeu ValThrAsnSer LeuAsnVal ProSerThr CysCysPheThr PheSerSer LysLysIle SerLeuGlnArg LeuLysSer
 601  TTGCACTAAG TCTTGCACTT GTCACGAATT CGCTCAACGT CCCATCTACT TGCTGCTTCA CATTTAGCAG TAAGAAGATC TCCTTGCAGA GGCTGAAGAG
          TyrValIle ThrThrSerArg CysProGln LysAlaVal IlePheArgThr LysLeuGly CysAlaAspPro LysGluLys TrpValGln
 701  CTATGTGATC ACCACCAGCA GGTGTCCCCA GAAGGCTGTC ATCTTCAGAA CCAAACTGGG CAAGGAGATC TGTGCTGACC CAAAGGAGAA GTGGGTCCAG
                                                                                                        human IgG1 Fc (constant region)
         AsnTyrMetLys HisLeuGly ArgLysAla HisThrLeuLys ThrAspLys CysHisThr ThrHisThr CysProProCys ProAlaPro GluLeuLeu GlyGlyProSer
 801  AATTATATGA AACACCTGGG CCGGAAAGCT CACACCCTGA AGACTGACAA AACTCACACA TGCCCACCGT GCCCAGCACC TGAACTCCTG GGGGGACCGT
         ValPheLeu PheProPro LysProLysAsp ThrLeuMet IleSerArg ThrProGluVal ThrCysVal ValValAsp ValSerHisGlu AspProGlu
 901  CAGTCTTCCT CTTCCCCCCA AAACCCAAGG ACACCCTCAT GATCTCCCGG ACCCCTGAGG TCACATGCGT GGTGGTGGAC GTGAGCCACG AAGACCCTGA
         ValLysPhe AsnTrpTyrVal AspGlyVal GluValHis AsnAlaLysThr LysProArg GluGluGln TyrAsnSerThr TyrArgVal ValSerVal
1001  GGTCAAGTTC AACTGGTACG TGGACGGCGT GGAGGTGCAT AATGCCAAGA CAAAGCCGCG GGAGGAGCAG TACAACAGCA CGTACCGTGT GGTCAGCGTC
         LeuThrValLeu HisGlnAsp TrpLeuAsn GlyLysGluTyr LysCysLys ValSerAsn LysAlaLeuPro AlaProIle GluLysThr IleSerLysAla
1101  CTCACCGTCC TGCACCAGGA CTGGCTGAAT GGCAAGGAGT ACAAGTGCAA GGTCTCCAAC AAAGCCCTCC CAGCCCCCAT CGAGAAAACC ATCTCCAAAG
         LysGlyGln ProArgGlu ProGlnValTyr ThrLeuPro ProSerArg GluGluMetThr LysAsnGln ValSerLeu ThrCysLeuVal LysGlyPhe
1201  CCAAAGGGCA GCCCCGAGAA CCACAGGTGT ACACCCTGCC CCCATCCCGG GAGGAGATGA CCAAGAACCA GGTCAGCCTG ACCTGCCTGG TCAAAGGCTT
         TyrProSer AspIleAlaVal GluTrpGlu SerAsnGly GlnProGluAsn AsnTyrLys ThrThrPro ProValLeuAsp SerAspGly SerPhePhe
1301  CTATCCCAGC GACATCGCCG TGGAGTGGGA GAGCAATGGG CAGCCGGAGA ACAACTACAA GACCACGCCT CCCGTGCTGG ACTCCGACGG CTCCTTCTTC
         LeuTyrSerLys LeuThrVal AspLysSer ArgTrpGlnGln GlyAsnVal PheSerCys SerValMetHis GluAlaLeu HisAsnHis TyrThrGlnLys
1401  CTCTACAGCA AGCTCACCGT GGACAAGAGC AGGTGGCAGC AGGGGAACGT CTTCTCATGC TCCGTGATGC ACGAGGCTCT GCACAACCAC TACACGCAGA
                                                                                                              AseI
         SerLeuSer LeuSerPro GlyLys***(SEQ ID NO:62)
1501  AGAGCCTCTC CCTGTCTCCG GGTAAATGAG TGCTAGCTGG CCAGACATGA TAAGATACAT TGATGAGTTT GGACAAACCA CAACTAGAAT GCAGTGAAAA
1601  AAATGCTTTA TTTGTGAAAT TTGTGATGCT ATTGCTTTAT TTGTAACCAT TATAAGCTGC AATAAACAAG TTAACAACAA CAATTGCATT CATTTTATGT
1701  TTCAGGTTCA GGGGGAGGTG TGGGAGGTTT TTTAAAGCAA GTAAAACCTC TACAAATGTG GTATGGAATT AATTCAAAAA TACAGCATAG CAAAACTTTA
1801  ACCTCCAAAT CAAGCCTCTA CTTGAATCCT TTTCTGAGGG ATGAATAAGG CATAGGCATC AGGGGCTGTT GCCAATGTGC ATTAGCTGTT TGCAGCCTCA
```

```
1901 CCTTCTTTCA TGGAGTTTAA GATATAGTGT ATTTTCCCAA GGTTTGAACT AGCTCTTTCAT TTCTTTATGT TTTAAATGCA CTGACCTCCC ACATTCCCTT
2001 TTTAGTAAAA TATTCAGAAA TAATTTAAAT ACATCATTGC AATGAAAATA AATGTTTTTT ATTAGGCAGA ATCAGATGC TCAAGCCCT TCATAATATC
2101 CCCCAGTTTA GTAGTTGGAC TTAGGGAACA AAGGAACCTT TAATAGAAAT TGGACAGCAA GAAAGCGAGC TTCTAGCTTA TCCTCAGTCC TGCTCCTCTG
2201 CCACAAAGTG CACGCAGTTG CCGGCCGGGT CGCGCAGGGC GAACTCCCGC CCCCACGCT GCTCGCCGAT CTCGGTCATG GCCGCCCGG AGGCGTCCCG
2301 GAAGTTCGTG GACACGACCT CCGACCACTC GGCGTACAGC TCGTCCAGGC CGCGCACCCA CACCCAGGCC AGGGTGTTGT CCGGCACCAC CTGGTCCTGG
2401 ACCCGCTGA TGAACAGGGT CACGTCGTCC CGGACCACAC CGGCGAAGTC GTCCTCCACG AAGTCCCGGG AGAACCCGAG CCGGTCGGTC CAGAACTCGA
2501 CCGCTCCGGC GACGTCGCGC GCGGTGAGCA CCGGAACGGC ACTGGTCAAC TTGGCCATGA TGGCTCCTCC TGTCAGGAGA GGAAAGAGAA GAAGGTTAGT

AseI
2601 ACAATTGCTA TAGTGAGTTG TATTATACTA TGCAGATATA CTATGCCAAT GATTAATTGT CAAAACTAGGG CATAGTGCCA CTTTTCCTGC
2701 ACTGCCCCAT CTCCTGCCCA CCCTTCCCA GGCATAGACA GTCAGTGACT TACCAAACTC ACAGGAGGGA GCTTGAGACA GACCCGCGGG
2801 ACCGCCGAAC TGCGAGGGGA CGTAGCTAGG GCGGCTTCTT TTATGGTGCG CCGGCCCTCG GAGGCAGGGC GCTCGGGGAG CCTAGCGGC CAATCTGCGG
2901 TGGCAGGAGG CGGGGCCGAA GGCCGTGCCT GACCAATCCG GGTTGGGCGC CTGACTAGTC AAAACAAACT CCCATTGACG AAGCAAGGG GAAGTCACGC GCCTGTAGCG
3001 CCAGTCGTGT GTGAAATGGG GGCTTGGGGG CCCATTGATG TACTGCACACG AGGCATCAT GCAATGTAATA TAGGGGTAAATA TCAATGGGGT GGAGACTTGG AAATCCCGT
3101 GAGTCAAACC GCTATCCACG CATGTACTGG GCATAATGCC AGGCGGGCCA CCATTGACGT TTTACCGTCA CATGGTAATA GCAATGACTA ATACGTAGAT GTACTGCCAA GTAGGAAAGT
3201 CCCATAAGGT CATGTACTGG GCATAATGCC AGGCGGGCCA CCATTGACGT TTTACCGTCA CAATGACTA TAGGGGTAATA TCCCTATTGG CGTTACTATG TGATACACTT GATGTACTGC
3301 CAAGTGGGCA GTTTACCGTA AATACTCCAC CCATTGACGT CAATGATATG GGAACATACG TCATTATTGA CGTCAATGGG
3401 CGGGGTCGT TGGGCGGTCA GCCAGGCGGG CCATTTACCG GTTTAGTATGT AACGCCTGCA GGTTAATTAA GAACATGTGA GCAAAAGGC AGCAAGGC
3501 CAGGAACCGT AAAAAGGCCG CGTTGCTGGC GTTTTTCCAT AGGCTCCGCC CCCCTGACGA GCATCACAAA AATCACGACGCT CAAGTCAGAG GTGGCGAAAC
3601 CCGACAGGAC TATAAAGATA CCAGGCGTTT CCCCCTGGAA GCTCCCTCGT GCGCTCTCCT GTTCCGACCCC TGCCGCTTAC CGGATACCTG TCCGCCTTTC
3701 TCCCTTCGGG AAGCGTGGCG CTTTCTCATA GCTCACGCTG TAGGTATCTC AGTTCGGTGT AGTCGTTCG CTCCAAGCTG GGCTGTGTGC ACGAACCCC
3801 CGTTCAGCCC GACCGCTGCG CCTTATCCGG TAACTATCGT CTTGAGTCCA ACCCGGTAAG ACACGACTTA TCGCCACTGG CAGCAGCCAC TGGTAACAGG
3901 ATTAGCAGAG CGAGGTATGT AGGCGGTGCT ACAGAGTTCT TGAAGTGGTG GCCTAACTAC GGCTACACTA GAAGAACAGT ATTTGGTATC TGCGCTCTGC
4001 TGAAGCCAGT TACCTTCGGA AAAAGAGTTG GTAGCTCTTG ATCCGGCAAA CAAACCACCG CTGGTAGCGG TGGTTTTTTT GTTTGCAAGC AGCAGATTAC
4101 GCGCAGAAAA AAGGATCTC AAGAAGATCC TTTGATCTTT TCTACGGGGT CTGACGCTCA GTGGAACGAA AACTCACGTT AAGGGATTTT GGTCATGCT
4201 AGTTAATTAA CATTTAAATC AGCGGCCGCA ATAAAATATC TTTATTTTCA TTACATCTGT GTGTTGGTTT TTTGTGTGAA TCGTAACTAA CATACGCTCT
4301 CCATCAAAAC AAAACGAAAC AAAACAAACT AGCAAAATAG GCTGTCCCCA GTGCAAGTGC AGGTGCCAGA ACATTTCTCT ATCGAA (SEQ ID NO:89)
```

IL2ss.CCL13(5-75).hIgG1Fc sequence
[Alanine substitutions for removal of GAG binding sites – Lys & His]

```
   1  GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101  GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201  GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301  GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401  GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                              SfoI
                                              NarI
                                              KasI
                                              BbeI
                                             ~~~~~~~                                   IL-2 secretion signal
                                                                                       MetTyrArg MetGlnLeu LeuSerCysIle
 501  TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                 EcoRI
                                 ~~~~~~~ CCL13 (5-75)
        AlaLeuSer LeuAlaLeu ValThrAsnSer LeuAsnVal ProSerThr CysCysPheThr PheSerSer LysLysIle SerLeuGlnArg LeuLysSer
 601  TTGCACTAAG TCTTGCACTT GTCACGAATT CGCTCAACGT CCCATCTACT TGCTGCTTCA CATTTAGCAG TAAGAAGATC TCCTTGCAGA GGCTGAAGAG
       TyrValIle ThrThrSerArg CysProGln LysAlaVal IlePheArgThr AlaLeuGly AlaGluIle CysAlaAspPro AlaGluAla TrpValGln
 701  CTATGTGATC ACCACCAGCA GGTGTCCCCA GAAGGCTGTC ATCTTCAGAA CCgccCTGGG CgcgGAGATC TGTGCTGACC CAgccGAGgc cTGGGTCCAG
                                                        human IgG1 Fc (constant region)
      AsnTyrMetAla AlaLeuGly ArgLysAla AlaThrLeuAla ThrAspLys ThrHisThr CysProProCys ProAlaPro GluLeuLeu GlyGlyProSer
 801  AATTATATGg cggctCTGGG CCGGAAAGCT gccACCCTGg ctACTGACAA AACTCACACA TGCCCACCGT GCCCAGCACC TGAACTCCTG GGGGGACCGT
        ValPheLeu PheProPro LysProLysAsp ThrLeuMet IleSerArg ThrProGluVal ThrCysVal ValValAsp ValSerHisGlu AspProGlu
 901  CAGTCTTCCT CTTCCCCCCA AAACCCAAGG ACACCCTCAT GATCTCCCGG ACCCCTGAGG TCACATGCGT GGTGGTGGAC GTGAGCCACG AAGACCCTGA
       ValLysPhe AsnTrpTyrVal AspGlyVal GluValHis AsnAlaLysThr LysProArg GluGluGln TyrAsnSerThr TyrArgVal ValSerVal
1001  GGTCAAGTTC AACTGGTACG TGGACGGCGT GGAGGTGCAT AATGCCAAGA CAAAGCCGCG GGAGGAGCAG TACAACAGCA CGTACCGTGT GGTCAGCGTC
      LeuThrValLeu HisGlnAsp TrpLeuAsn GlyLysGluTyr LysCysLys ValSerAsn LysAlaLeuPro AlaProIle GluLysThr IleSerLysAla
1101  CTCACCGTCC TGCACCAGGA CTGGCTGAAT GGCAAGGAGT ACAAGTGCAA GGTCTCCAAC AAAGCCCTCC CAGCCCCCAT CGAGAAAACC ATCTCCAAAG
        LysGlyGln ProArgGlu ProGlnValTyr ThrLeuPro ProSerArg GluGluMetThr LysAsnGln ValSerLeu ThrCysLeuVal LysGlyPhe
1201  CCAAAGGGCA GCCCCGAGAA CCACAGGTGT ACACCCTGCC CCCATCCCGG GAGGAGATGA CCAAGAACCA GGTCAGCCTG ACCTGCCTGG TCAAAGGCTT
       TyrProSer AspIleAlaVal GluTrpGlu SerAsnGly GlnProGluAsn AsnTyrLys ThrThrPro ProValLeuAsp SerAspGly SerPhePhe
1301  CTATCCCAGC GACATCGCCG TGGAGTGGGA GAGCAATGGG CAGCCGGAGA ACAACTACAA GACCACGCCT CCCGTGCTGG ACTCCGACGG CTCCTTCTTC
      LeuTyrSerLys LeuThrVal AspLysSer ArgTrpGlnGln GlyAsnVal PheSerCys SerValMetHis GluAlaLeu HisAsnHis TyrThrGlnLys
1401  CTCTACAGCA AGCTCACCGT GGACAAGAGC AGGTGGCAGC AGGGGAACGT CTTCTCATGC TCCGTGATGC ACGAGGCTCT GCACAACCAC TACACGCAGA
                                             NheI
                                             BmtI
        SerLeuSer LeuSerPro GlyLys***(SEQ ID NO:63)
1501  AGAGCCTCTC CCTGTCTCCG GGTAAATGAG TGCTAGCTGG CCAGACATGA TAAGATACAT TGATGAGTTT GGACAAACCA CAACTAGAAT GCAGTGAAAA
1601  AAATGCTTTA TTTGTGAAAT TTGTGATGCT ATTGCTTTAT TTGTAACCAT TATAAGCTGC AATAAACAAG TTAACAACAA CAATTGCATT CATTTTATGT
                                                                                   AseI
1701  TTCAGGTTCA GGGGGAGGTG TGGGAGGTTT TTTAAAGCAA GTAAAACCTC TACAAATGTG GTATGGAATT AATTCTAAAA TACAGCATAG CAAAACTTTA
```

|      |            |            |            |            |            |            |            |            |            |
|------|------------|------------|------------|------------|------------|------------|------------|------------|------------|
| 1801 | ACCTCCAAAT | CAAGCCTCTA | CTTGAATCCT | TTTCTGAGGG | ATGAATAAGG | CATAGGCATC | AGGGGCTGTT | GCCAATGTGC | ATTAGCTGTT | TGCAGCCTCA |
| 1901 | CCTTCTTTCA | TGGAGTTTAA | GATATAGTGT | ATTTTCCCAA | GGTTTGAACT | AGCTCTTCAT | TTCTTTATGT | TTTAAATGCA | CTGACCTCCC | ACATTCCCTT |
| 2001 | TTTAGTAAAA | TATTCAGAAA | TAATTTAAAT | ACATCATTGC | AATGAAAATA | AATGTTTTTT | ATTAGGCAGA | ATCCAGATGC | TCAAGGCCCT | TCATAATATC |
| 2101 | CCCAGTTTA  | GTAGTTGGAC | TTAGGAACA  | AAGGAACCTT | TAATAGAAAT | TGGACAGCAA | GAAAGCGAGC | TTCTAGCTTA | TCCTCAGTCC | TGCTCCTCTG |
| 2201 | CCACAAAGTG | CACGCAGTTG | CCGGCCGGGT | CGCCAGGGC  | GAACTCCCGC | CCCCACGGCT | GCTCGCCGAT | CTCGGTCATG | GCCGGCCGG  | AGGCGTCCCG |
| 2301 | GAAGTTCGTG | GACACGACCT | CACGACCACTC | CCGACCACTC | GGCGTACAGC | TCGTCCAGGC | CACCCAGGCC | AGGGTGTTGT | CCGGCACCAC | CTGGTCCTGG |
| 2401 | ACCGCGCTGA | TGAACAGGGT | CACGTCGTCC | CGGACCACAC | CGGCGAAGTC | CGGCCACCCA | AAGTCCCCGG | AGAACCCGAG | CCGTCGTC   | CAGAACTCGA |
| 2501 | CCGCTCCGGC | GACGTCGCGC | GCGGTGAGCA | CCGGAACGGC | ACTGGTCAAC | TTGGCCATGA | TGGCTCCTCC | TGTCAGGAGA | GGAAAGAGAA | GAAGGTTAGT |
| 2601 | ACAATTGCTA | TAGTGAGTTG | TATTATACTA | TGCAGATATA | CTATGCCAAT | GATTAATTGT | CAAACTAGGG | CTGCAGGGTT | CATAGTGCCA | CTTTTCCTGC |
| 2701 | ACTGCCCAT  | CTCCTGCCCA | CCCTTTCCCA | GGCATAGACA | GTCAGTGACT | TACCAAACTC | ACAGGAGGGA | GAAGGCAGAA | GCTTGAGACA | GACCCGGGGG |
| 2801 | ACCGCGAAC  | TGCGAGGGGA | CGTGGCTAGG | GCGGCTTCTT | TTATGGTGCG | CCGGCCCCTCG | GAGGCAGGGC | GCTCGGGGAG | GCCTAGCGGC | CAATCTGCGG |
| 2901 | TGGCAGGAGG | CGGGGCCGAA | GGCCGTGCCT | GACCAATCCG | GAGCACATAG | GAGTCTCAGC | CCCCGCCCC  | AAAGCAAGGG | GAAGTCACGC | GCCTGTAGCG |
| 3001 | CCAGTTCGTT | GTGAAATGGG | GGCTTGGGG  | GGTTGGGGCC | CTGACTAGTC | AAAACAAACT | CCCATTGACG | TCAATGGGGT | GGAGACTTGG | AAATCCCGT  |
| 3101 | GAGTCAAACC | GCTATCCACG | CCCATTGATG | TACTGCCAAA | ACCGCATCAT | CATGGTAATA | GCGATGACTA | ATACGTAGAT | GTACTGCCAA | GTAGGAAAGT |
| 3201 | CCCATAAGGT | CATGTACTGG | AGGCGGGCA  | CCATTGACGT | TTACCGTCA  | TGGGGGCGT  | ACTTGGCATA | TAGGGCATA  | TGATACACTT | GATGTACTGC |
| 3301 | CAAGTGGGCA | GTTTACCGTA | AATACTCCAC | CCATTGACGT | CAATGGGAAG | TCCCTATTGG | CGTTACTATG | GGAACATACG | TCATTATTGA | CGTCAATGGG |
| 3401 | CGGGGGTCGT | TGGGCGGTCA | GCCAGGCGGG | CCATTTACCG | TAAGTTATGT | AACGCCTGCA | GGTTAATTAA | GAACATGTGA | GCAAAAGGCC | AGCAAAAGGC |
| 3501 | CAGGAACCGT | AAAAAGGCCG | CGTTGCTGGC | GTTTTTCCAT | AGGCTCCGCC | CCCCTGACGA | GCATCACAAA | AATCGACGCT | CAAGTCAGAG | GTGGCGAAAC |
| 3601 | CCGACAGGAC | TATAAAGATA | CCAGGCGTTT | CCCCCTGGAA | GCTCCCTCGT | GCGCTCTCCT | GTTCCGACCC | TGCCGCTTAC | CGGATACCTG | TCCGCCTTTC |
| 3701 | TCCCTTCGGG | AAGCGTGGCG | CTTTCTCATA | GCTCACGCTG | TAGGTATCTC | AGTTCGGTGT | AGGTCGTTCG | CTCCAAGCTG | GGCTGTGTGC | ACGAACCCCC |
| 3801 | CGTTCAGCCC | GACCGCTGCG | CCTTATCCGG | TAACTATCGT | CTTGAGTCCA | ACCCGGTAAG | ACACGACTTA | TCGCCACTGG | CAGCAGCCAC | TGGTAACAGG |
| 3901 | ATTAGCAGAG | CGAGGTATGT | AGGCGGTGCT | ACAGAGTTCT | TGAAGTGGTG | GCCTAACTAC | GGCTACACTA | GAAGAACAGT | ATTTGGTATC | TGCGCTCTGC |
| 4001 | TGAAGCCAGT | TACCTTCGGA | AAAAGAGTTG | GTAGCTCTTG | ATCCGGCAAA | CAAACCACCG | CTGGTAGCGG | TGGTTTTTTT | GTTTGCAAGC | AGCAGATTAC |
| 4101 | GCGCAGAAAA | AAAGGATCTC | AAGAAGATCC | TTTGATCTTT | TCTACGGGGT | CTGACGCTCA | GTGGAACGAA | AACTCACGTT | AAGGGATTTT | GGTCATGCT  |
| 4201 | AGTTAATTAA | CATTTAAATC | AGCGGCCGCA | ATAAAATATC | TTTATTTTCA | TTACATCTGT | GTGTTGGTTT | TTTGTGTGAA | TCGTAACTAA | CATACGCTCT |
| 4301 | CCATCAAAC  | AAAACGAAAC | AGCAAACAACT |            | GCTGTCCCCA | GTGCAAGTGC | AGGTGCCAGA | ACATTTCTCT | ATCGAA     | (SEQ ID NO:90) |

AseI (above position 2606 area)

IL2ss.CCL25.hIgG1Fc sequence

```
   1  GGATCTGGCA TGGCTCCGGT CCCCCTCAGT GGGCAGAGCG CACATGCGCC ACAGTCCCCG AGAGTTGGG GGGAGGGGTC GGCAATTGAA CGGGTGCCTA
 101  GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201  GTGAACGTTC TTTTTCGCAA CGGGTTTGCC GCCAGAACAC TCGAGGGGCT CGCATCTCTC CGCATCCGGC CTTCACGCGC CCGCCGCCCT ACCTGAGGCC
 301  GCCATCCACG CCGGTTGAGT CCGGTTCTCC CGCCTCCCGC CTGTGGTGCC TCCTGAACTG CGTCCGCCGT CTAGGTAAGT CTTGCTCAAC GGTCGAGACC
 401  GGGCCTTTGT CCGGCCTCC CTTGGAGCCT CCTAGACTC AGCCGGCTCT ACCTACCTG CCACGCTTTG CCTGACCCTG CTTGCTCAAC TCTACGTCTT TGTTTCGTTT
                                            SfoI
                                            NarI
                                            KasI
                                            BbeI                                                       IL-2 secretion signal
                                                                                                       MetTyrArg MetGlnLeu LeuSerCysIle
 501  TCTGTTCTGC GCCGTTACAG ATCCAAGCTG TGAACGGCGC CTACCTGAGA TCACCGGCGA AGGAGGCCA CCATGTACAG GATGCAACTC CTGTCTTGCA
                            EcoRI
                                       ------ CCL25 (1-127)
                            AlaLeuSer LeuAlaLeu ValThrAsnSer ThrGlnGly ValPheGlu AspCysCysLeu AlaTyrHis TyrProIle GlyTrpAlaVal LeuArgHis
 601  TTGCACTAAG TCTTGCACTT GTCACGAATT CAACCCAAGG TGTCTTTGAG GACTGCTGCC TGGCCTACCA CTACCCCATT GGGTGGGCTG TGCTCCGGCA
                            AlaTrpThr TyrArgIleGln GluValSer GlySerCys AsnLeuProAla AlaIlePhe TyrLeuPro LysArgHisArg LysValCys GlyAsnPro
 701  CGCTGGACT TACCGGATCC AGGAGGTGAG TGGATCCTGC AATCTGCCTG CTGCGATATT CTACCTCCCC AAGAGACACA GGAAGGTGTG TGGGAACCCC
                            CysSerArgGlu ValGlnArg AlaMetLys ArgAsnLys ValPheAla LysLeuArgHis AsnThrGln ThrPheGln GlyProHisAla
 801  AAAGCAGGG AGTGCAGAG AGCATGAAG CTCCTGATG CTCGAAATAA GGTTTTTGCA AAGCTCCGCC ACACACGCA GACCTTCCAA GGCCCTCATG
                            LysProLys LeuSerPhe GlyAsnSerLys LeuSerPhe SerAsnProIle SerSerSer LysArgAsn ValSerAspLys ThrHisThr
                                                                                                                   human IgG1 Fc
                                                                                                                   (constant region)
 901  CTGTAAAGAA GTTGAGTTCT GGAAACTCCA AGTTATCATC GTCCAAGTTT AGCAATCCCA TCAGCAGCAG CAAGAGGAAT GTCTCCGACA AACTCACAC
                            CysProPro CysProAlaPro GluLeuLeu GlyGlyPro SerValPheLeu PheProPro LysProLys AspThrLeuMet IleSerArg ThrProGlu
1001  ATGCCACCG TGCCCAGCAC CTGAACTCCT GGGGGGACCG TCAGTCTTC TTCCTCCCCC CAAAACCCAAG GACACCCTCA TGATCTCCCG GACCCCTGAG
                            AleI
                            ValThrCysVal ValValAsp ValSerHis GluAspProGlu ValLysPhe AsnTrpTyr ValAspGlyVal GluValHis AsnAlaLys ThrLysProArg
1101  GTCACATGC GTGGTGGTGGA CGTGAGCCAC GAAGACCCTG AGGTCAAGTT CAACTGGTAC GTGGACGGCG TGGAGGTGCA TAATGCCAAG ACAAAGCCGC
                            GluGluGln TyrAsnSer ThrTyrArgVal ValSerVal LeuHisGlnAsp TrpLeuAsn GlyLysGlu TyrLysCysLys ValSerAsn
1201  GGGAGGAGCA GTACAACAGC ACGTACCGTG TGGTCAGCGT CCTCACCGTC CTGCACCAGG ACTGGCTGAA TGGCAAGGAG TACAAGTGCA AGGTCTCCAA
                            LysAlaLeu ProAlaProIle GluLysThr IleSerLys AlaLysGlyGln ProArgGlu ProGlnVal TyrThrLeuPro ProSerArg GluGluMet
1301  CAAAGCCCTC CCAGCCCCCA TCGAGAAAAC CATCTCCAAA GCCAAAGGGC AGCCCCGAGA ACCACAGGTG TACACCCTGC CCCCATCCCG GGAGGAGATG
                            ThrLysAsnGln ValSerLeu ThrCysLeu ValLysGlyPhe TyrProSer AspIleAla ValGluTrpGlu SerAsnGly GlnProGlu AsnAsnTyrLys
1401  ACCAAGAACC AGGTCAGCCT GACCTGCCTG GTCAAAGGCT TCTATCCCAG CGACATCGCC GTGGAGTGGG AGAGCAATGG GCAGCCGGAG AACAACTACA
                            ThrThrPro ProValLeu AspSerAspGly SerPhePhe LeuTyrSer LysLeuThrVal AspLysSer ArgTrpGln GlnGlyAsnVal PheSerCys
1501  AGACCACGCC TCCCGTGCTG GACTCCGACG GCTCCTTCTT CCTCTACAGC AAGCTCACCG TGGACAAGAG CAGGTGGCAG CAGGGGAACG TCTTCTCATG
                                                                                                    BmtI
                                                                                                    NheI
                            SerValMet HisGluAlaLeu HisAsnHis TyrThrGln LysSerLeuSer LeuSerPro GlyLys*** (SEQ ID NO:64)
1601  CTCCGTGATG CACGAGGCTC TGCACAACCA CTACACGCAG AAGAGCCTCT CCCTGTCTCC GGGTAAATGA GTGCTAGCTG GCCAGACATG ATAAGATACA
```

```
1701 TTGATGAGTT TGGACAAACC ACAACTAGAA TGCAGTGAAA AAATGCTTT ATTTGTGAAA TTTGTGATGC TATTGCTTTA TTTGTAACCA TTATAAGCTG
1801 CAATAAACAA GTTAACAACA ACAATTGCAT TCATTTTATG TTTCAGGTTC AGGGGAGGT GTGGGAGGTT ACTTGAAGCA AGTAAAACCT CTACAAATGT
         AseI
1901 GGTATGGAAT TAATTCTAAA ATACAGCATA GCAAAACTTT AACCTCCAAA TCAAGCCTCT ACTTGAATCC TTTTCTGAGG GATGAATAAG GCATAGGCAT
2001 CAGGGCTGT TGCCAATGTG CATTAGCTGT TTGCAGCCTC ACCTTCTTTC TTTTAGTTTA ATGGAGTTTA TATTTCCCA AGTTTGAAC TAGCTCTTCA
2101 TTTCTTTATG TTTTAAATGC CTGACCTCC CACATTCCCT TTTTAGTAAA ATATTCAGAA ATAATTAAA TACATCATTG CAATGAAAAT AAATGTTTTT
2201 TATTAGGCAG AATCCAGATG CTCAAGGCTC TTCATAATAT CCCCCAGTTT GCCACAAAGT GCACGCAGTT AAGGAAACCT TTAATAGAAA TTGGACAGCA
2301 AGAAAGCGAG CTTCTAGCTT ATCCTCAGTC CTGCTCCTCT GGAAGTTCGT GCACCGCAGT GCCGGCCGG TCGGCAGGG CGAACTCCG CCCGCACGC
2401 TGCTCGCCGA TCTCGGTCAT GGCCGCCCG GAGGCGTCCC GGAAGTTCGT GCACACGACC TCCGACCACT CGGGGTACAG CTCGTTCAGG CCGCCACCC
2501 ACACCCAGGC CAGGGTGTTG TCCGGCACCA CCTGGTCCTG GACCGCGCTG ATGAACAGGG ATGAACAGGG TCACGTCGTC CCGGCGAAGT CGTCCTCCAC
2601 GAAGTCCCGG GAGAACCCGA GCCGGTCGGT CCAGAACTCG ACCGCTCCGG CGACGTCGCG CGACGTGAGC CGCGGAACGG CACTGGTCAA CTTGGCCATG
                                                                                                      AseI
2701 ATGGCTCCTC CTGTCAGGAG AGGAAAGAGA AGAAGGTTAG TACAATTGCT ATAGTGAGTT ATGCAGATAT ATGCAGATAT ACTATGCCAA TGATTAATTG
2801 TCAAACTAGG GCTGCAGGGT TCATAGTGCC ACTTTTCCTG CACTGCCCCA TCTCCTGCCC AGGCATAGAC AGTCAGTGAC TTACCAAACT
2901 CACAGGAGGG AGAAGGCAGA AGCTTGAGAC AGACCCGCGG GACCGCCGAA CTGCGAGGGG ACGTGGCTAG GGCGGCTTCT TTATGGTGC GCCGGCCCTC
3001 GGAGGCAGGG CGCTCGGGGA GGCCTAGCGG GTGGCAGGAG GCCAGGCGTC GCGGGCCGA AGGCCGTGCC TGACCAATCC GGAGCACATA GGAGTCTCAG
3101 CCCCCGCCC CAAAGCAAGG GGAAGTCACG GAAGTCAAAC CGCTCGTAGC TGTGAAATGG GGCTTGGGGC CCTGACTAGT CAAAACAAAC
3201 TCCCATTGAC GTCAATGGGG TGGAGACTTG GAAATCCCCG AGTAGGAAAG CGCTATCCAC GCCCATTGAT GTACTGCCAA ACCGCATCA TCATGTGTAAT
3301 AGCGATGACT AATACGTAGA TGTACTGCCA AGTAGGAAAG TCCCATAAGG TCATGTACTG GGCATAATGC CAGGCGGGCC ATTACCGTC ATTGACGTCA
3401 ATAGGGGGCG TACTTGGCAT ATGATACACT CCAAGTGGGC AGTTTACCGT AGTTACGCT AAATACTCCA CCCATTGACG TCAATGGAAA GTCCCTATTG
3501 GCGTTACTAT GGGAACATAC GTCATTATTG ACGTCAATGG GCGGGGGTCG TTGGGCGGTC AGCCAGGCG GCCATTTACC GTAAGTTATG TAACGCTGC
3601 AGTTAATTA AGAACATGTG AGCAAAAGGC CAGCAAAAGG CCAGGAACCG TAAAAAGGCC GCGTTGCTGG CGTTTTTCCA TAGGCTCCGC CCCCCTGACG
3701 AGCATCACAA AAATCGACGC TCAAGTCAGA GGTGGCGAAA CCCGACAGGA CTATAAAGAT ACCAGGCGTT TCCCCCTGGA AGCTCCCTCG TGCGCTCTCC
3801 TGTTCCGACC CTGCCGCTTA CCGGATACCT GTCCGCCTTT CTCCCTTCGG GAAGCGTGGC GCTTTCTCAT AGCTCACGCT GTAGGTATCT CAGTTCGGTG
3901 TAGGTCGTTC GCTCCAAGCT GGGCTGTGTG CACGAACCCC CCGTTCAGCC CGACCGCTGC GCCTTATCCG GTAACTATCG TCTTGAGTCC AACCCGGTAA
4001 GACACGACTT ATCGCCACTG GCAGCAGCCA CTGGTAACAG GATTAGCAGA GCGAGGTATG TAGGCGGTGC TTGAAGTGGT GGCCTAACTA
4101 CGGCTACACT AGAAGAACAG TATTTGGTAT CTGCCTCTG CTGCAGCCAG TTACCTTCGG AAAAAGAGTT GGTAGCTCTT GATCCGGCAA ACAAACCACC
4201 GCTGGTAGCG GTGGTTTTTT TGTTTGCAAG CAGCAGATTA CGCGCAGAAA AAAAGGATCT CAAGAAGATC CTTTGATCTT TTCTACGGGG TCTGACGCTC
4301 AGTGGAACGA AAACTCACGT TAAGGGATTT TGGTCATGAG ATTATCAAAA AGGATCTTCA CCTAGATCCT TTTAAATTAA AAATGAAGTT TTAAATCAAT
4401 TGTGTTGGTT TTTTGTGTGA ATCGTAACTA ACATACGCTC TCCATCAAAA CAAAACGAAA CAAAACAAAC AATAAAATAT ATTACATCTG
4501 CAGGTGCCAG AACATTTCTC TATCGAA    (SEQ ID NO: 91)
```

IL2ss.CCL25(4-127).hIgG1Fc sequence

```
   1  GGATCTGCGA TCGCTCCGGT GCCCGTCAGT GCCCGTCCCG CACATGCCCC GGGCAGAGCG AGAAGTTGGG GGGAGGGGTC GGCAATTGAA CGGGTGCCTA
 101  GAGAAGGTGG CGCGGGGTAA ACTCGGAAAG TGATGTCGTG GCCAGAACAC AGTCTTTTCC GCCTTTTCCC CGAGGGTGGG GGAGAACCGT ATATAAGTGC
 201  GTGAACGTTC TTTTTCGCAA CGGGTTTGCC GGGTTTGCCC GCCAGAAGCT TCGAGGGGCT TCGAGCCTCT CGCATCCTCT CTTCACGCGC CCCGCGCCCT
 301  GCCATCCACG CCGGTTGAGT CCGGTCTGC CCGCTCCTGC CTGTGGTGCC TCCTGAACTG CGTCCGCCGT CGTGGTGAGT CTAGGTAAGT TTAAGCTCA GGTCGAGACC
 401  GGGCCTTTGT CCGGCGCTCC CTTGGAGCCT ACCTAGACTC AGCCGGCTCT CCAACGCTTG CCTGACCCTG CTTGCTCAAC TCTACGTCTT TGTTTCGTTT

IL-2 secretion signal
                                                                                                      MetTyrArg MetGlnLeu LeuSerCysIle
 501  TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                              EcoRI
                                        ------- CCL25 (4-127)
                                                                                        AlaLeuSer LeuAlaLeu ValThrAsnSer ValPheGlu AspCysCys LeuAlaTyrHis TyrProIle GlyTrpAla ValLeuArgHis AlaTrpThr
 601  TTGCACTAAG TCTTGCACTT GTCACGAATT CGGTCTTTGA AGACTGCTGC CTGGCCTACC ACTACCCCAT TGGCTGGGCT GTGCTCCGGC ACGCCTGGAC
                                                           TyrArgIle GlnGluValSer GlySerCys AsnLeuPro AlaAlaIlePhe TyrLeuPro LysAsnPro LysPheTyr GlyAsnPro LysSerArg
 701  TTACCGGATC CAGGAGGTGA GCGGGAGCTG CAATCTGCCT GCTGCGATAT TCTACCTGCC CAAGAACCCA AAGTTCTACG GGGAACCC CAAAAGCAGG
            GluValGlnArg AlaMetIys LeuLeuAsp AlaArgAsnLys ValPheAla LysLeuArg HisAsnThrGln ThrPheGln GlyProHis AlaValLysLys
 801  GAGGTGCAGA GAGCCATGAA GCTCCTGGAT GCTCGAAATA AGTTTTTGC AAAGCTCCGC CACAACCGC AGACCTTCCA AGGCCCTCAT GCTGTAAAGA
                                                                                                                      human IgG1 Fc (constant region)
            LeuSerSer GlyAsnSer LysLeuSer SerLeuSerPhe SerAsnPro IleSerSerSer LysLysAsp ValSerArg LysThrHisThr CysProPro
 901  AGTTGAGTTC TGGAAACTCC AAGTTATCAT CGTCCAAGTT TAGCAATCCC ATCAGCAGCA GCAAGAAGAA TGTCTCCGAC AAAACTCACA CATGCCCACC
                CysProAla ProGluLeuLeu GlyGlyPro SerValPhe LeuPheProPro LysProLys AspThrLeu MetIleSerArg ThrProGlu ValThrCys
1001  GTGCCCAGCA CCTGAACTCC TGGGGGGACC GTCAGTCTTC CTCTTCCCCC CAAAACCCAA GGACACCCTC ATGATCTCCC GGACCCCTGA GGTCACATGC
      ValValAsp ValSerHis GluAspPro GluValLysPhe AsnTrpTyr ValAspGly ValGluValHis AsnAlaLys ThrLysPro ArgGluGluGln
1101  GTGGTGGTGG ACGTGAGCCA CGAAGACCCT GAGGTCAAGT TCAACTGGTA CGTGGACGGC GTGGAGGTGC ATAATGCCAA GACAAAGCCG CGGGAGGAGC
      TyrAsnSer ThrTyrArg ValValSerVal LeuThrVal LeuHisGln AspTrpLeuAsn GlyLysGlu TyrLysCys LysValSerAsn LysAlaLeu
1201  AGTACAACAG CACGTACCGT GTGGTCAGCG TCCTCACCGT CCTGCACCAG GACTGGCTGA ATGGCAAGGA GTACAAGTGC AAGGTCTCCA ACAAAGCCCT
      ProAlaPro IleGluLysThr IleSerLys AlaLysGly GlnProArgGlu ProGlnVal TyrThrLeu ProProSerArg GluGluMet ThrLysAsn
1301  CCCAGCCCCC ATCGAGAAAA CCATCTCCAA AGCCAAAGGG CAGCCCCGAG AACCACAGGT GTACACCCTG CCCCCATCCC GGGAGGAGAT GACCAAGAAC
      GlnValSerLeu ThrCysLeu ValLysGly PheTyrProSer AspIleAla ValGluTrp GluSerAsnGly GlnProGlu AsnAsnTyr LysThrThrPro
1401  CAGGTCAGCC TGACCTGCCT GGTCAAAGGC TTCTATCCCA GCGACATCGC CGTGGAGTGG GAGAGCAATG GGCAGCCGGA GAACAACTAC AAGACCACGC
        ProValLeu AspSerAsp GlySerPhePhe LeuTyrSer LysLeuThr ValAspLysSer ArgTrpGln GlnGlyAsn ValPheSerCys SerValMet
1501  CTCCCGTGCT GGACTCCGAC GGCTCCTTCT TCCTCTACAG CAAGCTCACC GTGGACAAGA GCAGGTGGCA GCAGGGGAAC GTCTTCTCAT GCTCCGTGAT
                                                                                                     BmtI
                                                                                                     NheI
      HisGluAla LeuHisAsnHis TyrThrGln LysSerLeu SerLeuSerPro GlyLys*** (SEQ ID NO:65)
1601  GCACGAGGCT CTGCACAACC ACTACACGCA GAAGAGCCTC TCCCTGTCTC CGGGTAAATG ACTGCTAGTT GGGCCAGACAT GATAACATAC ATTGATCAGT
1701  TTGGACAAAC CACAACTAGA ATGCAGTGAA AAAATGCTTT TATTTGTGAA ATTTGTGATG CTATTGCTTT ATTTGTAACC ATTATAAGCT GCAATAAACA
                                                                                                                          AseI
```

```
1801 AGTTAACAAC AACAATTGCA TTCATTTTAT GTTTCAGGTT CAGGGGGAGG TGTGGGAGGT TTTTTAAAGC AAGTAAAACC TCTACAAATG TGGTATGGAA
     AseI
1901 TTAATTCTAA AATACAGCAT AGCAAAACTT TAACCTCCAA ATCAAGCCTC TACTTGAATC CTTTTCTGAG GGATGAATAA GGCATAGGCA TCAGGGGCTG
2001 TTGCCAATGT GCATTAGCTG TTTGCAGCCT CCACATTCCC TTTTTAGTAA CATGGAGTTT AAGATATAGT GTATTTTCCC AAGGTTTGAA CTAGCTCTTC ATTTCTTTAT
2101 GTTTTAAATG CACTGACCTC CTTCATAATA TCCCCCAGTT AATATTCAGA CAAAGGAAAC ATACATCATT GCAATGAAAA TAAATGTTTT TTATTAGGCA
2201 GAATCCAGAT GCTCAAGGCC CTTGCTCCTC TGCCACAAAG TAGTAGTTGG ACTTAGGGAA TGCCGGCCGG GTCGCGCAGG TTTAATAGAA ATTGGACAGC AAGAAAGCGA
2301 GCTTCTAGCT TATCCTCAGT CCTGCTCCTC GGAGGCGTCC TGCACGCAGT TGCCGACCAC CTCCGACCAC TCGGCGTACA GCTCGTCCAG GCCGCCACCC CTGCTCGCCG
2401 ATCTCGGTCA TGGCCGGCCC GTCCGGCACC ACCTGGTCCT CGGAAGTTCG TGGACACGAC TGGACACGAC GATGAACAGG GTCACGTCGT CCCGACCCAC GCCGCGCACC CACACCCAGG
2501 CCAGGGTGTT GTCCGGCACC ACCTGGTCCT CGGAAGTTCG CGACCGCGCT GATGAACAGG GTCACGTCGT CCCGACCCAC ACCGGCGAAG TGTCCTCCA CGAAGTCCCG
2601 GGAGAACCCG AGCCGGTCGG TCCAGAACTC GACCGCTCCG GACCGCTCCG GCGACGTCGC GCACCGGTGAG CACCGGAACG GCACTGGTCA ACTTGGCCAT GATGGCTCCT
                                                                                                              AseI
2701 CCTGTCAGGA GAGGAAAGAG AAGAAGGTTA GTACAATTGC TATAGTGAGT ATCTCCTGCC CACCCTTTCC TATGCAGATA TACTATGCCA ATGATTAATT GTCAAACTAG
2801 GGCTGCAGGG TTCATAGTGC CACTTTTCCT GCACTGCCCC ACTGCGAGGG ACTGCGAGGG ACGTGGCTA CAGGCATAGA CTTACCAAAC TCACAGGAGG
2901 GAGAAGGCAG AAGCTTGAGA CAGACCCGCG GGACCGCCGA ACTGCGAGGG ACTGCGAGGG GACGTGGCTA GGGGCGGCTTC CGCCGGCCCT CGGAGGCAGG
3001 GCGCTCGGGG AGGCCTAGCG GCCAATCTGC GGTGGCAGGA GGGGCGGCCG AAGGCCGTGC CTGACCAATC CGGAGCACAT AGGAGTCTCA GCCCCCGCC
3101 CCAAGCAAG GGGAAGTCAC GCGCTGTAG CGCCTGTAG TTGTGAAATG CGGCTATCCA CGGCCTTGGG GGGGTTGGGG CCCTGACTAG TCAAACAAA CTCCCATTGA
3201 CGTCAATGGG GTGGAGACTT GGAAATCCCC GTGAGTCAAA CGGCTATCCA GTGTACTGCA AAACCGCATC ATCATGGTAA TAGGGATGAC
3301 TAATACGTAG ATGTACTGCC AAGTAGGAAA GTCCCATAAG GTCCCATAAG GGCATAATG CCAGGCGGGC CATTTACCGT CATTGACGTC AATAGGGGC
3401 GTACTTGGCA TATGATACAC TTGATGTACT TTGATGTACT CAGTTTACCG TAAATACTCC ACCCATTGAC GTCAATGGA AGTCCCTATT GGCGTTACTA
3501 TGGGAACATA CGTCATTATT GACGTCAATG GGGCGGGGTC GTTGGGCGGT GTTGGGCGGT CAGCCAGGCG GGCCATTTAC CGTAAGTTAT GTAACGCCTG CAGGTTAATT
3601 AAGAACATGT GAGCAAAAG CCCAGAACCC GCCAGAACCC GCCAGGAACC ACTATAAAGA TACCAGGCGT TTCCCCCTGG AAGCTCCCTC CCCCCTGAC GAGCATCACA
3701 AAAATCGACG CTCAAGTCAG AGGTGGCGAA TGTCCGCCTT TCTCCCTTCG CGCTTCAGC AAGCGTGG CGCTTCAGC GCGCTTCAGC TACCAGCGT TAGCTCACGC TTCAGTATC GTGCGCTCTC CTGTTCCGAC
3801 CCTGCCGCTT ACCGGATACC TGTCCGCCTT TCTCCCTTCG CGCTTCAGC CCGCTTCAGC CCGCTTCAGC CGCTTCAGC CGCCTTATCC GGTAACTATC TCAGTTCGGT GTAGGTCGTT
3901 CGCTCCAAGC TGGGCTGTGT GCACGAACCC CCCGTTCAGC GGATTAGCAG GGATTAGCAG CCGACCGCTG AGCGAGGTAT GTAGGCGGTG CTACAGAGTT CAACCCGGTA AGACAGACT
4001 TATCGCCACT GGCAGCAGCC ACTGGTAACA TCTGCGCTCT GCTGAAGCCA GTTACCTTCG GAAAAAGAGT CTTGAAGTGG TGGCCTAACT ACGGCTACAC CGCTGGTAGC
4101 TAGAAGAACA GTATTTGGTA TTGTTTGCAA GCAGCAGATT ACGCGCAGAA AAAAAGGATC TCAAGAAGAT CCTTTGATCT TTTCTACGGG GTCTGACGCT CAGTGGAACG
4201 GGTGGTTTTT TTAAGGATT TTGGTCATGG CTAGTTAATT AACATTAAA TCAGCGCCG CAATAAAATA TCTTTATTT CATTACATCT GTGTGTTGGT
4301 AAAACTCACG AATCGTAACT AACATACGCT CTCCATCAAA ACAAAACGAA ACAAAACAAA CTAGCAAAT AGGCTGTCCC CAGTGCAAGT GCAGGTGCCA
4401 TTTTTGTGTG AATCGTAACT AACATACGCT CTCCATCAAA ACAAAACGAA ACAAAACAAA CTAGCAAAT AGGCTGTCCC CAGTGCAAGT GCAGGTGCCA
4501 GAACATTTCT CTATCGAA  (SEQ ID NO:92)
```

IL2ss.CCL25(4-127).hIgG1Fc sequence
[Alanine substitutions for GAG binding sites – Lys, Arg & His]

```
   1  GGATCTGCGA TCGCTCCGGT GCCCGTCAGT GGGAGAGCG CACATGCCCA ACAGTCCCCG AGAAGTTGGG GGGAGGGGTC GGCAATTGAA CGGGTGCCTA
 101  GAGAAGTGG CGCGGGGTAA ACTGGGAAAG TGATGTCGTG GCCAGAACAC TACTG

```
1701  TTGGACAAAC CACAACTAGA ATGCAGTGAA AAAAATGCTT TATTGTGAA ATTTGTGATG CTATTGCTTT ATTTGTAACC ATTATAAGCT GCAATAAACA
                                                                                                                    AseI
1801  AGTTAACAAC AACAATTGCA TTCATTTTAT GTTTCAGGTT CAGGGGGAGG TGTGGGAGGT TTTTTAAAGC AAGTAAAACC TCTACAAATG TGGTATGGAA
      AseI
1901  TTAATTCTAA AATACAGCAT AGCAAAACTT TAACCTCCAA ATCAAGCCTC TACTTGAATC CTTTTCTGAG CTTTTCTTTC GGCATAGGCA TCAGGGGCTG
2001  TTGCCAATGT GCATTAGCTG TTTGCAGCCT CACCTTCTTT CACCTGAGTT CATGGAGTTT AAGATATAGT GTATTTTCCC AAGGTTTGAA CTAGCTCTTC ATTTCTTTAT
2101  GTTTTAAATG CACTGACCTC CCACATTCCC TTTTTAGTAA AATATTCAGA AATAATTTAA ATACATCATT GCAATGAAAA TTTATGGTTT TTATTAGGCA
2201  GAATCCAGAT GCTCAAGGCC CTTCATAATA TCCCCCAGTT TAGTAGTTGG ACTTAGGGAA CAAAGGAACC TGCCGGCAGG GCGAACTCCC GCCCCACGG AAGAAAGGA
2301  GCTTCTAGCT TATCCTCAGT CCTGCTCCTC TGCCACAAAG TGCACGCAGT TGGACACGAC CTCCGACCAC GTCGCGTCCAG GCTCGTCCAG GCCGCCACC CTGCTCGCCG
2401  ATCTCGGTCA TGGCCGGCCC GGAAGGCGTCC CGGAAGTTCG TGGACACGAC CTCCGACCAC TCGCGGTACA GCTCGTCCAG GCCGCCACC CACACCAGG
2501  CCAGGGTGTT GTCCGGCACC ACCTGGTCCT GGACCGCGCT GATGAACAGG GTCACGTCGT CCCGGACCAC ACCGGCGAAG TCGTCCTCCA CGAAGTCCCG
2601  GGAGAACCCG AGCCGGTTGG TCCAGAACTC GACGCGTCGC GCGACGTCGC GCACGGTGAG GCACTGGTCA ACTTGGCCAT GATGGCTCCT
2701  CCTGTCAGGA GAGGAAAGAG AAGAAGGTTA GTACAATTGC TGTATTATAC TATAGTGAGT ATGATTAATT GTCAAACTAG
2801  GGCTGCAGGG TTCATAGTGC CACTTTTTCCT GCACTGCCCC ATCTCCTGCC CACCCCTTTCC CAGGCATAGA CTTACCAAAC TCACAGAGG
2901  GAGAAGGCAG AAGCTTGAGA CGACCCGCGT GGACCCGCGT GGGCGGGGGG GACGTGGCTC TTTTATGGTG CGCCGGCCCT CGGAGCAGG
3001  GCGCTCCGGG GCCAATTCTG GCCAATTCTG GCCAGTCAGG AAGGCCGCCCA CGGAGCACAT AGGAGTCTCA GCCCCCCGCC
3101  CCAAAGCTAC GGGAAGTGAC GCGCGTGTAG CGCCAGCGTG TTGTGAAATG CCGCTATCCA AAACCGCATC TCAAAACAAA CTCCCATTGA
3201  CGTCAATGGG GTGGAGACTT GGAAATCCCC GTGACATAAG GTCATATAAG GGGCATAATG CCAAGGCGGC CATTTACCGT CATTGACGTC TAGCGATGAC
3301  TAATACGTAG AATGTACTGCC AAGTAGAGAA GTCCCATAAG GTCATGTACT GCCATAATCC TAAATACTCC CATTTACCGT CATTGACGTC AATAGGGGC
3401  GTACTTGGCA TATGATACAC TTGATGTACT CAGTTTACCG GTTGGGCGGT CAGTTTACCG GCCATTGAC AGTCCCTATT GGCGTTACTA
3501  TGGGAACATA CGTCATTATT GACGTCAATG GGCGGGGGTC GTTGGGCGGT GTAAAAAAGC CAGCCAGGCG CGCCATTTAT GTAACGCCTG CAGGTAATT
3601  AAGAACATGT GAGCAAAAGG CCAGCAAAAG GCCAGGAACC GTAAAAAGGC ACTATAAAGA TACCAGGCGT TTCCCCCTGG AAGCTCCCTC GTGCGCTCTC CTGTTCCGAC
3701  CCTGCCGCTT ACCGGATACC CTGTCCGCCTT TCTCCCTTCG CCCGTTCAGC CCGACCCTG CGCTTTCTCA TAGCTCACGC TGTAGGTATC TCAGTTCGGT GTAGGTCGTT
3801  CGCTCCAAGC TGGGCTGTGT GCACGAACCC AGGTGGCGAA TGTCCGCCTT GCACGAACCC CCCGTTCAGC GGTAACTATC GTCTTGAGTC CAACCCGGTA AGACACGACT
3901  TATCGCCACT GGCAGCAGCC ACTGGTAACA GGATTAGCAG AGCGAGGTAT GTAGCGGGTG CTACACAGTT CTTGAAGTGG TGGCCTAACT ACGGCTACAC
4001  TAGAAGAACA GTATTGGTA TCTGCGCTCT GCTGAAGCCA GTTACCTTCG GAAAAAGAGT TGGTAGTCT TGATCCGGCA ACAAACCAC CGCTGGTAGC
4101  GGTGGTTTTT TTGTTTGCAA GCAGCAGATT ACGCGCAGAA AAAAAGGATC TCAAGAAGAT CCTTTGATCT TTTCTACGG GTCTGACGCT CAGTGGAACG
4201  AAAACTCACG TTAAGGGATT TTGGTCATGA GATTATCAAA AAGGATCTTC ACCTAGATCC TTTTAAATTA AAAATGAAGT TTTAAATCAA TCTAAAGTAT
4301  TTTTGTGTG AATCGTAACT AACATACGCT CTCCATCAGT AATATCAAAA AAGGATCCTT ACCTAGATCC TTTAAATTA AAAATGAAGT TCAGTGCAAGT GCAGTGCCA
4501  GAACATTTCT CTATCGAA     (SEQ ID NO:93)
```

IL2ss.CXCL11.hIgG1Fc sequence

```
   1  GGATCTGCGA TCGCTCCGGT GCCCGTCAGT GGGCAGAGCG CACATCCCCC ACAGTCCCCG AGAAGTTGGG GGGAGGGGTC GGCAATTGAA CCGGTGCCTA
 101  GAGAAGGTGG CCCGGGGTAA ACTGGGAAAG TGATGTCGTG GCCAGAACAC CGGCTTTTTCC GCCTTTTTTC CGAGGGTGGG GGAGAACCGT ATATAAGTGC AGTAGTCGCC
 201  GTGAACGTTC TTTTTCGCAA CGGGTTTGCC TCGAGGGGCT TCGAGGGGCT TCGACGCGCG CTTCACGCGC CGCCGCCCCT ACCTGAGGCC
 301  GCCATCCACG CCGGTTGAGT CGGTTCTGC CGGTGTGCC TCCTGAACTG CGTCCGCCGT CTAGGTAAGT CTTAAGCTCA GTCGAGACC
 401  GGGCCTTTGT CCGGCGCTCC CTTGGAGCCT AGCCGGGCCT ACCTAGCCT AGCGCCGTCT CCACGCTTTG CCTGACCCTG CTTGCTCAAC TCTACGTCTT TGTTTCGTTT

501  TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                            EcoRI                                          IL-2 secretion signal
                                             KasI                                          MetTyrArg MetGlnLeu LeuSerCysIle
                                             NarI
                                             SfoI
                                             BbeI
                                            ~~~~~~~ CXCL11 (1-73)
 601  AlaLeuSer LeuAlaLeu ValThrAsnSer PheProMet PheLysArg GlyArgCysLeu CysIleGly ProGlyVal LysAlaValLys ValAlaAsp
      TTGCACTAAG TCTTGCACTT GTCACGAATT CGTTCCCCAT GTTCAAAAGA GGACGCTGTC TTTGCATAGG CCCTGGGGTA AAAGCAGTGA AAGTGGCAGA
 701  IleGluLys AlaSerIleMet TyrProSer AsnAsnCys AspLysIleGlu ValIleIle ThrLeuLys GluAsnLysGly GlnArgCys LeuAsnPro
      TATTGAGAAA GCTTCCATAA TGTACCCAAG TAACAACTGT GACAAAATAG AAGTGATTAT TACCCTGAAA GAAAATAAAG GACAACGATG CCTAAATCCC
                                                                                              human IgG1 Fc (constant region)
 801  LysSerLysGln AlaArgLeu IleIleLys LysValGluArg LysAsnPhe AspLysThr HisThrCysPro AlaProGlu LeuLeuGlyGly
      AAATGAGAAGC AAGCAAGGCT TATAATCAAA AAAGTTGAAA GAAAGAATTT TGACAAAACT CACACATGCC CACCGTGCCC AGCACCTGAA CTCCTGGGGG
 901  ProSerVal PheLeuPhe ProProLysPro LysAspThr LeuMetIle SerArgThrPro GluValThr CysValVal ValAspValSer HisGluAsp
      GACCGTCAGT CTTCCTCTTC CCCCCAAAAC CCAAGGACAC CCTCATGATC TCCCGGACCC CTGAGGTCAC ATGCGTGGTG GTGGACGTGA GCCACGAAGA
1001  ProGluVal LysPheAsnTrp TyrValAsp GlyValGlu ValHisAsnAla LysThrLys ProArgGlu GluGlnTyrAsn SerThrTyr ArgValVal
      CCCTGAGGTC AAGTTCAACT GGTACGTGGA CGGCGTGGAG GTGCATAATG CCAAGACAAA GCCGCGGGAG GAGCAGTACA ACAGCACGTA CCGTGTGGTC
1101  SerValLeuThr ValLeuHis GlnAspTrp LeuAsnGlyLys GluTyrLys CysLysVal SerAsnLysAla LeuProAla ProIleGlu LysThrIleSer
      AGCGTCCTCA CCGTCCTGCA CCAGGACTGG CTGAATGGCA AGGAGTACAA GTGCAAGGTC TCCAACAAAG CCCTCCCAGC CCCCATCGAG AAAACCATCT
1201  LysAlaLys GlyGlnPro ArgGluProGln ValTyrThr LeuProPro SerArgGluGlu MetThrLys AsnGlnVal SerLeuThrCys LeuValLys
      CCAAAGCCAA AGGGCAGCCC CGAGAACCAC AGGTGTACAC CCTGCCCCCA TCCCGGGAGG AGATGACCAA GAACCAGGTC AGCCTGACCT GCCTGGTCAA
1301  GlyPheTyr ProSerAspIle AlaValGlu TrpGluSer AsnGlyGlnPro GluAsnAsn TyrLysThr ThrProProVal LeuAspSer AspGlySer
      AGGCTTCTAT CCCAGCGACA TCGCCGTGGA GTGGGAGAGC AATGGGCAGC CGGAGAACAA CTACAAGACC ACGCCTCCCG TGCTGGACTC CGACGGCTCC
1401  PhePheLeuTyr SerLysLeu ThrValAsp LysSerArgTrp GlnGlnGly AsnValPhe SerCysSerVal MetHisGlu AlaLeuHis AsnHisTyrThr
      TTCTTCCTCT ACAGCAAGCT CACCGTGGAC AAGAGCAGGT GGCAGCAGGG GAACGTCTTC TCATGCTCCG TGATGCACGA GGCTCTGCAC AACCACTACA
                                                                                                           BmtI
                                                                                                           NheI
1501  GlnLysSer LeuSerLeu SerProGlyLys ***(SEQ ID NO:67)
      CGCAGAAGAG CCTCTCCCTG TCTCCGGGTA AATGAGTGCT AGCTGGCCAG ACATGATAAT GAGTTTGGAC AAAACCACAC TAGAATGCAG
1601  TGAAAAAAT GCTTTATTTG TGAAATTTGT GATGCTATTG CTTTATTTGT AACCATTATA AGCTGCAATA AACAAGTAA CAACAACAAT TGCATTCATT
1701  TTATGTTTCA GGTTCAGGGG GAGGTGTGGG AGTTTTTTTA AAGCAAGTAA AACCTCTACA AATGTGGTAT CTAAAATACA GCATAGCAAA
1801  ACTTTAACCT CCAAATCAAG CCTCTACTTG AATCCTTTTC TGAGGGATGA ATAAGGCATA GGCTGTTGCCA ATGTGCATTA GCTGTTTGCA
```

```
1901  GCCTCACCTT CTTTCATGGA GTTTAAGATA TAGTGTATTT TCCCAAGGTT TGAACTAGCT CTTTCATTTCT TTATGTTTTA AATGCACTGA CCTCCCACAT
2001  TCCCTTTTTA GTAAAATATT CAGAAATAAT TTAAATACAT GCAACAAAGG AAACTTTAAT AGAAATTGGA CAGCAAGAAA GCGAGCTTCT AGCTTATCCT GGCCCTTCAT
2101  AATATCCCCC AGTTTAGTAG TTGGACTTAG CCGGGTCGCG CCGGTTGCCG TCCCGCCCCC ACGGCTGCTC GCCGATCTCG GTCATGGCCG CAGTCCTGCT
2201  CCTCTGCCAC AAAGTGCACG CAGTTGCCGA CCACTCGGCG TACAGCTCGT CCAGGCCGCG CACCCACACC CAGGCCAGGG TGTTGTCCGG GCCCGAGGC
2301  GTCCCGAAG TTCGTGGACA CGACCTCCGA CAGGGTCACG TGTCCCGGA CCACACCGGC GAAGTCGTCC TCCACGAAGT CCCGGAGAA TGTTGTCCGG CACCACCTGG
2401  TCCTGACCG CGCTGATGAA CAGGGTCACG TGTCCCGGA CCACACCGGC GAAGTCGTCC TCCACGAAGT CCCGGAGAA CCCGAGCCGG TCGGTCCAGA
2501  ACTCGACCGC TCCGGCGACG TCGCGCGCGG TGAAGCACTG GTCAACTTGG CCATGATGGC TCCTCCTGTC AGGAGAGGAA AGAGAAGAAG

AseI
2601  GTTAGTACAA TTGCTATAGT GAGTTGTATT ATACTATGCA GATATACTAT AATTGTCAAA CTAGGGCTGC AGGGTTCATA GTGCCACTTT
2701  TCCTGCACTG CCCATCTCC TGCCCACCCT TTCCCAGGCA TAGACAGTCA AAACTCACAG GAGGAGAAG GCAGAAGCTT GAGACAGACC
2801  CGCGGGACCG AGGAGGCGGG AGGGGACGTG GCTAGGGCGG CTTCTTTTAT GGTGCGCCGG CCCTCGGAGG CAGGGCGCTC GGGGAGGCCT AGCGGCCAAT
2901  CTGCCGGTAG AGGAGGGGCG GCCGAAGCCG CGTCCGAGC AATCCGGAGT CTAGCCCCCA CGCCCAAAG CTCAGCCCCA CAAGGGAAG TCACGCGCCT
3001  GTAGCGCCAG CGTGTTGTGA CGTGTTGTGA AATGGGGGCT GGGGCCCTGA CTAGTTTACT CAAACTCCCA GTAATAGCGA TTGACGTCAA TGGGGTGGAG ACTTGGAAAT
3101  CCCCGTGAGT CAAACCGCTA TTGATGTACT AATGCCAAGGC GCCAAAACCG CATCATCATG CCGTCAATAGG GGCGTACTT TGCCAAGTAG
3201  GAAAGTCCCA TAAGGTCATG TACTGGGCAT AATGCCAAGC GGGCCATTTA CCGTCAATTGA TATTGGCGTT GGCATATGAT ACACTTGATG
3301  TACTGCCAAG TGGGCAGTTT ACCGTAAATA CTCCACCCAT TGACGTCAAT GGAAAGTCCC TATTGGCGTT ACTATGGGAA CATACGTCAT TATTGACGTC
3401  AATGGGCGGG GGTCGTTGGG CGGGGCCAT TTACCGTAAG TTATGTAACG CCTGCAGGTT AATTAAGAAC ATGTGAGCAA AAGGCCAGCA
3501  AAAGGCCAGG AACCGTAAAA AGGCCGCGTT GCTGGCGTTT TTCCATAGGC TCCGCCCCCC TGACGAGCAT CACAAAAATC GACGCTCAAG TCAGAGGTGG
3601  CGAAACCCGA CAGGACTATA AAGATACCAG GCGTTTCCCC CTGGAAGCTC CCTCGTGCGC TCTCCTGTTC CGACCCTGCC GCTTACCGGA TACCTGTCCG
3701  CCTTTCTCCC TTCGGGAAGC GTGGCGCTTT CTCATAGCTC ACGCTGTAGG TATCTCAGTT CGGTGTAGGT CGTTCGCTCC AAGCTGGGCT GTGTGCACGA
3801  ACCCCCCGTT CAGCCCGACC GCTGCGCCTT ATCCGGTAAC TATCGTCTTG AGTCCAACCC GGTAAGACAC GACTTATCGC CACTGGCAGC AGCCACTGGT
3901  AACAGGATTA GCAGAGCGAG GTATGTAGGC GGTGCTACAG AGTTCTTGAA GTGGTGGCCT AACTACGGCT ACACTAGAAG AACAGATTTT GGTATCTGCG
4001  CTCTGCTGAA GCCAGTTACC TTCGGAAAAA GAGTTGGTAG CTCTTGATCC GGCAAACAAA CCACCGCTGG TAGCGGTGGT TTTTTTGTTT GCAAGCAGCA
4101  GATTACGCGC AGAAAAAAAG GATCTCAAGA AGATCCTTTG ATCTTTTCTA CGGGGTCTGA CGCTCAGTGG AACGAAAACT CACGTTAAGG GATTTTGGTC
4201  ATGAGCTAGT AATTAACATT TAAATCAGCG GCCGCAATAA AATATCTTTA TTTTCATTAC ATCTGTGTGT TGGTTTTTTG TGTGAATCGT AACTAACATA
4301  CGCTCTCCAT CAAACAAAA CGAAACTAGCA CAAACTAGCA AAATAGCAAA TCCCCAGTGC AAGTGCAGGT GCCAGAACAT TTCTCTATCG AA (SEQ ID NO:94)
```

IL2ss.CXCL11(4-73).hIgG1Fc sequence

```
   1  GGATCTGCGA TGCCTCCGGT GCCCGTCAGT GGGCAGAGCG CACATCGCCC ACAGTCCCCG AGAAGTTGGG GGGAGGGGTC GGCAATTGAA CGGGTGCCTA
 101  GAGAAGTGG  CGCGGGGTAA ACTGGGAAAG TGATGTCGTG TACTGGCT\CC GCCTTTTTCC CGAGGGTGGG GGAGAACCGT ATATAAGTGC AGTAGTCGCC
 201  GTGAACGTTC TTTTTCGCAA CGGGTTTGCC GCCAGAACAC AGCTGAAGCT TCGAGGGGCT CGCATCCTCT CTTCACGCGC CCGCCGCCCT ACCTGAGGCC
 301  GCCATCCACG CCGGTTGAGT CCGTTCCTGC CGCCTCCCGC TCCTGGTGCC CGTCCGCCGT CTAGGTAAGT CTTAAGCTCA GGTCAGACC
 401  GGGCCTTTGT CCGGCGCTCC CTTGGAGCCT AGCCGGCTCT CCACGCTTTG CCTGACCCTG CTTGCTCAAC TCTACGTCTT TGTTTCGTT
                                                            KasI
                                                            NarI
                                                            SfoI
                                                            BbeI
                                                                                                                   IL-2 secretion signal
                                                                                                                   MetTyrArg MetGlnLeu LeuSerCysIle
 501  TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                       EcoRI
                                       ~~~~~~ CXCL11 (4-73)
      AlaLeuSer LeuAlaLeu ValThrArg PheLysArg GlyArgCys LeuCysIleGly ProGlyVal LysAlaVal IleIleLys
 601  TTGCACTAAG TCTTGCACTT GTCACGAATT CGTTCAAAAG AGGAGCTGT CTTTGCATAG GCCCTGGGGT AAAAGCAGTG AAGTGGCAG ATATTGAGAA
      AlaSerIle MetTyrProSer AsnAsnCys AspLysIle GluValIleIle ThrLeuLys GluAsnLys GlyGlnArgCys LeuAsnPro LysSerLys
 701  AGCCTCCATA ATGTACCCAA GTAACAACTG TGACAAAATA GAAGTGATTA TTACCCTGAA AGAAAATAAA GGACAACGAT GCTAAATCC CAAATCGAAG
                                                                                              human IgG1 Fc (constant region)
                                                                                              ~~~~~~~~~~~
      GlnAlaArgLeu IleIleLys LysValGlu ArgLysAsnPhe AspLysThr HisThrCys ProProCysPro AlaProGlu LeuLeuGly GlyProSerVal
 801  CAAGCAAGGC TTATAATCAA AAAAGTTGAA AGAAAGAATT TTGACAAAAC TCACACATGC CCACCGTGCC CAGCACCTGA ACTCCTGGGG GGACCGTCAG
      PheLeuPhe ProProLys ProLysAspThr LeuMetIle SerArgThr ProGluValThr CysValVal ValAspVal SerHisGluAsp ProGluVal
 901  TTCTTCCTCT TCCCCCAAAA CCCAAGGACA CCCTCATGAT CTCCCGGACC CCTGAGGTCA CATGCGTGGT GGTGGACGTG AGCCACGAAG ACCCTGAGGT
      LysPheAsn TrpTyrValAsp GlyValGlu ValHisAsn AlaLysThrLys ProArgGlu GluGlnTyr AsnSerThrTyr ArgValVal SerValLeu
1001  CAAGTTCAAC TGGTACGTGG ACGGCGTGGA GGTGCATAAT GCCAAGACAA AGCCGCGGGA GGAGCAGTAC AACAGCACGT ACCGTGTGGT CAGCGTCCTC
      ThrValLeuHis GlnAspTrp LeuAsnGly LysGluTyrLys CysLysVal SerAsnLys AlaLeuProAla ProIleGlu LysThrIle SerLysAlaLys
1101  ACCGTCCTGC ACCAGGACTG GCTGAATGGC AAGGAGTACA AGTGCAAGGT CTCCAACAAA GCCCTCCCAG CCCCCATCGA GAAAACCATC TCCAAAGCCA
      GlyGlnPro ArgGluPro GlnValTyrThr LeuProPro SerArgAspGlu GluMetThrLys AsnGlnVal SerLeuThr CysLeuValLys GlyPheTyr
1201  AAGGGCAGCC CCGAGAACCA CAGGTGTACA CCCTGCCCCC ATCCCGGGAG GAGATGACCA AGAACCAGGT CAGCCTGACC TGCCTGGTCA AAGGCTTCTA
      ProSerAsp IleAlaValGlu TrpGluSer AsnGlyGln ProGluAsnAsn TyrLysThr ThrProPro ValLeuAspSer AspGlySer PhePheLeu
1301  TCCCAGCGAC ATCGCCGTGG AGTGGGAGAG CAATGGGCAG CCGGAGAACA ACTACAAGAC CACGCCTCCC GTGCTGGACT CCGACGGCTC CTTCTTCCTC
      TyrSerLysLeu ThrValAsp LysSerArg TrpGlnGlnGly AsnValPhe SerCysSer ValMetHisGlu AlaLeuHis AsnHisTyr ThrGlnLysSer
1401  TACAGCAAGC TCACCGTGGA CAAGAGCAGG TGGCAGCAGG GGAACGTCTT CTCATGCTCC GTGATGCACG AGGCTCTGCA CAACCACTAC ACGCAGAAGA
                                                                                                                   AseI
      LeuSerLeu SerProGly Lys***(SEQ ID NO:68)
1501  GCCTCTCCCT GTCTCCGGGT AAATGACTGC AGCTGGCCA CACATGATAA CATACATTGA AGCTGCAAT AAACAAGTTA CAAACCACAA CTAGAATGCA
1601  TGCTTTATTT GTGAAATTTG TGAAAATTTG TGATGCTATT GCTTATTTG TAACCATTAT AAGCTGCAAT AAACAAGTTA ACAACAACAA TTGCATTCAT TTTATGTTTC
1701  AGGTTCAGGG GGAGGTGTGG GAGGTTTTTT AAAGCAAGTA AAACCTCTAC AAATGTGGTA TGGAATTAAT TCTAAAAATAC AGCATAGCAA AACTTAACC
1801  TCCAAATCAA GCCTCTACTT GAATCCTTTT CTGAGGGATG AATAGCAGG GGCTGTTGCC AGCATGCATT AGTGTTTGC AGCCTCACCT
```

```
1901 TCTTTCATGG AGTTTAAGAT ATAGTGTATT TTCCCAAGGT TTGAACTAGC TCTTCATTTC TTTATGTTTT AAATGCACTG ACCTCCCACA TTCCCTTTTT
2001 AGTAAAATAT TCAGAAATAA TTTAAATACA TCATTGCAAT GAAAATAAAT GTTTTTTATT AGGCAGAATC CAGATGCTCA AGGCCCTTCA TAATATCCCG
2101 CAGTTTAGTA GTTGGACTTA GGGAACAAAG GAACCTTTAA TAGAAATTGG ACAGCAAGAA AGCGAGCTTC TAGCTTATCC TCAGTCCTGC TCCTCTGCCA
2201 CAAAGTGCAC GCAGTTGCCG GCCGGGTCGC CTCCCGCCCC CACGGCTGCT CGCCGATCTC GGTCATGGCC GCCCGGAGG CGTCCCGGAA
2301 GTTCGTGGAC ACGACCTCCG ACCACTCGGC GTACAGCTCG TCCAGGCCGC GCACCCACAC GCAGGCCAGG GTGTTGTCCG GCACCACCTG GTCCTGGACC
2401 GCGCTGATGA ACAGGGTCAC GTCGTCCCGG ACCACACCGG CGAAGTCGTC CTCCACGAAG TCCCGGAGA ACCCGAGCCG GTCGGTCCAG AACTCGACCG
2501 CTCCGGGCGAC GTCGCGCGG GTGAGCACCT GAACGGCACT GGTCAACTTG GCCATGATGG CTCCTCCTGT CAGGAGAGGA AAGAGAAGAA GGTTAGTACA
                                                                     AseI
2601 ATTGCTATAG TGAGTTGTAT TATACTATGC AGATATACTA TGCCAATGAT TAATTGTCAA ACTAGGGCTG CAGGGTTCAT AGTGCCACTT TTTCCTGCACT
2701 GCCCCATCTC CTGCCCACCC TTTCCCAGGC ATAGACAGTC AGTGACTTAC CAAACTCACA GGAGGAGAA GGCAGAAGCT TGAGACAGAC CCGCGGGACC
2801 GCCGAACTGC GAGGGGACGT GGCTAGGGCG GTTCTTTTA TGGTGCGCCG GCCCTCGGAG GCAGGGCGCT CGGGGAGGCC TAGCGGCCAA TCTGCGGTGG
2901 CAGGAGGCGG GGCCGAAGGC CGTGCCTGAC CAATCCGGAG CACATAGGAG TCTCAGCCCC CCGCCCAAA GCAGGGGAA GTCACGCGCC TGTAGCGCCA
3001 GCGTGTTGTG AAATGGGGGC TTGGGGGGGT ACTAGTCAAA ACAAACTCCC ATTGACGTCA ATGGGGTGGA GACTTGAAA TCCCCGTGAG
3101 TCAAACCGCT ATCCACGCCC ATTGATGTAC TGCCAAAACC GCATCATCAT GGTAATAGCG ATGACTAATA CGTAGATGTA CTGCCAAGTA GGAAAGTCCC
3201 ATAAGGTCAT GTACTGGGCA TAATGCCAGG CGGGCCATTT ACCGTCATTG ACGTCAATAG GGGGCGTACT TGGCATATGA TACACTTGAT GTACTGCCAA
3301 GTGGCAGTT TACCGTAAAT ACTCCACCCA TTGACGTCAA TGGAAAGTCC CTATTGGCGT TACTATGGAA ACATACGTCA TTATTGACGT CAATGGGCGG
3401 GGGTCGTTGG GCGGTCAGCC AGGCGGGCCA TTTACCGTAA GTTATGTAAC GCCTGCAGGT TAATTAAGAA CATGTGAGCA AAAGGCCAGC AAAAGGCCAG
3501 GAACCGTAAA AAGGCCGCGT TGCTGGCGTT TTTCCATAGG CTCCGCCCCC CTGACGAGCA TCACAAAAT CGACGCTCAA GTCAGAGGTG GCGAAACCCG
3601 ACAGGACTAT AAAGATACCA GGCGTTTCCC CCTGGAAGCT CCCTCGTGCG CTCTCCTGTT CCGACCCTGC CGCTTACCGG ATACCTGTCC GCCTTTCTCC
3701 CTTCGGAAG CGTGGCGCTT TCTCATAGCT CACGCTGTAG GTATCTCAGT TCGGTGTAGG TCGTTCGCTC CAAGCTGGGC TGTGTGCACG AACCCCCCGT
3801 TCAGCCCGAC CGCTGCGCCT TATCCGGTAA CTATCGTCTT GAGTCCAACC CGGTAAGACA CGACTTATCG CCACTGGCAG CAGCCACTGG TAACAGGATT
3901 AGCAGAGCGA GGTATGTAGG CGGTGCTACA GAGTTCTTGA AGTGGTGGCC TAACTACGGC TACACTAGAA GAACAGTATT TGGTATCTGC GCTCTGCTGA
4001 AGCCAGTTAC CTTCGGAAAA AGAGTTGGTA GCTCTTGATC GTCTTTTTCT ACGGGGTCTG ACCGCTCAGTG AACGAAAAC TCACGTTAAG GGATTTTGGT CAAGCAGCAG AGATTACGCG
4101 CAGAAAAAAA GGATCTCAAG AAGATCCTTT GATCTTTTCT ACGGGGTCTG ACGCTCAGTG GAACGAAAAC TCACGTTAAG GGATTTTGGT CATGAGATT
4201 TAATTAACAT TTAAATCAGC AGCCGCAATA AAATATCTTT ACGGGCTGTG TTGGTTTTT GTGTGAATCG TAACTAACAT ACGCTCTCCA
4301 TCAAACAAA ACGAAACAAA ACAAACAAGA GCTCGCAGTG CAAGTGCAGG TGCCAGAACA TTTCTCTATC GAA (SEQ ID NO:95)
```

IL2ss.CXCL11(4-73).hIgG1Fc sequence [Alanine substitutions for removal of GAG binding sites – Lys & His]

```
   1     GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101     GAGAAGGTGG CGCGGGGTAA ACTGGGAAAG TGATGTCGTG TACTGGCT\CC GCCTTTTTCC CGAGGGTGGG GGAGAACCGT ATATAAGTGC AGTAGTCGCC
 201     GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301     GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401     GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                                     KasI
                                                     NarI
                                                     SfoI
                                                     BbeI
                                                    ~~~~~~~                                    IL-2 secretion signal
                                                                                               MetTyrArg MetGlnLeu LeuSerCysIle
 501     TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                    EcoRI
                                    ~~~~~~~ CXCL11 (4-73)
          AlaLeuSer LeuAlaLeu ValThrAsnSer PheLysArg GlyArgCys LeuCysIleGly ProGlyVal LysAlaVal LysValAlaAsp IleGluAla
 601     TTGCACTAAG TCTTGCACTT GTCACGAATT CGTTCAAAAG AGGACGCTGT CTTTGCATAG GCCCTGGGGT AAAAGCAGTG AAAGTGGCAG ATATTGAGgc
         AlaSerIle MetTyrProSer AsnAsnCys AspLysIle GluValIleIle ThrLeuAla GluAsnAla GlyGlnAlaCys LeuAsnPro AlaSerAla
 701     cGCCTCCATA ATGTACCCAA GTAACAACTG TGACAAAATA GAAGTGATTA TTACCCTGgc aGAAAATgcc GGACAAgcaT GCCTAAATCC CgccTCGgca
                                                                human IgG1 Fc (constant region)
         GlnAlaAlaLeu IleIleAla AlaValGlu AlaAlaAsnPhe AspLysThr HisThrCys ProProCysPro AlaProGlu LeuLeuGly GlyProSerVal
 801     CAAGCAgccC TTATAATCgc agccGTTGAA gcagccAATT TTGACAAAAC TCACACATGC CCACCGTGCC CAGCACCTGA ACTCCTGGGG GGACCGTCAG
          PheLeuPhe ProProLys ProLysAspThr LeuMetIle SerArgThr ProGluValThr CysValVal ValAspVal SerHisGluAsp ProGluVal
 901     TCTTCCTCTT CCCCCCAAAA CCCAAGGACA CCCTCATGAT CTCCCGGACC CCTGAGGTCA CATGCGTGGT GGTGGACGTG AGCCACGAAG ACCCTGAGGT
         LysPheAsn TrpTyrValAsp GlyValGlu ValHisAsn AlaLysThrLys ProArgGlu GluGlnTyr AsnSerThrTyr ArgValVal SerValLeu
1001     CAAGTTCAAC TGGTACGTGG ACGGCGTGGA GGTGCATAAT GCCAAGACAA AGCCGCGGGA GGAGCAGTAC AACAGCACGT ACCGTGTGGT CAGCGTCCTC
         ThrValLeuHis GlnAspTrp LeuAsnGly LysGluTyrLys CysLysVal SerAsnLys AlaLeuProAla ProIleGlu LysThrIle SerLysAlaLys
1101     ACCGTCCTGC ACCAGGACTG GCTGAATGGC AAGGAGTACA AGTGCAAGGT CTCCAACAAA GCCCTCCCAG CCCCCATCGA GAAAACCATC TCCAAAGCCA
          GlyGlnPro ArgGluPro GlnValTyrThr LeuProPro SerArgGlu GluMetThrLys AsnGlnVal SerLeuThr CysLeuValLys GlyPheTyr
1201     AAGGGCAGCC CCGAGAACCA CAGGTGTACA CCCTGCCCCC ATCCCGGGAG GAGATGACCA AGAACCAGGT CAGCCTGACC TGCCTGGTCA AAGGCTTCTA
         ProSerAsp IleAlaValGlu TrpGluSer AsnGlyGln ProGluAsnAsn TyrLysThr ThrProPro ValLeuAspSer AspGlySer PhePheLeu
1301     TCCCAGCGAC ATCGCCGTGG AGTGGGAGAG CAATGGGCAG CCGGAGAACA ACTACAAGAC CACGCCTCCC GTGCTGGACT CCGACGGCTC CTTCTTCCTC
         TyrSerLysLeu ThrValAsp LysSerArg TrpGlnGlnGly AsnValPhe SerCysSer ValMetHisGlu AlaLeuHis AsnHisTyr ThrGlnLysSer
1401     TACAGCAAGC TCACCGTGGA CAAGAGCAGG TGGCAGCAGG GGAACGTCTT CTCATGCTCC GTGATGCACG AGGCTCTGCA CAACCACTAC ACGCAGAAGA
                                       BmtI
                                       NheI
          LeuSerLeu SerProGly Lys***(SEQ ID NO:69)
1501     GCCTCTCCCT GTCTCCGGGT AAATGAGTGC TAGCTGGCCA GACATGATAA GATACATTGA TGAGTTTGGA CAAACCACAA CTAGAATGCA GTGAAAAAAA
1601     TGCTTTATTT GTGAAATTTG TGATGCTATT GCTTTATTTG TAACCATTAT AAGCTGCAAT AAACAAGTTA ACAACAACAA TTGCATTCAT TTTATGTTTC
                                                                                     AseI
1701     AGGTTCAGGG GGAGGTGTGG GAGGTTTTTT AAAGCAAGTA AAACCTCTAC AAATGTGGTA TGGAATTAAT TCTAAAATAC AGCATAGCAA AACTTTAACC
1801     TCCAAATCAA GCCTCTACTT GAATCCTTTT CTGAGGGATG AATAAGGCAT AGGCATCAGG GGCTGTTGCC AATGTGCATT AGCTGTTTGC AGCCTCACCT
```

```
1901  TCTTTCATGG AGTTTAAGAT ATAGTGTATT TTCCCAAGGT TTGAACTAGC TCTTCATTTC TTTATGTTTT AAATGCACTG ACCTCCCACA TTCCCTTTTT
2001  AGTAAAATAT TCAGAAATAA TTTAAATACA GGGAACAAAG TCATTGCAAT GAAAATAAAT GTTTTTTATT AGGCAGAATC CAGATGCTCA AGGCCCTTCA TAATATCCCC
2101  CAGTTTAGTA GTTGGACTTA GCCGGTGCGC GCCGGTCGC GAACCTTTAA TAGAAATTGG ACAGCAAGAA AGCGAGCTTC CGCCGATCTC GGTCATGGCC GGTCCCGAGG TCCTCTGCCA
2201  CAAAGTGCAC GCAGTTGCCG ACCACTCCG GCAGGGCGAA CTCCGCCCC TCCAGGCCGC CCAGGCCAGG CGCCGATCTC CGCCGATCTC GGTCATGGCC GGTCCCGAGG CGTCCCGGAA
2301  GTTCGTGGAC ACGACCTCCG ACCACTCCG GTACAGCTCG GTACAGCTCG CCAGGCCAGG CGCCGATCTC GCCACCACAC CCAGGCCAGG GTGTTGTCCG GCACCACCTG GTCCTGACCC
2401  GCGCTGATGA ACAGGGTCAC GTCGTCCCGG ACCACACCGG CGAAGTCGTC CGAAGTCGTC CTCCACGAAG TCCCGGGAGA ACCCGAGCCG GTCGTTCAG AACTCGACCG
2501  CTCCGGCGAC GTCGCGCGCG GTGAGCACCT GAACGGCACT GGTCAACTTG GCCATGATGG CTCCTCCTGT CAGGAGAGGA AGAGAAGAA GGTTAGTACA
                                                                AseI
2601  ATTGCTATAG TGAGTTGTAT TATACTATGC AGATATACTA TGCCAATGAT TAATTGTCAA ACTAGGGCTG CAGGGTTCAT AGTGCCACTT TTTCCTGCACT
2701  GCCCCATCTC CTGCCACCC TTTCCAGGC ATAGACAGTC AGTGACTTAC CAAACTCACA GGAGGGAGAA GGCCAGAAGCT TGAGACAGAC CCGGGGACC
2801  GCCGAACTGC GAGGGACGT GGCTAGGGCG GCTTCTTTTA TGGTGCGCCG GCCCTCGGAG GCAGGGCGCT CGGGAGGCGC TAGCGGCCAA TCTGCGGTGG
2901  CAGGAGGCGG GGCCGAAGGC CGTGCCTGAC CAATCCGGAG CACATAGGAG TCTCAGCCCC CCGCCCAAA GCAAGGGGAA GTCACGCGCC TGTAGCGCCA
3001  GCGTGTTGTG AAATGGGGGG TTGGGCGGGT TGGGCCCTG ACTAGTCAAA ACAAACTCCC ATTGACGTCA ATGGGGTGA GACTTGGAAA TCCCCGTGAG
3101  TCAAACCGCT ATCCACGCCC ATTGATGTAC TGCCAAAACC GCATCATCAT GGTAATAGCG ATGACTAATA CGTAGATGTA CTGCCAAGTA GGAAAGTCCC
3201  ATAAGGTCAT GTACTGGGCA TACTGGGCA ACTCCACCA CCGTCATTG ACCGTCATTG GGGGCGTACT TGGCATATGA TTATTGACGT GTACTGCCAA
3301  GTGGGCAGTT TACCGTAAAT AGGCGGGCCA TTGACGTCAA GTTATGTAAC GCCTGCAGTT TACTATGGGA ACATACGTCA TTATTGACGT CAATGGGCGG
3401  GGGTCGTTGG GCGGTCGGGT TGCTGGCGTT TTTTCATAGG CTCCGCCCCC CTGACGAGCA GCCTGCAGTT TAATAAGAA CATGTGAGCA AAAGGCCAGC AAAAGGCCAG
3501  GAACCCTAAA AAGGCGCGT AAGATACCA GGCGTTTCCC CCTGGAAGCT CTCCTCTGTT CCGACCCTGC CGACGCTCAA GTCAGAGGTG GCGAAACCCG
3601  ACAGGACTAT AAAGATACCA GGCGTTTCCC TCTCATAGCT CACGCTGTAG GTATCTCAGT TCGGTGTAGG TCGTTCGCTC CAAGCTGGGC ATACCTGTCC GCCTTTCTCC
3701  CTTCGGGAAG CGTGGCGCTT TCTCATAGCT CTATCCGGTAA CTATCCGGTAA TATCCGGTAA GAGTTCGTCT CCGTAAGACA CGACTTATCG CCACTGGCAG CAGCCACTGG TAACAGGATT
3801  TCAGCCCGAC CGCTGCGCCT TATCCGGTAA CGGTGCTACA GAGTTCTTGA GATCCTTTCT ACGGGGTCTG AGCCCGAC AGGTGCTACA GAGTTCTTGA CGGTGCTACA GAGTTCTTGA CAGCCACTGG TAACAGGATT GCTCTGCTGA AGCCAGTTAC
3901  AGCAGAGCGA GGTATGTAGG CGGTGCTACA AGAGTTGGTA GCTCTTTTGA ACGGGGTCTG ACGCTCAGT CATCGTGTG AACACCGCTG GTAGCGGTGG TTTTTTTGTT TGCAAGCAGC AGATTACGCG
4001  AGCCAGTTAC CTTCGGAAAA AGAGTTGGTA GCTCTTTTGA ACGGGGTCTG ACGCTCAGT CATCGTGTG GAACACCGCTG GTAGCGGTGG TCACGTTAAG GGATTTTGGT CATGGCTAGT
4101  CAGAAAAAA GGATCTCAAG AAGATCCTTT ATTTCATTA ACGGGGTCTG ACGCTCAGT CATCGTGTG TTGGTTTTTT GTGTGAATCG TTTCTCTATC GAA (SEQ ID NO:96)
4201  TAATTAACAT TTAAATCAGC GGCCGCAATA ATTTCATTA ACGGGGTCTG ACGCTCAGT CATCGTGTG CAAGTGCAGG TTTCTCTATC GAA (SEQ ID NO:96)
4301  TCAAAACAAA ACGAAACAAA ACAAACTAGC AAAATAGGCT
```

IL2ss.CXCL11.hIgG4Fc sequence

```
   1  GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101  GAGAAGGTGG CGCGGGGTAA ACTGGGAAAG TGATGTCGTG TACTGGCTCC GCCTTTTTCC CGAGGGTGGG GAGAACCCGT CTTCACGCGC AGTAAGTGC
 201  GTGAACGTTC TTTTTCGCAA CGGGTTTGCC CCAGAACAC AGCTGAAGCT TCGAGGGGCT TGCATCTCTC CGCATCGCGC CGCCGCCCCT ACCTGAGGCC
 301  GCCATCCACG CCGGTTGAGT CGCCTCCCGC CGCCTTCTGC CGGTTCTCGC CTCTGGTGCC ACCGGGCTCT CCTGAACTG CGTCCGCCGT CTAGTAAGT GGTCGAGACC
 401  GGGCCTTTGT CCGGCGCTCC CTTGGAAGCCT CCTAGAGCCT AGCCGGCTCT CCACGCTTTG CCTGACCCTG CTTGCTCAAC TCTACGTCTT TGTTTCGTTT
                                        NarI
                                        SfoI
                                        KasI
                                        BbeI
                                                                                                IL-2 secretion signal
                                                                                      MetTyrArg MetGlnLeu LeuSerCysIle
 501  TCTGTTCTGC GCCGTTACAG ATCCAAGCTG TGACCGGCGC CTACCTGAGA TCACCGGACG AGGAGGGCCA CCATGTACAG GATGCAACTC CTGTCTTGCA
         ----- EcoRI                         -------- CXCL11 (1-73)
      AlaLeuSer LeuAlaLeu ValThrAsnSer PheProMet PheLysArg GlyArgCysLeu CysIleGly LysAlaValLys ValAlaAsp
 601  TTGCACTAAG TCTTGCACTT GTCACGAATT CGTTCCCCAT GTTCAAAAGA GGACGCTGTC TTTGCATAGG CCCTGGGGTA AAAGCAGTGA AAGTGGCAGA
      IleGluLys AlaSerIleMet TyrProSer AsnAsnCys AspLysIleGlu ThrLeuLys GluAsnLysGly GlnArgCys LeuAsnPro
 701  TATTGAGAAA GCCTCCATAA TGTACCCAAG TAACAACTGT GACAAAATAG AAGTGATTAT TACCCTGAAA GAAAATAAAG GACAACGATG CCTAAATCCC
                                                                               human IgG4 Fc (constant region)
      LysSerLysGln AlaArgLeu IleIleLys LysValGluArg LysAsnPhe ProProCys ProSerCysPro AlaProGlu PheLeuGly GlyProSerVal
 801  AAATCGAAGC AAGCAAGGCT TATAATCAAA AAAGTTGAAA GAAAGAATTT TCCCCCATGC CCATCATGCC CAGCACCTGA GTTCCTGGGG GGACCATCAG
      PheLeuPhe ProProLys ProLysAspThr LeuMetIle SerArgThr ProGluValThr CysValVal ValAspVal SerGlnGluAsp ProGluVal
 901  TCTTCCTGTT CCCCCCAAAA CCCAAGGACA CTCTCATGAT CTCCCGGACC CCTGAGGTCA CGTGCGTGGT GGTGGACGTG AGCCAGGAAG ACCCGAGGT
      GlnPheAsn TrpTyrValAsp GlyValGlu ValHisAsn AlaLysThrLys ProArgGlu GluGlnPhe AsnSerThrTyr ArgValVal SerValLeu
1001  CCAGTTCAAC TGGTACGTGG ATGGCGTGGA GGTGCATAAT GCCAAGACAA AGCCGCGGGA GGAGCAGTTC AACAGCACGT ACCGTGTGGT CAGCGTCCTC
      ThrValLeuHis GlnAspTrp LeuAsnGly LysGluTyrLys CysLysVal SerAsnLys GlyLeuProSer SerIleGlu LysThrIle SerLysAlaLys
1101  ACCGTCCTGC ACCAGGACTG GCTGAACGGC AAGGAGTACA AGTGCAAGGT CTCCAACAAA GGCCTCCCGT CCTCCATCGA GAAAACCATC TCCAAGGCCA
      GlyGlnPro ArgGluPro GlnValTyrThr LeuProPro SerGlnGlu GluMetThrLys AsnGlnVal SerLeuThr CysLeuValLys GlyPheTyr
1201  AAGGGCAGCC CCGAGAACCA CAGGTGTACA CCCTGCCCCC ATCCCAGGAG GAGATGACCA AGAACCAGGT CAGCCTGACC TGCCTGGTCA AAGGCTTCTA
      ProSerAsp IleAlaValGlu TrpGluSer AsnGlyGln ProGluAsnAsn TyrLysThr ThrProPro ValLeuAspSer AspGlySer PhePheLeu
1301  CCCCAGCGAC ATCGCCGTGG AGTGGGAGAG CAATGGGCAG CCGGAGAACA ACTACAAGAC CACGCCTCCC GTGCTGGACT CCGACGGCTC CTTCTTCCTC
      TyrSerArgLeu ThrValAsp LysSerArg TrpGlnGluGly AsnValPhe SerCysSer ValMetHisGlu AlaLeuHis AsnHisTyr ThrGlnLysSer
1401  TACAGCAGGC TAACCGTGGA CAAGAGCAGG TGGCAGGAGG GGAATGTCTT CTCATGCTCC GTGATGCATG AGGCTCTGCA CAACCACTAC ACACAGAAGA
                                                                                                                  AseI
      LeuSerLeu SerProGly Lys***(SEQ ID NO:70)
1501  GCCTCTCCCT GTCTCCGGGT AAATGAGTGC TAGCTGGCCA GACATGATAA GATACATTGA TGAGTTTGGA CAAACCACAA CTAGAATGCA GTGAAAAAAA
1601  TGCTTTATTT GTGAAATTTG TGATGCTATT GCTTTATTTG TAACCATTAT AAGCTGCAAT AAACAAGTTA ACAACAACAA TTGCATTCAT TTTATGTTTC
                                                                            AseI
1701  AGGTTCAGGG GGAGGTGTGG GAGGTTTTTT AAAGCAAGTA AAACCTCTAC AAATGTGGTA TGGAATTAAT TCTAAAATAC AGCATAGCAA AACTTTAACC
1801  TCCAAATCAA GCCCTACTT CCGAGGCCAT GAATCCTTGC CCGAGGCCAG CAATAAGGCAT GGCTGTTGCC AATGTGCATT AGCTGTTTGC AGCCTCACCT
```

```
1901  TCTTTCATGG AGTTTAAGAT ATAGTGTATT TCCCAAGGT TTGAACTAGC TCTTCATTTC TTTATGTTTT AAATGCACTG ACCTCCCACA TTCCCTTTTT
2001  AGTAAAATAT TCAGAAATAA TTTAAATACA TCATTGCAAT GAACCTTTAA TAGAAATTGG ACAGCAAGAA AGCGAGCTTC CAGATGCTCA AGGCCCTTCA TAATATCCCC
2101  CAGTTAGTA GTTGGACTTA GGGAACAAAG GCCGGTCGC CTCCCGCCCC CACGGCTGCT CGCCGATCTC TAGCTTATCC TCAGTCCTGC TCCTCTGCCA
2201  CAAAGTGCAC GCAGTTGCCG ACGACCTCCG ACCACTCGGC GTACAGCTCG TCCAGGCCGC GCACCACCAC CCAGGCCAGG GTCATGGCC GGCCCGGAGG CGTCCCGGAA
2301  GTTCGTGGAC ACGACCTCCG ACCACTCGGC GTACAGCTCG TCCAGGCCGC GCACCACCAC CCAGGCCAGG GTGTTGTCCG GTCCACCTG GTCCTGACC
2401  GCGCTGATGA ACAGGGTCAC GTCGTCCGGG ACCACGCACT CGAAGTCGTC CTCCACGAAG TCCCGGGAGA TCCCGGGAGA ACCCGACCCG GTCGTCAG AACTCGACCG
2501  CTCCGGCGAC GTCCGGGCGG GTGAGCACCG GAACGGCACT GGTCAACTTG GCCATGATGG CTCCTCCTGT CAGGAGAGGA AAGAGAGAA GGTTAGTACA

AseI
2601  ATTGCTATAG TGAGTTGTAT TATACTATGC AGATATACTA TGCCAATGAT TAATTGTCAA ACTAGGGCTG CAGGGTTCAT AGTGCCACTT TTCCTGCACT
2701  GCCCCATCTC CTGCCCACCC TTTCCCAGGC ATAGACAGTC AGTGACTTAC CAAAACTCAC GGAGGGAGAA GGCAGAAGCT TGAGACAGAC CCGCGGGACC
2801  GCCGAACTGC GAGGGGACGT GGCTAGGGCG GCTTCTTTTA TGGTGCGCCG GCCCTCGGAG GCAGGGGCT CGGGAGGCC TAGCGGCCAA TCTGCGGTGG
2901  CAGGAGGCGG GGCCGAAGGC CGTGCCTGAC CAATAGGAG CACATAGGAG TCTCAGCCTC CCGCCCAAA GCAAGGGGAA GTCACGGCC TGTAGCGCCA
3001  GCGTGTTGTG AAATGGGGGT TTGGGGGGGT TGGGGCCCTG ACTAGTCAAA ACAAACTCCC ATTGACGTCA ATGGGTGGA GACTTGGAAA TCCCCGTGAG
3101  TCAAACCGCT ATCCACGCCC ATTGATGTAC TGCCAAAACC GCATCATCAT GGTAATAGCG ATGACTAATA CGTAGATGTA CTGCCAAGTA GGAAAGTCCC
3201  ATAAGGTCAT GTACTGGGCA TAATGCCAGG CGGGCCATTT ACCGTCATTG TGGAAAGTCC ACGTCAATAG GGGCGTACT TGGCATATGA TACACTTGAT GTACTGCCAA
3301  GTGGCAGTT TACCGTAAAT ACTCCACCCA TTGACGTCAA GTTATGTAAC GCCTGCAGGT TACTATGGGA ACATACGTCA TTATTGACGT CAATGGGCGG
3401  GGGTCGTTGG GCGGTCAGCC AGGCGGGCCA TTTACCGTAA CTCCGCCCCC CTGACGAGCA TCACAAAAAT CATGTGAGCA AAAGGCCAGC AAAAGGCCAG
3501  GAACCGTAAA AAGGCCGCGT TGCTGGCGTT TTTCCATAGG CTCCGCCCCC CTGACGAGCA CATGTGAGCA AAAGGCCAGC AAAAGGCCAG GCGAAACCCG
3601  ACAGGACTAT AAAGATACCA GGCGTTTCCC CCTGGAAGCT CCCTCGTGCG CTCTCCTGTT CCGACCCTGC CGCTTACCGG ATACCTGTCC GCCTTTCTCC
3701  CTTCGGGAAG CGTGGCGCTT TCTCATAGCT CACGCTGTAG GTATCTCAGT TCGGTGTAGG TCGTTCGCTC CAAGCTGGGC TGTGTGCACG AACCCCCCGT
3801  TCAGCCCGAC CGCTGCGCCT TATCCGGTAA CTATCGTCTT GAGTCCAACC CGGTAAGACA CGACTTATCG CCACTGGCAG CAGCCACTGG TAACAGGATT
3901  AGCAGAGCGA GGTATGTAGG CGGTGCTACA GAGTTCTTGA AGTGGTGGCC TAACTACGGC TACACTAGAA GAACAGTATT TGGTATCTGC GCTCTGCTGA
4001  AGCCAGTTAC CTTCGGAAAA AGAGTTGGTA GCTCTTGATC CGGCAAACAA ACCACCGCTG GTAGCGGTGG TTTTTTTGTT TGCAAGCAGC AGATTACGCG
4101  CAGAAAAAAA GGATCTCAAG AAGATCCTTT GATCTTTTCT ACGGGGTCTG ACGCTCAGTG GAACGAAAAC TCACGTTAAG GGATTTTGGT CATGCTAGT
4201  TAATTAACAT TTAAATCAGC GGCCGCAATA AAATATCTTT ATTTTCATTA CATCTGTGTG TTGGTTTTT GTGTGAATCG TAACTAACAT ACGCTCTCCA
4301  TCAAAACAAA ACGAAACAAA ACAAACTAGC AAAATAGGCT GTCCCCAGTG CAAGTGCAGG TGCCAGAACA TTTCTCTATC GAA (SEQ ID NO:97)
```

IL2ss.CXCL11(4-73).hIgG4Fc sequence

```
   1  GGATCTGCGA TGCTCCGGT GCCCGTCAGT GGGCAGAGCG CACAATCGCCC ACAGTCCCCG AGAAGTTGGG GGGAGGGGTC GGCAATTGAA CGGGTGCCTA
 101  GAGAAGGTGG CGCGGGGTAA ACTGGGAAAG TGATGTCGTG GCCAGAACAC AGCTTGAACT CTGAGGGGCT TCGAGGGCGT CGCATTCTCT CGAGGGTGGG GGAGAACCGT ATATAAGTGC AGTAGTCGCC
 201  GTGAACGTTC TTTTTCGCAA CGGGTTTGCC CCGTTCTCTGC CCGGTTGAGT CCGGCCTCCG CTTGGAGCCT ACCTAGAGTC AGCCGGCTCT CCCACGCTTT GCATCCGGGC CGTCCGCGGT TTAAGCTCA GGTCGAGACC
 301  GCCATCCACG CCGGTTGAGT CCGCCTCCC CCTTGCCCG CTTGCCC CCACGCTTTG CTAGGTAAGT CTTAAGCTCA GGTCGAGACC
 401  GGGCCTTTGT CCGGGCCTCC CTTGGAGCCT ACCTAGAGCT AGCCGGCTCT CCCACGCTTT GCATCCGGGC CGTCCGCGGT CTTGCTCAAC TCTACGTCTT TGTTTCGTTT
             KasI
             SfoI
             NarI
             BbeI
                                                                     IL-2 secretion signal
                                                                     MetTyrArg MetGlnLeu LeuSerCysIle
 501  TCTGTTCTGC GCCGTTACAG ATCCAAGCTG TGACCGGCGC CTACCTGAGA AGGAGGGCCA CCATGTACAG GATGCAACTC CTGTCTTGCA
      EcoRI
             ~~~~~~~ CXCL11 (4-73)
      AlaLeuSer LeuAlaLeu ValThrAsnSer PheLysArg GlyArgCys LeuCysIleGly ProGlyVal LysAlaVal LysValAlaAsp IleGluLys
 601  TTGCACTAAG TCTTGACTT GTCACGAATT CGTTCAAAAG AGGAGCGTGT CTTTGCATAG GCCCTGGGGT AAAAGCAGTG AAGTGGCAG ATATTGAGAA
      AlaSerIle MetTyrProSer AsnAsnCys AspLysIle ThrLeuLys GluLysLys GlyGlnArgCys LeuAsnPro LysSerLys
 701  AGCCTCCATA ATGTACCCAA GTAACAACTG TGACAAGATA TTACCCTGAA AGAAAATAAA GGACAACGAT GCCTAAATCC CAAATCGAAG
                                             human IgG4 Fc (constant region)
      GlnAlaArgLeu IleIleLys LysValGlu ArgLysAsnPhe ProProCys ProSerCys ProAlaProGlu PheLeuGly GlyProSer ValPheLeuPhe
 801  CAAGCAAGGC TTATAATCAA AAAAGTTGAA AGAAAGAATT TCCCCCCATG CCCATCATGC CCAGCACCTG AGTTCCTGGG GGGACCATCA GTCTTCCTGT
      ProProLys ProLysAsp ThrLeuMetIle SerArgThr ProGluVal ThrCysValVal ValAspVal SerGlnGlu AspProGluVal GlnPheAsn
 901  TCCCCCCAAA ACCCAAGGAC ACTCTCATGA TCTCCCGGAC CCCTGAGGTC ACGTGCGTGG TGGTGGACGT GAGCCAGGAA GACCCCGAGG TCCAGTTCAA
      TrpTyrVal AspGlyValGlu ValHisAsn AlaLysThr LysProArgGlu GluGlnPhe AsnSerThr TyrArgValVal SerValLeu ThrValLeu
1001  CTGGTACGTG GATGGCGTGG AGGTGCATAA TGCCAAGACA AAGCCGCGGG AGGAGCAGTT CAACAGCACG TACCGTGTGG TCAGCGTCCT CACCGTCCTG
      HisGlnAspTrp LeuAsnGly LysGluTyr LysCysLysVal SerAsnLys GlyLeuPro SerSerIleGlu LysThrIle SerLysAla LysGlyGlnPro
1101  CACCAGGACT GGCTGAACGG CAAGGAGTAC AAGTGCAAGG TCTCCAACAA AGGCCTCCCG TCCTCCATCG AGAAAACCAT CTCCAAAGCC AAAGGGCAGC
      ArgGluPro GlnValTyr ThrLeuProPro SerGlnGlu GluMetThr LysAsnGlnVal SerLeuThr CysLeuVal LysGlyPheTyr ProSerAsp
1201  CCCGAGAGCC ACAGGTGTAC ACCCTGCCCC CATCCCAGGA GGAGATGACC AAGAACCAGG TCAGCCTGAC CTGCCTGGTC AAAGGCTTCT ACCCCAGCGA
      IleAlaVal GluTrpGluSer AsnGlyGln ProGluAsn AsnTyrLysThr ThrProPro ValLeuAsp SerArgGlySer PhePheLeu TyrSerArg
1301  CATCGCCGTG GAGTGGGAGA GCAATGGGCA GCCGGAGAAC AACTACAAGA CCACGCCTCC CGTGCTGGAC TCCGACGGCT CCTTCTTCCT CTACAGCAGG
      LeuThrValAsp LysSerArg TrpGlnGlu GlyAsnValPhe SerCysSer ValMetHis GluAlaLeuHis AsnHisTyr ThrGlnLys SerLeuSerLeu
1401  CTAACCGTGG ACAAGAGCAG GTGGCAGGAG GGGAATGTCT TCTCATGCTC CGTGATGCAT GAGGCTCTGC ACAACCACTA CACACAGAAG AGCCTCTCCC
                                                                                                          AseI
      SerProGly Lys***(SEQ ID NO:71)
1501  TGTCTCCGGG TAAATGAGTG CTAGCTGCCC AGAGCATGATA AGATACATTG ATGAGTTTGG ACAAACCACA ACTAGAATGC AGTGAAAAAA ATGCTTTATT
1601  TGTGAAATTT GTGATGCTAT TGCTTTATTT GTAACCATTA TAAGCTGCAA TAAACAAGTT AACAACAACA ATTGCATTCA TTTTATGTTT CAGGTTCAGG
```

```
1701 GTGAGTGTG GGAGGTTTTT TAAAGCAAGT CAAATGTGGT ATGGAATTAA TTCTAAAATA CAGCATAGCA AAACTTTAAC CTCCAAATCA
1801 AGCCCTACT TGAATCCTTT TCTGAGGGAT GAATAAGGCA TAGGCATCAG GGGCTGTTGC CAATGTGCAT TAGCTGTTTG CAGCCTCACC TTCTTTCATG
1901 GAGTTTAAGA TATAGTGTAT TTTCCAAGG TTTGAACTAG CTCTTCATTT CTTTATGTTT TAAATGCACT GACCTCCCAC ATTCCCTTTT TAGTAAAATA
2001 TTCAGAAATA ATTTAAATAC ATCATTGCAA TGAAAATAAA TGTTTTTTAT CAGCAGAAT CCAGATGCTC AAGGCCCTTC ATAATATCCC CCAGTTTAGT
2101 AGTTGGACTT AGGGAACAAA GGAACCTTTA ATAGAAATTG GACAGCAAGA AAGCGAGCTT CTAGCTTATC CTCAGTCCTG CTCCCTGCC ACAAAGTGCA
2201 CGCAGTTGCC GGCCGGGTCG CGCAGGGCGA ACTCCCGCCC CGCCAGGCTGC CCCAGGCCAG CGGTCATGGC CGGCCCGGAG GCCACCACCT AGTTCGTGGA
2301 CACGACCTCC GACCACTCGG CGTACAGCTC GTCCAGGCCG CGCACCCACA CCCCACGAA GTCCCGGGAG GGCACCACCT GGTCCTGGAC CGGCGTGATG
2401 AACAGGGTCA CGTCGTCCCG GACCACACCG GCGAAGTCGT CCTCCACGAA GTCCCGGGAG GTCGGTCA GAACTCGACC GCTCCGGCGA
2501 CGTCGCGCGC GGTGAGCACC GGAACGGCAC TGGTCAACTT GGCCATGATG GCTCCTTCCTG TCAGGAGAGG AAAGAGAAGA AGTTAGTAC AATTGCTATA
      AseI
2601 GTGAGTGTA TTATACTATG CAGATATACT ATGCCAATGA TTAATTGTCA AACTAGGGCT GCAGGGTTCA TAGTGCCACT TTTCCTGCAC TGCCCCATCT
2701 CCTGCCACC CTTTCCCAGG CATAGACAGT CAGTGACTTA CCAAACTCAC AGGAGGGAGA AGGCAGAAGC TTGAGACAGA CCCGCGGGAC CGCCGAACTG
2801 CGAGGGACG TGGCTAGGGC GGCTTCTTTT ATGGTGCGCC GGCCCTCGGA GCAGGGCGC TCGGGAAGGC CTAGCGGTG ATCTGCGGTG GCAGGAGCGG
2901 GGGCCGAAGG CCGTGCCTGA CCAATCCGGA GCACATAGGA GTCTCAGCGC CCCGCCCAA AGCAAGGGGA AGTCACGCGC CTGTAGCGCC AGCGTGTTGT
3001 GAAATGGGG CTTGGGGGG TTGGGCCCT GACTAGTCAA AACAAACTCC CATTGACGTC AATGGGGTGG AGACTTGAA ATCCCCGTGA GTCAAACCGC
3101 TATCCACGCC CATTGATGTA CTGCCAAAAC CGCATCATCA TGGTAATAGC GATGACTAAT ACGTAGATGT ACTGCCAAGT AGGAAAGTCC CATAAGGTCA
3201 TGTACTGGGC ATAATGCCAG GCGGGCCATT TACCGTCATT TGGCATATG TGGCATATG TGGCATATG ATACACTTGA TGTACTGCCA AGTGGCCAGT
3301 TTACCGTAAA TACTCCACCC ATTGACGTCA ATGGAAAGTC CCTATTGGCG TTACTATGG AACATACGTC ATTATTGACG CAAAAGGCCA GGGTCGTTTG
3401 GGCGGTCAGC CAGGGCGG ATTTACCGTA AGTTATGTAA CGCCTGCAGC CCTGACCCTG TTAATTAAGA ACATGTGAGC AAAAGGCCAG GAACCGTAA
3501 AAAGCCGCG TTGCTGGCGT TTTTCCATAG GCTCCGCCCC CTGACGAGC ATCACAAAAA TCGACGCTCA AGTCAGAGGT GGCGAAACCC GACAGACTA
3601 TAAAGATACC AGGCGTTTCC CCCTGGAAGC TCCCTCGTGC GCTCTCCTGT TCCGACCCTG CCGCTTACCG GATACCTGTC CGCCTTTCTC CCTTCGGGAA
3701 GCGTGGCGCT TTCTCATAGC TCACGCTGTA GGTATCTCAG TTCGGTGTAG GTCGTTCGCT CCAAGCTGGG CTGTGTGCAC GAACCCCCCG TTCAGCCCGA
3801 CCGCTGCGCC TTATCCGGTA ACTATCGTCT ACTACTAGA AGTTGTGGCC CGGTAAGAC GCCACTGGCA GCAGCCACTG GTAACAGGAT TAGCAGAGCG
3901 AGGTATGTAG GCGGTGCTAC AGAGTTCTTG AAGTGGTGGC CTAACTAGAA AACCACCGCT GGTAGCGGTG GTTTTTTGT CGCTCTGCTG AAGCCAGTTA
4001 CCTTCGGAAA AAGAGTTGGT AGCTCTTGAT CCGGCAAACA AACCACCGCT GACGCTCAGT GGAACGAAAA CTCACGTTAA GGGATTTTGG TCATGAGCAG
4101 AGGATCTCAA GAAGATCCTT TGATCTTTTC TACGGGTCT TATTTTCATT GACGCTCAGT GTTGGTTTT TGTGTGAATC GTAACTAACA TACGCTCTCC
4201 TTTAAATCAG CGGCCGCAAT AAAATATCTT TATTTTCATT ACATCTGTGT GTTGGTTTT TGTGTGAATC GTAACTAACA TACGCTCTCC ATCAAAACAA
4301 AACGAAACAA AACAAACTAG CAAAATAGGC TGTCCCCAGT GCAAGTGCAG GTGCCAGAAC ATTCTCTAT CGAA    (SEQ ID NO:98)
```

IL2ss.CXCL11(4-73).hIgG4Fc sequence [Alanine substitutions for GAG binding sites – Arg, Lys & His]

```
   1   GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101   GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201   GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301   GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401   GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                           KasI
                                           SfoI
                                           NarI
                                           BbeI
                                          ~~~~~~~                                        IL-2 secretion signal
                                                                                         MetTyrArg MetGlnLeu LeuSerCysIle
 501   TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                EcoRI
                                ~~~~~~~ CXCL11 (4-73)
        AlaLeuSer LeuAlaLeu ValThrAsnSer PheLysArg GlyArgCys LeuCysIleGly ProGlyVal LysAlaVal LysValAlaAsp IleGluAla
 601   TTGCACTAAG TCTTGCACTT GTCACGAATT CGTTCAAAAG AGGACGCTGT CTTTGCATAG GCCCTGGGGT AAAAGCAGTG AAAGTGGCAG ATATTGAGgc
        AlaSerIle MetTyrProSer AsnAsnCys AspLysIle GluValIleIle ThrLeuAla GluAsnAla GlyGlnAlaCys LeuAsnPro AlaSerAla
 701   cGCCTCCATA ATGTACCCAA GTAACAACTG TGACAAAATA GAAGTGATTA TTACCCTGgc aGAAAATgcc GGACAAgcaT GCCTAAATCC CgccTCGgca
                                                    human IgG4 Fc (constant region)
       GlnAlaAlaLeu IleIleAla AlaValGlu AlaAlaAsnPhe ProProCys ProSerCys ProAlaProGlu PheLeuGly GlyProSer ValPheLeuPhe
 801   CAAGCAgccC TTATAATCgc agccGTTGAA gcagccAATT TTCCCCCATG CCCATCATGC CCAGCACCTG AGTTCCTGGG GGGACCATCA GTCTTCCTGT
         ProProLys ProLysAsp ThrLeuMetIle SerArgThr ProGluVal ThrCysValVal ValAspVal SerGlnGlu AspProGluVal GlnPheAsn
 901   TCCCCCCAAA ACCCAAGGAC ACTCTCATGA TCTCCCGGAC CCCTGAGGTC ACGTGCGTGG TGGTGGACGT GAGCCAGGAA GACCCCGAGG TCCAGTTCAA
        TrpTyrVal AspGlyValGlu ValHisAsn AlaLysThr LysProArgGlu GluGlnPhe AsnSerThr TyrArgValVal SerValLeu ThrValLeu
1001   CTGGTACGTG GATGGCGTGG AGGTGCATAA TGCCAAGACA AAGCCGCGGG AGGAGCAGTT CAACAGCACG TACCGTGTGG TCAGCGTCCT CACCGTCCTG
       HisGlnAspTrp LeuAsnGly LysGluTyr LysCysLysVal SerAsnLys GlyLeuPro SerSerIleGlu LysThrIle SerLysAla LysGlyGlnPro
1101   CACCAGGACT GGCTGAACGG CAAGGAGTAC AAGTGCAAGG TCTCCAACAA AGGCCTCCCG TCCTCCATCG AGAAAACCAT CTCCAAAGCC AAAGGGCAGC
         ArgGluPro GlnValTyr ThrLeuProPro SerGlnGlu GluMetThr LysAsnGlnVal SerLeuThr CysLeuVal LysGlyPheTyr ProSerAsp
1201   CCCGAGAGCC ACAGGTGTAC ACCCTGCCCC CATCCCAGGA GGAGATGACC AAGAACCAGG TCAGCCTGAC CTGCCTGGTC AAAGGCTTCT ACCCCAGCGA
        IleAlaVal GluTrpGluSer AsnGlyGln ProGluAsn AsnTyrLysThr ThrProPro ValLeuAsp SerAspGlySer PhePheLeu TyrSerArg
1301   CATCGCCGTG GAGTGGGAGA GCAATGGGCA GCCGGAGAAC AACTACAAGA CCACGCCTCC CGTGCTGGAC TCCGACGGCT CCTTCTTCCT CTACAGCAGG
       LeuThrValAsp LysSerArg TrpGlnGlu GlyAsnValPhe SerCysSer ValMetHis GluAlaLeuHis AsnHisTyr ThrGlnLys SerLeuSerLeu
1401   CTAACCGTGG ACAAGAGCAG GTGGCAGGAG GGGAATGTCT TCTCATGCTC CGTGATGCAT GAGGCTCTGC ACAACCACTA CACACAGAAG AGCCTCTCCC
                             BmtI
                             NheI
                            ~~~~~~~
         SerProGly Lys***(SEQ ID NO:72)
1501   TGTCTCCGGG TAAATGAGTG CTAGCTGGCC AGACATGATA AGATACATTG ATGAGTTTGG ACAAACCACA ACTAGAATGC AGTGAAAAAA ATGCTTTATT
1601   TGTGAAATTT GTGATGCTAT TGCTTTATTT GTAACCATTA TAAGCTGCAA TAAACAAGTT AACAACAACA ATTGCATTCA TTTTATGTTT CAGGTTCAGG
                                                                       AseI
                                                                      ~~~~~~~
```

```
1701  GGGAGGTGTG GGAGGTTTTT TAAAGCAAGT AAAACCTCTA CAAATGTGGT ATGGAATTAA TTCTAAAATA CAGGATAGCA AAACTTTAAC CTCCAAATCA
1801  AGCCTTACT  TGAATCCTTT TCTGAGGGAT GAATAAGGCA TAGGCATCAG GGGCTGTTGC CAATGTGCAT TAGCTGTTTG CAGCCTCACC TTCTTTCATG
1901  GAGTTTAAGA TATAGTGTAT TTTCCAAGG  TTTGAACTAG CTCTTCATTT CTTTATGTTT TAAATGCACT GACTCCCAC  ATTCCTTTT  TAGTAAAATA
2001  TTCAGAAATA ATTTAAATAC ATCATTGCAA TGAAAAATTG TGTTTTTTAT TAGGCAGAAT CCAGATGCTC AAGGCCCTTC ATAATATCCC CCAGTTTAGT
2101  AGTTGGACTT AGGGAACAAA GGAACCTTTA ATAGAAATTG GACAGCAAGA AAGCGAGCTT CTAGCTTATC CTCAGTCCTG CTCCTCTGCC ACAAAGTGCA
2201  CGCAGTTGCC GGCGGGTCG  CGCAGGGCGA ACTCCCGCCC TGCCGGCTGC TCGCCGATCT CGGTCATGGC CGGCCCGGAG GCGTCCCGGA AGTTCGTGGA
2301  CACGACCTCC GACCACTCGG CGTACAGCTC GTCCAGGCCG GCACCCACA  CCCAGGCCAG GGTGTTGTCC GGCACCACCT GGTCCTGGAC GCGCTGATG
2401  AACAGGGTCA CGTCGTCCCG GACCACACCG GCGAAGTCGT CCTCCACGAA GTCCCGGGAG AACCCGAGCC GGTCGGTCCA GAACTCGACC GCTCCGGCGA
2501  CGTCGCGCGC GGTGAGCACC GGAACGGCAC TGGTCAACTT GGCCATGATG GCTCCTCCTG TCAGGAGAGG AAAGAGAAGA AGGTTAGTAC AATTGCTATA
                                                  AseI
2601  GTGAGTTGTA TTATACTATG CAGATATACT ATGCCAATGA TTAATTGTCA AACTAGGGCT GCAGGGTTCA TAGTGCCACT TTTCCTGCAC TGCCCCATCT
2701  CCTGCCACC  CTTTCCCAGG CATAGACAGT CAGTGACTTA CCAAACTCAC AGGAGGGAGA AGGCAGAAGC TTGAGACAGA CCCGCGGGAC CGCCGAACTG
2801  CGAGGGACG  TGGCTAGGGC GGCTTCTTTT ATGGTGCGCC GGCCCTCGGA GGCAGGGCGC TCGGGGAGGC CTAGCGGCCA ATCTGCGGTG GCAGGAGGCG
2901  GGGCCGAAGG CCGTGCCTGA CCAATCCGGA GCACATAGGA GTCTCAGCCC CCCGCCCCAA AGCAAGGGGA AGTCACGCGC CTGTAGCGCC AGCGTGTTGT
3001  GAAATGGGGG CTTGGGGGG  TTGGGCCCT  GACTAGTCAA AACAAACTCC CATTGACGTC AATGGGGTGG AGACTTGGAA ATCCCCGTGA GTCAAACCGC
3101  TATCCACGCC CATTGATGTA CTGCCAAAAC CGCATCATCA TGGTAATAGC GATGACTAAT ACGTAGATGT ACTGCCAAGT AGGAAAGTCC CATAAGGTCA
3201  TGTACTGGGC ATAATGCCAG GCGGGCCATT TACCGTCATT GACGTCAATA GGGGCGTAC  TTGGCATATG ATACACTTGA TGTACTGCCA AGTGGGCAGT
3301  TTACCGTAAA TACTCCACCC ATTGACGTCA ATGGAAAGTC CCTATTGGCG TTACTATGGG AACATACGTC ATTATTGACG TCAATGGGCG GGGGTCGTTG
3401  GGCGGTCAGC CAGGCGGGCC ATTTACCGTA AGTTATGTAA CGCCTGCAGG TTAATTAAGA ATCACAAAAA TGACGCTCA  AGTCAGAGGT GGCGAAACCC GACAGACTA
3501  AAAGGCCGCG TTGCTGGCGT TTTTCCATAG GCTCCGCCCC TCCCTGCGTC GTCCTCCTGT TCCGACCCTG CGCCTTACCG GATACGTGTC CGCCTTTCTC CCTTCGGGAA
3601  TAAGATACC  AGGCGTTTCC CCCTGGAAGC TCCCTCGTGC GCTCTCCTTC GGTGTAG   GTCGTTCGCT CCAAGCTGGG CTGTGTGCAC GAACCCCCCG TTCAGCCCGA
3701  GCGCTGCGCT TTCTCATAGC TCACGCTGTA GGTATCTCAG TTCGGTGTAG GTCGTTCGCT CCAAGCTGGG CTGTGTGCAC GAACCCCCCG TTCAGCCCGA
3801  CCGCTGCGCC TTATCCGGTA ACTATCGTCT TGAGTCCAAC CCGGTAAGAC ACGACTTATC GCCACTGGCA GCAGCCACTG GTAACAGGAT TAGCAGAGCG
3901  AGGTATGTAG GCGGTGCTAC AGAGTTCTTG AAGTGGTGGC CTAACTACGG CTACACTAGA AGAACAGTAT TGGTATCTG  CGCTCTGCTG AAGCCAGTTA
4001  CCTTCGGAAA AAGAGTTGGT AGCTCTTGAT CCGGCAAACA AACCACCGCT GGTAGCGGTG GTTTTTTTGT TTGCAAGCAG CAGATTACGC GCAGAAAAAA
4101  AGGATCTCAA GAAGATCCTT TGATCTTTTC TACGGGGTCT GACGCTCAGT GGAACGAAAA CTCACGTTAA GGGATTTTGG TCATGCTAG  TTAATTAACA
4201  TTTAAATCAG CGGCCGCAAT AAAATATCTT TATTTTCATT ACATCTGTGT GTTGGTTTTT TGTGTGAATC GTAACTAACA TACGCTCTCC ATCAAAACAA
4301  AACGAAACAA AACAAACTAG CAAAATAGGC TGTCCCCAGT GCAAGTGCAG ATTTCTCTAT CGAA   (SEQ ID NO:99)
```

FIG.7E (CONT)

FIG. 8A
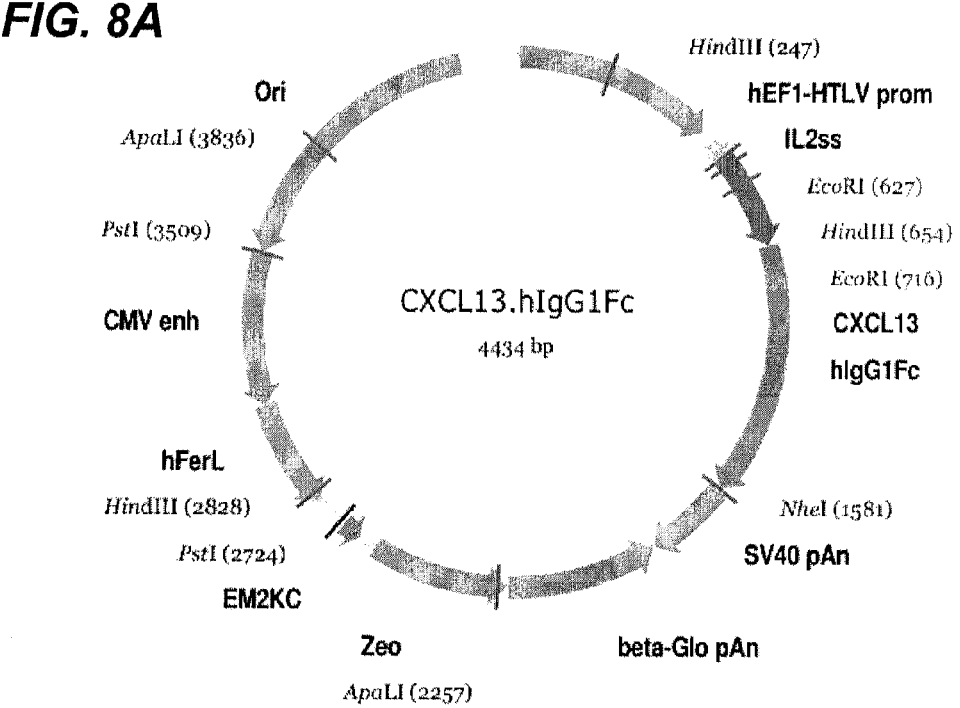
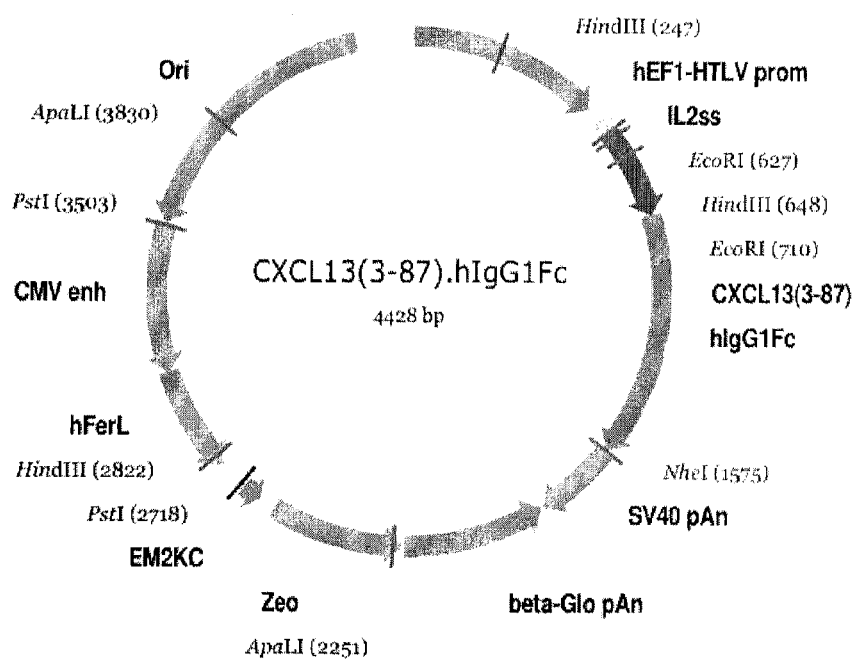
FIG. 8B

FIG. 8C

IL2ss.CXCL13.hIgG1Fc sequence

```
   1 GGATCTGCGA TCGCTCCGGT GCCCGTCAGT GGGCAGAGCG CACATGCCCC ACAGTCCCCG AGAAGTTGGG GGGAGGGGTC GGCAATTGAA CGGGTGCCTA
 101 GAGAAGGTGG CGCGGGGTAA ACTGGGAAAG TGATGTCGTG GCCAGAACGT TCTTCGGCTC CGAGGGTGGG CGAGGGTGGG CTTCACGCGC ATATAAGTGC AGTAGTCGCC
 201 GTGAACGTTC TTTTTCGCAA CGGGTTTGCC GCCAGAACAC AGCTGAAGCT TCGAGGGGCT CGCATCTCTC CGCATCGCGC CGCCGCCCT ACCTGAGGC
 301 GCCATCCACG CCGGTTGAGT CCGGTTCTGC CGCGTCCCGC CGTGGTGCC TCCTGAACTG GCCTTCCGCC CGTCCGCCGT CTAGGTAAGT TTAAAGCTCA GGTCGAGACC
 401 GGGCCTTTGT CCGGCGCTCC CTTGGAGCCT ACCTAGAGCCT AGCCGGCTCT CCACGCTTTG CCTGACCCTG CTGGCTCAAC TCTACGTCTT TGTTTCGTTT

501 TCTGTTCTGC GCCGTTACAG ATCCAAGCTG TGACCGGCGC CTACCCTGAGA TCACCGGCGA AGGAGGCCCA CCATGTACAG GATGCAACTC CTGTCTTGCA
                                                                                IL-2 secretion signal
                                                                                MetTyrArg MetGlnLeu LeuSerCysIle
                       EcoRI       KasI
                                   NarI
                                   SfoI
                                   BbeI
                                                CXCL13 (1-87)
 601 TTGCACTAAG TCTTGCACTT GTCACGAATT CGGTTCTGGA GTGTAGATG ACAAGTTGA TGTCCAAGAG AGCTCAGTCT TTATCCCTAG
                                   EcoRI
     AlaLeuSer LeuAlaLeu ValThrAsnSer ValLeuGlu ValTyrTyr ThrSerLeuArg CysArgCys ValGlnGlu SerSerValPhe IleProArg
 701 ACGCTTCATT GATCGAATTC AAATCTTGCC CCGTGGGAAT GGTTGTCCAA GAAAAGAAAT CATAGTCTGG AAGAAGAACA AGTCAATTGT GTGTGTGGAC
     ArgPheIle AspArgIleGln IleLeuPro ArgGlyAsn GlyCysProArg LysLysLys IleValTrp LysLysAsnLys SerIleVal CysValAsp
                                                                                                          human IgG1 Fc
                                                                                                          (constant region)
 801 CCTCAAGCTG AATGGATACA AAGAATGATG GAAGTATTGA GAAAAGAAG TTCTTCAACT CTACCAGTTC CAGTGTTTAA GAGAAAGATT CCCGAAAGAA
     ProGlnAlaGlu TrpIleGln ArgMetMet GluValLeuArg LysArgSer SerSerThr LeuProValPro ValPheLys ArgLysIle ProAspLysThr
 901 CTCACACATG CCCACCGTGC CCAGCACCTG AACTCCTGGG GGGACCGTCA GTCTTCCTCT TCCCCCCAAA ACCCAAGGAC ACCCTCATGA TCTCCCGGAC
     HisThrCys ProProCys ProAlaProGlu LeuLeuGly GlyProSer ValPheLeuPhe ProProLys ProLysAsp ThrLeuMetIle SerArgThr
1001 CCCTGAGGTC ACATGCGTGG TGGTGGACGT GAGCCACGAA GACCCTGAGG TCAAGTTCAA CTGGTACGTG GACGGCGTGG AGGTGCATAA TGCCAAGACA
     ProGluVal ThrCysValVal ValAspVal SerHisGlu AspProGluVal LysPheAsn TrpTyrVal AspGlyValGlu ValHisAsn AlaLysThr
1101 AAGCCGCGGG AGGAGCAGTA CAACAGCACG TACCGTGTGG TCAGCGTCCT CACCGTCCTG CACCAGGACT GGCTGAATGG CAAGGAGTAC AAGTGCAAGG
     LysProArgGlu GluGlnTyr AsnSerThr TyrArgValVal SerValLeu ThrValLeu HisGlnAspTrp LeuAsnGly LysGluTyr LysCysLysVal
1201 TCTCCAACAA AGCCCTCCCA GCCCCCATCG AGAAAACCAT CTCAAAAGCC AAAGGGCAGC CCCGAGAACC ACAGGTGTAC ACCCTGCCCC CATCCCGGGA
     SerAsnLys AlaLeuPro AlaProIleGlu LysThrIle SerLysAla LysGlyGlnPro ArgGluPro GlnValTyr ThrLeuProPro SerArgGlu
1301 GGAGATGACC AAGAACCAGG TCAGCCTGAC CTGCCTGGTC AAAGGCTTCT ATCCCAGCGA CATCGCCGTG GAGTGGGAGA GCAATGGGCA GCCGGAGAAC
     GluMetThr LysAsnGlnVal SerLeuThr CysLeuVal LysGlyPheTyr ProSerAsp IleAlaVal GluTrpGluSer AsnGlyGln ProGluAsn
1401 AACTACAAGA CCACGCCTCC CGTGCTGGAC TCCGACGGCT CCTTCTTCCT CTACAGCAAG CTCACCGTGG ACAAGAGCAG GTGGCAGCAG GGGAACGTCT
     AsnTyrLysThr ThrProPro ValLeuAsp SerAspGlySer PhePheLeu TyrSerLys LeuThrValAsp LysSerArg TrpGlnGln GlyAsnValPhe
                                                                                                        BmtI
                                                                                                        NheI
1501 TCTCATGCTC CGTGATGCAC GAGGCTCTG CACAACCACTA CACGCAGAAG AGCCTCTCCC TGTCTCCGGG TAAATGAGTC CTAGCTGGCC CTAGCTGGCC
     SerCysSer ValMetHis GluAlaLeuHis AsnHisTyr ThrGlnLys SerLeuSerLeu SerProGly Lys*** (SEQ ID NO:73)
1601 AGATACATG ATGGTTTGG ACAAACCACA ACTAGAATGC AGTGAAAAAA ATGCTTATT TGTGAAATTT GTGATGCTAT TGCTTTATTT GTAACCATTA
1701 TAAGCTGCAA TAAACAAGTT AACAACAACA ATTGCATTCA TTTAATGTT CAGTTCAGG GGGAGGTGTG GGAGGTTTTT TAAAGCAAGT AAAACCTCTA
```

```
                 AseI
1801  CAAATGTGGT ATGGAATTAA TTCTAAAATA CAGCATAGCA AAACTTTAAC CTCCAAATCA AGCCTCTACT TGAATCCTTT TCTGAGGGAT GAATAAGGCA
1901  TAGGCATCAG GGGCTGTTGC CAGCTGTTTG TAGCTGCAT  GACCTCCAC  ATTCCCTTTT TTCTTTCATG GAGTTTAAGA TATAGTGTAT TTTCCCAAGG TTTGAACTAG
2001  CTCTTCATTT CTTTATGTTT TAAATGCACT CAGCCCCAC  ATTCCCTTTT ATAATATCCC TAGTAAAATA TTCAGAAATA ATTTAAATAC ATCATTGCAA TGAAAATAAA
2101  TGTTTTTAT  TAGGCAGAAT CCAGATGCTC AAGGCCCTTC CTCAGTCCTG CTCCTCTGCC ACAAAGTGCA CAGTTTAGT  AGTTGGACTT AGGAACCTTA ATAGAAATTG
2201  GACAGCAAGA AAGCGAGCTT CTAGCTTATC CGGTCATGGC CGGTCCCGGA GGTCCTCGGA AGTTCGTGGA CGCAGTTGCC CACGACCTCC GACCACTCGG GCAGGGCGA  ACTCCCGCCC
2301  CCACGGCTGC TCGCCGATCT CGGTCATGGC GGTGTTGTCC GGCACCACCT GGTCCTTGGA CACGACCTCG AACAGGGTCA CGTCGTCCCG GACCACACCG GTCCAGGCCG
2401  CGCACCACA  CCCAGGCCAG GTCCCGGGAG AACCCGAGCC GGTCGGTCCA GAACTCGGCA GCTCCGGCGA CGTCGCGCGC GGTGAGCACC GGAACGCACC TGGTCAACTT GCGAAGTCGT
2501  CCTCCACGAA GTCCCGGGAG AACCCGAGCC GGTCGGTCCA GAACTCGGCA GCTCCGGCGA CGTCGCGCGC GGTGAGCACC GGAACGCACC TGGTCAACTT
2601  GGCCATGATG GCTCCTCCTG TCAGGAGAGG AAAGAGAAGA AGGTTAGTAC AATTGCTATA GTGAGTTGTA TTATACTATG CAGATATACT ATGCAATGA
      AseI
2701  TTAATTGTCA AACTAGGGCT GCAGGGTTCA TAGTGCCACT TTTCCTGCAC TGCCCCATCT CCTGCCCACC CTTTCCCACC CATAGACAGT CAGTGACTTA
2801  CCAAACTCAC AGGAGGGAGA AGGCAGAAGC TTGAGACAGA CCCGGGGAC  CGCCGAACTG TGGCTAGGGC GGCTTCTTTT ATGGTGCGCC
2901  GGCCCTCGGA GGCAGGGCGC TCGGGGAGGC CTAGCGGCCA ATCTGCGGTG GCAGGAGGCG GGGCCGAAGG CCGTGCCTGA CCAATCCGGA GCACATAGGA
3001  GTCTCAGCGC CCCGCCCCAA AGCAAGGGGA AGTCACGCGC CTGTAGCGCG AGCGTGTTGT GAAATGGGGG CTTGGGGCCT TTGGGCCCT  GACTAGTCAA
3101  AACAAACTCC CATTGACGTC AATGGGGTGG AGACTTGGAA ATCCCCGTGA GTCAAACCGC TATCCACGCC CATTGATGTA CTGCCAAAAC CGCATCATCA
3201  TGGTAATAGC GATGACTAAT ACGTAGATGT ACTGCCAAGT AGGAAAGTCC CATAAGGTCA TGTACTGCCA ATAATGCCAG GCGGGCCATT TACCGTCATT
3301  GACGTCAATA GGGGCGTAC  TTGGCATATG AACATACGTC ATTATTGACG TGTACTGCAA AGTGGGCAGT TTACTCCACCC ATTGACGTCA ATGAAAGTC
3401  CCTATTGGCG TTACTATGGG TTAATTAAGA ACATGTGAGC AAAAGGCCAG CAAAAGGCCA GGAACCGTAA AAAGGCCGCG TTGCTGGCGT TTTTCCATAG GCTCCGCCCC
3501  CGCTGCAGG  TTAATTAAGA ACATGTGAGC AAAAGGCCAG CAAAAGGCCA GGAACCGTAA AAAGGCCGCG TTGCTGGCGT TTTTCCATAG GCTCCGCCCC
3601  CCTGACGAGC ATCACAAAAA TCGACGCTCA AGTCAGAGGT GGCGAAACCC GACAGGACTA TAAAGATACC AGGCGTTTCC CCCTGGAAGC TCCCTCGTGC
3701  GCTCTCCTGT TCCGACCCTG CCGCTTACCG GATACCTGTC CGCCTTTCTC CCTTCGGGAA GCGTGGCGCT TTCTCATAGC TCACGCTGTA GGTATCTCAG
3801  TTCGGTGTAG GTCGTTCGCT CCAAGCTGGG CTGTGTGCAC GAACCCCCCG TTCAGCCCGA CCGCTGCGCC TTATCCGGTA ACTATCGTCT TGAGTCCAAC
3901  CCGGTAAGAC ACGACTTATC GCCACTGGCA GCAGCCACTG GTAACAGGAT TAGCAGAGCG AGGTATGTAG GCGGTGCTAC AGAGTTCTTG AAGTGGTGGC
4001  CTAACTACGG CTACACTAGA AGAACAGTAT TTGGTATCTG CGCTCTGCTG AAGCCAGTTA CCTTCGGAAA AGAGTTGGT  AGCTCTTGAT CCGGCAAACA
4101  AACCACCGCT GGTAGCGGTG GTTTTTTTGT TTGCAAGCAG CAGATTACGC GCAGAAAAAA AGGATCTCAA GAAGATCCTT TGATCTTTTC TACGGGTCT
4201  GACGCTCAGT GGAACGAAAA CTCACGTTAA GGGATTTTGG TCATGGCTAG TTAATTAACA TTTAAATCAG CGGCCGCAAT AAAATATCTT TATTTTCATT
4301  ACATCTGTGT GTTGGTTTTT TGTGTGAATC GTAACGTTAA TACGCTCTCC ATCAAAACAA AACGAAACAA CAAAACTAG  CAAAATAGGC TGTCCCCAGT
4401  GCAAGTGCAG GTGCCAGAAC ATTTCTCTAT CGAA       (SEQ ID NO:100)
```

IL2ss.CXCL13(3-87).hIgG1Fc sequence

```
   1 GGATCTGCGA TCGCTCCGGT GCCGTCAGT GGGCAGAGCG CACATCGCCC ACAGTCCCCG AGAAGTTGGG GGGAGGGGTC GGCAATTGAA CGGGTGCCTA
 101 GAGAAGGTGG CGCGGGTAA ACTGGGTAAG TGATGTCGTG GCCAGAACCT TACTGGCTCC GCCTTTTTCC CGAGGGTGGG GGAGAACCGT CTTCACGCGC ATATAAGTGC AGTAGTCGCC
 201 GTGAACGTTC TTTTTCGCAA CGGGTTTGCC GCCAGAACAC AGCTGAAGCT TCGAGGGGCT TCGCATCTCT CGCACGCGC CCGCCGCCCT ACCTGAGGCC
 301 GCCATCCACG CCGGTTGAGT CCGGTTCTGC CCGCCTCCGC CCGCCCGCC CTGTGGTGCC TCCTGAACTG CGTCCGCCGT CTAGGTAAGT TTAAAGCTCA GGTCGAGACC
 401 GGGCCCTTTGT CCGGCGCTCC CTGGAGCCT AGCCGGCTCT AGCCGGCCT CCACGCTTTG CCTGACCCTG CTTGCTCAAC TCTACGTCTT TGTTTCGTTT
                                     KasI
                                     NarI
                                     SfoI
                                     BbeI
                                                                                          IL-2 secretion signal
                                                                                       MetTyrArg MetGlnLeu LeuSerCysIle
 501 TCTGTTTCTGC GCCGTTACAG ATCCAAGCTG TGACCGGCGC CTACCTGAGA TCACCGGCGA AGGAGGCCA CCATGTACAG GATGCAACTC CTGTCTTGCA
                                                                            EcoRI
                                                                           ~~~~~~~ CXCL13 (3-87)
               AlaLeuSer LeuAlaAla ValThrAsnSer GluValTyr TyrThrSer LeuArgCysArg CysValGln GluSerSer ValPheIlePro ArgArgPhe
 601 TTGCACTAAG TCTTGCACTT GTCACGAATT CGGAGGTCTA TTACACAAGC TTGAGGTGTA GATGTGTCCA AGAGAGCTCA GTCTTTATCC CTAGACGCTT
      IleAspArg IleGlnIleLeu ProArgGly AsnGlyCys ProGlyLysGlu IleIleVal TrpLysLys AsnLysSerIle ValCysVal AspProGln
 701 CATTGATCGA ATTCAAATCT TGCCCCGTGG GAATGGTTGT CCAAGAAAAG AAATCATAGT CTGGAAGAAG AACAAGTCAA TTGTGTGTGT GGACCCTCAA
     AlaGluTrpIle GlnArgMet MetGluVal LeuArgLysArg SerSerSer ThrLeuPro ValProValPhe LysArgLys IleProAsp LysThrHisThr
 801 GCTCAATGGA TACAAAGAAT GATGGAAGTA TTGAGAAGAAA GAAGTTCTTC AACTCTACCA GTTCCAGTGT TTAAGAGAAA GATTCCCGAC AAAACTCACA
     CysProPro CysProAla ProGluLeuLeu GlyGlyPro SerValPhe LeuPheProPro LysProLys AspThrLeu MetIleSerArg ThrProGlu
 901 TGTCCACCC GTGCCCAGCA CCTGAACTCC TGGGGGGACC GTCAGTCTTC CTCTTCCCCC CAAAACCCAA GGACACCCTC ATGATCTCCC GGACCCCTGA
     ValThrCys ValValValAsp ValSerHis GluAspPro GluValLysPhe AsnTrpTyr ValAspGly ValGluValHis AsnAlaLys ThrLysPro
1001 GGTCACATGC GTGGTGGTGG ACGTGAGCCA CGAAGACCCT GAGGTCAAGT TCAACTGGTA CGTGGACGGC GTGGAGGTGC ATAATGCCAA GACAAAGCCG
     ArgGluGluGln TyrAsnSer ThrTyrArg ValValSerVal LeuThrVal LeuHisGln AspTrpLeuAsn GlyLysGlu TyrLysCys LysValSerAsn
1101 CGGGAGGAGC AGTACAACAG CACGTACCGT GTGGTCAGCG TCCTCACCGT CCTGCACCAG GACTGGCTGA ATGGCAAGGA GTACAAGTGC AAGGTCTCCA
     LysAlaLeu ProAlaPro IleGluLysThr IleSerLys AlaLysGly GlnProArgGlu ProGlnVal TyrThrLeu ProProSerArg GluGluMet
1201 ACAAAGCCC CCCAGCCCCC ATCGAGAAAA CCATCTCCAA AGCCAAAGGG CAGCCCCGAG AACCACAGGT GTACACCCTG CCCCCATCCC GGGAGGAGAT
     ThrLysAsn GlnValSerLeu ThrCysLeu ValLysGly PheTyrProSer AspIleAla ValGluTrp GluSerAsnGly GlnProGlu AsnAsnTyr
1301 GACCAAGAAC CAGGTGAGCC TGACCTGCCT GGTCAAAGGC TTCTATCCCA GCGACATCGC CGTGGAGTGG GAGAGCAATG GGCAGCCGGA GAACAACTAC
     LysThrThrPro ProValLeu AspSerAsp GlySerPhePhe LeuTyrSer LysLeuThr ValAspLysSer ArgTrpGln GlnGlyAsn ValPheSerCys
1401 AAGACCACGC CTCCCGTGCT GGACTCCGAC GGCTCCTTCT TCCTCTACAG CAAGCTCACC GTGGACAAGA GCAGGTGGCA GCAGGGGAAC GTCTTCTCAT
                                                                                                     BmtI
                                                                                                     NheI
     SerValMet HisGluAla LeuHisAsnHis TyrThrGln LysSerLeu SerLeuSerPro GlyLys***(SEQ ID NO:74)
1501 GCTCCGTGAT GCACGAGGCT CTGCACAACC ACTACACGCA GAAGAGCCTC TCCCTGTCTC CGGGTAAATG AGTGCTAGCT GGCCAGACAT GATAAGATAC
1601 ATTGATGAGT TTGGACAAAC CACAACTAGA ATGCAGTGAA AAAAATGCTT TATTTGTGAA ATTTGTGATG CTATTGCTTT AATTGTAACC TATATAAGCT
1701 GCAATAAACA AGTTAACAAC AACAATTGCA TTCATTTTAT GTTTCAGGTT CAGGGGGAGG TGTGGGAGGT TTTTTAAAGC AAGTAAAACC TCTACAAATG
                 AseI
```

```
1801  TGGTATGGAA TTAATTCTAA AATACAGCAT AGCAAAACTT TAACCTCCAA ATCAAGCCTC TACTTGAATC CTTTTCTGAG GGATGAATAA GGCATAGGCA
1901  TCAGGGGCTG TTGCCAATGT GCATTAGCTG TTTGCAGCCT CCACATTCCC TTTTTAGTAA CATGGAGTTT AAGATATAGT GTATTTTCCC AAGGTTTGAA CTAGCTCTTC
2001  ATTTCTTTAT GTTTTAAATG CACTGACCTC CTTCATAATA TCCCCAGTT ACTTAGTTGG AATAATTCAGA ATACATCATT CAAAGAAACC TTTAATAGAA ATTGGACAGC
2101  TTATTAGGCA GAATCCAGAT GCTCAAGGCC CCTGCTCCTC TGCACAAAAG TGCACGCAGT TAGTAGTTGG TGCCGGCCGG GTCGCGCAGG GCGAACTCCC GCCCCCACGG
2201  AAGAAAGCGA GCTTCTAGCT TATCCTCAGT TGGCCGGCCC GGAGGCGTCC CGGAAGTTCG TGGACACGAC CTCCGACCAC TCGGCGTACA GCTCGTCCAG GCCGGCACC
2301  CTGCTCGCCG ATCTCGGTCA TGGCCGGTGT GTCCGGCACC ACCTGGTCCT GGACCGCGCT GATGAACAGG GTCACGTCGT CCCGGACCAC ACCGGCGAAG TCGTCCTCCA
2401  CACACCCAGG CCAGGGTGTT GTCCGGCACC ACCTGGTCCT GGACCGCGCT GATGAACAGG GTCACGTCGT CCCGGACCAC ACCGGCGAAG TCGTCCTCCA
2501  CGAAGTCCCG GGAGAACCCG AGCCGGTCGG TCCAGAACTC TCCAGAACTC GACCGCTCCG GCGACGTCGC GCGCGGTGAG CACCGGAACG GCACTGGTCA ACTTGGCCAT
                                                                                                                  AseI
2601  GATGGCTCCT CCTGTCAGGA GAGGAAAGAG GTACAATTGC TATAGTGAGT TATGCAGATA TACTATGCCA ATGATTAATT
2701  GTCAAACTAG GGCTGCAGGG TTCATAGTGC CACTTTTCCT GCACTGCCCC ATCTCCTGCC CACCCTTTCC CAGGCATAGA CAGTCAGTGA CTTACCAAAC
2801  TCACAGGAGG GAGAAGGCAG AAGCTTGAGA CAGACCCGG ACTGCGAGGG GACGTGGCTA GGGCGGCTTC TTTATGGTG CGCCGGCCCT
2901  CGGAGGCAGG GCGCTCGGGG AGGCCTAGCG GCCAATCTGC GGTGGCAGGA GGCGGGGCCG AAGGCCGTGC CTGACCAATC CGGACCACAT AGGAGTCTCA
3001  GCCCCCCGCC CCAAAGCAAG GGGAAGTCAC GCGCCTGTAG CGCCAGCGTG TTGTGAAATG GGGCTTGGGG CCCTGACTAG AAACCGCATC TCAAAACAAA
3101  CTCCCATTGA CGTCAATGGG GTGGAGACTT GGAAATCCCC GTGACTATGA CGCTATCCA AAGTAGGAAA GTCATGTACT CAGGCGGGC CATTTACCGT ATCATGGTAA
3201  TAGCGATGAC TAATACGTAG ATGTACTGCC AAGTAGGAAA GTCATGTACT GCCAAGTGGG TAAATACTCC ACCATTGAC GTCAATGGAA AGTCCTATT
3301  AATAGGGGC GTACTTGGCA TATGATACAT TTGATGTACT GCCAAGTGGG TAAATACTCC ACCATTGAC GTCAATGGAA AGTCCTATT
3401  GGCGTTACTA TGGGAACATA CGTCATTATT GACGTCAATG GGCGGGGGTC GTTGGGCGGT CAGCCAGGCG GGCCATTTAC CGTAAGTTAT GTAACGCTG
3501  CAGTTAATT AAGAACATGT GAGCAAAAGG CCAGGAACC ACCAGGAACC ACCCGACAGG ACTATAAAGA TACCAGGCGT TTCCCCCTGG AAGCTCCCTC GTGCGCTCTC
3601  GAGCATCACA AAAATCGACG CTCAAGTCAG AGGTGGCGAA ACCCGACAGG ACTATAAAGA TACCAGGCGT TTCCCCCTGG AAGCTCCCTC GTGCGCTCTC
3701  CTGTTCCGAC CCTGCCGCTT ACCGGATACC TGTCCGCCTT TCTCCCTTCG GGAAGCGTGG CGCTTTCTCA TAGCTCACGC TGTAGGTATC TCAGTTCGGT
3801  GTAGGTCGTT CGCTCCAAGC TGGGCTGTGT GCACGAACCC CCCGTTCAGC CCGACCGCTG CCCTTATCC CGGTAACTATC GTCTTGAGTC CAACCCGGTA
3901  AGACACGACT TATCGCCACT GGCAGCAGCC ACTGGTAACA GGATTAGCAG AGCGAGGTAT GTAGGCGGTG CTACAGAGTT CTTGAAGTGG TGGCCTAACT
4001  ACGGCTACAC TAGAAGAACA GTATTTGGTA TCTGCCTCT GCTGAAGCCA GTTACCTTCG GAAAAAGAGT TGGTAGCTCT TGATCCGGCA AACAAACCA
4101  CCGCTGGTAG CGGTGGTTTT TTTGTTTGCA ACAGCAGATT ACGCGCAGAA AAAAAGGATC TCAAGAAGAT CCTTTGATCT TTTCTACGGG GTCTGACGCT
4201  CAGTGGAACG AAAACTCACG TTAAGGGATT TTGGTCATGA CTAGTTAATT AACATTTAAA AACATTTAAA TCAGCGCCG CAATAAAATA TCTTATTT CATTACATCT
4301  GTGTGTTGGT TTTTTGTGTG AATCGTAACT AACATACGCT CTCCATCAAA ACAAAACGAA ACAAAACGAA ACAAACACAA CTAGCAAAAT AGGCCTGTCCC CAGTGCAAGT
4401  GCAAGGTGCCA GAACATTTCT CTATCGAA (SEQ ID NO:101)
```

IL2ss.CXCL13(3-87).hIgG1Fc sequence [Alanine substitutions for removal of GAG binding sites – Lys & His]

```
   1  GGATCTGCGA TGCTCCGGT GCCCGTCAGT GGGCAGAGCG CACATCGCCC ACAGTCCCCG AGAAGTTGGG GGGAGGGGTC GGCAATTGAA CGGGTGCCTA
 101  GAGAAGGTGG CGGGGGTAA ACTGCGAAAG TGATGTCGTG GCCAGAACAC CGGGTTTGCC TACTGGCTCC GCCTTTTTCC CGAGGGTGGG GGAAGAACCGT ATATAAGTGC AGTAGTCGCC
 201  GTGAACGTTC TTTTTCGCAA CGGGTTTGCC GCCAGAACAC AGCTGAAGCT TCGAGGGGCT CGCATTCTCC CCATCCGCGC CCGGCGCCCT ACCTGAGCC
 301  GCCATCCACG CCGGTGAGT CCGTTCTGC CGGTTCTGC CTGTGGTGCC CCTGAACTG CGTCCGGCGT CCACCTTTG AGCCGGCTCT ACCTAGACT GCCCTGAACC CTTGCTCAAC TCTACGTCTT GTTTCGTTT
 401  GGGCCTTTGT CCGGGCTCC CTTGGAGCCT ACCTAGACTC AGCCGGCTCT CCACGCTTTG CCTGACCCTG CTTGCTCAAC TCTACGTCTT GTTTCGTTT
                                      KasI
                                      NarI
                                      SfoI
                                      BbeI
                                                                                                                            IL-2 secretion signal
                                                                                                                            MetTyrArg MetGlnLeu LeuSerCysIle
 501  TCTGTTCTGC GCCGTTACAG ATCCAAGCTG TGACCGGCGC CTACCTGAGA TCACGGGCGA AGGAGGGCCA CCATGTACAG GATGCAACTC CTGTCTTGCA
                          EcoRI
                                      ----- CXCL13 (3-87)
 601  TTGCACTAAG TCTTGCACTT GTCAGAATT CGGAGGTCTA TTACACAAGC TTGAGGTGTA GATGTGTCCA AGAGAGCTCA GTCTTTATCC CTAGACGCTT
        EcoRI
                 AlaLeuSer LeuAlaLeu ValThrAsnSer GluValTyr TyrThrSer LeuArgCysArg CysValGln GluSerSer ValPheIlePro ArgArgPhe
 701  ATTGATGCC ATTCAAATCT TGCCCCGTGG GAATGGTTGT CCAAGAAAAG AAATCATAGT CTGGCTGCG AACGCTCAA TTGTGTGT GGACCCTCAA
                 IleAspAla IleGlnIleLeu ProArgGly AsnGlyCys ProArgLysGlu IleIleVal TrpAlaAla AsnAlaSerIle ValCysVal AspProGln
                                                                                                                            human IgG1 Fc
                                                                                                                            (constant region)
 801  AlaGluTrpIle GlnAlaMet MetGluVal LeuAlaAlaAla SerSerSer ThrLeuPro ValThrHisThr LysThrHisThr
      GCTGAATGGA TACAAGCCAT GATGGAAGTA TTGGCTGCGG CTAGTTCTTC AACTCTACCA GTTCCAGTGT TGCCGCTGGG GATTCCCGAC AAAACTCACA
                 CysProPro CysProAla ProGluLeuLeu GlyGlyPro SerValPhe LeuPheProPro LysProLys AspThrLeu MetIleSerArg ThrProGlu
 901  CATGCCCACC GTGCCCAGCA CCTGAACTCC TGGGGGGACC GTCAGTCTTC CTCTTCCCCC CAAAACCCAA GGACACCCTC ATGATCTCCC GGACCCCTGA
                 ValThrCys ValValValAsp ValSerHis GluAsPro GluValLysPhe AsnTrpTyr ValAsPGly ValGluValHis AsnAlaLys ThrLysPro
1001  GGTCACATGC GTGGTGGTG ACGTGAGCCA CGAAGACCCT GAGGTCAAGT TCAACTGGTA CGTGGACGGC GTGGAGGTGC ATAATGCCAA GACAAAGCCG
                 ArgGluGluGln TyrAsnSer ThrTyrArg ValValSerVal LeuThrVal LeuHisGln AspTrpLeuAsn GlyLysGlu TyrLysCys LysValSerAsn
1101  CGGGAGGAGC AGTACAACAG CACGTACCGT GTGGTCAGTG TCCTCACCGT CCTGCACCAG GACTGGCTGA ATGGCAAGGA GTACAAGTGC AAGGTCTCCA
                 LysAlaLeu ProAlaPro IleGluLysThr IleSerLys AlaLysGly GlnProArgGlu ProGlnVal TyrThrLeu ProProSerArg GluGluMet
1201  ACAAAGCCCT CCCAGCCCCC ATCGAGAAAA CCATCTCCAA AGCCAAAGGG CAGCCCCGA GAACCAGT GTACACCCTG CCCCCATCCC GGGAGGAGAT
                 ThrLysAsn GlnValSerLeu ThrCysLeu ValLysGly PheTyrProSer AspIleAla ValGluTrp GluSerAsnGly GlnProGlu AsnAsnTyr
1301  GACCAAGAAC CAGGTCAGCC TGACCTGCCT GGTCAAAGGC TTCTATCCCA GCGACATCGC CGTGGAGTGG GAGAGCAATG GGCAGCCGGA GAACAACTAC
                 LysThrThrPro ProValLeu AspSerAsp GlySerPhePhe LeuTyrSer LysLeuThr ValAspLysSer ArgTrpGln GlnGlyAsn ValPheSerCys
1401  AAGACCACGC CTCCCGTGCT GGACTCCGAC GGCTCCTTCT TCCTCTACAG CAAGCTCACC GTGGACAAGA GCAGGTGGCA GCAGGGGAAC GTCTTCTCAT
                                                                                                                            BmtI
                                                                                                                            NheI
                 SerValMet HisGluAla LeuHisAsnHis TyrThrGln LysSerLeu SerLeuSerPro GlyLys***(SEQ ID NO:75)
1501  GCTCCGTGAT GCACGAGGCT CTGCACAACA CTACACGGA GAAGAGCCTC TCCCTGTCTC CGGGTAAATG AGTGCTAGCT GGCCAGACAT GATAAGATAC
1601  ATTGAGAGT TTGGACAAAC CACAACTAGA ATGCAGTGAA AAAAATGCTT TATTTGTGAA ATTTGTGATG CTATTGCTTT ATTTGTAACC ATTATAAGCT
1701  GCAATAAACA AGTTAACAAC AACAATTGCA TTCATTTTAT GTTTCAGGTT CAGGGGGAGG TGTGGGAGGT TTTTTAAAGC AAGTAAAACC TCTACAAATG
```

```
         AseI
1801 TGGTATGGAA TTAATTCTAA AATACAGCAT AGCAAAAACTT TAACCTCCAA ATCAAGCCTC TACTTGAATC CTTTTCTGAG GGATGAATAA GGCATAGGCA
1901 TCAGGGGCTG TTGCCAATGT GCATTAGCTG TTTGCAGCCT CACCTTCTTT CATGGAGTTT AAGATATAGT AATAATTTAA GTATTTCCC AAGGTTTGAA CTAGCTCTTC
2001 ATTTCTTTAT GTTTTAAATG CACTGACCTC CCACATTCCC CTTTTAGTAA AATATTCAGA ACTTAGGGAA ATACATCATT CAAAGGAACC TTTAATAGAA TAAATGTTTT
2101 TTATTAGGCA GAATCCAGAT GCTCAAGGCC CTTCATAATA TCCCCCAGTT TAGTAGTTGG TGCACGCAGT TGCCGGCAGG GTCCGGCAGG GCGAACTCCC GCCCCACGG
2201 AAGAAAGCGA GCTTCTAGCT TATCCTCAGT CCTGCTCCTC TGCCACAAAG TGCACGCAGT TGGACACGAC CTCCGACCAC TGGGCGTACA GCTCGTCCAG GCCGCACC
2301 CTGCTCGCCG ATCTCGGTCA TGGCCGGCCC GGAGGCGTCC CGGAAGTTCG TGGACACGAC GATGAACAGG GTCACGTCGT CCCGACCAC ACCGGCGAAG TGTCCTCCA
2401 CACACCCAGG CCAGGGTGTT GTCCGGCACC ACCTGGTCCT GGACCGCGCT GATGAACAGG GTCACGTCGT CCCGACCAC ACCGGCGAAG TGTCCTCCA
2501 CGAAGTCCCG GGAGAACCCG AGCCGGTCGG TCCAGAACTC GACCGCTCCG GACCGGTCGAG GCGACGTCGC GCCGGTCA ACTTGGCCAT
                                                                                                        AseI
2601 GATGGCTCCT CCTGTCAGGA GAGGAAAGAG AAGAAGGTTA GTACAATTGC TATAGTGAGT TGTATTATAC TATGCAGATA TACTATGCCA ATGATTAATT
2701 GTCAAACTAG GGCTGCAGGG TTCATAGTGC CACTTTTCCT GCACTCCTGCC ATCTCCTGCC GACGTGGCTA CAGTCAGTGA CTTACCAAAC
2801 TCACAGGAGG GAGAAGGCAG AAGCTTGAGA CAGACCCGCG GGACCGCCGA ACTGCGAGGG GACGTGGCTA AAGGCCGTGC CGGAGCACAT AGGAGTCTCA
2901 CGGAGGCAGG GCGCTGGGGG GCCTAGCG GCCAATCTGC GGTGGCAGGA CGCCAGCGTG TTGTGAAATG GGGCTTGGG CCCTGACTAG TCAAAACAAA
3001 GCCCCCGCC CAAAGCACA GGGAAGTCAC GCGCCTGTAG GTGAGTCAAA CCGCTATCCA TGTACTGCCA AAACCGCATC ATCATGTAA
3101 CTCCCATTGA CGTCAATGGG GTGGAGACTT AAGTAGGAAA GTCCCATAAG CCGCATAATG CAGGCGGGC CATTACCGT CATTGACGTC
3201 TAGGCGATGAC TAATACGTAG ATGTACTGCC TTGATGTACT GCCAAGTGGG TAAATACTCC GTCAATGGAA AGTCCCTATT
3301 AATAGGGGGC GTACTTGGCA TATGATACAC CGTCATTATT GGGGGGGGTC GTTGGGCGGT CAGCCAGGGG CGGTTTTTCC GTAACGCTG
3401 GGCGTTACTA TGGGAACATA CGTCATTATT GAGCAAAAGG GCCAGGAACC GTAAAAAGC ACTATAAAGA TACCAGGCGT TCCCCCTGG AAGCTCCCTC GTGCGCTCTC
3501 CAGGTTAATT AAGAACATGT GAGCAAAAGG CCAGGAACC GTAAAAAGC ACTATAAAGA TACCAGGCGT TTCCCCCTGG AAGCTCCCTC GTGCGCTCTC
3601 GAGCATCACA AAAATCGACG CTCAAGTCAG AGGTGGCGAA ACCGACAGG TCTCCCCTTCG GAAGCGTGG CCGACCGCTG TAGCGATATC GTCTTGAGTC CAACCGGTA
3701 CTGTTCCGAC CCTGCCGCTT ACCGGATACC TGTCCGCCTT GCACGAACCC CCCGTTCAGC GGATTAGCAG AGCGAGGTAT GTAGGCGGTG CTTGAAGTGG TGGCCTAACT
3801 GTAGGTCGTT CGCTCCAAGC TGGGCTGTGT GCACAGACC ACTGGTAACA GTATTTGGTA TCTGCGCTCT GCTGAAGCCA ACGGGCAGAT TCAAGAAGAT CCTTTGATCT
3901 AGACACGACT TATGCCACT GGCAGCAGCC GTATTTGGTA TCTGCGCTCT GCTGAAGCCA ACGGGCAGAT TCAAGAAGAT CCTTTGATCT TTTCTACGG GTCTGACGCT
4001 ACGGCTACAC TAGAAGAACA GTATTTGGTA TTGTTTGCAA GCAGCAGATT ACGCGCAGAA AAAAAGGATC TCAAGAAGAT CCTTTGATCT TTTCTACGG GTCTGACGCT
4101 CGCTGGTAGC GGTGGTTTTT TTGTTTGCAA GCAGCAGATT ACGCGCAGAA AAAAAGGATC TCAAGAAGAT CCTTTGATCT TTTCTACGG GTCTGACGCT
4201 CAGTGGAACG AAAACTCACG TTAAGGGATT TTGGTCATGA CTAGTTAATT AACATTTAAA TCAGCGGCCG CAATAAAATA TCTTTATTTT CATTACATCT
4301 GTGTGTTGGT TTTTTGTGTG AATCGTAACT AACATACGCT CTCCATCGAA ACAAAACGAA ACAAAACAAA CTAGCAAAAT AGGCTGTCCC CAGTGCAAGT
4401 GCAGGTGCCA GAACATTTCT CTATCGAA (SEQ ID NO:102)
```

IL2ss.CXCL13.hIgG4Fc sequence

```
   1  GGATTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101  GAGAAGGTGG CCGGGGTAA ACTGCGAAAG TGATGTCGTG AGCTGAACCT CGCCTTTTCC CGAGGGTGGG GGAGAACCGT CTTCACGCGC ATATAAGTGC
 201  GTGAACGTTC TTTTTGCAA CGGGTTGCC AGCAGAACAC AGCTGAAGCT TCGAGGGGCT CGCATCCTC CGCATCCGGC CTTCACGCGC ACTGAGGCC
 301  GCCATCCACG CCGGTTCTGC CGCTTCCCGC CGTGTGGCC CCTGAACTG CGTCCGCCCT CGTCCGCCC CTAGTAAGT TTAAAGCTCA GGTCGAGACC
 401  GGGCCTTTGT CCGGCGCTCC CTTGGAGCCT ACCTAGACTC AGCCGGCTCT AGCCGGCTCT CTTGACCCTG CTTGCTCAAC TCTACGTCTT TGTTTCGTTT
                                                   KasI
                                                   NarI
                                                   SfoI
                                                   BbeI
                                                                                          IL-2 secretion signal
                                                                                          MetTyrArg MetGlnLeu LeuSerCysIle
 501  TCTGTTCTGC GCCGTTACAG ATCCAAGCTG TGACCGGCGC CTACCGGAGA TCACCGGCGA AGGAGGGCCA CCATGTACAG GATGCAACTC CTGTCTTGCA
                                      EcoRI
                                      ~~~~~~~ CXCL13 (1-87)
      AlaLeuSer LeuAlaAla ValThrAsnSer ValLeuGlu ValTyrTyr ThrSerLeuArg CysArgCys ValGlnGlu SerSerValPhe IleProArg
 601  TTGCACTAAG TCTTGCACTT GTCACGAATT CGGTTCTGGA GGTCTAGATG ACAAGCTTGA TGTCCAAGAG AGTCAGTCT TTATCCCTAG
      ArgPheIle AspArgIleGln IleLeuPro ArgGlyAsn GlyCysProArg LysLeuValTrp LysLysAsnLys SerIleVal CysValAsp
 701  ACGTTCATT GATCGAATTC AAATCTTGCC CCGTGGGAAT GGTTGTCCAA GAAAAGAACA AGTCAATTGT GTGTGTGGAC
                                                                                          human IgG4 Fc
                                                                                          (constant region)
      ProGlnAlaGlu TrpIleGln ArgMetMet GluValLeuArg LysArgSer SerSerThr LeuProValPro ValPheLys ArgLysIle ProProProCys
 801  CCTCAAGCTG AATGGATACA AAGAATGATG GAAGTATTGA GAAAAGAAG TTCTTCAACT CTACCAGTTC CAGTGTTAA GAGAAAGATT CCCCCCCCAT
      ProSerCys ProAlaPro GluPheLeuGly GlyProSer ValPheLeu PheProProLys ProLysAsp ThrLeuMet IleSerArgThr ProGluVal
 901  CCAGCTGC CCCAGCACCT GAGTTCCTGG GGGGACCATC AGTCTTCCTG TTCCCCCAA AACCCAAGGA CACTCTCATG ATCTCCCGGA CCCCTGAGGT
      ThrCysVal ValValAspVal SerGlnGlu AspProGlu ValGlnPheAsn TrpTyrVal AspGlyVal GluValHisAsn AlaLysThr LysProArg
1001  CACGTGCGTG GTGGTGGACG TGAGCCAGGA AGACCCCGAG GTCCAGTTCA ACTGGTACGT GGATGGCGTG GAGGTGCATA ATGCCAAGAC AAAGCCGCGG
      GluGluGlnPhe AsnSerThr TyrArgVal ValSerValLeu ThrValLeu HisGlnAsp TrpLeuAsnGly LysGluTyr LysCysLys ValSerAsnLys
1101  GAGGAGCAG TTCAACAGC ACGTACCGTG GTCAGCGTGC TCACCGTGCT GCACCAGGAC TGGCTGAACG GCAAGGAGTA CAAGTGCAAG GTCTCCAACA
      GlyLeuPro SerSerIle GluLysThrIle SerLysAla LysGlyGln ProArgGluPro GlnValTyr ThrLeuPro ProSerGlnGlu GluMetThr
1201  AAGGCCTCCC GTCCTCCATC GAGAAAACCA TCTCCAAAGC CAAAGGGCAG CCCCGAGAGC CACAGGTGTA CACCCTGCCC CCATCCCAGG AGGAGATGAC
      LysAsnGln ValSerLeuThr CysLeuVal LysGlyPhe TyrProSerAsp IleAlaVal GluTrpGlu SerAsnGlyGln ProGluAsn AsnTyrLys
1301  CAAGAACCAG GTCAGCCTGA CCTGCCTGGT CAAAGGCTTC TACCCCAGCG ACATCGCCGT GGAGTGGGAG AGCAATGGGC AGCCGGAGAA CAACTACAAG
      ThrThrProPro ValLeuAsp SerArgGly SerPhePheLeu TyrSerArg LeuThrVal AspLysSerArg TrpGlnGlu GlyAsnVal PheSerCysSer
1401  ACCACGCCTC CCGTGCTGGA CTCCGACGGC TCCTTCTTCC TCTACAGCAG GCTAACCGTG GACAAGAGCA GGTGGCAGGA GGGGAATGTC TTCTCATGCT
                                                                                          BmtI
                                                                                          NheI
      ValMetHis GluAlaLeu HisAsnHisTyr ThrGlnLys SerLeuSer LeuSerProGly Lys***(SEQ ID NO:76)
1501  CCGTGATGCA TGAGGCTCTG CACAACCACT ACACACAGAA GAGCCTCTCC CTGTCTCCGG GTAAATGAGT GCTAGCTGGC CAGACATGAT AAGATACATT
1601  GATGAGTTTG GACAAACCAC AACTAGAATG CAGTGAAAA ATGCTTTATT TGTGAAATT TGTGATGCTA TTGCTTTATT TGTAACCATT ATAAGCTGCA
1701  ATAAACAAGT TAACAACAAC AATTGCATTC ATTTTATGTT TCAGGTTCAG GGGGAGGTGT GGGAGGTTTT TAAAGCAAG TAAAACCCTCT ACAAATGTGG
```

```
                 AseI
1801  TATGGAATTA  ATTCTAAAAT  ACAGCATAGC  AAAACTTTAA  CCTCCAAATC  AAGCCTCTAC  TTGAATCCTT  TTCTGAGGGA  TGAATAAGGC  ATAGGCATCA
1901  GGGGCTGTTG  CCAATGTGCA  TTAGCTGTTT  GCAGCCCTCAC CTTCTTTCAT  GGAGTTAAG   ATATAGTGTA  TTTTCCCAAG  GTTTGAACTA  GCTCTTCATT
2001  TCTTTATGTT  TTAAATGCAC  TGACCTCCCA  CATTCCCTTT  TTAGTAAAAT  ATTCAGAAAT  AATTAAATA   CATCATTGCA  ATGAAAATAA  ATGTTTTTA
2101  TTAGGCAGAA  TCCAGATGCT  CAAGGCCCTT  CATAATATCC  CCCAGTTTAG  TAGTTGGACT  TAGGGAACAA  AGGAACCTTT  AATAGAAATT  GGACAGCAAG
2201  AAAGCGAGCT  TCTAGCTTAT  CCTCAGTCCT  GCTCCCTCTGC CACAAAGTGC  ACGCAGTTGC  CGGCCGGGTC  GCCCAGGGCG  AACTCCCGCC  CCACGGCTG
2301  CTCGCCGATC  TCGGTCATGG  CCGGCCCGGA  GGCGTCCCGG  AAGTTCGTGG  ACACGACCTC  CGATACAGCT  GCGTACAGCT  CGTCCAGGCC  GCGCACCAC
2401  ACCCAGGCCA  GGGTGTTGTC  CGGCACCACC  TGGTCCTGGA  CCGCGCTGAT  GAACAGGGTC  ACGTCGTCCC  GGACCACACC  GGCGAAGTCG  TCCTCCACGA
2501  AGTCCCGGGA  GAACCCGAGC  CGGTCGGTCC  AGAACTCGAC  CGCTCCGGCG  ACGTCGGCGG  CGGTGAGCAC  CGGAACGGCA  CTGGTCAACT  TGGCCATGAT
                                                                                                              AseI
2601  GGCTCCTCCT  GTCAGGAGAG  GAAAGAGAAG  AAGGTTAGTA  CAATTGCTAT  AGTGAGTTGT  ATTATACTAT  GCAGATATAC  TATGCCAATG  ATTAATTGTC
2701  AAACTAGGGC  TGCAGGGTTC  ATATGCCAC   CTTGAGAACAG ACCCGCGGGA  CTGCCCCATC  TCCTGCCCAC  CCTTTCCCAG  GCATAGACAG  TCAGTGACTT  ACCAAACTCA
2801  CAGGAGGGAG  AAGGCAGAAG  CTTGAGACAG  ACCCGCGGGA  CGGCGCGAACT GCGAGGGGAC  GTGGCTAGGG  CGGCTTCTTT  TATGGTGCGC  CGGCCCTCGG
2901  AGGCAGGGCG  CTCGGGGAGG  CCTAGCGGCC  AATCTGCGGT  GGCAGGAGGC  GGGGCCGAAG  GCCGTGCCTG  ACCAATCCGG  AGCACATAGG  AGTCTCAGCC
3001  CCCCCGCCCA  AGCAAGGGGG  AAGTCACGCG  CCTGTAGCGC  CAGCGTGTTG  TGAAATGGGG  GCTTGGGGCCC GTTGGGGCCC  TGACTAGTCA  AAACAAACTC
3101  CCATTGACGT  CAATGGGGTG  GAGACTTGGA  AATCCCCGTG  AGTCAACCGTG CCATAAGGTC  CATTGATGT   ACTGCCAAAA  CCGCATCATC  ATGGTAATAG
3201  CGATGACTAA  TACGTAGATG  TACTGCCAAG  TAGGAAAAGTC CCATAAGGTC  ATGTACTGCC  GGCGGGCCAT  TTACCGTCAT  TGACGTCAAT
3301  AGGGGCGTA   CTTGGCATAT  GATACATTGC  ATGTACTGCC  AAGTGGGCAG  TTTACCGTAA  ATACTCCACC  CATTGACGTC  AATGGAAAGT  CCCTATTGGC
3401  GTTACTATGG  GAACATACGT  GTCAATGGC   GCAAAAGGCC  GGGGGTCGTT  GGGGCGGGCC  CCAGGCGGGC  CATTTACCGT  AAGTTATGTA  ACGCCTGCAG
3501  GTTAATTAAG  AACATGTGAG  CAAAAGGCCA  GCAAAAGGCC  AGGAACCGTA  AAAAGGCCGC  GTTGCTGGCG  TTTTTCCATA  GGCTCCGCCC  CCCTGACGAG
3601  CATCACAAAA  ATCGACGCTC  AAGTCAGAGG  TGGCGAAACC  CGACAGGACT  ATAAAGATAC  CAGGCGTTTC  CCCCTGAAG   CTCCCTCGTG  CGCTCTCCTG
3701  TTCCGACCCT  GCCGCTTACC  GGATACCTGT  CCGCCTTTCT  CCCTTCGGGA  AGCGTGGCGC  TTTCTCATAG  CTCACGCTGT  AGGTATCTCA  GTTCGGTGTA
3801  GGTCGTTCGC  TCCAAGCTGG  GCTGTGTGCA  CGAACCCCCC  GTTCAGCCCG  ACCGCTGCGC  CTTATCCGGT  AACTATCGTC  TTGAGTCCAA  CCCGGTAAGA
3901  CACGACTTAT  CGCCACTGGC  AGCAGCCACT  GGTAACAGGA  TTAGCAGAGC  GAGGTATGTA  GGCGGTGCTA  CAGAGTTCTT  GAAGTGGTGG  CCTAACTACG
4001  GCTACACTAG  AAGAACAGTA  TTTGGTATCT  GCGCTCTGCT  GAAGCCAGTT  ACCTTCGGAA  AAAGAGTTGG  TAGCTCTTGA  TCCGGCAAAC  AAACCACCGC
4101  TGGTAGCGGT  GGTTTTTTG   TTTGCAAGCA  GCAGATTACG  CGCAGAAAAA  AAGGATCTCA  AGAAGATCCT  TTGATCTTTT  CTACGGGGTC  TGACGCTCAG
4201  TGGAACGAAA  ACTCACGTTA  AGGGATTTTG  GTCATGAGAT  TATCAAATGG  CATCAAATCA  GCGGCCGCAA  AACAAACTA   TAAAATATCT  TACATCTGTG
4301  TGTTGGTTTT  TGTGTGAAT   ATACGCTCTC  CATCAAAACA  AAACGAAACA  AAACAAACTA  AACAAACTA   CTATTTTCAT  TACATCTGTG  TACATCTGTG
4401  GGTGCCAGAA  CATTTCTCTA  TCGAA  (SEQ ID NO:103)
```

IL2ss.CXCL13(3-87).hIgG4Fc sequence

```
   1  GGATCTGCGA TCGCTCCGGT GCCGTCCAGT GGGCAGAGCG CACATCGCCC ACAGTCCCCG AGAAGTTGGG GGGAGGGGTC GGCAATTGAA CGGGTGCCTA
 101  GAGAAGGTGG CGCGGGGTAA ACTGGGAAAG TGATGTCGTG GCCAGAACAC CGGGTTTGCC AGCTGAAGCT TCGAGGGGCT CGAAGAGTGG CCGAGAACCT CTTCACGCGC GGAGGGGCCT AGTAGTCGCC
 201  GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301  GCCATCCACG CCGGTGAGT CGCTTCTGC CGCTTCTGC TCGTGTGCC TCCTGAACTG CGTCCGCGT CTAGGTAAGT TTAAAGCTCA GGTCGAGACC
 401  GGGCCTTTGT CCGGCGCTCC CTTGGAGCCT ACCTAGCTCT AGCCGGCTCT ACCTAGCTCT CCTGACCCTG CCTGCTCAAC TCTACGTCTT TGTTCCTTT

NarI
                                                      KasI
                                                      SfoI
                                                      BbeI
                                                                                                 IL-2 secretion signal
                                                                                      MetTyrArg MetGlnLeu LeuSerCysIle 501  TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                          EcoRI
                                   ~~~~~ CXCL13 (3-87)
             AlaLeuSer LeuAlaAla ValThrAsnSer GluValTyr TyrThrSer LeuArgCysArg CysValGln GluSerSer ValPheIlePro ArgArgPhe
 601  TTGCACTAAG TCTTGCACTT GTCACGAATT CGGAGGTCTA TTACACAAGC TTGAGGTGTA GATGTGTCCA AGAGAGCTCA GTCTTTATCC CTAGACGTT
                                     EcoRI
             IleAspArg IleGlnIleLeu ProArgGly AsnGlyCys ProArgLysGlu IleIleVal TrpLysLys AsnLysSerIle ValCysVal AspProGln
 701  CATTGATCGA ATTCAAATCT TGCCCCGTGG GAATGGTTGT CCAAGAAAAG AAATCATAGT CTGGAAGAAG AACAAGTCAA TTGTGTGTGT GGACCCTCAA AlaGluTrpIle GlnArgMet MetGluVal LeuArgLysArg SerSerSer ThrLeuPro ValProValPhe LysArgLys IleProPro ProCysProSer
 801  GCTGAATGGA TACAAAGAT GATGGAAGTA TTGAGAAGA GAAGTTCTTC AACTTACTCA GTTCCAGTGT TTAAGAGAAA GATTCCCCC CCATGCCCAT
             CysProAla ProGluPhe LeuGlyGlyPro SerValPhe LeuPhePro ProLysProLys AspThrLeu MetIleSer ArgThrProGlu ValThrCys
 901  TGCCCAGCT CCTGAGTTC CTGGGGGGAC CATCAGTCTT CCTGTTCCCC CCAAAACCCA AGGACACTCT CATGATCTCC CGGACCCCTG AGGTCACGTG
             ValValVal AspValSerGln GluAspPro GluValGln PheAsnTrpTyr ValAspGly ValGluVal HisAsnAlaLys ThrLysPro ArgGluGlu
1001  CGTGGTGGTG GACGTGAGCC AGGAAGACCC CGAGGTCCAG TTCAACTGGT ACGTGGATGG CGTGGAGGTG CATAATGCCA AGACAAAGCC GCGGGAGGAG
             GlnPheAsnSer ThrTyrArg ValValSer ValLeuThrVal LeuHisGln AspTrpLeu AsnGlyLysGlu TyrLysCys LysValSer AsnLysGlyLeu
1101  CAGTTCAACA GCACGTACCG TGTGGTCAGC GTCCTCACCG TCCTGCACCA GGACTGGCTG AACGGCAAGG AGTACAAGTG CAAGGTCTCC AACAAAGGCC
             ProSerSer IleGluLys ThrIleSerLys AlaLysGly GlnProArg GluProGlnVal TyrThrLeu ProProSer GlnGluGluMet ThrLysAsn
1201  TCCCGTCCTC CATCGAGAAA ACCATCTCCA AAGCCAAAGG GCAGCCCCGA GAGCCACAGG TGTACACCCT GCCCCCATCC CAGGAGGAGA TGACCAAGAA
             GlnValSer LeuThrCysLeu ValLysGly PheTyrPro SerAspIleAla ValGluTrp GluSerAsn GlyGlnProGlu AsnAsnTyr LysThrThr
1301  CCAGGTCAGC CTGACCTGCC TGGTCAAAGG CTTCTACCCC AGCGACATCG CCGTGGAGTG GGAGAGCAAT GGGCAGCCGG AGAACAACTA CAAGACCACG
             ProProValLeu AspSerAsp GlySerPhe PheLeuTyrSer ArgLeuThr ValAspLys SerArgTrpGln GluGlyAsn ValPheSer CysSerValMet
1401  CCTCCCGTGC TGGACTCCGA CGGCTCCTTC TTCCTCTACA GCAGGCTAAC CGTGGACAAG AGCAGGTGGC AGGAGGGGAA TGTCTTCTCA TGCTCCGTGA
                                                                                                        BmtI
                                                                                                        NheI
             HisGluAla LeuHisAsn HisTyrThrGln LysSerLeu SerLeuSer ProGlyLys***(SEQ ID NO:77)
1501  TGCATGAGGC TCTGCACAAC CACTACACAC AGAAGAGCCT CTCCCTGTCT CCGGGTAAAT GAGTGCTAGC TGCCCAGACA TGATAAGATA CATTGATGAG
1601  TTGGACAAA CCACAACTAG AATGCAGTGA AAAAAATGCT TTATTTGTGA AATTTGTGAT GCTATTGCTT TATTTGTAAC CATTATAAGC TGCAATAAAC
1701  AAGTTAACAA CAACAATTGC ATTCATTTTA TGTTTCAGGT TCAGGGGGAG GTGTGGGAGG TTTTTTAAAG CAAGTAAAAC CTCTACAAAT GTGGTATGGA
      AseI
```

```
1801  ATTAATTCTA AAATACAGCA TAGCAAAACT TTAACCTCCA AATCAAGCCT CTACTTGAAT CCTTTTCTGA GGGATGAATA AGGCATAGGC ATCAGGGCT
1901  GTTGCCAATG TGCATTAGCT GTTTGCAGCC TCACCTTCTT TCATGGAGTT TAAGATATAG TGTATTTTCC CAAGGTTTGA ACTAGCTCTT CATTTCTTTA
2001  TGTTTTAAAT GCACTGACCT CCCACATTCC CTTTTTAGTA AAATATTCAG GACTTAGGGA AAATAATTTA AATACATCAT TGCAATGAAA ATAAATGTTT TTTATTAGGC
2101  AGAATCCAGA TGCTCAAGGC CCTTCATAAT ATCCCCAGT TTAGTAGTTG GACTTAGGGA ACAAAGGAAC CTTTAATAGA GGCGAACTCC CGCCCCCACG CAAGAAAGCG
2201  AGCTTCTAGC TTATCCTCAG TCCTGCTCCT CTGCCACAAA GTGCACGCAG TTGCCGCCG GGTCGCGGAG AGCTCGTCCA GGCCGCGCAC GCTGCTCGCC
2301  GATCTCGGTC ATGGCCGGCC CGGAGGCGTC CGGAAGTTC GTGGACACGA CCTCCGACCA CTCGGCCTAC AGCTCGTCCA CACCGGCGAC GTCGTCCTCC ACGAAGTCCC
2401  GCCAGGGTGT TGTCCGGCAC CACCTGGTCC TGATGACGCG TGATGAACAG GGTCACGTCG TCCCGACCA CACCGGCGAC GTCGTCCTCC ACGAAGTCCC
2501  GGGAGAACCC GAGCCGGTCG GTCCAGAACT CGACCGCTCC CGACCGCTGA CGCGCCGGTGA GCACCGGAAC GGCACTGGTC AACTTGGCCA TGATGCTCC

AseI
2601  TCCTGTCAGG AGAGGAAAGA GAAGAAGGTT AGTACAATTG CTATAGTGAG TTGTATTATA CTATGCAGAT ATACTATGCC AATGATTAAT TGTCAAACTA
2701  GGGCTGCAGG GTTCATAGTG CCACTTTTCC TGCACTGCCC CATCTCCTGC CCACCCTTTC CCAGGCATAG ACAGTCAGTG ACTTACCAAA CTCACAGGAG
2801  GGAGAAGGCA GAAGCTTGAG ACAGACCGC GGGACCGCCG AACTGCGAGG GGACGTGGCT AGGGCGGCTT CTTTTATGGT GCGCCGGCCC TCGGAGGCAG
2901  GGCGCTCGGG GAGGCCTAGC GGCCAATCTG CGGTGGCAGG GCGGGGGC GAAGGCCGTG CCTGACCAAT AGGGGTTTGG CCGGAGCACA TAGGAGTCTC AGCCCCCGC
3001  CCCAAAGCAA GGGGAAGTCA CGCGCCTGTA GCGCCAGCGT GTTGTGAAAT GGGGCTTGG GTCAAAACAA GTCAAAACAA ACTCCCATTG
3101  ACGTCAATGG GGTGGAGACT TGGAAATCCC CGTGAGTCAA ACCGCTATCC ACGCCATTG ATGTACTGCC AAAACCGAT CATCATGGTA ATAGCGATGA
3201  CTAATACGTA GATGTACTGC CAAGTAGGAA AGTCCCATAA GGTCATGTAC TGGGCATAAT GCCAGGCGGG CCATTACCG TCATTGACGT CAATAGGGGG
3301  CGTACTTGGC ATATGATACA CTTGATGTAC TGCCAAGTGG GCAGTTTACC GTAAATACTC CACCCATTGA CGTCAATGGA AAGTCCCTAT TGGCGTTACT
3401  ATGGAACAT ACGTCATTAT TGACGTCAAT GGGCGGGGGT CGTTGGGCGG TCAGCCAGGC GGGCCATTTA CCGTTACTCC CGTAAGTTA TGTAACGCCT GCAGGTTAAT
3501  TAAGAACATG TGAGCAAAAG GCCAGCAAAA GGCCAGGAAC CGTAAAAAGG CCGCGTTGCT GGCGTTTTTC CATAGGCTC GAAGCTCCCT GCCCCCTGA CGAGCATCAC
3601  AAAAATCGAC GCTCAAGTCA GAGGTGGCGA AACCCGACAG GACTATAAAG ATACCAGGCG TTTCCCCCTG GAAGCTCCCT CGTGCGCTCT CCTGTTCCGA
3701  CCCTGCCGCT TACCGGATAC CTGTCCGCCT TTCTCCCTTC GGGAAGCGTG GCGCTTTCTC ATAGCTCACG CTGTAGGTAT CGTCAGTTCGG TGTAGGTCGT
3801  TCGCTCCAAG CTGGGCTGTG TGCACGAACC CCCGGTTCAG CCCGACCGCT GCGCCTTATC GCGGCCTAAC CCAACCCGGT AAGACACGAC TACGGCTACA
3901  TTATCGCCAC TGGCAGCAGC CACTGGTAAC AGGATTAGCA GAGCGAGGTA AGTTACCTTC GGAAAAAGAG TTGGTAGCTC TTGATCCGGC AAACAAACCA CCGCTGGTAG
4001  CTAGAAGAAC AGTATTTGT TTTGTTTGCA ACCAGCAGAT TACGCGCAGA AAAAAAGGAT CTCAAGAAGA TCCTTTGATC TTTTCTACGG GGTCTGACGC TCAGTGGAAC
4101  CGGTGGTTTT GTTAAGGGAT TTTGGTCATG AATGCGGTAAC TTTGTCATG TAACATTAA TAACATTTAA AACAAAACGA ACTAAACAA TAGGCTGTCC CCAGTGCAAG TGCAGGTGCC
4201  GAAAACTCAC GTTAAGGGAT TTTGGTCATG GCTAGTTAAT AACATTTAA AACAAAACGA ACTAAACAA TAGGCTGTCC CCAGTGCAAG TGCAGGTGCC
4301  TTTTTTGTGT GAATCGTAAC TAACATACGC TCTCCATCAA AACAAAACGA ACTAAACAA TAGGCTGTCC CCAGTGCAAG TGCAGGTGCC
4401  AGAACATTTC TCTATCGAA (SEQ ID NO: 104)
```

IL2ss.CXCL13(3-87).hIgG4Fc sequence [Alanine substitutions for removal of GAG binding sites – Lys & His]

```
   1  GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101  GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201  GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301  GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401  GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                               NarI
                                               KasI
                                               SfoI
                                               BbeI
                                               ~~~~~~~                           IL-2 secretion signal
                                                                                 MetTyrArg MetGlnLeu LeuSerCysIle
 501  TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                               EcoRI
                               ~~~~~~~ CXCL13 (3-87)
       AlaLeuSer LeuAlaLeu ValThrAsnSer GluValTyr TyrThrSer LeuArgCysArg CysValGln GluSerSer ValPheIlePro ArgArgPhe
 601  TTGCACTAAG TCTTGCACTT GTCACGAATT CGGAGGTCTA TTACACAAGC TTGAGGTGTA GATGTGTCCA AGAGAGCTCA GTCTTTATCC CTAGACGCTT
           EcoRI
      IleAspAla IleGlnIleLeu ProArgGly AsnGlyCys ProArgLysGlu IleIleVal TrpAlaAla AsnAlaSerIle ValCysVal AspProGln
 701  CATTGATgcc ATTCAAATCT TGCCCCGTGG GAATGGTTGT CCAAGAAAAG AAATCATAGT CTGGgctgcg AACgctTCAA TTGTGTGTGT GGACCCTCAA
                                                                                              human IgG4 Fc
                                                                                              (constant region)
      AlaGluTrpIle GlnAlaMet MetGluVal LeuAlaAlaAla SerSerSer ThrLeuPro ValProValPhe AlaAlaAla IleProPro ProCysProSer
 801  GCTGAATGGA TACAAgccAT GATGGAAGTA TTGgctgcgg ctAGTTCTTC AACTCTACCA GTTCCAGTGT TTgccgctgc gATTCCCCCC CCATGCCCAT
       CysProAla ProGluPhe LeuGlyGlyPro SerValPhe LeuPhePro ProLysProLys AspThrLeu MetIleSer ArgThrProGlu ValThrCys
 901  CATGCCCAGC ACCTGAGTTC CTGGGGGGAC CATCAGTCTT CCTGTTCCCC CCAAAACCCA AGGACACTCT CATGATCTCC CGGACCCCTG AGGTCACGTG
      ValValVal AspValSerGln GluAspPro GluValGln PheAsnTrpTyr ValAspGly ValGluVal HisAsnAlaLys ThrLysPro ArgGluGlu
1001  CGTGGTGGTG GACGTGAGCC AGGAAGACCC CGAGGTCCAG TTCAACTGGT ACGTGGATGG CGTGGAGGTG CATAATGCCA AGACAAAGCC GCGGGAGGAG
      GlnPheAsnSer ThrTyrArg ValValSer ValLeuThrVal LeuHisGln AspTrpLeu AsnGlyLysGlu TyrLysCys LysValSer AsnLysGlyLeu
1101  CAGTTCAACA GCACGTACCG TGTGGTCAGC GTCCTCACCG TCCTGCACCA GGACTGGCTG AACGGCAAGG AGTACAAGTG CAAGGTCTCC AACAAAGGCC
       ProSerSer IleGluLys ThrIleSerLys AlaLysGly GlnProArg GluProGlnVal TyrThrLeu ProProSer GlnGluGluMet ThrLysAsn
1201  TCCCGTCCTC CATCGAGAAA ACCATCTCCA AAGCCAAAGG GCAGCCCCGA GAGCCACAGG TGTACACCCT GCCCCCATCC CAGGAGGAGA TGACCAAGAA
      GlnValSer LeuThrCysLeu ValLysGly PheTyrPro SerAspIleAla ValGluTrp GluSerAsn GlyGlnProGlu AsnAsnTyr LysThrThr
1301  CCAGGTCAGC CTGACCTGCC TGGTCAAAGG CTTCTACCCC AGCGACATCG CCGTGGAGTG GGAGAGCAAT GGGCAGCCGG AGAACAACTA CAAGACCACG
      ProProValLeu AspSerAsp GlySerPhe PheLeuTyrSer ArgLeuThr ValAspLys SerArgTrpGln GluGlyAsn ValPheSer CysSerValMet
1401  CCTCCCGTGC TGGACTCCGA CGGCTCCTTC TTCCTCTACA GCAGGCTAAC CGTGGACAAG AGCAGGTGGC AGGAGGGGAA TGTCTTCTCA TGCTCCGTGA
                                                                             BmtI
                                                                             NheI
       HisGluAla LeuHisAsn HisTyrThrGln LysSerLeu SerLeuSer ProGlyLys***(SEQ ID NO:78)
1501  TGCATGAGGC TCTGCACAAC CACTACACAC AGAAGAGCCT CTCCCTGTCT CCGGGTAAAT GAGTGCTAGC TGGCCAGACA TGATAAGATA CATTGATGAG
1601  TTTGGACAAA CCACAACTAG AATGCAGTGA AAAAAATGCT TTATTTGTGA AATTTGTGAT GCTATTGCTT TATTTGTAAC CATTATAAGC TGCAATAAAC
1701  AAGTTAACAA CAACAATTGC ATTCATTTTA TGTTTCAGGT TCAGGGGGAG GTGTGGGAGG TTTTTTAAAG CAAGTAAAAC CTCTACAAAT GTGGTATGGA
```

```
                 AseI
1801  ATTAATTCTA AAATACAGCA TAGCAAAAACT TTAACCTCCA AATCAAGCCT CTACTTGAAT CCTTTTCTGA GGGATGAATA AGGCATAGCC ATCAGGGCT
1901  GTTGCCAATG TGCATTAGCT GTTTGCAGCC CCCACATTCC TCACCTTCTT TCATGGAGTT TAAGATATAG TGTATTTTCC CAAGGTTTGA ACTAGTCTT CATTCTTTA
2001  TGTTTTAAAT GCACTGACCT CCCACATTCC CTTTTAGTA AAATATTCAG AAATAATTTA GACTTAGGGA ACAAAGAAC TGCAATGAAA CTTTAATGTTT TTTATTAGC
2101  AGAATCCAGA TGCTCAAGGC CCTTCATAAT ATCCCCAGT TTAGTAGTTG GTCACGCAG CCTCCGACCA TTGCCGGCCG GGCGAACTCC CTTTAATAGA CGCCCCCACG CAAGAAAGCG
2201  AGCTTCTAGC TTATCCTCAG TCCTGCTCCT CTGCCACAAA GTGCACGCAG CCTCCGACCA CTCAGCCGAC AGCTGTCCA GGCGAACTCC GCCCCCACG GCTGCTCCGC
2301  GATCTCGGTC ATGGCCGGCC CGGAGGCGTC GTGACACGA CCCGACCA GGTCACGTCG TCCCGGACCA CACCGGCGAA GTCGTCCTCC CCACACCCAG
2401  GCCAGGGTGT TGTCCGGCAC CACCTGGTCC TGGACCGCGC TGATGAACAG GGTCACGTCG TCCCGGACCA CACCGGCGAA GTCGTCCTCC ACGAAGTCCC
2501  GGGAGAACCC GAGCCGGTCG GTCCAGAACT CGACCGCTCC GGCGACGTCG CGCGGGTGA GCACCGGAAC GGCACTGGTC AACTTGGCCA TGATGGCTCC
                                                                                                        AseI
2601  TCCTGTGTCAGG AGAGGAAAGA GAAGAAGGTT AGTACAATTG CTATAGTGAG TTGTATTATA CTATGCAGAT ATACTATGCC AATGATTAAT TGTCAAACTA
2701  GGGCTGCAGG GTTCATAGTG CCACTTTTCC TGCACTGCCC CATCTCCTGC CCACCCTTTC CCAGGCATAG ACAGTCAGTG ACTTACCAAA CTCACAGGAG
2801  GGAGAAGGCA GAAGCTTGAG ACAGACCCGC GGGACCGCG AACTGCGAGG AGGGCCTGCT AGGGCCGCTT CTTTTATGGT GCGCCGGCCC TCGGAGGCAG
2901  GGGCTCGGG GAGGCCTAGC GCCCAATCTG CGGTGGCAGG AGGGCGGGCC CCTGACCAAT CCTGACCGTG CCGAGCACA TAGGAGTCTC AGCCCCCGC
3001  CCCAAAGCAA GGGGAAGTCA CGGCCCTGTA GCGCCAGCGT GTTGTGAAAT GGGGGCTTGG GGGGTTGGG GCCCTGACTA GTCAAAACAA ACTCCATTG
3101  ACGTCAATGG GGTGGAGACT TGGAAATCCC CGTGAGTCAA ACCGCTATCC ACGCCCATTG ATGTACTGCC AAAACCGCAT CATCATGGTA ATAGCGATGA
3201  CTAATACGTA GATGTACTGC CAAGTAGGAA AGTCCCATAA TGGGCATAAT CCCAGGCGGG GTAAATACTC GCCAGGCGGG CCATTACCG TCATTGACGT CAATAGGGGG
3301  CGTATTGGGC ATATGATACA CTTGATGTAC TGCCAAGTGG GCAGTTTACC GTAAGCTTTA CCCCATTGA CGTCAATGGA AGTCCCTAT TGGCCTTACT
3401  ATGGAACAT AGTCATTAT TGACGTCAAT GCCAGCAAAG GGCCAGCAAAG AACCCGACCG CGTTGGGGT TCAGCCAGGC CCGTAAGTTA TGTAACGCCT GCAGTTAAT
3501  TAAGAACATG TGAGCAAAAG GCCAGCAAAG GCCAGGAACC AACCCGACAG GACTATAAG CCGCGTTGCT CGGCGTTTTC CATAGGCTCC GCCCCCCTGA CGAGCATCAC
3601  AAAAATCGAC GCTCAAGTCA GAGGTGGCGA AACCCGACAG GACTATAAG ATACCAGGCG TTTCCCCCTG GAAGCTCCT CGTGCGCTCT CCTGTTCCGA
3701  CCCTGCCGCT TACCGGATAC CTGTCCGCCT TTCTCCCTTC GGGAAGCGTG GCGCTTTCTC ATAGCTCACG CTGTAGGTAT CTCAGTTCGG TGTAGGTCGT
3801  TCGCTCCAAG CTGGGCTGTG TGCACGAACC CCCCGTTCAG CCCGACCGCT GCGCCTTATC CGGTAACTATC CGGCCTTATC CAACCCGGT AAGACACGAC
3901  TTATGCCAC TGGCAGCAGC CACTGGTAAC AGGATTAGCA GAGCGAGGTA TGTAGGCGGT GCTACAGAGT TCTTGAAGTG GTGGCCTACA ACGCTGGTAG
4001  CTAGAAGAAC AGTATTTGGT ATCTGCGCTC TGCTGAAGCC AGTTACCTTC GGAAAAAGAG TTGATCCGGC AAACAAACCA CCGCTGGTAG
4101  CGGTGGTTTT TTTGTTTGCA AGCAGCAGAT TACGCGCAGA AAAAAAGGAT CTCAAGAAGA TCCTTTGATC TTTTCTACGG GGTCTGACGC TCAGTGAAC
4201  GAAAACTCAC GTTAAGGGAT TTTGGTCATG GCTAGTTAAT TAACATTTAA GCAATAAAAT ATCTTTATTT TCATTACATC TGTGTGTGG
4301  TTTTTGTGT GAATCGTAAC TAACATACGC TCTCCATCAA AACAAAACGA ACTAGCAAAA TAGGCTGTCC CCAGTGCAAG TGCAGGTGCC
4401  AGAACATTTC TCTATCGAA (SEQ ID NO:105)
```

KineMap #3

⚡ indicate potential sites for pegylation of CXCL11.

CCL1      NP_002972        SEQ ID NO:1
mqiittalvc lllagmwped vdsksmqvpf srccfsfaeq eiplrailcy rntssicsne
glifklkrgk eacaldtvgw vqrhrkmlrh cpskrk

CCL2      NP_002973        SEQ ID NO:2
mkvsaallcl lliaatfipq glaqpdaina pvtccynftn rkisvqrlas yrritsskcp
keavifktiv akeicadpkq kwvqdsmdhl dkqtqtpkt

CCL3      NP_002974        SEQ ID NO:3
mqvstaalav llctmalcnq fsaslaadtp taccfsytsr qipqnfiady fetssqcskp
gvifltkrsr qvcadpseew vqkyvsdlel sa

CCL4      NP_002975        SEQ ID NO:4
mklcvtvlsl lmlvaafcsp alsapmgsdp ptaccfsyta rklprnfvvd yyetsslcsq
pavvfqtkrs kqvcadpses wvqeyvydle ln

CCL4L1    NP_001001435     SEQ ID NO:5
mklcvtvlsl lvlvaafcsl alsapmgsdp ptaccfsyta rklprnfvvd yyetsslcsq
pavvfqtkrg kqvcadpses wvqeyvydle ln

CCL5      NP_002976        SEQ ID NO:6
mkvsaaalav iliatalcap asaspyssdt tpccfayiar plprahikey fytsgkcsnp
avvfvtrknr qvcanpekkw vreyinslem s

CCL7      NP_006264        SEQ ID NO:7
mkasaallcl lltaaafspq glaqpvgint sttccyrfin kkipkqrles yrrttsshcp
reavifktkl dkeicadptq kwvqdfmkhl dkktqtpkl

CCL8      NP_005614        SEQ ID NO:8
mkvsaallcl llmaatfspq glaqpdsvsi pitccfnvin rkipiqrles ytritniqcp
keavifktkr gkevcadpke rwvrdsmkhl dqifqnlkp

CCL11     CAG33702         SEQ ID NO:9
mkvsaallwl lliaaafspq glagpasvpt tccfnlanrk iplqrlesyr ritsgkcpqk
avifktklak dicadpkkkw vqdsmkyldq ksptpkp

CCL13     NP_005399        SEQ ID NO:10
mkvsavllcl llmtaafnpq glaqpdalnv pstccftfss kkislqrlks yvittsrcpq
kavifrtklg keicadpkek wvqnymkhlg rkahtlkt

CCL14-1   NP_116739        SEQ ID NO:11
mkisvaaipf fllitialgt ktesssrgpy hpseccftyt tykiprqrim dyyetnsqcs
kpgivfitkr ghsvctnpsd kwvqdyikdm ken

CCL14-2   NP_116738        SEQ ID NO:12
mkisvaaipf fllitialgt ktesssqtgg kpkvvkiqlk lvggpyhpse ccftyttyki
prqrimdyye tnsqcskpgi vfitkrghsv ctnpsdkwvq dyikdmken

FIG. 12 (CONT)

CCL15    NP_116741    SEQ ID NO:13
mkvsvaalsc lmlvavlgsq aqfindaete lmmsklplen pvvlnsfhfa adcctsyisq
sipcslmksy fetssecskp gvifltkkgr qvcakpsgpg vqdcmkklkp ysi

CCL16    NP_004581    SEQ ID NO:14
mkvseaalsl lvliliitsa srsqpkvpew vntpstcclk yyekvlprrl vvgyrkalnc
hlpaiifvtk rnrevctnpn ddwvqeyikd pnlpllptrn lstvkiitak ngqpqllnsq

CCL17    NP_002978    SEQ ID NO:15
maplkmlalv tlllgaslqh ihaargtnvg reccleyfkg aiplrklktw yqtsedcsrd
aivfvtvqgr aicsdpnnkr vknavkylqs lers

CCL18    NP_002979    SEQ ID NO:16
mkglaaallv lvctmalcsc aqvgtnkelc clvytswqip qkfivdyset spqcpkpgvi
lltkrgrqic adpnkkwvqk yisdlklna

CCL19    NP_006265    SEQ ID NO:17
malllalsll vlwtspaptl sgtndaedcc lsvtqkpipg yivrnfhyll ikdgcrvpav
vfttlrgrql cappdqpwve riiqrlqrts akmkrrss

CCL20-1    NP_004582    SEQ ID NO:18
mcctksllla almsvlllhl cgeseaasnf dcclgytdri lhpkfivgft rqlanegcdi
naiifhtkkk lsvcanpkqt wvkyivrlls kkvknm

CCL20-2    NP_001123518    SEQ ID NO:19
mcctksllla almsvlllhl cgeseasnfd cclgytdril hpkfivgftr qlanegcdin
aiifhtkkkl svcanpkqtw vkyivrllsk kvknm

CCL21    NP_002980    SEQ ID NO:20
maqslalsll ilvlafgipr tqgsdggaqd cclkysqrki pakvvrsyrk qepslgcsip
ailflprkrs qaelcadpke lwvqqlmqhl dktpspqkpa qgcrkdrgas ktgkkgkgsk
gckrtersqt pkgp

CCL22    NP_002981    SEQ ID NO:21
mdrlqtallv vlvllavalq ateagpygan medsvccrdy vryrlplrvv khfywtsdsc
prpgvvlltf rdkeicadpr vpwvkmilnk lsq

CCL23-1    NP_665905    SEQ ID NO:22
mkvsvaalsc lmlvtalgsq arvtkdaete fmmsklplen pvlldrfhat sadccisytp
rsipcslles yfetnsecsk pgvifltkkg rrfcanpsdk qvqvcvrmlk ldtriktrkn

CCL23-2    NP_005055    SEQ ID NO:23
mkvsvaalsc lmlvtalgsq arvtkdaete fmmsklplen pvlldmlwrr kigpqmtlsh
aagfhatsad ccisytprsi pcsllesyfe tnsecskpgv ifltkkgrrf canpsdkqvq
vcvrmlkldt riktrkn

CCL24    NP_002982    SEQ ID NO:24
maglmtivts llflgvcahh iiptgsvvip spccmffvsk ripenrvvsy qlssrstclk
agvifttkkg qqfcgdpkqe wvqrymknld akqkkaspra ravavkgpvq rypgnqttc

FIG. 12 (CONT)

CCL25-1   NP_005615   SEQ ID NO:25
mnlwllaclv agflgawapa vhtqgvfedc clayhypigw avlrrawtyr iqevsgscnl
paaifylpkr hrkvcgnpks revqramkll darnkvfakl hhntqtfqag phavkklssg
nsklssskfs npissskrnv sllisansgl

CCL25-2   NP_683686   SEQ ID NO:26
mnlwllaclv agflgawapa vhtqgvfedc clayhypigw avlrrawtyr iqevsgscnl
paairpscck evefwklqvi ivqv

CCL25-3   EAW68951   SEQ ID NO:27
mnlwllaclv agflgawapa vhtqgvfedc clayhypigw avlrrawtyr iqevsgscnl
paairpscck evefwklqvi iiqv

CCL26   NP_006063   SEQ ID NO:28
mmglslasav llasllslhl gtatrgsdis ktccfqyshk plpwtwvrsy eftsnscsqr
avifttkrgk kvcthprkkw vqkyisllkt pkql

CCL27   NP_006655   SEQ ID NO:29
mkgpptfcsl lllslllspd ptaafllpps tacctqlyrk plsdkllrkv iqvelqeadg
dchlqafvlh laqrsicihp qnpslsqwfe hqerklhgtl pklnfgmlrk mg

CCL28   NP_683513   SEQ ID NO:30
mqqrglaiva lavcaalhas eailpiassc ctevshhisr rllervnmcr iqradgdcdl
aavilhvkrr ricvsphnht vkqwmkvqaa kkngkgnvch rkkhhgkrns nrahqgkhet
yghktpy

CXCL1   NP_001502   SEQ ID NO:31
maraalsaap snprllrval lllllvaagr raagasvate lrcqclqtlq gihpkniqsv
nvkspgphca qteviatlkn grkaclnpas pivkkiiekm lnsdksn

CXCL2   NP_002080   SEQ ID NO:32
maratlsaap snprllrval lllllvaasr raagaplate lrcqclqtlq gihlkniqsv
kvkspgphca qteviatlkn gqkaclnpas pmvkkiiekm lkngksn

CXCL3   NP_002081   SEQ ID NO:33
mahatlsaap snprllrval lllllvaasr raagasvvte lrcqclqtlq gihlkniqsv
nvrspgphca qteviatlkn gkkaclnpas pmvqkiieki lnkgstn

CXCL4   NP_002610   SEQ ID NO:34
mssaagfcas rpgllflgll llplvvafas aeaeedgdlq clcvkttsqv rprhitslev
ikagphcpta qliatlkngr kicldlqapl ykkiikklle s

CXCL5   NP_002985   SEQ ID NO:35
msllssraar vpgpssslca llvlllllltq pgpiasagpa aavlrelrcv clqttqgvhp
kmisnlqvfa igpqcskvev vaslkngkei cldpeapflk kviqkildgg nken

CXCL6   NP_002984   SEQ ID NO:36
mslpssraar vpgpsgslca llalllllltp pgplasagpv savltelrct clrvtlrvnp
ktigklqvfp agpqcskvev vaslkngkqv cldpeapflk kviqkildsg nkkn

FIG. 12 (CONT)

CXCL7        NP_002695          SEQ ID NO:37
mslrldttps cnsarplhal qvlllllslll talasstkgq tkrnlakgke esldsdlyae
lrcmciktts gihpkniqsl evigkgthcn qveviatlkd grkicldpda prikkivqkk
lagdesad

CXCL8        NP_000575          SEQ ID NO:38
mtsklavall aaflisaalc egavlprsak elrcqcikty skpfhpkfik elrviesgph
canteiivkl sdgrelcldp kenwvqrvve kflkraens

CXCL9        NP_002407          SEQ ID NO:39
mkksgvlfll giilllvligv qgtpvvrkgr cscistnqgt ihlqslkdlk qfapspscek
ieiiatlkng vqtclnpdsa dvkelikkwe kqvsqkkkqk ngkkhqkkkv lkvrksqrsr
qkktt

CXCL10       NP_001556          SEQ ID NO:40
mnqtailicc lifltlsgiq gvplsrtvrc tcisisnqpv nprsleklei ipasqfcprv
eiiatmkkkg ekrclnpesk aiknllkavs kerskrsp

CXCL11       NP_005400          SEQ ID NO:41
msvkgmaial avilcatvvq gfpmfkrgrc lcigpgvkav kvadiekasi mypsnncdki
eviitlkenk gqrclnpksk qarliikkve rknf

CXCL12       NP_000600          SEQ ID NO:42
mnakvvvvlv lvltalclsd gkpvslsyrc pcrffeshva ranvkhlkil ntpncalqiv
arlknnnrqv cidpklkwiq eylekalnkr fkm

CXCL13       NP_006410          SEQ ID NO:43
mkfistslll mllvsslspv qgvlevyyts lrcrcvqess vfiprrfidr iqilprgngc
prkeiivwkk nksivcvdpq aewiqrmmev lrkrssstlp vpvfkrkip

CXCL16       NP_071342          SEQ ID NO:44
msgsqsevap spqsprspem grdlrpgsrv llllllllllv yltqpgngne gsvtgscycg
krissdspps vqfmnrlrkh lrayhrclyy trfqllswsv cggnkdpwvq elmscldlke
cghaysgiva hqkhllptsp pisqasegas sdihtpaqml lstlqstqrp tlpvgslssd
keltrpnett ihtaghslaa gpeagenqkq peknagptar tsatvpvlcl laiifiltaa
lsyvlckrrr gqspqsspdl pvhyipvapd snt

XCL1         AAH69817           SEQ ID NO:45
mrllilallg icsltayive gvgsevsdkr tcvslttqrl pvsriktyti tegslravif
itkrglkvca dpqatwvrdv vrsmdrksnt rnnmiqtkpt gtqqstntav tltg

XCL2         NP_003166          SEQ ID NO:46
mrllilallg icsltayive gvgsevshrr tcvslttqrl pvsriktyti tegslravif
itkrglkvca dpqatwvrdv vrsmdrksnt rnnmiqtkpt gtqqstntav tltg

FIG. 12 (CONT)

CX3CL1        NP_002987          SEQ ID NO:47
mapislswll rlatfchltv llagqhhgvt kcnitcskmt skipvallih yqqnqascgk
raiiletrqh rlfcadpkeq wvkdamqhld rqaaaltrng gtfekqigev kprttpaagg
mdesvvlepe atgesssslep tpssqeaqra lgtspelptg vtgssgtrlp ptpkaqdggp
vgtelfrvpp vstaatwqss aphqpgpslw aeaktseaps tqdpstqast asspapeena
psegqrvwgq gqsprpensl ereemgpvpa htdafqdwgp gsmahvsvvp vssegtpsre
pvasgswtpk aeepihatmd pqrlgvlitp vpdaqaatrr qavgllaflg llfclgvamf
tyqslqgcpr kmagemaegl ryiprscgsn syvlvpv

IgG1Fc        CBX54381.1         SEQ ID NO:48
sepkscdkth tcppcpapel lggpsvflfp pkpkdtlmis rtpevtcvvv dvshedpevk
fnwyvdgvev hnaktkpree qynstyrvvs vltvlhqdwl ngkeykckvs nkalpapiek
tiskakgqpr epqvytlpps rdeltknqvs ltclvkgfyp sdiavewesn gqpennyktt
ppvldsdgsf flyskltvdk srwqqgnvfs csvmhealhn hytqkslsls pgk

IgG2Fc        CBX54382.1         SEQ ID NO:49
erkccvecpp cpappvagps vflfppkpkd tlmisrtpev tcvvvdvshe dpevqfnwyv
dgvevhnakt kpreeqfnst frvvsvltvv hqdwlngkey kckvsnkglp apiektiskt
kgqprepqvy tlppsreemt knqvsltclv kgfypsdiav ewesngqpen nykttppmld
sdgsfflysk ltvdksrwqq gnvfscsvmh ealhnhytqk slslspgk

IgG3Fc        CBX54383.1         SEQ ID NO:50
elktplgdtt htcprcpepk scdtpppcpr cpepkscdtp ppcprcpepk scdtpppcpr
cpapellggp svflfppkpk dtlmisrtpe vtcvvvdvsh edpevqfkwy vdgvevhnak
tkpreeqfns tfrvvsvltv lhqdwlngke ykckvsnkal papiektisk tkgqprepqv
ytlppsreem tknqvsltcl vkgfypsdia vewessgqpe nnynttppml dsdgsfflys
kltvdksrwq qgnifscsvm healhnrftq kslslspgk

IgG4Fc        CBX54384.1         SEQ ID NO:51
eskygppcps cpapeflggp svflfppkpk dtlmisrtpe vtcvvvdvsq edpevqfnwy
vdgvevhnak tkpreeqfns tyrvvsvltv vhqdwlngke ykckvsnkgl pssiektisk
akgqprepqv ytlppsqeem tknqvsltcl vkgfypsdia vewesngqpe nnykttppvl
dsdgsfflys rltvdksrwq egnvfscsvm healhnhytq kslslslgk

US 8,541,564 B2

CHEMOKINE-IMMUNOGLOBULIN FUSION POLYPEPTIDES, COMPOSITIONS, METHOD OF MAKING AND USE THEREOF

This application claims the priority of U.S. Provisional Patent Application No. 61/492,260, filed on Jun. 1, 2011. The entirety of the aforementioned application is incorporated herein by reference.

FIELD

The present application generally relates to compositions that can be used for treating chemokine receptor-mediated disorders and modulating inflammation, inflammatory cell motility, cancer cell motility, or cancer cell survival.

BACKGROUND

Chemokines are chemotactic cytokines, of molecular weight 6-15 kDa, that are released by a wide variety of cells to attract and activate, among other cell types, macrophages, T and B lymphocytes, eosinophils, basophils and neutrophils. There are four classes of chemokines, CXC, CC, C, and CX3C, depending on whether the first two cysteines in the amino acid sequence are separated by a single amino acid (CXC) or are adjacent (CC). Unlike other chemokines, C chemokines have only two cysteines; one N-terminal and one downstream cysteine. The only CX3C chemokine, CX3CL1, has three amino acids between two N-terminal cysteines. The CXC chemokines, such as interleukin-8 (IL-8/CXCL8), neutrophil-activating protein-2 (NAP-2/CXCL7) and melanoma growth stimulatory activity protein (MGSA/CXCL1) are chemotactic primarily for neutrophils and T lymphocytes, whereas the CC chemokines, such as RANTES/CCL5, MIP-1α/CCL3, MJP-1β/CCL4, the monocyte chemotactic proteins (MCP-1/CCL2, MCP-2/CCL8, MCP-3/CCL7, MCP-4/CCL13, and MCP-5/CCL12) and the eotaxins (−1/CCL11 and −2/CCL24) are chemotactic for, among other cell types, macrophages, T lymphocytes, eosinophils, dendritic cells, and basophils. There also exist the chemokines lymphotactin-1/XCL1, lymphotactin-2/XCL2 (both C chemokines), and fractalkine/CX3CL1 (a CX3C chemokine) that do not fall into either of the major chemokine subfamilies, CXC and CC.

Chemokines bind to specific cell-surface receptors belonging to the family of G-protein-coupled seven-transmembrane-domain proteins, which are termed "chemokine receptors." On binding to their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration.

Chemokine receptors have been implicated as being important mediators of inflammatory, infectious, and immunoregulatory disorders and diseases, including cancer, asthma and allergic diseases, as well as autoimmune pathologies such as rheumatoid arthritis and atherosclerosis. For example, the chemokine receptor CCR3 plays a pivotal role in attracting eosinophils to sites of allergic inflammation and in subsequently activating these cells. The chemokine ligands for CCR3 induce a rapid increase in intracellular calcium concentration, increased expression of cellular adhesion molecules, cellular degranulation, and the promotion of eosinophil migration. Another chemokine receptor, CCR2, contributes to cancer progression and can induce tumor cell proliferation or chemotaxis. Accordingly, agents which modulate chemokine receptors would be useful in such disorders and diseases.

Chemokines have also been implicated in the pathogenesis of cell proliferative disorders, including for example induction of tumor angiogenesis and growth. Many tumor cells have also been shown to express chemokine receptors, such as CXCR1, CXCR2, CXCR3, CXCR4, CXCR5, CXCR6, CXCR7, CX3CL1, CCR2, CCR5, and CCR9, and thus tumor cells may also stimulate their own growth, migration, and/or invasion when responding to secreted chemokines.

Chemokines are critical for leukocyte recruitment to injured tissues and play an important role in the wound healing process. Impaired wound healing in diabetic patients is accompanied by decreased early inflammatory cell infiltration, but persistence of neutrophils and macrophages leading to chronic, nonhealing wounds. Chemokines may have both direct and inflammatory-mediated effects on many different aspects of diabetic wound healing, including: impairments in growth factor expression, angiogenesis, extracellular matrix formation, and reepithelialization. Certain chemokine receptor expression in wounds may accelerate healing, and be beneficial in the context of surgery, chronic ulcers, and other conditions.

Chemokine receptors therefore represent promising targets for the development of novel anti-inflammatory and anti-tumor as well as angiostatic, angiogenic, and wound healing agents. Thus, there remains a need for compositions that are capable of modulating activity of chemokine receptors.

SUMMARY

One aspect of the present application relates to an isolated chemokine-immunoglobulin fusion polypeptide having a chemokine moiety and an immunoglobulin moiety, wherein the chemokine moiety comprises a chemokine selected from the group consisting of human CCL1, CCL2, CCL3, CCL4, CCL4L1, CCL5, CCL7, CCL8, CCL11, CCL13, CCL14-1, CCL14-2, CCL15, CCL16, CCL17, CCL 18, CCL19, CCL20-1, CCL20-2, CCL21, CCL22, CCL23-1, CCL23-1, CCL24, CCL25-1, CCL25-2, CCL25-3, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof and wherein the immunoglobulin moiety comprises a peptide selected from the group consisting of the constant region of human Ig G1, the constant region of human Ig G2, the constant region of human Ig G3, the constant region of human Ig G4, and functional variants thereof. In one embodiment, the isolated chemokine-immunoglobulin fusion polypeptide is a pegylated chemokine-immunoglobulin fusion polypeptide.

In one particular embodiment, the chemokine-immunoglobulin fusion polypeptide is selected from the group consisting of CCL2-IgG1Fc, CCL2(5-76)-IgG1Fc, CCL2(5-76K/H→A)-IgG1Fc, CCL2-IgG4Fc, CCL2(5-76)-IgG4Fc, CCL2(5-76K/H→A)-IgG4Fc, CCL7-IgG1Fc, CCL7(5-76)-IgG1Fc, CCL7(5-76K/H→A)-IgG1Fc, CCL7-IgG4Fc, CCL7(5-76)-IgG4Fc, CCL7(5-76K/H→A)-IgG4Fc, CCL8-IgG1Fc, CCL8(5-76)-IgG1Fc, CCL8(5-76K/H/R→A)-IgG1Fc, CCL8-IgG4Fc, CCL8(5-76)-IgG4Fc, CCL8(5-76K/H/R→A)-IgG4Fc, CCL13-IgG1Fc, CCL13(5-75)-IgG1Fc, CCL13(5-75K/H→A)-IgG1Fc, CCL13-IgG4Fc, CCL13(5-75)-IgG4Fc, CCL13(5-75K/H→A)-IgG4Fc, CCL25-IgG1Fc, CCL25(4-127)-IgG1Fc, CCL25(4-127K/H/R→A)-IgG1Fc, CCL25-IgG4Fc, CCL25(4-127)-IgG4Fc, CCL25(4-127K/H/R→A)-IgG4Fc, CXCL11-IgG1Fc, CXCL11(4-73)-IgG1Fc, CXCL11(4-73K/H/R→A)-IgG1Fc, CXCL11-IgG4Fc, CXCL11(4-73)-IgG4Fc, CXCL11(4-73K/R→A)-IgG4Fc, CXCL12α-IgG1Fc, CXCL12α(3-67)-IgG1Fc, CXCL12α(3-67K/R→A)-IgG1Fc, CXCL12α-IgG4Fc, CXCL12α(3-67)-IgG4Fc, CXCL12α(3-67K/R→A)-IgG4Fc, CXCL13-IgG1Fc, CXCL13(3-87)-IgG1Fc, CXCL13(3-87K/R→A)-IgG1Fc, CXCL13-IgG4Fc, CXCL13(3-87)-IgG4Fc, and CXCL13(3-87K/R→A)-IgG4Fc.

Another aspect of the present application is directed to an isolated polynuecleotide encoding a chemokine-immunoglobulin fusion polypeptide having a chemokine moiety and an immunoglobulin moiety, wherein the chemokine moiety comprises a chemokine selected from the group consisting of human CCL1, CCL2, CCL3, CCL4, CCL5, CCL7, CCL8, CCL11, CCL13, CCL14, CCL15, CCL16, CCL17, CCL19, CCL21, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, XCL1, XCL2, CX3CL1 and functional variants thereof and wherein the immunoglobulin moiety comprises a peptide selected from the group consisting of the constant regions of human IgG1 (hIgG1Fc), the constant regions of human IgG2 (hIgG2Fc), the constant regions of human IgG3 (hIgG3Fc), the constant regions of human IgG4 (hIgG4Fc), and functional variants thereof.

In a particular embodiment, the isolated polynuecleotide encoding a cchemokine-immunoglobulin fusion polypeptide is selected from the group consisting of CCL2-IgG1Fc, CCL2 (5-76)-IgG1Fc, CCL2(5-76K/H→A)-IgG1Fc, CCL2-IgG2Fc, CCL2(5-76)-IgG2Fc, CCL2(5-76K/H→A)-IgG2Fc, CCL2-IgG3Fc, CCL2(5-76)-IgG3Fc, CCL2(5-76K/H→A)-IgG3Fc, CCL2-IgG4Fc, CCL2(5-76)-IgG4Fc, CCL2(5-76K/H→A)-IgG4Fc, CCL7-IgG1Fc, CCL7(5-76)-IgG1Fc, CCL7(5-76K/H→A)-IgG1Fc, CCL7-IgG2Fc, CCL7(5-76)-IgG2Fc, CCL7(5-76K/H→A)-IgG2Fc, CCL7-IgG3Fc, CCL7(5-76)-IgG3Fc, CCL7(5-76K/H→A)-IgG3Fc, CCL7-IgG4Fc, CCL7(5-76)-IgG4Fc, CCL7(5-76K/H→A)-IgG4Fc, CCL8-IgG1Fc, CCL8(5-76)-IgG1Fc, CCL8(5-76K/H/R→A)-IgG1Fc, CCL8-IgG1Fc, CCL8(5-76)-IgG1Fc, CCL8(5-76K/H/R→A)-IgG1Fc, CCL8-IgG2Fc, CCL8(5-76)-IgG2Fc, CCL8(5-76K/H/R→A)-IgG2Fc, CCL8-IgG3Fc, CCL8(5-76)-IgG3Fc, CCL8(5-76K/H/R→A)-IgG3Fc, CCL8-IgG4Fc, CCL8(5-76)-IgG4Fc, CCL8(5-76K/H/R→A)-IgG4Fc, CCL13-IgG1Fc, CCL13(5-75)-IgG1Fc, CCL13(5-75K/H→A)-IgG1Fc, CCL13-IgG2Fc, CCL13(5-75)-IgG2Fc, CCL13(5-75K/H→A)-IgG2Fc, CCL13-IgG3Fc, CCL13(5-75)-IgG3Fc, CCL13(5-75K/H→A)-IgG3Fc, CCL13-IgG4Fc, CCL13(5-75)-IgG4Fc, CCL13(5-75K/H→A)-IgG4Fc, CCL25-IgG1Fc, CCL25(4-127)-IgG1Fc, CCL25(4-127K/H/R→A)-IgG1Fc, CCL25-IgG2Fc, CCL25(4-127)-IgG2Fc, CCL25(4-127K/H/R→A)-IgG2Fc, CCL25-IgG3Fc, CCL25(4-127)-IgG3Fc, CCL25(4-127K/H/R→A)-IgG3Fc, CCL25-IgG4Fc, CCL25(4-127)-IgG4Fc, CCL25(4-127K/H/R→A)-IgG4Fc, CXCL11-IgG1Fc, CXCL11(4-73)-IgG1Fc, CXCL11(4-73K/R→A)-IgG1Fc, CXCL11-IgG2Fc, CXCL11(4-73)-IgG2Fc, CXCL11(4-73K/R→A)-IgG2Fc, CXCL11-IgG3Fc, CXCL11(4-73)-IgG3Fc, CXCL11(4-73K/R→A)-IgG3Fc, CXCL11-IgG4Fc, CXCL11(4-73)-IgG4Fc, CXCL11(4-73K/R→A)-IgG4Fc, CXCL12α-IgG1Fc, CXCL12α(3-67)-IgG1Fc, CXCL12α(3-67K/R→A)-IgG1Fc, CXCL12α-IgG2Fc, CXCL12α(3-67)-IgG2Fc, CXCL12α(3-67K/R→A)-IgG2Fc, CXCL12α-IgG3Fc, CXCL12α(3-67)-IgG3Fc, CXCL12α(3-67K/R→A)-IgG3Fc, CXCL12α-IgG4Fc, CXCL12α(3-67)-IgG4Fc, CXCL12α(3-67K/R→A)-IgG4Fc, CXCL13-IgG1Fc, CXCL13(3-87)-IgG1Fc, CXCL13(3-87K/R→A)-IgG1Fc, CXCL13-IgG2Fc, CXCL13(3-87)-IgG2Fc, CXCL13(3-87K/R→A)-IgG2Fc, CXCL13-IgG3Fc, CXCL13(3-87)-IgG3Fc, CXCL13(3-87K/R→A)-IgG3Fc, CXCL13-IgG4Fc, CXCL13(3-87)-IgG4Fc, and CXCL13(3-87K/R→A)-IgG4Fc.

A further aspect of the present application is directed to a pharmaceutical composition comprising (1) a chemokine-immunoglobulin fusion polypeptide of the present application or an expression vector encoding a chemokine-immunoglobulin fusion polypeptide of the present application, and (2) a pharmaceutically acceptable carrier.

A further aspect of the present application is directed to a method for treating a chemokine receptor-mediated disorder in a subject, comprising administering to said subject an effective amount of the pharmaceuical composition of the present application.

Another aspect of the present application relates to a method for modulating inflammation in a subject, comprising comprising administering to said subject an effective amount of the pharmaceuical composition of the present application.

Another aspect of the present application relates to a method for treating a chemokine receptor-mediated disorder in a subject, comprising administering to said subject an effective amount of a pegylated chemokine, wherein the chemokine is selected from the group consisting of human CCL1, CCL2, CCL3, CCL4, CCL5, CCL7, CCL8, CCL11, CCL13, CCL14, CCL15, CCL16, CCL17, CCL19, CCL21, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, XCL1, XCL2, CX3CL1 and functional variants thereof.

In a further embodiment, the pegylated chemokine is selected from the group consisting of CCL2-PEG, var-CCL2-PEG, CCL7-PEG, var-CCL7-PEG, CCL8-PEG, var-CCL8-PEG, CCL13-PEG, var-CCL13-PEG, CCL25-PEG, var-CCL25-PEG, CXCL11-PEG, var-CXCL11-PEG, CXCL13-PEG, var-CXCL13-PEG, CXCL16-PEG, and var-CXCL16-PEG.

BRIEF DESCRIPTION OF THE DRAWINGS

FIG. 1C shows the nuceotide sequence of the expression vector pCCL2.hIgG1Fc.

FIG. 1D shows the nuceotide sequence of the expression vector pCCL2(5-76).hIgG1Fc.

FIG. 1E shows the nuceotide sequence of the expression vector pCCL2(5-76).hIgG1Fc with alanine substitutions for removal of GAG binding sites—lys and his.

FIG. 2C shows the nuceotide sequence of the expression vector pCCL7.hIgG1Fc.

FIG. 2D shows the nuceotide sequence of the expression vector pCCL7(5-76).hIgG1Fc.

FIG. 2E shows the nuceotide sequence of the expression vector pCCL7(5-76).hIgG1Fc with alanine substitutions for removal of GAG binding sites—lys and his.

FIG. 3A depicts the expression vector pCCL8.hIgG1Fc.

FIG. 3B depicts the expression vector pCCL8(5-76).hIgG1Fc.

FIG. 3C shows the nuceotide sequence of the expression vector pCCL8.hIgG1Fc.

FIG. 3D shows the nuceotide sequence of the expression vector pCCL8(5-76).hIgG1Fc.

FIG. 3E shows the nuceotide sequence of the expression vector pCCL8(5-76).hIgG1Fc with alanine substitutio

FIG. 4C shows the nuceotide sequence of the expression vector pCCL13.hIgG1Fc.

FIG. 4D shows the nuceotide sequence of the expression vector pCCL13(5-75).hIgG1Fc.

FIG. 4E shows the nuceotide sequence of the expression vector pCCL13(5-76).hIgG1Fc with alanine substitutios for removal of GAG binding sites—lys and his.

FIG. 5C shows the nuceotide sequence of the expression vector pCCL25.hIgG1Fc.

FIG. 5D shows the nuceotide sequence of the expression vector pCCL25(4-127).hIgG1Fc.

FIG. 5E shows the nuceotide sequence of the expression vector pCCL25(4-127).hIgG1Fc with alanine substitutios for removal of GAG binding sites—lys and his.

FIG. 6C shows the nuceotide sequence of the expression vector pCXCL11.hIgG1Fc.

FIG. 6D shows the nuceotide sequence of the expression vector pCXCL11(4-73).hIgG1Fc.

FIG. 6E shows the nuceotide sequence of the expression vector pCXCL11(4-127).hIgG1Fc with alanine substitutios for removal of GAG binding sites—lys and his.

FIG. 7C shows the nuceotide sequence of the expression vector pCXCL11.hIgG4Fc.

FIG. 7D shows the nuceotide sequence of the expression vector pCXCL11(4-73).hIgG4Fc.

FIG. 7E shows the nuceotide sequence of the expression vector pCXCL11(4-127).hIgG4Fc with alanine substitutios for removal of GAG binding sites—lys and his.

FIG. 8A depicts the expression vector pCXCL13.hIgG1Fc.

FIG. 8B depicts the expression vector pCXCL13(3-87).hIgG1Fc.

FIG. 8C shows the nuceotide sequence of the expression vector pCXCL13.hIgG1Fc.

FIG. 8D shows the nuceotide sequence of the expression vector pCXCL13(4-73).hIgG1Fc.

FIG. 8E shows the nuceotide sequence of the expression vector pCXCL13(4-127).hIgG1Fc with alanine substitutios for removal of GAG binding sites—lys and his.

FIG. 9C shows the nuceotide sequence of the expression vector pCXCL13.hIgG4Fc.

FIG. 9D shows the nuceotide sequence of the expression vector pCXCL13(3-87).hIgG4Fc.

FIG. 9E shows the nuceotide sequence of the expression vector pCXCL11(4-127).hIgG4Fc with alanine substitutios for removal of GAG binding sites—lys and his.

FIG. 11 depicts a cartoon of the structure of CXCL11 indication potential pegylation sites.

FIG. 12 shows the amino acid sequences of the chemokines and human IgG Fc fragments listed in Table 1.

DETAILED DESCRIPTION

Figure 1A:
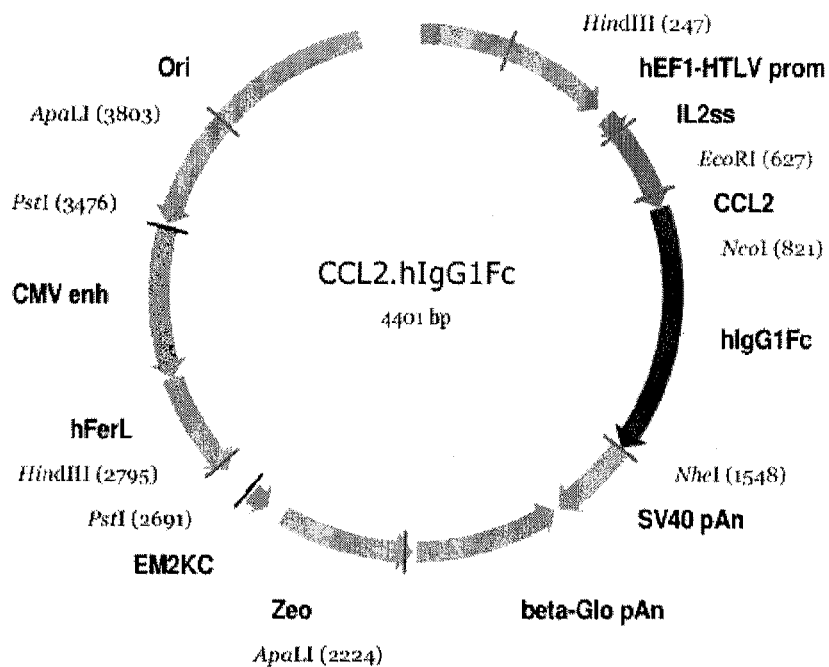
FIG. 1A depicts the expression vector pCCL2.hIgG1Fc. The Fc region comprises the CH2 and CH3 domains of the IgG heavy chain and the hinge region. The hinge serves as a flexible spacer between the two parts of the Fc-fusion protein, allowing each part of the molecule to function independently. hEF1-HTLV prom is a composite promoter comprising the Elongation Factor-1α (EF-1α) core promoter1 and the R segment and part of the U5 sequence (R-U5') of the Human T-Cell Leukemia Virus (HTLV) Type 1 Long Terminal Repeat2. The EF-1α promoter exhibits a strong activity and yields long lasting expression of a transgene in vivo. The R-U5' has been coupled to the EF-1α core promoter to enhance stability of RNA. MCS: The multiple cloning site. SV40 pAn: the Simian Virus 40 late polyadenylation signal. ori: a minimal *E. coli* origin of replication. CMV enh/hFerL prom: This composite promoter combines the human cytomegalovirus immediate-early gene 1 enhancer and the core promoter of the human ferritin light chain gene. This ubiquitous promoter drives the expression of the Zeocin™-resistance gene in mammalian cells. EM2KC is a bacterial promoter that enables the constitutive expression of the antibiotic resistance gene in *E. coli*. EM2KC is located within an intron and is spliced out in mammalian cells. Zeo: Resistance to Zeocin™ is conferred by the Sh ble gene from *Streptoalloteichus hindustanus*. The same resistance gene confers selection in both mammalian cells and *E. coli*. βGlo pAn: The human beta-globin 3'UTR and polyadenylation sequence allows efficient arrest of the transgene transcription4

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

Unless otherwise defined, scientific and technical terms used in connection with the present invention shall have the meanings that are commonly understood by those of ordinary skill in the art. Although any methods, devices, and materials similar or equivalent to those described herein can be used in the practice or testing of the presently disclosed subject matter, representative methods, devices, and materials are now described. Further, unless otherwise required by context, singular terms shall include pluralities and plural terms shall include the singular.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

The present application generally relates to compositions and methods for treating chemokine receptor-mediated disorders and modulating inflammation. Particularly, the present application relates to chemokine-immunoglobulin fusion polypeptides, chemokine-polymer conjugates, and uses thereof to modulate immunity, cancer progression, and inflammation as well as treat chemokine receptor-mediated disorders, including tissue regeneration, wound repair, stem cell homeostasis, cell proliferative disorders, and inflammatory.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The terms "treat," "treating" or "treatment" as used herein, refers to a method of alleviating or abrogating a disorder and/or its attendant symptoms. The terms "prevent", "preventing" or "prevention," as used herein, refer to a method of barring a subject from acquiring a disorder and/or its attendant symptoms. In certain embodiments, the terms "prevent," "preventing" or "prevention" refer to a method of reducing the risk of acquiring a disorder and/or its attendant symptoms.

In a pharmacological sense, in the context of the present invention, an "effective amount" of a composition efers to an amount effective in the prevention or treatment of a disorder for the treatment of which the composition is effective. A "disorder" is any condition that would benefit from treatment with the composition.

"Mammal" for purposes of treatment refers to any animal classified as a mammal, including humans, non-human primates, domestic and farm animals, and zoo, sports, or pet animals, such as dogs, horses, cats, cows, etc. Preferably, the mammal is human.

The term "inhibits" is a relative term, an agent inhibits a response or condition if the response or condition is quantitatively diminished following administration of the agent, or if it is diminished following administration of the agent, as compared to a reference agent. Similarly, the term "prevents" does not necessarily mean that an agent completely eliminates the response or condition, so long as at least one characteristic of the response or condition is eliminated. Thus, a composition that reduces or prevents an infection or a response, such as a pathological response, can, but does not necessarily completely eliminate such an infection or response, so long as the infection or response is measurably diminished, for example, by at least about 50%, such as by at least about 70%, or about 80%, or even by about 90% of (that is to 10% or less than) the infection or response in the absence of the agent, or in comparison to a reference agent.

Chemokine-Immunoglobulin Fusion Polypeptides

Chemokines have been demonstrated to mediate a number of cellular functions involving motility, invasion, adherence, proliferation, and survival. At the appropriate levels and expression, these chemotactic cytokines promote proper wound healing, neovascularization or immunity. If inappropriately expressed, these factors can dictate chronic diseases like keloid formation, angiogenesis, metastasis/drug resistance of cancer cells, autoimmunity, graft rejection, inflammation (e.g., arthritis, ulcerative colitis, Crohn's disease, multiple sclerosis, COPD, etc.), diabetes. Both beneficial and deleterious functions are mediated by binding and activation of chemokine receptors, which are class A, G protein coupled receptors.

A number of small molecule antagonists have been constructed to block the action of these receptors. Remarkably, many of these compounds have high affinities (5-50 nM) and specificities for their target. However, these inhibitors have two major limitations: (i) hydrophobicity and possible liver retention/toxicity and (ii) relative short serum-half life or bioavailability (<6 hours).

The present application provides isolated chemokine-immunoglobulin fusion polypeptides for clinical use. The fusion polypeptides comprise a wild-type human chemokine or a variant thereof fused to the constant region (i.e., CH2 and CH3) of a human immunoglobulin (Ig) G or a variant thereof. The chemokine-immunoglobulin fusion polypeptide can bind with specificity to one or more particular chemokine receptors and thereby modulate one or more biological activities (e.g., receptor activation) of the receptor(s).

One aspect of the present invention relates to an isolated chemokine-immunoglobulin fusion polypeptide having a chemokine moiety and an immunoglobulin moiety, wherein the chemokine moiety comprises a chemokine selected from the group consisting of human CCL1, CCL2, CCL3, CCL4, CCL4L1, CCL5, CCL7, CCL8, CCL11, CCL13, CCL14-1, CCL14-2, CCL15, CCL16, CCL17, CCL 18, CCL19, CCL20-1, CCL20-2, CCL21, CCL22, CCL23-1, CCL23-1, CCL24, CCL25-1, CCL25-2, CCL25-3, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof and wherein the immunoglobulin moiety comprises a peptide selected from the group consisting of the constant region (Fc) of human IgG1, the constant region of human IgG2, the constant region of human IgG3, the constant region of human IgG4, and functional variants thereof. The complete amino acid sequences of the above-described chemokines and the Fc regions of human IgG1, IgG2, IgG3 and IgG4 are listed in Table 1 below and shown in FIG. 12.

TABLE 1

| Chemokine/Receptor | Protein Accession No. | SEQ ID NO: |
|---|---|---|
| CCL1 | NP_002972 | 1 |
| CCL2 | NP_002973 | 2 |
| CCL3 | NP_002974 | 3 |
| CCL4 | NP_002975 | 4 |
| CCL4L1 | NP_001001435 | 5 |
| CCL5 | NP_002976 | 6 |
| CCL7 | NP_006264 | 7 |
| CCL8 | NP_005614 | 8 |
| CCL11 | CAG33702 | 9 |
| CCL13 | NP_005399 | 10 |
| CCL14-1 | NP_116739 | 11 |
| CCL14-2 | NP_116738 | 12 |
| CCL15 | NP_116741 | 13 |
| CCL16 | NP_004581 | 14 |
| CCL17 | NP_002978 | 15 |
| CCL18 | NP_002979 | 16 |
| CCL19 | NP_006265 | 17 |
| CCL20-1 | NP_004582 | 18 |
| CCL20-2 | NP_001123518 | 19 |
| CCL21 | NP_002980 | 20 |
| CCL22 | NP_002981 | 21 |
| CCL23-1 | NP_665905 | 22 |
| CCL23-2 | NP_005055 | 23 |
| CCL24 | NP_002982 | 24 |
| CCL25-1 | NP_005615 | 25 |
| CCL25-2 | NP_683686 | 26 |

TABLE 1-continued

| Chemokine/Receptor | Protein Accession No. | SEQ ID NO: |
|---|---|---|
| CCL25-3 | EAW68951 | 27 |
| CCL26 | NP_006063 | 28 |
| CCL27 | NP_006655 | 29 |
| CCL28 | NP_683513 | 30 |
| CXCL1 | NP_001502 | 31 |
| CXCL2 | NP_002080 | 32 |
| CXCL3 | NP_002081 | 33 |
| CXCL4 | NP_002610 | 34 |
| CXCL5 | NP_002985 | 35 |
| CXCL6 | NP_002984 | 36 |
| CXCL7 | NP_002695 | 37 |
| CXCL8 | NP_000575 | 38 |
| CXCL9 | NP_002407 | 39 |
| CXCL10 | NP_001556 | 40 |
| CXCL11 | NP_005400 | 41 |
| CXCL12 | NP_000600 | 42 |
| CXCL13 | NP_006410 | 43 |
| CXCL16 | NP_071342 | 44 |
| XCL1 | AAH69817 | 45 |
| XCL2 | NP_003166 | 46 |
| CX3CL1 | NP_002987 | 47 |
| IgG1Fc | CBX54381.1 | 48 |
| IgG2Fc | CBX54382.1 | 49 |
| IgG3Fc | CBX54383.1 | 50 |
| IgG4Fc | CBX54384.1 | 51 |

Without wishing to be bound by any particular theory of operation, the immunoglobulin region can increase serum-half life or bioavailability of the fusion polypeptide and the precise polypeptide sequences of the Fc portion can be selected to maximize serum-half life and/or bioavailability. In addition, Fc regions from different IgG subclasses (e.g., IgG1, IgG2, IgG3, and IgG4) exhibit different immunological activities, and therefore the IgG Fc region can be selected based on a desired immunological activity. For example, the Fc region of IgG1 can activate complement, while the Fc region of IgG4 has reduced complement activity.

Thus, a particular Fc region can be selected for a particular application based on the desired immunological activities manifested by each region. In some particular embodiments, the Fc region can be the Fc region of human IgG1, IgG2, IgG3 or IgG4. As such, the chemokine-immunoglobulin fusion polypeptide find utility in enhancing immunity, suppressing autoimmunity, suppressing inflammation, and/or inhibiting growth/metastasis of proliferative disorder cells. The present application further provides isolated polynucleotide which encode the chemokine-immunoglobulin fusion polypeptide disclosed herein and expression vectors capable of expressing the chemokine-immunoglobulin fusion polypeptide in vivo.

The term "isolated", when applied to a protein or polynucleotide, denotes that the protein or polynucleotide is essentially free of other cellular components with which it is associated in the natural state. It can be in a homogeneous state although it can be in either a dry or aqueous solution. Homogeneity and whether a molecule is isolated can be determined using analytical chemistry techniques such as polyacrylamide gel electrophoresis or high performance liquid chromatography. A protein that is the predominant species present in a preparation is substantially isolated. The term "isolated" denotes that a protein or polynucleotide gives rise to essentially one band in an electrophoretic gel. Particularly, it means that the protein or polynucleotide is in some embodiments at least about 50% pure, in some embodiments at least about 85% pure, and in some embodiments at least about 99% pure.

The term "polynucleotide" refers to deoxyribonucleotides or ribonucleotides and polymers thereof in either single- or double-stranded form. Unless specifically limited, the terms encompass nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues. The term "polynucleotide" or "polynucleotide sequence" can also be used interchangeably with gene, open reading frame (ORF), cDNA, and mRNA encoded by a gene.

The terms "polypeptide", "protein", and "peptide", which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide" and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

The chemokine portion of the chemokine-immunoglobulin fusion polypeptide can be selected based on the chemokine receptor or receptors to which it exhibits binding specificity. This provides for the selective targeting of the chemokine-immunoglobulin fusion polypeptide to one or more specific chemokine receptors to thereby modulate activation and subsequent biological activities of the receptor(s). Table 1 (adapted from Allen et al. (2007) Annu. Rev. Immunol. 25:787-820) provides an exemplary list of receptors that can be targeted by one or more chemokines, which can be incorporated into the chemokine-immunoglobulin fusion polypeptide of the presently-disclosed subject matter.

As disclosed in Table 2, certain chemokines can specifically bind more than one chemokine receptor. For example, CXCL11 can bind with specificity to chemokine receptors CXCR3-A, CXCR3-B, CXCR7, and DARC/Duffy. As such, if it is desirable to target more than one chemokine receptor, a particular chemokine, such as CXC11, can be selected for incorporation into the chemokine-immunoglobulin fusion polypeptide of the presently-disclosed subject matter. In some embodiments of the presently disclosed subject matter, the chemokine-immunoglobulin fusion polypeptide can comprise of a chemokine portion selected from the group consisting of CCL2, CCL7, CCL8, CCL13, CCL25, CXCL11, CXCL13, and mutations thereof. "Mutations" of the polypeptides include variants and fragments of the reference polypeptides.

TABLE 2

Chemokine receptors and their ligands

| Receptor | Ligands |
|---|---|
| CCR1 | CCL3, CCL5, CCL7, CCL13, CCL14, CCL15, CCL16, CCL23 |
| CCR2 | CCL2, CCL7, CCL8, CCL13, CCL16 |

TABLE 2-continued

Chemokine receptors and their ligands

| Receptor | Ligands |
|---|---|
| CCR3 | CCL5, CCL7, CCL8, CCL11, CCL13, CCL15, CCL16, CCL24, CCL26, CCL28 |
| CCR4 | CCL17, CCL22 |
| CCR5 | CCL3, CCL4, CCL5, CCL8, CCL11, CCL14, CCL16 |
| CCR6 | CCL20 |
| CCR7 | CCL19, CCL21 |
| CCR8 | CCL1 |
| CCR9 | CCL25 |
| CCR10 | CCL27, CCL28 |
| CXCR1 | CXCL6, CXCL7, CXCL8 |
| CXCR2 | CXCL1, CXCL2, CXCL3, CXCL5, CXCL6, CXCL7, CXCL8 |
| CXCR3-A | CXCL9, CXCL10, CXCL11, CCL11 |
| CXCR3-B | CXCL4, CXCL9, CXCL10, CXCL11, CCL11 |
| CXCR4 | CXCL12 |
| CXCR5 | CXCL13 |
| CXCR6 | CXCL16 |
| CXCR7 | CXCL12, CXCL11 |
| XCR1 | XCL1, XCL2 |
| $CX_3CR1$ | $CX_3CL1$ |
| CCX-CKR | CCL19, CCL21, CCL25 |
| D6 | CCL2, CCL3L1, CCL4, CCL5, CCL7, CCL8, CCL11, CCL13, CCL14, CCL17, CCL22 |
| DARC/Duffy | CCL2, CCL7, CCL8, CCL11, CCL13, CCL14, CCL16, CCL17, CXCL1, CXCL5, CXCL6, CXCL7, CXCL8, CXCL9, CXCL11, CXCL13 |

The term "functional variant" refers to protein or polypeptide that is different from the reference protein or polypeptide by one or more amino acids, e.g., one or more amino acid substitutions, but substaintially maintains the biological function of the reference protein or polypeptide. As used herein, a functional variant of a chemokine is a variant that maintains the receptor binding function of the original chemokine and a functional variant of the Fc region of IgG is a variant that maintains the immunologivla activities of the original Fc region.

A functional variant of a polypeptide may be a fragment of the original polypeptide. The term "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both. Fragments typically are at least 3, 5, 6, 8 or 10 amino acids long, at least 14 amino acids long, at least 20, 30, 40 or 50 amino acids long, at least 75 amino acids long, or at least 100, 150, 200, or more amino acids long.

The term "functional variant" further includes conservatively substituted variants. The term "conservatively substituted variant" refers to a peptide comprising an amino acid residue sequence that differs from a reference peptide by one or more conservative amino acid substitution, and maintains some or all of the activity of the reference peptide as described herein. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another, such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. The phrase "conservatively substituted variant" also includes peptides wherein a residue is replaced with a chemically derivatized residue, provided that the resulting peptide maintains some or all of the activity of the reference peptide as described herein.

In some particular embodiments, the chemokine-immunoglobulin fusion polypeptides disclosed herein include functional variants to the chemokine portion that introduce amino acid substitutions to eliminate glycosaminoglycan (e.g., heparin, laminin, GAG)-binding, which can thereby increase the serum half-life of the polypeptide. For example, in some embodiments one or more alanines can be substituted for lysines, arginines and/or histidines within GAG binding sites of the chemokine portions.

Specific chemokine-immunoglobulin fusion polypeptides disclosed herein that include a chemokine variant having one or more mutations in the chemokine sequence are named accordingly to indicate the particular mutation. For example "var-" before the chemokine name (e.g., var-CCL2) is indicative of a variant having an engineered mutation to the chemokine portion that results in a polypeptide sequence that differs from the reference chemokine sequence (e.g., CCL2). A fragment mutation resulting from a truncation is notated be the sequence remaining after truncation. For example, a truncation of the N-terminal 4 amino acids of the 76 amino acid CCL2 chemokine would be notated as "var-CCL2" or "CCL2 (5-76)". A variant mutation resulting from one or more amino acid substitutions would be notated as a parenthetical after the chemokine name in the form "X#Y" or "X→Y", wherein the amino acid X (in standard one letter amino acid code, as is known in the art) in the reference polypeptide is substituted with the amino acid Y either at a particular residue (#) or throughout the polypeptide, or a particular region of the polypeptide (X→Y), such as for example a GAG-binding region of the chemokine polypeptide. In some embodiments, a mutation can include both a variant and a fragment of the reference chemokine polypeptide. These mutants are indicated in the named polypeptide in succession in a parenthetical following the chemokine name. For example, "CCL2(5-76K/H→A)" indicates a chemokine-immunoglobulin fusion polypeptide including in the chemokine portion a mutant CCL2 polypeptide that has been truncated at the N-terminus to remove residues 1-4 and also mutated to substitute alanines (A) for lysines (K) and histidines (H) within the sequence. Finally, in reference to nomenclature, the chemokine-immunoglobulin fusion polypeptides disclosed herein are named according to the chemokine portion (A) and the immunoglobulin portion (B) fused together (i.e. A-B). Thus, for example, CCL2-IgG1Fc refers to a chemokine-immunoglobulin fusion polypeptide comprising a wild-type CCL2 chemokine portion fused with an Fc constant region of an IgG class 1 immunoglobulin.

In some embodiments, the present application provides a human chemokine polypeptide fused to a human immunoglobulin polypeptide. In some embodiments, the present application provides the following novel isolated chemokine-immunoglobulin fusion polypeptides: CCL2-IgG1Fc, var-CCL2-IgG1Fc, CCL2-IgG2Fc, var-CCL2-IgG2Fc, CCL2-IgG3Fc, var-CCL2-IgG3Fc, CCL2-IgG4Fc, var-CCL2-IgG4Fc, CCL7-IgG1Fc, var-CCL7-IgG1Fc, CCL7-IgG2Fc, var-CCL7-IgG2Fc, CCL7-IgG3Fc, var-CCL7-IgG3Fc, CCL7-IgG4Fc, var-CCL7-IgG4Fc, CCL8-IgG1Fc, var-CCL8-IgG1Fc, CCL8-IgG2Fc, var-CCL8-IgG2Fc, CCL8-IgG3Fc, var-CCL8-IgG3Fc, CCL8-IgG4Fc, var-CCL8-IgG4Fc, CCL13-IgG1Fc, var-CCL13-IgG1Fc, CCL13-

IgG2Fc, var-CCL13-IgG2Fc, CCL13-IgG3Fc, var-CCL13-IgG3Fc, CCL13-IgG4Fc, var-CCL13-IgG4Fc, CCL25-IgG1Fc, var-CCL25-IgG1Fc, CCL25-IgG2Fc, var-CCL25-IgG2Fc, CCL25-IgG3Fc, var-CCL25-IgG3Fc, CCL25-IgG4Fc, var-CCL25-IgG4Fc, CXCL11-IgG1Fc, var-CXCL11-IgG1Fc, CXCL11-IgG2Fc, var-CXCL11-IgG2Fc, CXCL11-IgG3Fc, var-CXCL11-IgG3Fc, CXCL11-IgG4Fc, var-CXCL11-IgG4Fc, CXCL13-IgG1Fc, var-CXCL13-IgG1Fc, CXCL13-IgG2Fc, var-CXCL13-IgG2Fc, CXCL13-IgG3Fc, var-CXCL13-IgG3Fc, CXCL13-IgG4Fc, and var-CXCL13-IgG4Fc.

In particular embodiments, the present application provides the following novel isolated chemokine-immunoglobulin fusion polypeptides: CCL2-IgG1Fc (SEQ ID NO:52), CCL2(5-76)-IgG1Fc (SEQ ID NO:53), CCL2(5-76K/H→A)-IgG1Fc (SEQ ID NO:54), CCL7-IgG1Fc (SEQ ID NO:55), CCL7(5-76)-IgG1Fc (SEQ ID NO:56), CCL7(5-76K/H→A)-IgG1Fc (SEQ ID NO:57), CCL8-IgG1Fc (SEQ ID NO:58), CCL8(5-76)-IgG1Fc (SEQ ID NO:59), CCL8(5-76K/H→A)-IgG1Fc (SEQ ID NO:60), CCL13-IgG1Fc (SEQ ID NO:61), CCL13(5-75)-IgG1Fc (SEQ ID NO:62), CCL13(5-75K/H→A)-IgG1Fc (SEQ ID NO:63), CCL25-IgG1Fc (SEQ ID NO:64), CCL25(4-127)-IgG1Fc (SEQ ID NO:65), CCL25(4-127K/H→A)-IgG1Fc (SEQ ID NO:66), CXCL11-IgG1Fc (SEQ ID NO:67), CXCL11(4-73)-IgG1Fc (SEQ ID NO:68), CXCL11(4-73K/H→A)-IgG1Fc (SEQ ID NO:69), CXCL11-IgG4Fc (SEQ ID NO:70), CXCL11(4-73)-IgG4Fc (SEQ ID NO:71), CXCL11(4-73K/H→A)-IgG4Fc (SEQ ID NO:72), CXCL13-IgG1Fc (SEQ ID NO:73), CXCL13(3-87)-IgG1Fc (SEQ ID NO:74), CXCL13(3-87K/H→A)-IgG1Fc (SEQ ID NO:75), CXCL13-IgG4Fc (SEQ ID NO:76), CXCL13(3-87)-IgG4Fc (SEQ ID NO:77), and CXCL13(3-87K/H→A)-IgG4Fc (SEQ ID NO:78).

The novel chemokine-immunoglobulin fusion polypeptides disclosed herein can be produced using any of a variety of peptide production techniques generally known in the art. For example, recombinant genetic techniques can be utilized to produce the fusion polypeptides disclosed herein. As such, in some embodiments, an isolated nucleic acid molecule which encodes a chemokine-immunoglobulin fusion polypeptide selected from the group consisting of CCL2-IgG1Fc, var-CCL2-IgG1Fc, CCL2-IgG2Fc, var-CCL2-IgG2Fc, CCL2-IgG3Fc, var-CCL2-IgG3Fc, CCL2-IgG4Fc, var-CCL2-IgG4Fc, CCL7-IgG1Fc, var-CCL7-IgG1Fc, CCL7-IgG2Fc, var-CCL7-IgG2Fc, CCL7-IgG3Fc, var-CCL7-IgG3Fc, CCL7-IgG4Fc, var-CCL7-IgG4Fc, CCL8-IgG1Fc, var-CCL8-IgG1Fc, CCL8-IgG2Fc, var-CCL8-IgG2Fc, CCL8-IgG3Fc, var-CCL8-IgG3Fc, CCL8-IgG4Fc, var-CCL8-IgG4Fc, CCL13-IgG1Fc, var-CCL13-IgG1Fc, CCL13-IgG2Fc, var-CCL13-IgG2Fc, CCL13-IgG3Fc, var-CCL13-IgG3Fc, CCL13-IgG4Fc, var-CCL13-IgG4Fc, CCL25-IgG1Fc, var-CCL25-IgG1Fc, CCL25-IgG2Fc, var-CCL25-IgG2Fc, CCL25-IgG3Fc, var-CCL25-IgG3Fc, CCL25-IgG4Fc, var-CCL25-IgG4Fc, CXCL11-IgG1Fc, var-CXCL11-IgG1Fc, CXCL11-IgG2Fc, var-CXCL11-IgG2Fc, CXCL11-IgG3Fc, var-CXCL11-IgG3Fc, CXCL11-IgG4Fc, var-CXCL11-IgG4Fc, CXCL13-IgG1Fc, var-CXCL13-IgG1Fc, CXCL13-IgG2Fc, var-CXCL13-IgG2Fc, CXCL13-IgG3Fc, var-CXCL13-IgG3Fc, CXCL13-IgG4Fc, and var-CXCL13-IgG4Fcis provided.

In particular embodiments, the isolated nucleic acid molecule encodes a chemokine-immunoglobulin fusion polypeptide selected from the group consisting of CCL2-IgG1Fc, CCL2(5-76)-IgG1Fc, CCL2(5-76K/H→A)-IgG1Fc, CCL2-IgG2Fc, CCL2(5-76)-IgG2Fc, CCL2(5-76K/H→A)-IgG2Fc, CCL2-IgG3Fc, CCL2(5-76)-IgG3Fc, CCL2(5-76K/H→A)-IgG3Fc, CCL2-IgG4Fc, CCL2(5-76)-IgG4Fc, CCL2(5-76K/H→A)-IgG4Fc, CCL7-IgG1Fc, CCL7(5-76)-IgG1Fc, CCL7(5-76K/H→A)-IgG1Fc, CCL7-IgG2Fc, CCL7(5-76)-IgG2Fc, CCL7(5-76K/H→A)-IgG2Fc, CCL7-IgG3Fc, CCL7(5-76)-IgG3Fc, CCL7(5-76K/H→A)-IgG3Fc, CCL7-IgG4Fc, CCL7(5-76)-IgG4Fc, CCL7(5-76K/H→A)-IgG4Fc, CCL8-IgG1Fc, CCL8(5-76)-IgG1Fc, CCL8(5-76K/H→A)-IgG1Fc, CCL8-IgG2Fc, CCL8(5-76)-IgG2Fc, CCL8(5-76K/H→A)-IgG2Fc, CCL8-IgG3Fc, CCL8(5-76)-IgG3Fc, CCL8(5-76K/H→A)-IgG3Fc, CCL8-IgG4Fc, CCL8(5-76)-IgG4Fc, CCL8(5-76K/H→A)-IgG4Fc, CCL13-IgG1Fc, CCL13(5-75)-IgG1Fc, CCL13(5-75K/H→A)-IgG1Fc, CCL13-IgG2Fc, CCL13(5-75)-IgG2Fc, CCL13(5-75K/H→A)-IgG2Fc, CCL13-IgG3Fc, CCL13(5-75)-IgG3Fc, CCL13(5-75K/H→A)-IgG3Fc, CCL13-IgG4Fc, CCL13(5-75)-IgG4Fc, CCL13(5-75K/H→A)-IgG4Fc, CCL25-IgG1Fc, CCL25(4-127)-IgG1Fc, CCL25(4-127K/H→A)-IgG1Fc, CCL25-IgG2Fc, CCL25(4-127)-IgG2Fc, CCL25(4-127K/H→A)-IgG2Fc, CCL25-IgG3Fc, CCL25(4-127)-IgG3Fc, CCL25(4-127K/H→A)-IgG3Fc, CCL25-IgG4Fc, CCL25(4-127)-IgG4Fc, CCL25(4-127K/H→A)-IgG4Fc, CXCL11-IgG1Fc, CXCL11(4-73)-IgG1Fc, CXCL11(4-73K/H→A)-IgG1Fc, CXCL11-IgG2Fc, CXCL11(4-73)-IgG2Fc, CXCL11(4-73K/H→A)-IgG2Fc, CXCL11-IgG3Fc, CXCL11(4-73)-IgG3Fc, CXCL11(4-73K/H→A)-IgG3Fc, CXCL11-IgG4Fc, CXCL11(4-73)-IgG4Fc, CXCL11(4-73K/H→A)-IgG4Fc, CXCL13-IgG1Fc, CXCL13(3-87)-IgG1Fc, CXCL13(3-87K/H→A)-IgG1Fc, CXCL13-IgG2Fc, CXCL13(3-87)-IgG2Fc, CXCL13(3-87K/H→A)-IgG2Fc, CXCL13-IgG3Fc, CXCL13(3-87)-IgG3Fc, CXCL13(3-87K/H→A)-IgG3Fc, CXCL13-IgG4Fc, CXCL13(3-87)-IgG4Fc, and CXCL13(3-87K/H→A)-IgG4Fc. Recombinant cloning techniques may also be used to construct the heterologous gene sequences that encode for the fusion polypeptide gene product, as is known in the art.

Expression Vectors

Recombinant exprtession vectors comprising nucleic acid molecules which encode the polypeptides disclosed herein are also provided. Particularly useful vectors are contemplated to be those vectors in which the coding portion of the DNA segment is positioned under the control of a promoter. The promoter may be in the form of the promoter which is naturally associated with the chemokine or immunoglobulin gene, e.g., in mammalian tissues, as may be obtained by isolating the 5' non-coding sequences located upstream of the coding segment or exon, for example, using recombinant cloning and/or PCR technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a chemokine or immunoglobulin gene in its natural environment. Such promoters may include promoters isolated from plant, insect, bacterial, viral, eukaryotic, fish, avian or mammalian cells. Naturally, it will be important to employ a promoter that effectively directs the expression of the DNA segment in the cell type chosen for expression. The use of promoter and cell type combinations for protein expression is generally known to those of skill in the art of molecular biology. The promoters employed may be constitutive, or inducible, and can be used under the appropriate conditions to direct high level expression of the introduced DNA segment, such as is advantageous in the large-scale production of recombinant proteins or peptides.

Expression vectors generally contain sequences for transcriptional termination, and may additionally contain one or more elements positively affecting mRNA stability. An expression vector may further include an internal ribosome entry site (IRES) between adjacent protein coding regions to facilitate expression two or more proteins from a common mRNA in an infected or transfected cell. Additionally, the expression vectors may further include nucleic acid sequence encoding a marker product. This marker product may be used to determine if the gene has been delivered to the cell and is being expressed. Preferred marker genes are the *E. coli* lacZ gene, which encodes β-galactosidase, and green fluorescent protein (GFP).

In some embodiments, the expression vectors of the present application are plasmid expression vectors that are capable of expressing the chemokine-immunoglobulin fusion polypeptides of the present application in an in vitro setting. The expressed fusion polypeptide is then isolated and purified using methods well known to a person skilled in the art.

In other embodiments, the expression vectors of the present application are plasmid expression vectors that are capable of expressing the chemokine-immunoglobulin fusion polypeptides of the present application in an in vivo setting. These expression vectors may be introduced into a subject using delivery systems such as liposomes, including cationic liposomes (e.g., DOTMA, DOPE, DC-cholesterol) and anionic liposomes, microcapsules, nanoparticles and electroporation. In some embodiments, the expression vectors are targeted to a particular cell type via antibodies, receptors, or receptor ligands. Vehicles such as "stealth" and other antibody conjugated liposomes (including lipid mediated drug targeting to cells of interest), receptor mediated targeting of DNA through cell specific ligands or viral vectors targeting e.g., lymphoid, epithelial or endothelial cells. In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor level regulation. Many receptors follow more than one intracellular pathway, depending on the cell type, receptor concentration, type of ligand, ligand valency, and ligand concentration.

In yet other embodiments, the expression vectors of the present application are virus-based expression vectors that are capable of expressing the chemokine-immunoglobulin fusion polypeptides of the present application in an in vivo setting. Exemplary viral vectors may include or be derived from adenovirus, adeno-associated virus, herpesvirus, vaccinia virus, poliovirus, poxvirus, HIV virus, lentivirus, retrovirus, Sindbis and other RNA viruses, and the like. Also preferred are any viral families which share the properties of these viruses which make them suitable for use as vectors. Retroviruses include Murine Moloney Leukemia virus (MMLV), HIV and other lentivirus vectors. Adenovirus vectors are relatively stable and easy to work with, have high titers, and can be delivered in aerosol formulation, and can transfect non-dividing cells. Poxviral vectors are large and have several sites for inserting genes, they are theimostable and can be stored at room temperature. Viral delivery systems typically utilize viral vectors having one or more genes removed and with and an exogenous gene and/or gene/promotor cassette being inserted into the viral genome in place of the removed viral DNA. The necessary functions of the removed gene(s) may be supplied by cell lines which have been engineered to express the gene products of the early genes in trans.

In other embodiments, the expression vectors are phage DNA, yeast plasmids or baculovirus.

Figure 1B:
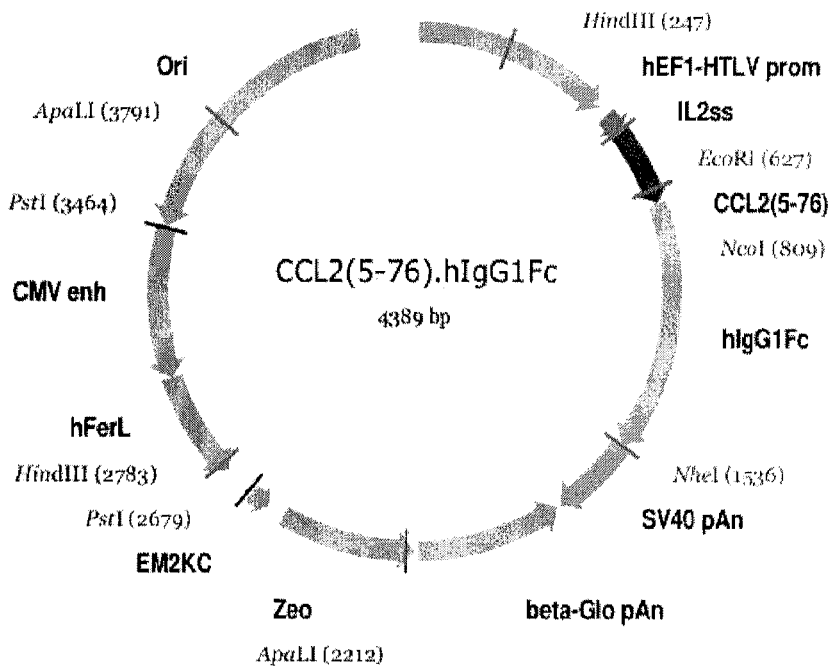
FIG. 1B depicts the expression vector pCCL2(5-76).hIgG1Fc.
Figure 1D:
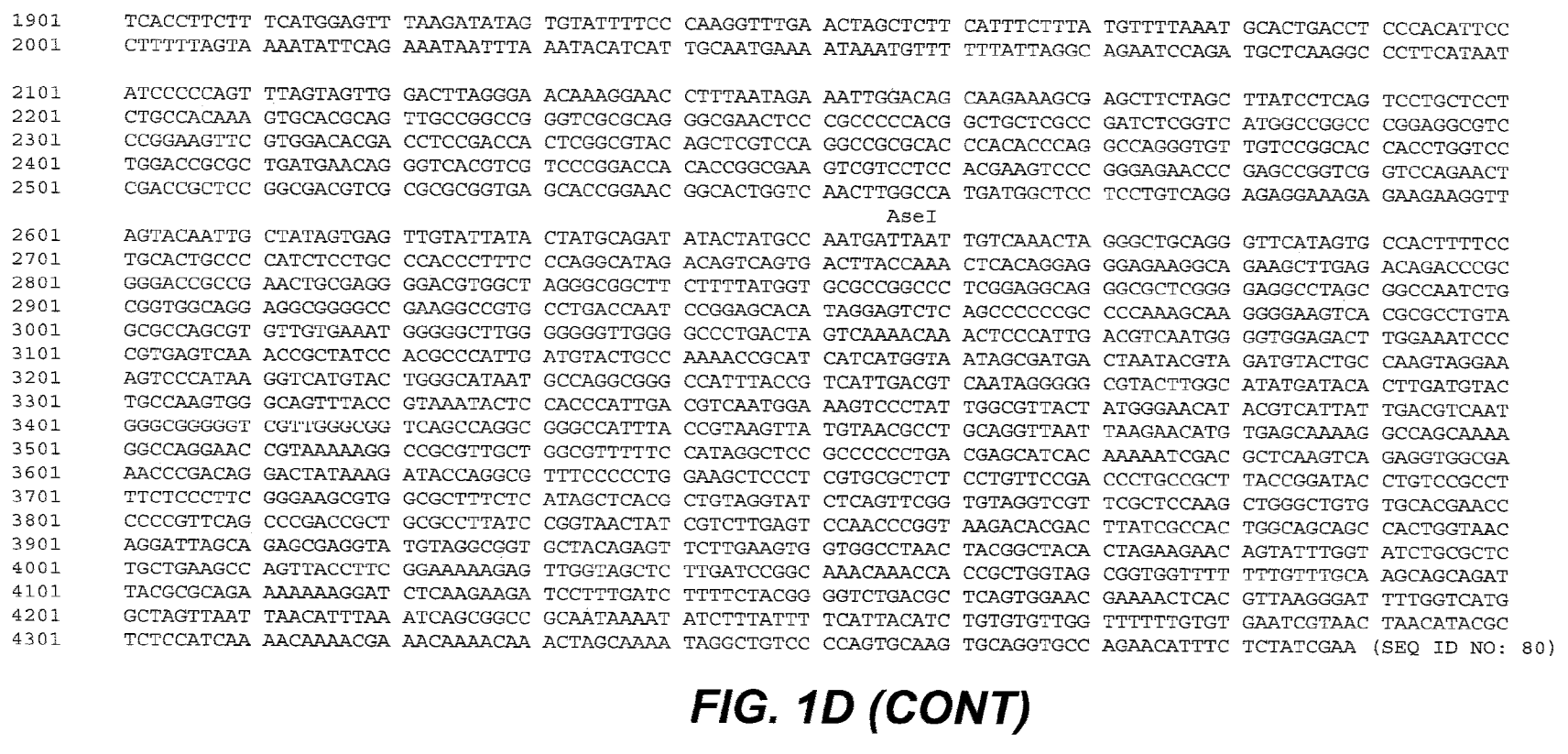
Figure 2A:
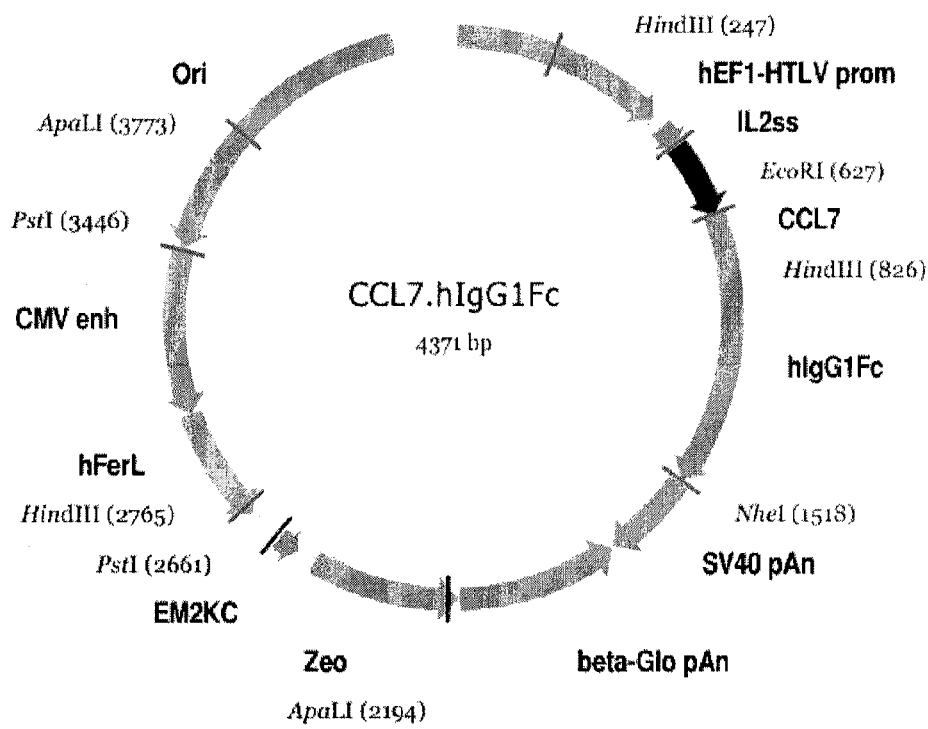
FIG. 2A depicts the expression vector pCCL7.hIgG1Fc.
Figure 2B:
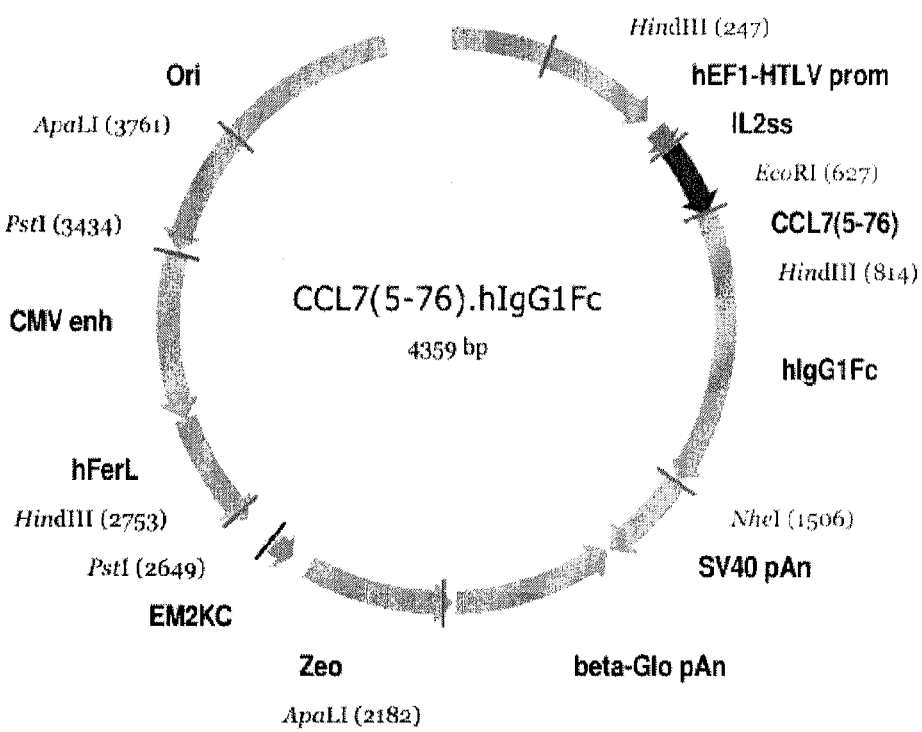
FIG. 2B depicts the expression vector pCCL7(5-76).hIgG1Fc.
Figure 4A:
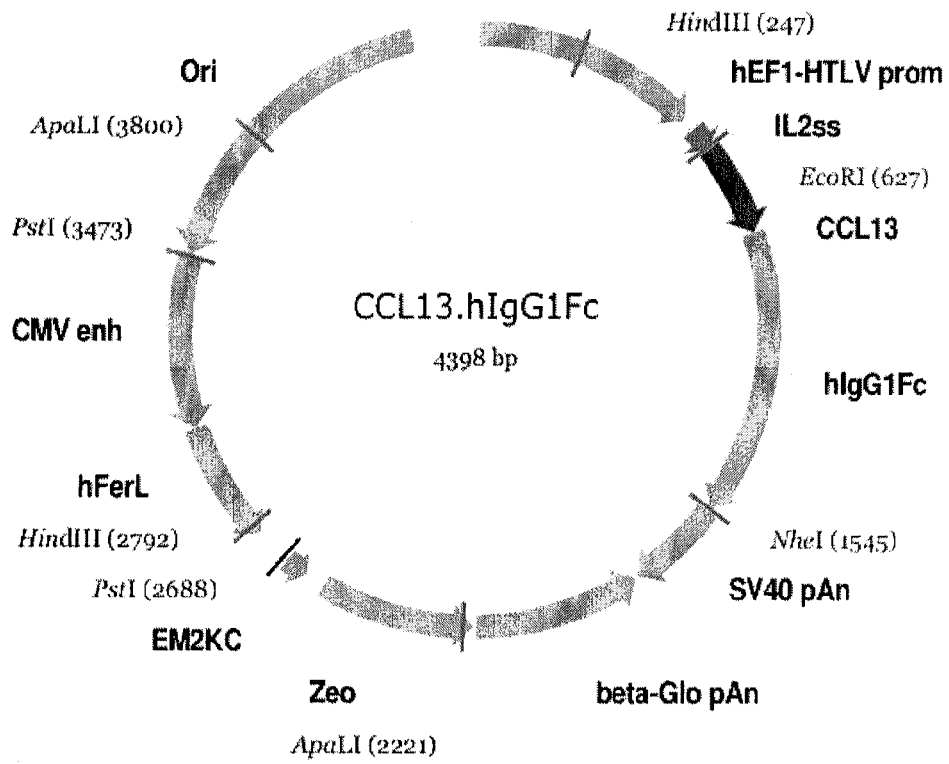
FIG. 4A depicts the expression vector pCCL13.hIgG1Fc.
Figure 4B:
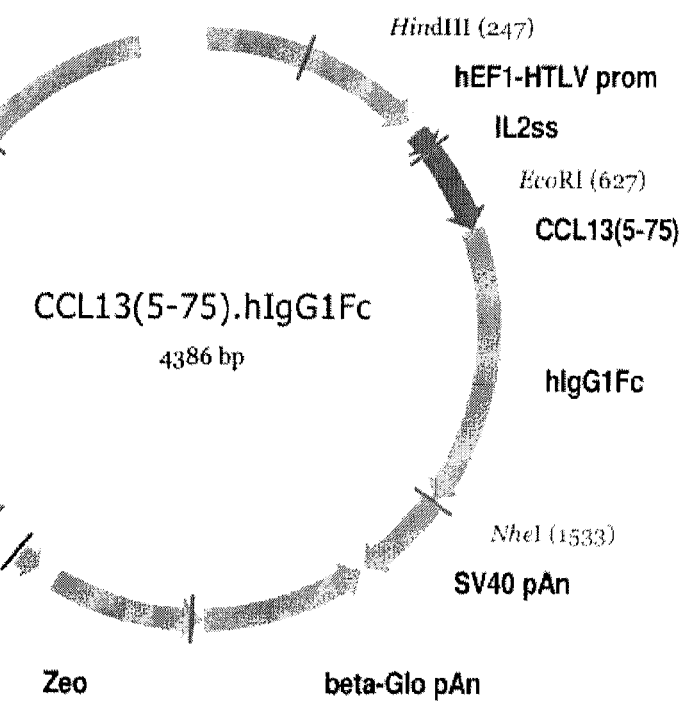
FIG. 4B depicts the expression vector pCCL13(5-75).hIgG1Fc.
Figure 5A:
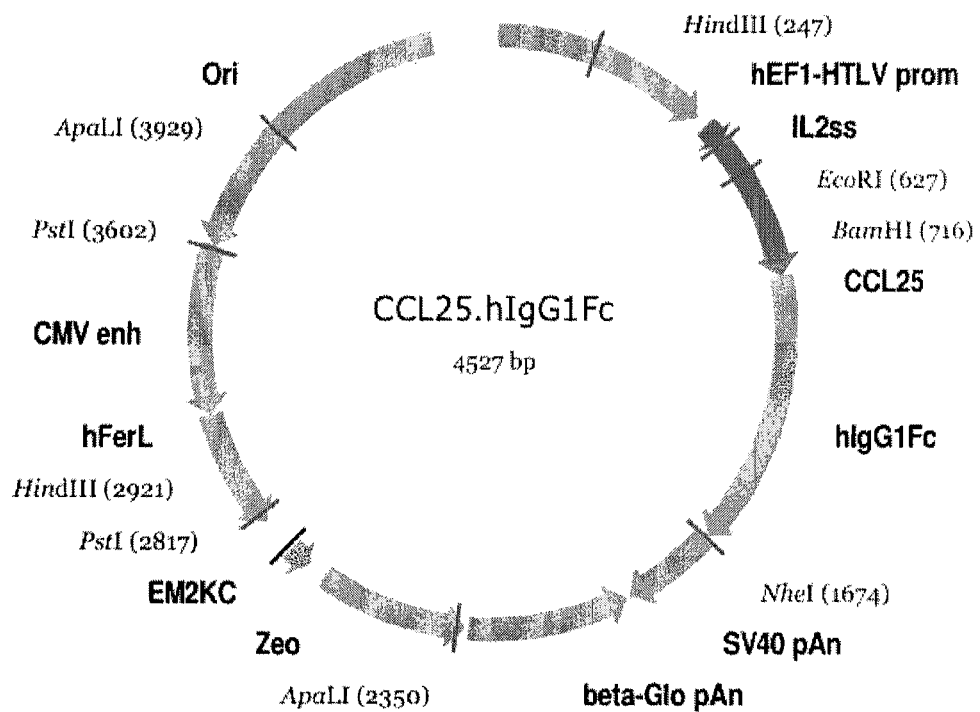
FIG. 5A depicts the expression vector pCCL25.hIgG1Fc.
Figure 5B:
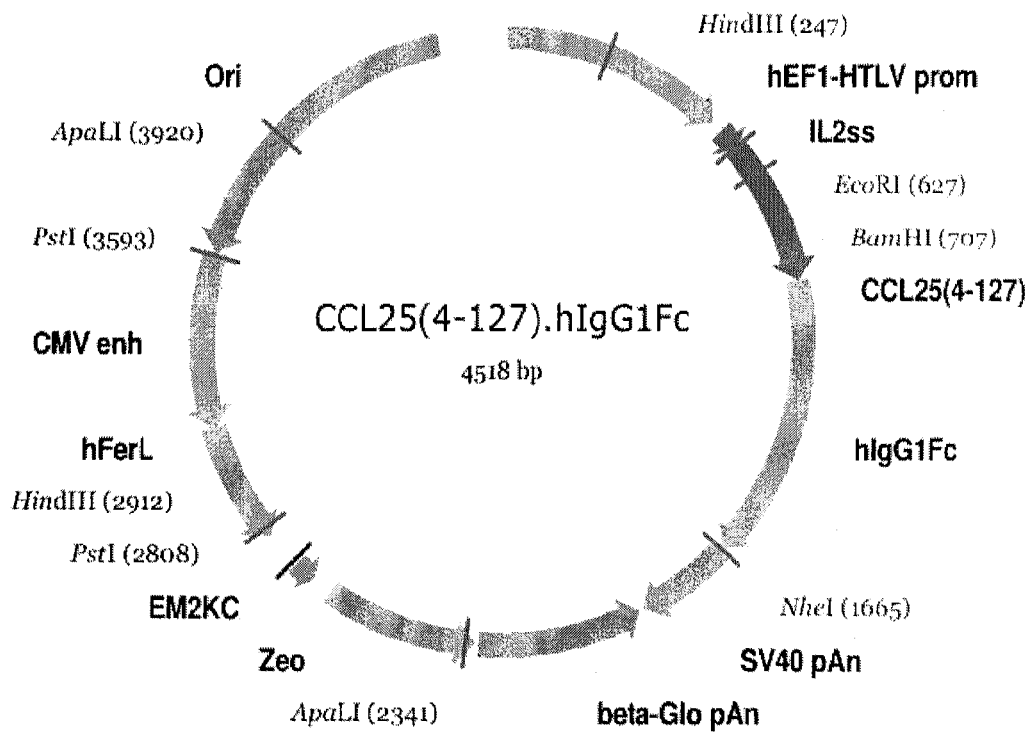
FIG. 5B depicts the expression vector pCCL25(4-127).hIgG1Fc.
Figure 6A:
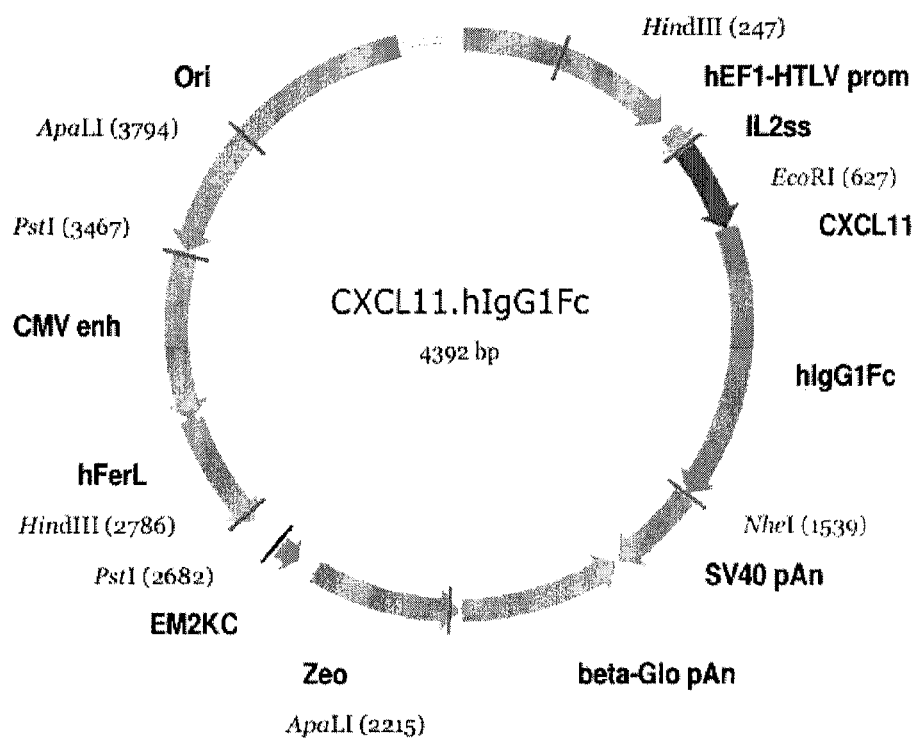
FIG. 6A depicts the expression vector pCXCL11.hIgG1Fc.
Figure 6B:
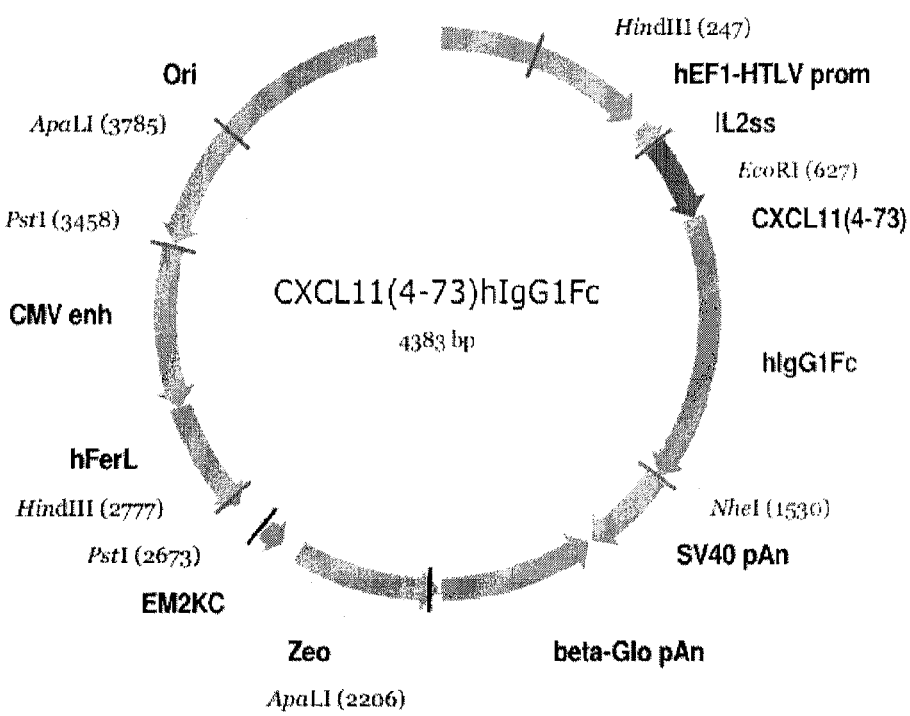
FIG. 6B depicts the expression vector pCXCL11(4-73).hIgG1Fc.
Figure 7A:
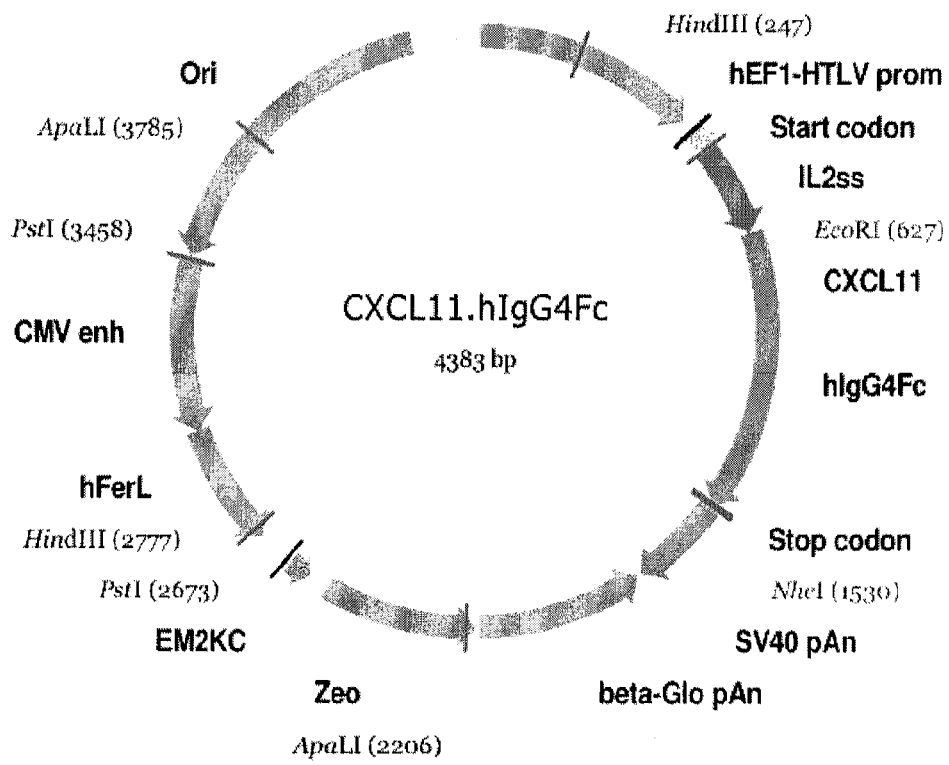
FIG. 7A depicts the expression vector pCXCL11.hIgG4Fc.
Figure 7B:
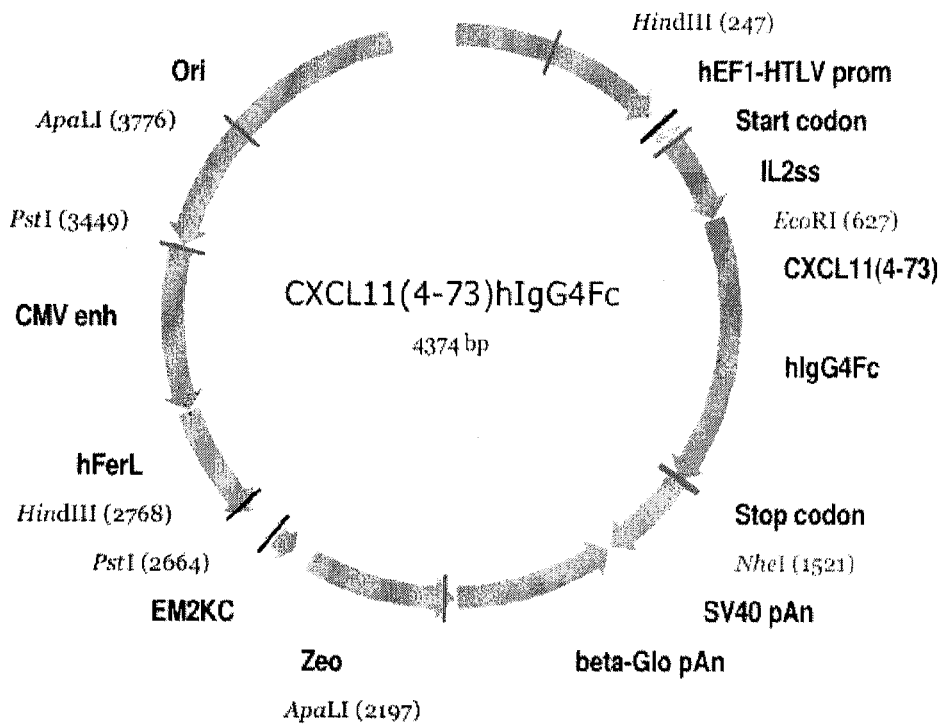
FIG. 7B depicts the expression vector pCXCL11(4-73).hIgG4Fc.
Figure 9A:
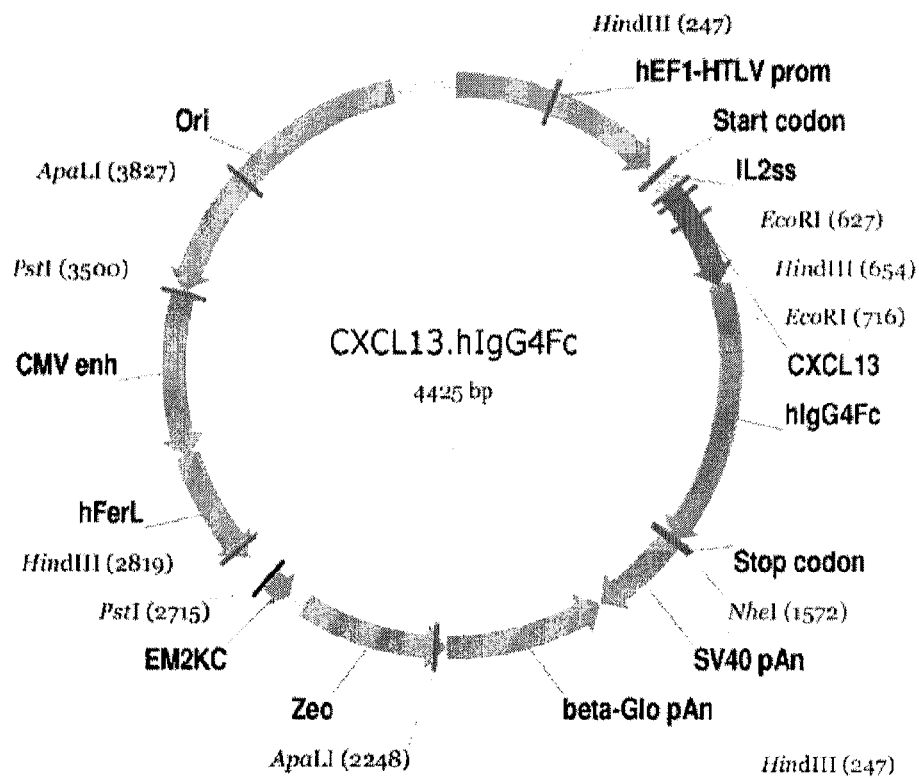
FIG. 9A depicts the expression vector pCXCL13.hIgG4Fc.
Figure 9B:
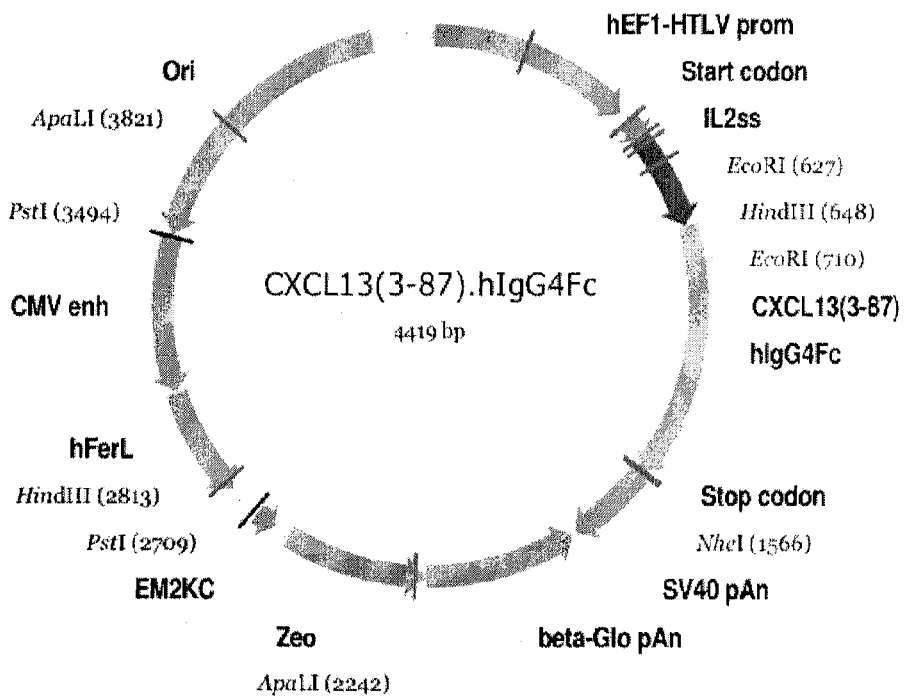
FIG. 9B depicts the expression vector pCXCL13(3-87).hIgG4Fc.
Figure 10A:
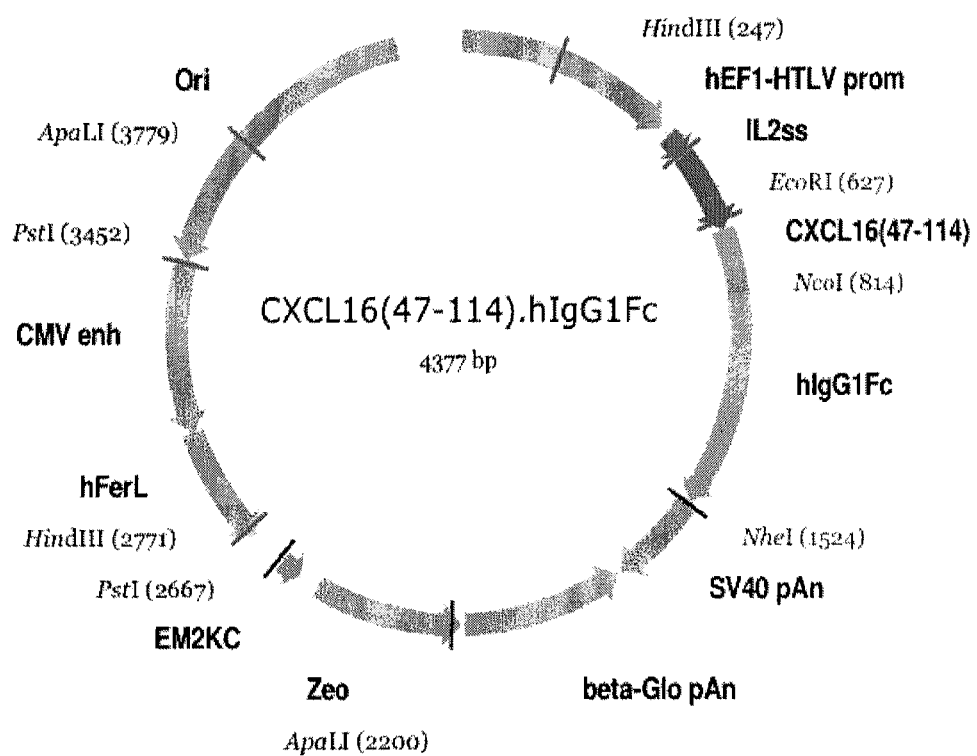
FIG. 10A depicts the expression vector pCXCL16(47-114).hIgG1Fc.

Exemplary expression vector constructs comprising polynucleotides which encode chemokine-immunoglobulin fusion polypeptides disclosed herein are shown in FIGS. 1-10. These expression vectors include pCCL2-IgG1Fc (SEQ ID NO:79), pCCL2(5-76)-IgG1Fc (SEQ ID NO:80), pCCL2(5-76K/H→A)-IgG1Fc (SEQ ID NO:81), pCCL7-IgG1Fc (SEQ ID NO:82), pCCL7(5-76)-IgG1Fc (SEQ ID NO:83), pCCL7(5-76K/H→A)-IgG1Fc (SEQ ID NO:84), pCCL8-IgG1Fc (SEQ ID NO:85), pCCL8(5-76)-IgG1Fc (SEQ ID NO:86), pCCL8(5-76K/H→A)-IgG1Fc (SEQ ID NO:87), pCCL13-IgG1Fc (SEQ ID NO:88), pCCL13(5-75)-IgG1Fc (SEQ ID NO:89), pCCL13(5-75K/H→A)-IgG1Fc (SEQ ID NO:90), pCCL25-IgG1Fc (SEQ ID NO:91), pCCL25(4-127)-IgG1Fc (SEQ ID NO:92), pCCL25(4-127K/H→A)-IgG1Fc (SEQ ID NO:93), pCXCL11-IgG1Fc (SEQ ID NO:94), pCXCL11(4-73)-IgG1Fc (SEQ ID NO:95), pCXCL11(4-73K/H→A)-IgG1Fc (SEQ ID NO:96), pCXCL11-IgG4Fc (SEQ ID NO:97), pCXCL11(4-73)-IgG4Fc (SEQ ID NO:98), pCXCL11(4-73K/H→A)-IgG4Fc (SEQ ID NO:99), pCXCL13-IgG1Fc (SEQ ID NO:100), pCXCL13(3-87)-IgG1Fc (SEQ ID NO:101), pCXCL13(3-87K/H→A)-IgG1Fc (SEQ ID NO:102), pCXCL13-IgG4Fc (SEQ ID NO:103), pCXCL13(3-87)-IgG4Fc (SEQ ID NO:104), and CXCL13(3-87K/H→A)-IgG4Fc (SEQ ID NO:105). It is understood that additional combinations of vectors and genes than those specifically disclosed above are contemplated by the presently-disclosed subject matter, as would be understood by one of ordinary skill in the art.

Protein Conjugates

In some embodiments, the chemokine-immunglobulin fusion polypeptides of the present application, as well as certain chemokines and variants thereof, are conjugated to a non-protein polymer to form protein-polymer conjugates. Unless specifically indicated to the contrary, the term "non-protein polymer" is defined as a molecule formed by covalent linkage of two or more monomers, wherein none of the monomers is contained in the group consisting of alanine (Ala), cysteine (Cys), aspartic acid (Asp), glutamic acid (Glu), phenylalanine (Phe), glycine (Gly), histidine (His), isoleucine (Ile), lysine (Lys), leucine (Leu), methionine (Met), asparagine (Asn), proline (Pro), glutamine (Gln), arginine (Arg), serine (Ser), threonine (Thr), valine (Val), tryptophan (Trp), and tyrosine (Tyr) residues. Serum soluble non-protein polymers, such as polyethylene glycol, and tissue or fat soluble polymers, such as polycaprolactone, can be used for delivery, release, and/or retention of polypeptides. In some embodiments, the protein-polymer conjugate is a pegylated chemokine-immunglobulin fusion polypeptide, chemokine or a variant thereof.

In one aspect, the presetn application encompass a conjugate having any molar ratio of polymer to chemokine or fragment thereof that endows the conjugate with an apparent size in the desired range as taught herein. The apparent size of the conjugate will depend in part upon the size and shape of the polymer used, the size and shape of the chemokine or fragment thereof used, the number of polymer molecules attached to the chemokine or fragment thereof, and the location of such attachment site(s) on the chemokine or fragment thereof. These parameters can easily be identified and maximized to obtain the conjugate with the desired apparent size for any type of chemokine or fragment thereof, polymer and linkage system.

In some embodiments, the protein-polymer conjugate of the present application has an effective size of at least about 500,000 D, or at least about 800,000 D, or at least about 900,000 D, or at least about 1,000,000 D, or at least about 1,200,000 D, or at least about 1,400,000 D, or at least about 1,500,000 D, or at least about 1,800,000 D, or at least about 2,000,000 D, or at least about 2,500,000 D. In one embodiment, the polymer is PEG.

In other embodiments, the protein-polymer conjugate of the present application has an effective size of at or about 500,000 D to at or about 10,000,000 D, or an effective size of at or about 500,000 D to at or about 8,000,000 D, or an effective size of at or about 500,000 D to at or about 5,000,000 D, or an effective size of at or about 500,000 D to at or about 4,000,000 D, or an effective size of at or about 500,000 D to at or about 3,000,000 D, or an effective size of at or about 500,000 D to at or about 2,500,000 D, or an effective size of at or about 500,000 D to at or about 2,000,000 D, or an effective size of at or about 500,000 D to at or about 1,800,000 D, or an effective size of at or about 500,000 D to at or about 1,600,000 D, or an effective size of at or about 500,000 D to at or about 1,500,000 D, or an effective size of at or about 500,000 D to at or about 1,000,000 D. In one embodiment, the polymer is PEG.

In a further embodiment, the protein-polymer conjugate has an effective size that is at least about 8 fold greater, or at least about 10 fold greater, or at least about 12 fold greater, or at least about 15 fold greater, or at least about 18 fold greater, or at least about 20 fold greater, or at least about 25 fold greater, or at least about 28 fold greater, or at least about 30 fold greater, or at least about 40 fold greater, than the effective size of the unconjugated chemokine-immunglobulin fusion polypeptide, chemokine or variant thereof. In one embodiment, the polymer is PEG.

In another embodiment, the protein-polymer conjugate has an effective size that is about 8 fold to about 100 fold greater, or is about 8 fold to about 80 fold greater, or is about 8 fold to about 50 fold greater, or is about 8 fold to about 40 fold greater, or is about 8 fold to about 30 fold greater, or is about 8 fold to about 28 fold greater, or is about 8 fold to about 25 fold greater, or is about 8 fold to about 20 fold greater, or is about 8 fold to about 18 fold greater, or is about 8 fold to about 15 fold greater, than the effective size of the unconjugated chemokine-immunglobulin fusion polypeptide, chemokine or variant thereof. In one embodiment, the polymer is PEG.

In another embodiment, the protein-polymer conjugate has an effective size that is about 25 fold to about 100 fold greater, or is about 25 fold to about 80 fold greater, or is about 25 fold to about 50 fold greater, or is about 25 fold to about 40 fold greater, or is about 25 fold to about 30 fold greater, or is about 25 fold to about 28 fold greater, than the effective size of the unconjugated chemokine-immunglobulin fusion polypeptide, chemokine or variant thereof. In one embodiment, the polymer is PEG.

In another embodiment, the protein-polymer conjugate has a polymer-to-protein molar ratio of no more than about 10:1, or no more than about 5:1, or no more than about 4:1, or no more than about 3:1, or no more than about 2:1, or no more than 1:1. In one embodiment, the polymer is PEG.

In still another embodiment, the protein-polymer conjugate is a chemokine-immunglobulin fusion polypeptide, chemokine or variant thereof covalently attached to at least one polymer having an actual MW of at least about 20,000 D. In one embodiment, the polymer is PEG.

In a further embodiment, the conjugate is a chemokine-immunglobulin fusion polypeptide, chemokine or variant thereof covalently attached to at least one polymer having an actual MW of at least about 30,000 D. In one embodiment, the polymer is PEG.

In yet another embodiment, the conjugate is a chemokine-immunglobulin fusion polypeptide, chemokine or variant thereof covalently attached to at least one polymer having an actual MW of at least about 40,000 D. In one embodiment, the polymer is PEG.

In another embodiment, the conjugate is a chemokine-immunglobulin fusion polypeptide, chemokine or variant thereof covalently attached to at least one polymer having an actual MW that is at or about 20,000 D to at or about 300,000 D, or is at or about 30,000 D to at or about 300,000 D, or is at or about 40,000 D to at or about 300,000 D. In one embodiment, the polymer is PEG.

The conjugates of the present application can be made using any suitable technique now known or hereafter developed for derivatizing chemokines or fragments thereof with polymers. It will be appreciated that the invention is not limited to conjugates utilizing any particular type of linkage between a chemokine or fragment thereof and a polymer.

The conjugates of the present application include species wherein a polymer is covalently attached to a non-specific site or non-specific sites on a chemokine-immunoglobulin fusion polypeptide, a chemokine or a variant thereof (i.e. the polymer attachment is not targeted to a particular region or a particular amino acid residue in the unconjugated chemokine or fragment thereof). In such embodiments, the coupling chemistry can, for example, utilize the free epsilon amino groups of lysine residues in the unconjugated antibody as attachment sites for the polymer, wherein such lysine residue amino groups are randomly derivatized with polymer.

In addition, the conjugates of the invention include species wherein a polymer is covalently attached to a specific site or specific sites on the unconjugated chemokine or fragment thereof (i.e. a polymer attachment is targeted to a particular region or a particular amino acid residue or residues in the unconjugated chemokine or fragment thereof). FIG. 11 depicts a cartoon of the structure of CXCL11 indication potential pegylation sites. In such embodiments, the coupling chemistry can, for example, utilize the free sulfhydryl group of a cysteine residue not in a disulfide bridge in the unconjugated chemokine or fragment thereof. In one embodiment, one or more cysteine residue(s) is (are) engineered into a selected site or sites in the unconjugated chemokine or fragment thereof for the purpose of providing a specific attachment site or sites for polymer. The polymer can be activated with any functional group that is capable of reacting specifically with the free sulfhydryl or thiol group(s) on the unconjugated antibody, such as maleimide, sulfhydryl, thiol, triflate, tesylate, aziridine, exirane, and 5-pyridyl functional groups. The polymer can be coupled to the unconjugated chemokine or fragment thereof using any protocol suitable for the chemistry of the coupling system selected.

In another embodiment, polymer attachment is targeted to the receptor binding site of the unconjugated chemokine or fragment thereof. In another embodiment, polymer attachment is targeted to a site on the chemokine or fragment thereof away from the receptor binding site of the unconjugated chemokine or fragment thereof.

In certain embodiments, the protein portion of the protein-polymer conjugate is selected from the group consisting of human CCL1, CCL2, CCL3, CCL4, CCL4L1, CCL5, CCL7, CCL8, CCL11, CCL13, CCL14-1, CCL14-2, CCL15, CCL16, CCL17, CCL 18, CCL19, CCL20-1, CCL20-2, CCL21, CCL22, CCL23-1, CCL23-1, CCL24, CCL25-1, CCL25-2, CCL25-3, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof and the polymer portion of the protein-polymer conjugate is PEG. FIG. 11 depicts a cartoon of the structure of CXCL11 indication potential pegylation sites.

In other embodiments, the protein portion of the protein-polymer conjugate is a chemokine-immunoglobulin fusion polypeptide wherein the chemokine moiety is selected from the group consisting of a human CCL1, CCL2, CCL3, CCL4, CCL4L1, CCL5, CCL7, CCL8, CCL11, CCL13, CCL14-1, CCL14-2, CCL15, CCL16, CCL17, CCL 18, CCL19, CCL20-1, CCL20-2, CCL21, CCL22, CCL23-1, CCL23-1, CCL24, CCL25-1, CCL25-2, CCL25-3, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof and the immunoglobulin moiety is selected from the group consisting of the Fc region of human IgG1, the Fc region of human IgG2, the Fc region of human IgG3, the Fc region of human IgG4 and variants thereof.

In some embodiments, the protein-polymer conjugate is a serum labile polypeptide selected from the group consisting of CCL2-PEG, var-CCL2-PEG, CCL7-PEG, var-CCL7-PEG, CCL8-PEG, var-CCL8-PEG, CCL13-PEG, var-CCL13-PEG, CCL25-PEG, var-CCL25-PEG, CXCL11-PEG, var-CXCL11-PEG, CXCL13-PEG, var-CXCL13-PEG, CXCL16-PEG, and var-CXCL16-PEG.

In particular embodiments, the protein-polymer conjugate is a serum labile polypeptide selected from the group consisting of CCL2-PEG, CCL2(5-76)-PEG, CCL2(5-76K/H→A)-PEG, CCL7-PEG, CCL7(5-76)-PEG, CCL7(5-76K/H→A)-PEG, CCL8-PEG, CCL8(5-76)-PEG, CCL8(5-76K/H-A)-PEG, CCL13-PEG, CCL13(5-75)-PEG, CCL13(5-75K/H→A)-PEG, CCL25-PEG, CCL25(4-127)-PEG, CCL25(4-127K/H→A)-PEG, CXCL11-PEG, CXCL11(4-73)-PEG, CXCL11(4-73K/H→A)-PEG, CXCL11-IgG4Fc, CXCL11(4-73)-IgG4Fc, CXCL11(4-73K/H→A)-IgG4Fc, CXCL13-PEG, CXCL13(3-87)-PEG, CXCL13(3-87K/H→A)-PEG, CXCL16-PEG, CXCL16(3-87)-PEG, and CXCL16(3-87K/H→A)-PEG.

It is believed that the serum half-life, MRT and/or serum clearance rate of any chemokine or fragment thereof can be greatly improved by derivatizing the chemokine or fragment thereof with polymer as taught herein. In a preferred embodiment, the conjugate contains a chemokine or fragment thereof selected from the group consisting of CCL2, CCL7, CCL8, CCL13, CCL25, CXCL11, CXCL12α, CXCL13, and mutations, variants and fragments thereof.

Methods of Producing Chemokine-Immunoglobulin Fusion Polypeptides

The chemokine-immunglobulin fusion polypeptides or variants thereof may be produced using methods well known in the art. In certain embodiments, the chemokine-immunglobulin fusion polypeptide or variants thereof are produced by chemical synthesis. Briefly, a chemokine-immunglobulin fusion polypeptide may be synthesized by coupling the carboxyl group or C-terminus of one amino acid to the amino group or N-terminus of another. Due to the possibility of unintended reactions, protecting groups are usually necessary. Chemical peptide synthesis starts at the C-terminal end of the peptide and ends at the N-terminus. This is the opposite of protein biosynthesis, which starts at the N-terminal end.

In some embodiments, the chemokine-immunglobulin fusion polypeptide may be synthesized using traditional liquid- or solid-phase synthesis. Fmoc and t-Boc solid phase peptide synthesis (SPPS) can be employed to grow the peptides from carboxy to amino-terminus. In certain embodiments, the last "amino acid" added to the reaction is pegylated. This last amino acid is often referred to as a carboxyl-PEG-amine, carboxyl-PEO-amine, or amine-PEG-acid, whereby the amine is blocked to protect against reaction and the acid is free to react with the amine group from the previously added amino acid in the reaction.

In other embodiments, the chemokine-immunglobulin fusion polypeptides or variants thereof are produced using recombinant DNA technologies. Procedures for the expression and purification of recombinant proteins are well established.

In certain embodiments, the chemokine-immunglobulin fusion polypeptides are expressed using the expression vectors such as bacterial plasmids; phage DNA; baculovirus; yeast plasmids; vectors derived from combinations of plasmids and phage DNA, and viral vectors ushc as vaccinia, adenovirus, fowl pox virus, pseudorabies, adenovirus, adeno-associated virus, retroviruses and many others viruses.

Expression vectors carrying the chemokine-immunoglobulin fusion polypeptides can be introduced into host cells by any of a variety of well-known procedures, such as electroporation, liposome mediated transfection, calcium phosphate precipitation, infection, transfection and the like, depending on the selection of vectors and host cells.

Host cells that contain expression vectors of chemokine-immunoglobulin fusion polypeptides are, thus, also a feature of this disclosure. Favorable host cells include prokaryotic (i.e., bacterial) host cells, such as *E. coli*, as well as numerous eukaryotic host cells, including fungal (e.g., yeast, such as *Saccharomyces cerevisiae* and Picchia pastoris) cells, insect cells, plant cells, and mammalian cells (such as CHO cells). Examples of appropriate expression hosts include: bacterial cells, such as *E. coli*, *Streptomyces*, and *Salmonella typhimurium*; fungal cells, such as *Saccharomyces cerevisiae*, *Pichia pastoris*, and *Neurospora crassa*; insect cells such as *Drosophila* and *Spodoptera frugiperda*; mammalian cells such as 3T3, COS, CHO, BHK, HEK 293 or Bowes melanoma; plant cells, including algae cells, etc.

The host cells can be cultured in conventional nutrient media modified as appropriate for activating promoters, selecting transformants, or amplifying the inserted polynucleotide sequences. The culture conditions, such as temperature, pH and the like, are typically those previously used with the host cell selected for expression, and will be apparent to those skilled in the art and in the references cited herein. The chemokine-immunoglobulin fusion polypeptides can also be produced in non-animal cells such as plants, yeast, fungi, bacteria and the like. In bacterial systems, a number of expression vectors can be selected depending upon the use intended for the expressed product. For example, when large quantities of a polypeptide or fragments thereof are needed for the production of antibodies, vectors which direct high level expression of fusion polypeptides that are readily purified are favorably employed. Such vectors include, but are not limited to, multifunctional *E. coli* cloning and expression vectors such as BLUESCRIPT (Stratagene), in which the coding sequence of interest, e.g., a polynucleotide of the invention as described above, can be ligated into the vector in-frame with sequences for the amino-terminal translation initiating Methionine and the subsequent 7 residues of beta-galactosidase producing a catalytically active beta galactosidase fusion polypeptide; pIN vectors (Van Heeke & Schuster (1989) J Biol Chem 264:5503-5509); pET vectors (Novagen, Madison Wis.), in which the amino-terminal methionine is ligated in frame with a histidine tag; and the like.

Similarly, in yeast, such as *Saccharomyces cerevisiae*, a number of vectors containing constitutive or inducible promoters such as alpha factor, alcohol oxidase and PGH can be used for production of the desired expression products. In mammalian host cells, a number expression systems, including both plasmids and viral-based systems, can be utilized.

For long-term, high-yield production of the chemokine-immunglobulin fusion polypeptides, stable expression systems are typically used. For example, polynucleotides encoding a the chemokine-immunglobulin fusion polypeptide are introduced into the host cell using expression vectors which contain viral origins of replication or endogenous expression elements and a selectable marker gene. Following the introduction of the vector, cells are allowed to grow for 1-2 days in an enriched media before they are switched to selective media. The purpose of the selectable marker is to confer resistance to selection, and its presence allows growth and recovery of cells, which successfully express the introduced sequences. For example, resistant groups or colonies of stably transformed cells can be proliferated using tissue culture techniques appropriate to the cell type. Host cells transformed with a nucleic acid encoding a c the chemokine-immunglobulin fusion polypeptide are optionally cultured under conditions suitable for the expression and recovery of the encoded protein from cell culture.

Following transduction of a suitable host cell line and growth of the host cells to an appropriate cell density, the selected promoter is induced by appropriate means (e.g., temperature shift or chemical induction) and cells are cultured for an additional period. The secreted polypeptide product is then recovered from the culture medium. Alternatively, cells can be harvested by centrifugation, disrupted by physical or chemical means, and the resulting crude extract retained for further purification. Eukaryotic or microbial cells employed in expression of proteins can be disrupted by any convenient method, including freeze-thaw cycling, sonication, mechanical disruption, or use of cell lysing agents, or other methods, which are well know to those skilled in the art.

Expressed the chemokine-immunglobulin fusion polypeptides can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems noted herein), hydroxylapatite chromatography, and lectin chromatography. Protein refolding steps can be used, as desired, in completing configuration of the mature protein. Finally, high performance liquid chromatography (HPLC) can be employed in the final purification steps. In addition to the references noted above, a variety of purification methods are well known in the art.

In another example, a polynucleotide sequence that encodes the chemokine-immunglobulin fusion polypeptide is introduced into insect cells using a Baculovirus Expression Vector System (BEVS). Recombinant baculovirus capable of infecting insect cells can be generated using commercially available vectors, kits and/or systems, such as the BD BaculoGold system from BD BioScience. Briefly, the polynucleotide sequence encoding the chemokine-immunglobulin fusion polypeptide is inserted into the pAcSG2 transfer vector. Then, host cells SF9 (*Spodoptera frugiperda*) are co-transfected by pAcSG2-chimer plasmid and BD BaculoGold, containing the linearized genomic DNA of the baculovirus *Autographa californica* nuclear polyhedrosis virus (Ac-NPV). Following transfection, homologous recombination occurs between the pACSG2 plasmid and the Baculovirus genome to generate the recombinant virus. In one example, the chemokine-immunglobulin fusion polypeptide is expressed under the regulatory control of the polyhedrin promoter (pH). Similar transfer vectors can be produced using other promoters, such as the basic (Ba) and p10 promoters. Similarly, alternative insect cells can be employed, such as SF21, which is closely related to the Sf9, and the High Five (Hi5) cell line derived from a cabbage looper, *Trichoplusia ni*. Following transfection and induction of expression (according to the selected promoter and/or enhancers or other regulatory elements), the expressed the chemokine-immunglobulin fusion polypeptides are recovered (e.g., purified or enriched) and renatured to ensure folding into a biologically active conformation.

In yet other embodiments, the chemokine-immunglobulin fusion polypeptides are expressed in vivo by a plasmid vector or a viral vector.

Treatment Methods

The present application further provides methods of using the chemokine-immunoglobulin fusion polypeptides disclosed herein to modulate inflammation and/or treat chemokine receptor-mediated disorders. In some embodiments, a method for treating a chemokine receptor-mediated disorder in a subject is provided. In some embodiments, the method comprises administering an effective amount of a chemokine-immunoglobulin fusion polypeptide disclosed herein to a subject in need thereof.

As used herein, the terms "treatment" or "treating" relate to any treatment of a chemokine receptor-mediated disorder, including but not limited to prophylactic treatment and therapeutic treatment. As such, the terms "treatment" or "treating" include, but are not limited to: preventing a chemokine receptor-mediated disorder or the development of a chemokine receptor-mediated disorder; inhibiting the progression of a chemokine receptor-mediated disorder; arresting or preventing the development of a chemokine receptor-mediated disorder; reducing the severity of a chemokine receptor-mediated disorder; ameliorating or relieving symptoms associated with a chemokine receptor-mediated disorder; and causing a regression of the chemokine receptor-mediated disorder or one or more of the symptoms associated with the chemokine receptor-mediated disorder.

The embodiments of the therapeutic compounds exhibit activity in the treatment of chemokine receptor-mediated disorders and inflammation, when administered in effective amounts. An effective amount of a composition disclosed herein is a nontoxic, but sufficient amount of the composition, such that the desired prophylactic or therapeutic effect is produced. The exact amount of the composition that is required will vary from subject to subject, depending on the species, age, condition of the animal, severity of the inflammation or chemokine receptor-mediated disorder in the animal, the particular carrier or adjuvant being used, its mode of administration, and the like. Accordingly, the effective amount of any particular therapeutic composition disclosed herein will vary based on the particular circumstances, and an appropriate effective amount can be determined in each case of application by one of ordinary skill in the art using only routine experimentation. The compositions disclosed herein can be administered in amounts ranging from about 0.1 µg to about 100 mg per kilogram of body weight. For example, the dosage regimen could be from about 1 µg to about 10 mg per kilogram of body weight, and such dosage units could be employed so that a total of from about 7 µg to about 700 mg of the composition is administered to a subject of about 70 kg of body weight.

A dosage regimen can be adjusted to provide an optimum therapeutic response and can be administered daily, biweekly, weekly, bimonthly, monthly, or at other appropriate time intervals. For example, compositions disclosed herein can be administered from once a day to once a week in dosages of about 5-250 mg per administration. For another example, several divided doses can be administered daily or the dose can be proportionally reduced as indicated by the exigencies of the therapeutic situation. One practical advantage is that the compound can be administered in a convenient manner such as intravenously, intratumorally, subcutaneously, transdermally, intraperitoneally or orally.

In some embodiments, the active composition is administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. The form should be sterile and fluid to the extent that easy syringability exists. It should be stable under the conditions of manufacture and storage and should be preserved against the contaminating action of microorganisms, such as bacteria and fungi. The pharmaceutical carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, the inclusion of isotonic agents can be desirable, for example, sugars or sodium chloride. Prolonged absorption of the injectable compositions can be brought about by the use in the compositions of agents, delaying absorption, for example, aluminum monostearate and gelatin.

Sterile injectable solutions can be prepared by incorporating the composition in the required amount in the appropriate solvent with various of the other ingredients enumerated above, followed by filtered sterilization. Generally, dispersions can be prepared by incorporating the various sterilized active ingredient into a sterile vehicle containing the basic dispersion medium and the required other ingredients from those enumerated above. In the case of sterile powders for the preparation of sterile injectable solutions, methods of preparation include vacuum drying and freeze drying techniques, which yield a powder of the active ingredient plus any additional desired ingredient from previously sterile filtered solution thereof.

As used herein, "pharmaceutically acceptable carrier" and "pharmaceutical carrier" are used interchangeably and include solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Parenteral compositions may be formulated in dosage-unit form for ease of administration and uniformity of dosage. Dosage-unit form, as used herein, refers to physically discrete units suited as unitary dosages for the subjects to be treated, each unit containing a predetermined quantity of active material calculated to produce the desired therapeutic effect in association with the required pharmaceutical carrier. The specification for the dosage-unit forms of the present application can be chosen based upon: (a) the unique characteristics of the active material and the particular therapeutic effect to be achieved, and (b) the limitations inherent in the art of compounding such an active material for the treatment of conditions in living subjects having a condition in which bodily health is impaired as described herein.

The active ingredient can be compounded for convenient and effective administration in effective amounts with a suitable pharmaceutically acceptable carrier in dosage unit form as described herein. A unit dosage form can, for example, contain the principle active compound in amounts ranging from, for example, about 0.1 to about 1000 mg or, for another example, from about 5 to about 500 mg. Expressed in proportions, the compound is generally present in from about 1 to about 100 mg/ml of carrier. In the case of compositions containing supplementary active ingredients, the dosages can be determined by reference to the usual dose and manner of administration of the ingredients.

Further, with respect to the therapeutic methods of the presently disclosed subject matter, a preferred subject is a vertebrate subject. A preferred vertebrate is warm-blooded; a preferred warm-blooded vertebrate is a mammal A preferred mammal is most preferably a human. As used herein, the term "subject" includes both human and animal subjects. Thus, veterinary therapeutic uses are provided in accordance with the presently disclosed subject matter.

As such, the presently application provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

In some embodiments of the presently-disclosed subject matter, the chemokine receptor-mediated disorder treated is a cell proliferative disorder, such as tumor or cancer. The present application provides chemokine-immunoglobulin fusion polypeptides that can target specific chemokine receptors expressed on cells of proliferative disorders disclosed herein. Cancer cells express functionally active chemokine receptors that may support adhesion, invasion, and cell survival. Chemokine receptor signaling and aggregation following binding of chemokines is coupled to integrin clustering, which enhances cell survival and firm cell adhesion. Without wishing to be bound by theory, the novel chemokine-immunoglobulin fusion polypeptides disclosed herein can bind chemokine receptors on these diseased cells and inhibit cellular events, including cell survival, migration, invasion, adhesion, or combinations thereof, and thereby treat the cell proliferative disorder. Table 3 lists various cancers and associations of the listed cancers with particular chemokines and chemokine receptors.

TABLE 3

Chemokine, Chemokine Receptor and Cancer Association (dependent of stage of disease)

| Cancer | Chemokine | Chemokine Receptor |
| --- | --- | --- |
| Carcinoma | CCL1, CCL4, CCL17, CCL19, CCL21, CCL22, CCL25, CXCL1, CXCL2, CXCL5, CXCL8, CXCL11, CXCL12, CXCL13, CXCL16 | CCR7, CCR8, CCR9, CXCR1, CXCR2, CXCR3, CXCR4, CXCR5, CXCR6, CXCR7, CX3CR1 |
| Leukemia | CCL1, CCL4, CCL17, CCL19, CCL21, CCL22, CCL25, CXCL12 | CCR7, CCR8, CCR9, CXCR4 |
| Lymphoma | CXCL12, CXCL13 | CXCR4, CXCR5 |
| Melanoma | CCL25, CCL27, CXCL1, CXCL2, CXCL3, CXCL5, CXCL6, CXCL7, CXCL8, CXCL12, CXCL13, CXCL16 CX3CL1 | CCR9, CCR10, CXCR1, CXCR2, CXCR4, CXCR5, CXCR6, CX3CR1 |
| Sarcoma | CCL1, CCL3, CCL4, CCL5, CCL7, CCL8, CCL11, CCL13, CCL17, CCL19, CCL22, CCL24, CXCL12, CX3CL1 | CCR3, CCR5, CCR8, CXCR4 CX3CR1, CCXCKR |

"Cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is neoplasm or tumor, which is an abnormal growth of tissue. "Cancer" refers to any of various malignant neoplasms characterized by the proliferation of cells that have the capability to invade surrounding tissue and/or metastasize to new colonization sites, and includes leukemias, carcinomas, melanoma, and sarcomas. Examples of cancers are cancer of the brain, bladder, breast, cervix, colon, head and neck, kidney, lung, non-small cell lung, mesothelioma, ovary, prostate, sarcoma, stomach, uterus and medulloblastoma.

By "leukemia" is meant broadly progressive, malignant diseases of the blood-forming organs and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" generally refers to a tumor which is made up of a substance like the embryonic connective tissue and is generally composed of closely packed cells embedded in a fibrillar or homogeneous substance. Sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphomas (e.g., Non-Hodgkin Lymphoma), immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Additional cancers include, for example, Hodgkin's Disease, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, pre-malignant skin lesions, testicular cancer, thyroid cancer, neuroblastoma, esophageal cancer, genitourinary tract cancer, malignant hypercalcemia, cervical cancer, endometrial cancer, and adrenal cortical cancer.

In other embodiments, the chemokine receptor-mediated disorder treated is an inflammatory disorder. Without wishing to be bound by theory, the novel chemokine-immunoglobulin fusion polypeptides disclosed herein can bind chemokine receptors on these cells and inhibit cellular events that can result in inflammation and inflammatory disorders. Table 4 lists various exemplary inflammatory disorders and associations of the listed disorders with particular chemokines and chemokine receptors. Targeting of the listed chemokine receptors with chemokine-immunoglobulin fusion polypeptides disclosed herein that act as specific ligands of the receptors can be useful for treating the listed inflammatory disorders.

TABLE 4

Chemokine, Chemokine Receptor and Inflammatory Disorder Association (dependent of stage of disease)

| Inflammatory Disorder | Chemokine | Chemokine Receptor |
|---|---|---|
| Allergies (Skin, Food & Respiratory) | CCL1, CCL2, CCL5, CCL7, CCL8, CCL11, CCL13, CCL17, CCL22, CCL24, CCL25, CCL26 | CCR3, CCR4, CCR8, CCR9 |
| Asthma | CCL3, CCL4, CCL5, CCL7, CCL8, CCL11, CCL15, CCL17, CCL22, CCL24, CCL26 | CCR3, CCR4, CCR5 |
| Septic Shock, Anaphylaxis | CXCL1, CXCL2, CXCL3, CXCL5, CXCL6, CXCL7, CXCL8, CXCL9, CXCL10, CXCL11, CCL5 | CXCR1, CXCR2, CXCR3 |
| Arthritis (septic, rheumatoid, psoriatic) | CXCL9, CXCL10, CXCL11, CXCL12, CXCL13 | CXCR3, CXCR4, CXCR5 |
| | CCL20 | CCR6 |
| | XCL1 | XCR1 |
| | CX3CL1 | CX3CR1 |
| Osteoarthritis | CXCL1, CXCL2, CXCL3, CXCL5, CXCL6, CXCL7, CXCL8, CXCL12, CXCL13 | CXCR1, CXCR2 |
| | CCL2, CCL3, CCL4, CCL7, CCL8, CCL13, CCL5, CCL18 | CCR2, CCR5 |
| Atherosclerosis | CXCL1, CXCL2, CXCL3, CXCL4, CXCL5, CXCL8 | CXCR1, CXCR2 |
| | CCL2, CCL3, CCL4, CCL8, CCL12, CCL13, CCL17, CCL22 | CCR2, CCR8 |
| | CX3CL1 | CX3CR1 |
| Dermatitis & Delayed-Typed Hypersensitivity | CXCL9, CXCL10, CXCL11 | CXCR3 |
| | CCL2, CCL3, CCL4, CCL5, CCL17, CCL20, CCL22, CCL27 | CCR4, CCR5, CCR6, CCR10 |
| Diabetes | CXCL9, CXCL10, CXCL11 | CXCR3 |
| | CCL2, CCL9 | CCR2, CCR4 |
| | CX3CL1 | CX3CR1 |
| Graft rejection | CXCL9, CXCL10, CXCL11 | CXCR3 |
| | CCL3, CCL4, CCL5 | CCR5 |
| | XCL1, XCL2 | XCR1 |
| Inflammatory Bowel Disorders | CXCL9, CXCL10, CXCL11 | CXCR3 |
| | CCL3, CCL4, CCL5, CCL25 | CCR5 |
| Interstitial Cystitis | CXCL9, CXCL10, CXCL11 | CXCR3 |
| | CCL3, CCL4, CCL5 | CCR5 |
| Multiple Sclerosis | CXCL9, CXCL10, CXCL11 | CXCR3 |
| | CCL3, CCL4, CCL5, CCL7, CCL14, CCL15, CCL23 | CCR1, CCR5 |

TABLE 4-continued

Chemokine, Chemokine Receptor and Inflammatory Disorder Association
(dependent of stage of disease)

| Inflammatory Disorder | Chemokine | Chemokine Receptor |
|---|---|---|
| Myasthemia gravis, Grave's disease, & Hashimoto thyroiditis | CXCL9, CXCL10, CXCL11<br>CCL3, CCL4, CCL5<br>XCL1, XCL2 | CXCR3<br>CCR5<br>XCR1 |
| Nephritis & Systemic Lupus Erthematosus | CXCL9, CXCL10, CXCL11, CXCL13<br>CCL2, CCL3, CCL4, CCL5, CCL8, CCL12, CCL13<br>CX3CL1 | CXCR3, CXCR5<br>CCR2, CCR4<br><br>CX3CR1 |
| Pneumonitis, Chronic Obstructive Pulmonary Disease, & Chronic Bronchitis | CXCL1, CXCL2, CXCL3, CXCL5, CXCL7, CXCL8<br>CCL3, CCL5, CCL7, CCL8, CCL11, CCL13, CCL24, CCL26 | CXCR2, CXCR3<br><br>CCR3 |

As used herein, the term "inflammatory disorder" includes diseases or disorders which are caused, at least in part, or exacerbated, by inflammation, which is generally characterized by increased blood flow, edema, activation of immune cells (e.g., proliferation, cytokine production, or enhanced phagocytosis), heat, redness, swelling, pain and/or loss of function in the affected tissue or organ. The cause of inflammation can be due to physical damage, chemical substances, micro-organisms, tissue necrosis, cell proliferative disorders, or other agents Inflammatory disorders include acute inflammatory disorders, chronic inflammatory disorders, and recurrent inflammatory disorders. Acute inflammatory disorders are generally of relatively short duration, and last for from about a few minutes to about one to two days, although they can last several weeks. Characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or longer, and are associated histologically with the presence of lymphocytes and macrophages and with proliferation of blood vessels and connective tissue. Recurrent inflammatory disorders include disorders which recur after a period of time or which have periodic episodes. Some inflammatory disorders fall within one or more categories. Exemplary inflammatory disorders include, but are not limited to, inflammatory disorders of the central or peripheral nervous system (e.g., abscess, AIDS related infections, Alzheimer's disease, chronic fatigue syndrome, congenital infections, encephalitis, ischemia, meningitis, multiple sclerosis, traumatic brain injury, etc.); inflammatory disorders of the urogenital system (e.g., endometriosis, glomerulosclerosis, infections of the vagina and cervix, intra-amniotic infection, pelvic inflammatory disease, renal inflammation/nephritis, sexually transmitted diseases, urethritis, urinary tract infections, yeast infection, etc.); inflammatory disorders of the digestive system (e.g., colon cancer, hepatitis, inflammatory bowel disease, interstitial cystitis, irritable bowel syndrome, ulcers, etc.); inflammatory disorders of the respiratory system (e.g., chronic lung disease, asthma, tuberculosis, pneumonia, etc.); inflammatory disorders of the skin, integument and musculoskeletal system (e.g., Behçet's disease, Crohn's disease, dermatitis, gingivitis, gout, myalgias, osteoarthritis, periodontitis, psoriasis, rheumatoid arthritis, spondyloarthropathies, skin sunburn, etc.); inflammatory disorders of the cardiovascular system (e.g., atherosclerosis, pericarditis, endocarditis, Kawasaki's disease, myocarditis, rheumatic fever, vasculitis); autoimmune disorders; cat scratch disease; infections of the eye; Lyme disease; lymphadenopathy; lymphatic inflammation; radiation-induced inflammation; sarcoidosis; Sjogren's syndrome; systemic lupus erythematosus and related disorders; and inflammatory disorders resulting from infections by microorganisms and inflammatory molecules. As used herein, the term "microorganism" refers to any species or type of microorganism, including but not limited to, bacteria, viruses, archaea, fungi, protozoans, mycoplasma, prions, and parasitic organisms. The term microorganism encompasses both those organisms that are in and of themselves pathogenic to another organism (e.g., animals, including humans, and plants) and those organisms that produce agents that are pathogenic to another organism, while the organism itself is not directly pathogenic or infective to the other organism. As noted, an inflammatory disorder is often caused, at least in part, or exacerbated by, inflammation, which may be characterized by symptoms and/or manifestations of the inflammatory disorder which may include, but are not limited to, increased blood flow, edema, activation of immune cells (e.g., proliferation, cytokine production, or enhanced phagocytosis), heat, redness, swelling, pain and loss of function in the affected tissue and organ. As such, the present application further provides methods of modulating inflammation. The term "modulating inflammation" refers to either inducement of inflammation or alleviating inflammation where inflammation is pathological, as occurs in inflammatory disorders. The term "alleviating" as used herein refers to preventing the symptoms and/or manifestations of inflammation or the development of the symptoms and/or manifestations of inflammation; inhibiting the progression of the symptoms and/or manifestations of inflammation; arresting or preventing the development of the symptoms and/or manifestations of inflammation; reducing the severity of symptoms and/or manifestations inflammation; ameliorating or relieving the symptoms and/or manifestations associated with inflammation; and/or causing a regression of the symptoms and/or manifestations of inflammation. The present invention is further illustrated by the following examples that should not be construed as limiting. The following examples may include compilations of data that are representative of data gathered at various times during the course of development and experimentation related to the present subject matter.

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

EXAMPLE 1

Generation of Plasmid Expression Vectors

Expression vectors capable of expressing a chemokine-immunoglobulin fusion polypeptide are generated from pFUSE-hIgG1-Fc1, pFUSE-hIgG2-Fc1, pFUSE-hIgG3-Fc1 and pFUSE-hIgG4-Fc1 vectors from InvivoGen (San Diego, Calif.) using standard molecular biology procedures. Examples of the expression vectors are shown in FIGS. 1-10.

EXAMPLE 2

Expression of Chemokine Receptors in Breast Cancer Cell Lines

Experiments are conducted to compare expression levels of CXCR7 and CXCR3 in breast cancer tissue of various stages, in non-neoplstic breast tissue. Non-neoplastic breast tissue does not express detectable levels of CXCR7. CXCR7 expression is significantly higher in tissues with advanced breast cancer, comparing to non-neoplastic breast tissue. CXCR7 and CXCR3 mRNAs are also elevated in breast cancer cell lines (MDA-MB-231), compared to normal breast cells (MCF-10A).

EXAMPLE 3 var-CXCL11-IgG Fusion Polypeptide Inhibits CXCR7 and CXCR3 Activation in Breast Cancer Cells Using Amnis ImageStream analysis, we found that CXCL11 stimulates CXCR3 and CXCR7 aggregation and rapid desensitization, that CXCL12 modulates modest CXCR7 clustering, and that adrenomedullin (AM) stimulates CXCR3 and CXCR7 clustering. CXCL11-IgG fusion polypeptide abrogates CXCR3 and CXCR7, but not CXCR4, clustering and desensitization by CXCL11, CXCL12 and AM.

The above description is for the purpose of teaching the person of ordinary skill in the art how to practice the present invention, and is not intended to detail all those obvious modifications and variations of it that will become apparent to the skilled worker upon reading the description. It is intended, however, that all such obvious modifications and variations be included within the scope of the present invention, which is defined by the following embodiments. The embodiments are intended to cover the components and steps in any sequence that is effective to meet the objectives there intended, unless the context specifically indicates the contrary. All the references cited in the specification are herein incorporated by reference in their entirely.

---

What is claimed is:

1. An isolated chemokine-immunoglobulin fusion polypeptide, comprising
a chemokine moiety from human CLXCL11 and
an immunoglobulin moiety from the constant region of human IgG1 (IgG1Fc), wherein the chemokine-immunoglobulin fusion polypeptide comprises an amino acid sequence selected from the group consisting of SEQ ID NO:67, SEQ ID NO:68 and SEQ ID NO:69.

2. The isolated chemokine-immunoglobulin fusion polypeptide of claim 1, wherein said fusion polypeptide is a pegylated fusion polypeptide.

3. The isolated chemokine-immunoglobulin fusion polypeptide of claim 2, wherein said pegylated fusion polypeptide has a molecular weight of at least about 500,000 daltons.

4. The isolated chemokine-immunoglobulin fusion polypeptide of claim 2, wherein said pegylated fusion polypeptide comprises PEG molecules having a collective molecular weight of at least about 20,000 daltons.

5. The isolated chemokine-immunoglobulin fusion polypeptide of claim 2, wherein said pegylated fusion polypeptide has a PEG-to-fusion polypeptide molar ratio of no more than about 10:1.

6. The isolated chemokine-immunoglobulin fusion polypeptide of claim 2, wherein said pegylated fusion polypeptide has a PEG-to-fusion polypeptide molar ratio of no more than about 5:1.

7. The isolated chemokine-immunoglobulin fusion polypeptide of claim 2, wherein said pegylated fusion polypeptide has a PEG-to-fusion polypeptide molar ratio of no more than about 2:1.

8. An isolated polynucleotide, encoding the chemokine-immunoglobulin fusion polypeptide of claim 1.

9. An expression vector, comprising:
a regulatory element; and
a polynucleotide operately linked to said regulatory element,
wherein said polynucleotide encodes the chemokine-immunoglobulin fusion polypeptide of claim 1.

10. The expression vector of claim 9, wherein said vector is a plasmid-based expression vector.

11. The expression vector of claim 9, wherein said vector is a virus-based expression vector.

12. A pharmaceutical composition, comprising:
the chemokine-immunoglobulin fusion polypeptide of claim 1; and
a pharmaceutically acceptable carrier.

13. A composition, comprising:
the expression vector of claim 9; and
a pharmaceutically acceptable carrier.

* * * * *

SEQUENCE LISTING

<160> NUMBER OF SEQ ID NOS: 106

<210> SEQ ID NO 1
<211> LENGTH: 96
<212> TYPE: PRT
<213> ORGANISM: Homo sapiens

<400> SEQUENCE: 1

```
Met Gln Ile Ile Thr Thr Ala Leu Val Cys Leu Leu Leu Ala Gly Met
1               5                   10                  15

Trp Pro Glu Asp Val Asp Ser Lys Ser Met Gln Val Pro Phe Ser Arg
            20                  25                  30

Cys Cys Phe Ser Phe Ala Glu Gln Glu Ile Pro Leu Arg Ala Ile Leu
        35                  40                  45

Cys Tyr Arg Asn Thr Ser Ser Ile Cys Ser Asn Glu Gly Leu Ile Phe
    50                  55                  60

Lys Leu Lys Arg Gly Lys Glu Ala Cys Ala Leu Asp Thr Val Gly Trp
65                  70                  75                  80

Val Gln Arg His Arg Lys Met Leu Arg His Cys Pro Ser Lys Arg Lys
                85                  90                  95
```

<210> SEQ ID NO 2
<211> LENGTH: 99
<212> TYPE: PRT
<213> ORGANISM: Homo sapiens

<400> SEQUENCE: 2

```
Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45
```

```
Ala Ser Tyr Arg Arg Ile Thr Ser Ser Lys Cys Pro Lys Glu Ala Val
        50                  55                  60

Ile Phe Lys Thr Ile Val Ala Lys Glu Ile Cys Ala Asp Pro Lys Gln
 65                  70                  75                  80

Lys Trp Val Gln Asp Ser Met Asp His Leu Asp Lys Gln Thr Gln Thr
                     85                  90                  95

Pro Lys Thr

<210> SEQ ID NO 3
<211> LENGTH: 92
<212> TYPE: PRT
<213> ORGANISM: Homo sapiens

<400> SEQUENCE: 3

Met Gln Val Ser Thr Ala Ala Leu Ala Val Leu Leu Cys Thr Met Ala
  1               5                  10                  15

Leu Cys Asn Gln Phe Ser Ala Ser Leu Ala Ala Asp Thr Pro Thr Ala
                 20                  25                  30

Cys Cys Phe Ser Tyr Thr Ser Arg Gln Ile Pro Gln Asn Phe Ile Ala
             35                  40                  45

Asp Tyr Phe Glu Thr Ser Ser Gln Cys Ser Lys Pro Gly Val Ile Phe
         50                  55                  60

Leu Thr Lys Arg Ser Arg Gln Val Cys Ala Asp Pro Ser Glu Glu Trp
 65                  70                  75                  80

Val Gln Lys Tyr Val Ser Asp Leu Glu Leu Ser Ala
                 85                  90

<210> SEQ ID NO 4
<211> LENGTH: 92
<212> TYPE: PRT
<213> ORGANISM: Homo sapiens

<400> SEQUENCE: 4

Met Lys Leu Cys Val Thr Val Leu Ser Leu Leu Met Leu Val Ala Ala
  1               5                  10                  15

Phe Cys Ser Pro Ala Leu Ser Ala Pro Met Gly Ser Asp Pro Pro Thr
                 20                  25                  30

Ala Cys Cys Phe Ser Tyr Thr Ala Arg Lys Leu Pro Arg Asn Phe Val
             35                  40                  45

Val Asp Tyr Tyr Glu Thr Ser Ser Leu Cys Ser Gln Pro Ala Val Val
         50                  55                  60

Phe Gln Thr Lys Arg Ser Lys Gln Val Cys Ala Asp Pro Ser Glu Ser
 65                  70                  75                  80

Trp Val Gln Glu Tyr Val Tyr Asp Leu Glu Leu Asn
                 85                  90

<210> SEQ ID NO 5
<211> LENGTH: 92
<212> TYPE: PRT
<213> ORGANISM: Homo sapiens

<400> SEQUENCE: 5

Met Lys Leu Cys Val Thr Val Leu Ser Leu Leu Val Leu Val Ala Ala
  1               5                  10                  15

Phe Cys Ser Leu Ala Leu Ser Ala Pro Met Gly Ser Asp Pro Pro Thr
                 20                  25                  30

Ala Cys Cys Phe Ser Tyr Thr Ala Arg Lys Leu Pro Arg Asn Phe Val
             35                  40                  45
```

```
Val Asp Tyr Tyr Glu Thr Ser Ser Leu Cys Ser Gln Pro Ala Val Val
    50                  55                  60

Phe Gln Thr Lys Arg Gly Lys Gln Val Cys Ala Asp Pro Ser Glu Ser
65                  70                  75                  80

Trp Val Gln Glu Tyr Val Tyr Asp Leu Glu Leu Asn
                85                  90

<210> SEQ ID NO 6
<211> LENGTH: 91
<212> TYPE: PRT
<213> ORGANISM: Homo sapiens

<400> SEQUENCE: 6

Met Lys Val Ser Ala Ala Leu Ala Val Ile Leu Ile Ala Thr Ala
1               5                   10                  15

Leu Cys Ala Pro Ala Ser Ala Ser Pro Tyr Ser Ser Asp Thr Thr Pro
                20                  25                  30

Cys Cys Phe Ala Tyr Ile Ala Arg Pro Leu Pro Arg Ala His Ile Lys
                35                  40                  45

Glu Tyr Phe Tyr Thr Ser Gly Lys Cys Ser Asn Pro Ala Val Val Phe
    50                  55                  60

Val Thr Arg Lys Asn Arg Gln Val Cys Ala Asn Pro Glu Lys Lys Trp
65                  70                  75                  80

Val Arg Glu Tyr Ile Asn Ser Leu Glu Met Ser
                85                  90

<210> SEQ ID NO 7
<211> LENGTH: 99
<212> TYPE: PRT
<213> ORGANISM: Homo sapiens

<400> SEQUENCE: 7

Met Lys Ala Ser Ala Ala Leu Leu Cys Leu Leu Leu Thr Ala Ala Ala
1               5                   10                  15

Phe Ser Pro Gln Gly Leu Ala Gln Pro Val Gly Ile Asn Thr Ser Thr
                20                  25                  30

Thr Cys Cys Tyr Arg Phe Ile Asn Lys Lys Ile Pro Lys Gln Arg Leu
                35                  40                  45

Glu Ser Tyr Arg Arg Thr Thr Ser Ser His Cys Pro Arg Glu Ala Val
    50                  55                  60

Ile Phe Lys Thr Lys Leu Asp Lys Glu Ile Cys Ala Asp Pro Thr Gln
65                  70                  75                  80

Lys Trp Val Gln Asp Phe Met Lys His Leu Asp Lys Lys Thr Gln Thr
                85                  90                  95

Pro Lys Leu

<210> SEQ ID NO 8
<211> LENGTH: 99
<212> TYPE: PRT
<213> ORGANISM: Homo sapiens

<400> SEQUENCE: 8

Met Lys Val Ser Ala Ala Leu Leu Cys Leu Leu Leu Met Ala Ala Thr
1               5                   10                  15

Phe Ser Pro Gln Gly Leu Ala Gln Pro Asp Ser Val Ser Ile Pro Ile
                20                  25                  30

Thr Cys Cys Phe Asn Val Ile Asn Arg Lys Ile Pro Ile Gln Arg Leu
                35                  40                  45
```

Glu Ser Tyr Thr Arg Ile Thr Asn Ile Gln Cys Pro Lys Glu Ala Val
            50                  55                  60

Ile Phe Lys Thr Lys Arg Gly Lys Glu Val Cys Ala Asp Pro Lys Glu
 65                  70                  75                  80

Arg Trp Val Arg Asp Ser Met Lys His Leu Asp Gln Ile Phe Gln Asn
                85                  90                  95

Leu Lys Pro

<210> SEQ ID NO 9
<211> LENGTH: 97
<212> TYPE: PRT
<213> ORGANISM: Homo sapiens

<400> SEQUENCE: 9

Met Lys Val Ser Ala Ala Leu Leu Trp Leu Leu Leu Ile Ala Ala Ala
 1               5                  10                  15

Phe Ser Pro Gln Gly Leu Ala Gly Pro Ala Ser Val Pro Thr Thr Cys
                20                  25                  30

Cys Phe Asn Leu Ala Asn Arg Lys Ile Pro Leu Gln Arg Leu Glu Ser
                35                  40                  45

Tyr Arg Arg Ile Thr Ser Gly Lys Cys Pro Gln Lys Ala Val Ile Phe
            50                  55                  60

Lys Thr Lys Leu Ala Lys Asp Ile Cys Ala Asp Pro Lys Lys Lys Trp
 65                  70                  75                  80

Val Gln Asp Ser Met Lys Tyr Leu Asp Gln Lys Ser Pro Thr Pro Lys
                85                  90                  95

Pro

<210> SEQ ID NO 10
<211> LENGTH: 98
<212> TYPE: PRT
<213> ORGANISM: Homo sapiens

<400> SEQUENCE: 10

Met Lys Val Ser Ala Val Leu Leu Cys Leu Leu Leu Met Thr Ala Ala
 1               5                  10                  15

Phe Asn Pro Gln Gly Leu Ala Gln Pro Asp Ala Leu Asn Val Pro Ser
                20                  25                  30

Thr Cys Cys Phe Thr Phe Ser Ser Lys Lys Ile Ser Leu Gln Arg Leu
                35                  40                  45

Lys Ser Tyr Val Ile Thr Thr Ser Arg Cys Pro Gln Lys Ala Val Ile
            50                  55                  60

Phe Arg Thr Lys Leu Gly Lys Glu Ile Cys Ala Asp Pro Lys Glu Lys
 65                  70                  75                  80

Trp Val Gln Asn Tyr Met Lys His Leu Gly Arg Lys Ala His Thr Leu
                85                  90                  95

Lys Thr

<210> SEQ ID NO 11
<211> LENGTH: 93
<212> TYPE: PRT
<213> ORGANISM: Homo sapiens

<400> SEQUENCE: 11

Met Lys Ile Ser Val Ala Ala Ile Pro Phe Phe Leu Leu Ile Thr Ile
 1               5                  10                  15

Ala Leu Gly Thr Lys Thr Glu Ser Ser Ser Arg Gly Pro Tyr His Pro

-continued

```
                    20                  25                  30
Ser Glu Cys Cys Phe Thr Tyr Thr Thr Tyr Lys Ile Pro Arg Gln Arg
            35                  40                  45

Ile Met Asp Tyr Tyr Glu Thr Asn Ser Gln Cys Ser Lys Pro Gly Ile
50                  55                  60

Val Phe Ile Thr Lys Arg Gly His Ser Val Cys Thr Asn Pro Ser Asp
65                  70                  75                  80

Lys Trp Val Gln Asp Tyr Ile Lys Asp Met Lys Glu Asn
                85                  90

<210> SEQ ID NO 12
<211> LENGTH: 109
<212> TYPE: PRT
<213> ORGANISM: Homo sapiens

<400> SEQUENCE: 12

Met Lys Ile Ser Val Ala Ala Ile Pro Phe Phe Leu Leu Ile Thr Ile
1               5                   10                  15

Ala Leu Gly Thr Lys Thr Glu Ser Ser Ser Gln Thr Gly Gly Lys Pro
                20                  25                  30

Lys Val Val Lys Ile Gln Leu Lys Leu Val Gly Gly Pro Tyr His Pro
            35                  40                  45

Ser Glu Cys Cys Phe Thr Tyr Thr Thr Tyr Lys Ile Pro Arg Gln Arg
        50                  55                  60

Ile Met Asp Tyr Tyr Glu Thr Asn Ser Gln Cys Ser Lys Pro Gly Ile
65                  70                  75                  80

Val Phe Ile Thr Lys Arg Gly His Ser Val Cys Thr Asn Pro Ser Asp
                85                  90                  95

Lys Trp Val Gln Asp Tyr Ile Lys Asp Met Lys Glu Asn
                100                 105

<210> SEQ ID NO 13
<211> LENGTH: 113
<212> TYPE: PRT
<213> ORGANISM: Homo sapiens

<400> SEQUENCE: 13

Met Lys Val Ser Val Ala Ala Leu Ser Cys Leu Met Leu Val Ala Val
1               5                   10                  15

Leu Gly Ser Gln Ala Gln Phe Ile Asn Asp Ala Glu Thr Glu Leu Met
                20                  25                  30

Met Ser Lys Leu Pro Leu Glu Asn Pro Val Val Leu Asn Ser Phe His
            35                  40                  45

Phe Ala Ala Asp Cys Cys Thr Ser Tyr Ile Ser Gln Ser Ile Pro Cys
50                  55                  60

Ser Leu Met Lys Ser Tyr Phe Glu Thr Ser Ser Glu Cys Ser Lys Pro
65                  70                  75                  80

Gly Val Ile Phe Leu Thr Lys Lys Gly Arg Gln Val Cys Ala Lys Pro
                85                  90                  95

Ser Gly Pro Gly Val Gln Asp Cys Met Lys Lys Leu Lys Pro Tyr Ser
                100                 105                 110

Ile

<210> SEQ ID NO 14
<211> LENGTH: 120
<212> TYPE: PRT
<213> ORGANISM: Homo sapiens
```

-continued

<400> SEQUENCE: 14

Met Lys Val Ser Glu Ala Ala Leu Ser Leu Leu Val Leu Ile Leu Ile
1               5                   10                  15

Ile Thr Ser Ala Ser Arg Ser Gln Pro Lys Val Pro Glu Trp Val Asn
            20                  25                  30

Thr Pro Ser Thr Cys Cys Leu Lys Tyr Tyr Glu Lys Val Leu Pro Arg
        35                  40                  45

Arg Leu Val Val Gly Tyr Arg Lys Ala Leu Asn Cys His Leu Pro Ala
    50                  55                  60

Ile Ile Phe Val Thr Lys Arg Asn Arg Glu Val Cys Thr Asn Pro Asn
65                  70                  75                  80

Asp Asp Trp Val Gln Glu Tyr Ile Lys Asp Pro Asn Leu Pro Leu Leu
                85                  90                  95

Pro Thr Arg Asn Leu Ser Thr Val Lys Ile Ile Thr Ala Lys Asn Gly
            100                 105                 110

Gln Pro Gln Leu Leu Asn Ser Gln
        115                 120

<210> SEQ ID NO 15
<211> LENGTH: 94
<212> TYPE: PRT
<213> ORGANISM: Homo sapiens

<400> SEQUENCE: 15

Met Ala Pro Leu Lys Met Leu Ala Leu Val Thr Leu Leu Gly Ala
1               5                   10                  15

Ser Leu Gln His Ile His Ala Ala Arg Gly Thr Asn Val Gly Arg Glu
            20                  25                  30

Cys Cys Leu Glu Tyr Phe Lys Gly Ala Ile Pro Leu Arg Lys Leu Lys
        35                  40                  45

Thr Trp Tyr Gln Thr Ser Glu Asp Cys Ser Arg Asp Ala Ile Val Phe
    50                  55                  60

Val Thr Val Gln Gly Arg Ala Ile Cys Ser Asp Pro Asn Asn Lys Arg
65                  70                  75                  80

Val Lys Asn Ala Val Lys Tyr Leu Gln Ser Leu Glu Arg Ser
                85                  90

<210> SEQ ID NO 16
<211> LENGTH: 89
<212> TYPE: PRT
<213> ORGANISM: Homo sapiens

<400> SEQUENCE: 16

Met Lys Gly Leu Ala Ala Ala Leu Leu Val Leu Val Cys Thr Met Ala
1               5                   10                  15

Leu Cys Ser Cys Ala Gln Val Gly Thr Asn Lys Glu Leu Cys Cys Leu
            20                  25                  30

Val Tyr Thr Ser Trp Gln Ile Pro Gln Lys Phe Ile Val Asp Tyr Ser
        35                  40                  45

Glu Thr Ser Pro Gln Cys Pro Lys Pro Gly Val Ile Leu Leu Thr Lys
    50                  55                  60

Arg Gly Arg Gln Ile Cys Ala Asp Pro Asn Lys Lys Trp Val Gln Lys
65                  70                  75                  80

Tyr Ile Ser Asp Leu Lys Leu Asn Ala
                85

<210> SEQ ID NO 17

<211> LENGTH: 98
<212> TYPE: PRT
<213> ORGANISM: Homo sapiens

<400> SEQUENCE: 17

Met Ala Leu Leu Leu Ala Leu Ser Leu Leu Val Leu Trp Thr Ser Pro
1               5                   10                  15

Ala Pro Thr Leu Ser Gly Thr Asn Asp Ala Glu Asp Cys Cys Leu Ser
            20                  25                  30

Val Thr Gln Lys Pro Ile Pro Gly Tyr Ile Val Arg Asn Phe His Tyr
        35                  40                  45

Leu Leu Ile Lys Asp Gly Cys Arg Val Pro Ala Val Val Phe Thr Thr
    50                  55                  60

Leu Arg Gly Arg Gln Leu Cys Ala Pro Pro Asp Gln Pro Trp Val Glu
65                  70                  75                  80

Arg Ile Ile Gln Arg Leu Gln Arg Thr Ser Ala Lys Met Lys Arg Arg
                85                  90                  95

Ser Ser

<210> SEQ ID NO 18
<211> LENGTH: 96
<212> TYPE: PRT
<213> ORGANISM: Homo sapiens

<400> SEQUENCE: 18

Met Cys Cys Thr Lys Ser Leu Leu Leu Ala Ala Leu Met Ser Val Leu
1               5                   10                  15

Leu Leu His Leu Cys Gly Glu Ser Glu Ala Ala Ser Asn Phe Asp Cys
            20                  25                  30

Cys Leu Gly Tyr Thr Asp Arg Ile Leu His Pro Lys Phe Ile Val Gly
        35                  40                  45

Phe Thr Arg Gln Leu Ala Asn Glu Gly Cys Asp Ile Asn Ala Ile Ile
    50                  55                  60

Phe His Thr Lys Lys Lys Leu Ser Val Cys Ala Asn Pro Lys Gln Thr
65                  70                  75                  80

Trp Val Lys Tyr Ile Val Arg Leu Leu Ser Lys Lys Val Lys Asn Met
                85                  90                  95

<210> SEQ ID NO 19
<211> LENGTH: 95
<212> TYPE: PRT
<213> ORGANISM: Homo sapiens

<400> SEQUENCE: 19

Met Cys Cys Thr Lys Ser Leu Leu Leu Ala Ala Leu Met Ser Val Leu
1               5                   10                  15

Leu Leu His Leu Cys Gly Glu Ser Glu Ala Ser Asn Phe Asp Cys Cys
            20                  25                  30

Leu Gly Tyr Thr Asp Arg Ile Leu His Pro Lys Phe Ile Val Gly Phe
        35                  40                  45

Thr Arg Gln Leu Ala Asn Glu Gly Cys Asp Ile Asn Ala Ile Ile Phe
    50                  55                  60

His Thr Lys Lys Lys Leu Ser Val Cys Ala Asn Pro Lys Gln Thr Trp
65                  70                  75                  80

Val Lys Tyr Ile Val Arg Leu Leu Ser Lys Lys Val Lys Asn Met
                85                  90                  95

<210> SEQ ID NO 20

-continued

```
<211> LENGTH: 134
<212> TYPE: PRT
<213> ORGANISM: Homo sapiens

<400> SEQUENCE: 20

Met Ala Gln Ser Leu Ala Leu Ser Leu Ile Leu Val Leu Ala Phe
1               5                   10                  15

Gly Ile Pro Arg Thr Gln Gly Ser Asp Gly Ala Gln Asp Cys Cys
                20                  25                  30

Leu Lys Tyr Ser Gln Arg Lys Ile Pro Ala Lys Val Val Arg Ser Tyr
            35                  40                  45

Arg Lys Gln Glu Pro Ser Leu Gly Cys Ser Ile Pro Ala Ile Leu Phe
50                  55                          60

Leu Pro Arg Lys Arg Ser Gln Ala Glu Leu Cys Ala Asp Pro Lys Glu
65                  70                  75                  80

Leu Trp Val Gln Gln Leu Met Gln His Leu Asp Lys Thr Pro Ser Pro
                85                  90                  95

Gln Lys Pro Ala Gln Gly Cys Arg Lys Asp Arg Gly Ala Ser Lys Thr
            100                 105                 110

Gly Lys Lys Gly Lys Gly Ser Lys Gly Cys Lys Arg Thr Glu Arg Ser
        115                 120                 125

Gln Thr Pro Lys Gly Pro
    130

<210> SEQ ID NO 21
<211> LENGTH: 93
<212> TYPE: PRT
<213> ORGANISM: Homo sapiens

<400> SEQUENCE: 21

Met Asp Arg Leu Gln Thr Ala Leu Leu Val Val Leu Val Leu Leu Ala
1               5                   10                  15

Val Ala Leu Gln Ala Thr Glu Ala Gly Pro Tyr Gly Ala Asn Met Glu
                20                  25                  30

Asp Ser Val Cys Cys Arg Asp Tyr Val Arg Tyr Arg Leu Pro Leu Arg
            35                  40                  45

Val Val Lys His Phe Tyr Trp Thr Ser Asp Ser Cys Pro Arg Pro Gly
50                  55                  60

Val Val Leu Leu Thr Phe Arg Asp Lys Glu Ile Cys Ala Asp Pro Arg
65                  70                  75                  80

Val Pro Trp Val Lys Met Ile Leu Asn Lys Leu Ser Gln
                85                  90

<210> SEQ ID NO 22
<211> LENGTH: 120
<212> TYPE: PRT
<213> ORGANISM: Homo sapiens

<400> SEQUENCE: 22

Met Lys Val Ser Val Ala Ala Leu Ser Cys Leu Met Leu Val Thr Ala
1               5                   10                  15

Leu Gly Ser Gln Ala Arg Val Thr Lys Asp Ala Glu Thr Glu Phe Met
                20                  25                  30

Met Ser Lys Leu Pro Leu Glu Asn Pro Val Leu Leu Asp Arg Phe His
            35                  40                  45

Ala Thr Ser Ala Asp Cys Cys Ile Ser Tyr Thr Pro Arg Ser Ile Pro
50                  55                  60

Cys Ser Leu Leu Glu Ser Tyr Phe Glu Thr Asn Ser Glu Cys Ser Lys
```

```
                65                  70                  75                  80
Pro Gly Val Ile Phe Leu Thr Lys Lys Gly Arg Arg Phe Cys Ala Asn
                    85                  90                  95

Pro Ser Asp Lys Gln Val Gln Val Cys Val Arg Met Leu Lys Leu Asp
                    100                 105                 110

Thr Arg Ile Lys Thr Arg Lys Asn
                    115                 120

<210> SEQ ID NO 23
<211> LENGTH: 137
<212> TYPE: PRT
<213> ORGANISM: Homo sapiens

<400> SEQUENCE: 23

Met Lys Val Ser Val Ala Ala Leu Ser Cys Leu Met Leu Val Thr Ala
1               5                   10                  15

Leu Gly Ser Gln Ala Arg Val Thr Lys Asp Ala Glu Thr Glu Phe Met
                20                  25                  30

Met Ser Lys Leu Pro Leu Glu Asn Pro Val Leu Leu Asp Met Leu Trp
            35                  40                  45

Arg Arg Lys Ile Gly Pro Gln Met Thr Leu Ser His Ala Ala Gly Phe
50                  55                  60

His Ala Thr Ser Ala Asp Cys Cys Ile Ser Tyr Thr Pro Arg Ser Ile
65                  70                  75                  80

Pro Cys Ser Leu Leu Glu Ser Tyr Phe Glu Thr Asn Ser Glu Cys Ser
                    85                  90                  95

Lys Pro Gly Val Ile Phe Leu Thr Lys Lys Gly Arg Arg Phe Cys Ala
                    100                 105                 110

Asn Pro Ser Asp Lys Gln Val Gln Val Cys Val Arg Met Leu Lys Leu
                    115                 120                 125

Asp Thr Arg Ile Lys Thr Arg Lys Asn
            130                 135

<210> SEQ ID NO 24
<211> LENGTH: 119
<212> TYPE: PRT
<213> ORGANISM: Homo sapiens

<400> SEQUENCE: 24

Met Ala Gly Leu Met Thr Ile Val Thr Ser Leu Leu Phe Leu Gly Val
1               5                   10                  15

Cys Ala His His Ile Ile Pro Thr Gly Ser Val Val Ile Pro Ser Pro
                20                  25                  30

Cys Cys Met Phe Phe Val Ser Lys Arg Ile Pro Glu Asn Arg Val Val
            35                  40                  45

Ser Tyr Gln Leu Ser Ser Arg Ser Thr Cys Leu Lys Ala Gly Val Ile
50                  55                  60

Phe Thr Thr Lys Lys Gly Gln Gln Phe Cys Gly Asp Pro Lys Gln Glu
65                  70                  75                  80

Trp Val Gln Arg Tyr Met Lys Asn Leu Asp Ala Lys Gln Lys Lys Ala
                    85                  90                  95

Ser Pro Arg Ala Arg Ala Val Ala Val Lys Gly Pro Val Gln Arg Tyr
                    100                 105                 110

Pro Gly Asn Gln Thr Thr Cys
            115

<210> SEQ ID NO 25
```

```
<211> LENGTH: 150
<212> TYPE: PRT
<213> ORGANISM: Homo sapiens

<400> SEQUENCE: 25

Met Asn Leu Trp Leu Leu Ala Cys Leu Val Ala Gly Phe Leu Gly Ala
1               5                   10                  15

Trp Ala Pro Ala Val His Thr Gln Gly Val Phe Glu Asp Cys Cys Leu
            20                  25                  30

Ala Tyr His Tyr Pro Ile Gly Trp Ala Val Leu Arg Arg Ala Trp Thr
        35                  40                  45

Tyr Arg Ile Gln Glu Val Ser Gly Ser Cys Asn Leu Pro Ala Ala Ile
50                  55                  60

Phe Tyr Leu Pro Lys Arg His Arg Lys Val Cys Gly Asn Pro Lys Ser
65                  70                  75                  80

Arg Glu Val Gln Arg Ala Met Lys Leu Leu Asp Ala Arg Asn Lys Val
                85                  90                  95

Phe Ala Lys Leu His His Asn Thr Gln Thr Phe Gln Ala Gly Pro His
            100                 105                 110

Ala Val Lys Lys Leu Ser Ser Gly Asn Ser Lys Leu Ser Ser Ser Lys
        115                 120                 125

Phe Ser Asn Pro Ile Ser Ser Ser Lys Arg Asn Val Ser Leu Leu Ile
130                 135                 140

Ser Ala Asn Ser Gly Leu
145                 150

<210> SEQ ID NO 26
<211> LENGTH: 84
<212> TYPE: PRT
<213> ORGANISM: Homo sapiens

<400> SEQUENCE: 26

Met Asn Leu Trp Leu Leu Ala Cys Leu Val Ala Gly Phe Leu Gly Ala
1               5                   10                  15

Trp Ala Pro Ala Val His Thr Gln Gly Val Phe Glu Asp Cys Cys Leu
            20                  25                  30

Ala Tyr His Tyr Pro Ile Gly Trp Ala Val Leu Arg Arg Ala Trp Thr
        35                  40                  45

Tyr Arg Ile Gln Glu Val Ser Gly Ser Cys Asn Leu Pro Ala Ala Ile
50                  55                  60

Arg Pro Ser Cys Cys Lys Glu Val Glu Phe Trp Lys Leu Gln Val Ile
65                  70                  75                  80

Ile Val Gln Val

<210> SEQ ID NO 27
<211> LENGTH: 84
<212> TYPE: PRT
<213> ORGANISM: Homo sapiens

<400> SEQUENCE: 27

Met Asn Leu Trp Leu Leu Ala Cys Leu Val Ala Gly Phe Leu Gly Ala
1               5                   10                  15

Trp Ala Pro Ala Val His Thr Gln Gly Val Phe Glu Asp Cys Cys Leu
            20                  25                  30

Ala Tyr His Tyr Pro Ile Gly Trp Ala Val Leu Arg Arg Ala Trp Thr
        35                  40                  45

Tyr Arg Ile Gln Glu Val Ser Gly Ser Cys Asn Leu Pro Ala Ala Ile
50                  55                  60
```

```
Arg Pro Ser Cys Cys Lys Glu Val Glu Phe Trp Lys Leu Gln Val Ile
 65                  70                  75                  80

Ile Ile Gln Val
```

<210> SEQ ID NO 28
<211> LENGTH: 94
<212> TYPE: PRT
<213> ORGANISM: Homo sapiens

<400> SEQUENCE: 28

```
Met Met Gly Leu Ser Leu Ala Ser Ala Val Leu Leu Ala Ser Leu Leu
  1               5                  10                  15

Ser Leu His Leu Gly Thr Ala Thr Arg Gly Ser Asp Ile Ser Lys Thr
                 20                  25                  30

Cys Cys Phe Gln Tyr Ser His Lys Pro Leu Pro Trp Thr Trp Val Arg
             35                  40                  45

Ser Tyr Glu Phe Thr Ser Asn Ser Cys Ser Gln Arg Ala Val Ile Phe
         50                  55                  60

Thr Thr Lys Arg Gly Lys Lys Val Cys Thr His Pro Arg Lys Lys Trp
 65                  70                  75                  80

Val Gln Lys Tyr Ile Ser Leu Leu Lys Thr Pro Lys Gln Leu
                 85                  90
```

<210> SEQ ID NO 29
<211> LENGTH: 112
<212> TYPE: PRT
<213> ORGANISM: Homo sapiens

<400> SEQUENCE: 29

```
Met Lys Gly Pro Pro Thr Phe Cys Ser Leu Leu Leu Ser Leu Leu
  1               5                  10                  15

Leu Ser Pro Asp Pro Thr Ala Ala Phe Leu Pro Pro Ser Thr Ala
                 20                  25                  30

Cys Cys Thr Gln Leu Tyr Arg Lys Pro Leu Ser Asp Lys Leu Leu Arg
             35                  40                  45

Lys Val Ile Gln Val Glu Leu Gln Glu Ala Asp Gly Asp Cys His Leu
         50                  55                  60

Gln Ala Phe Val Leu His Leu Ala Gln Arg Ser Ile Cys Ile His Pro
 65                  70                  75                  80

Gln Asn Pro Ser Leu Ser Gln Trp Phe Glu His Gln Glu Arg Lys Leu
                 85                  90                  95

His Gly Thr Leu Pro Lys Leu Asn Phe Gly Met Leu Arg Lys Met Gly
                100                 105                 110
```

<210> SEQ ID NO 30
<211> LENGTH: 127
<212> TYPE: PRT
<213> ORGANISM: Homo sapiens

<400> SEQUENCE: 30

```
Met Gln Gln Arg Gly Leu Ala Ile Val Ala Leu Ala Val Cys Ala Ala
  1               5                  10                  15

Leu His Ala Ser Glu Ala Ile Leu Pro Ile Ala Ser Ser Cys Cys Thr
                 20                  25                  30

Glu Val Ser His His Ile Ser Arg Arg Leu Leu Glu Arg Val Asn Met
             35                  40                  45

Cys Arg Ile Gln Arg Ala Asp Gly Asp Cys Asp Leu Ala Ala Val Ile
         50                  55                  60
```

Leu His Val Lys Arg Arg Ile Cys Val Ser Pro His Asn His Thr
65                  70                  75                  80

Val Lys Gln Trp Met Lys Val Gln Ala Ala Lys Lys Asn Gly Lys Gly
                85                  90                  95

Asn Val Cys His Arg Lys Lys His His Gly Lys Arg Asn Ser Asn Arg
            100                 105                 110

Ala His Gln Gly Lys His Glu Thr Tyr Gly His Lys Thr Pro Tyr
        115                 120                 125

<210> SEQ ID NO 31
<211> LENGTH: 107
<212> TYPE: PRT
<213> ORGANISM: Homo sapiens

<400> SEQUENCE: 31

Met Ala Arg Ala Ala Leu Ser Ala Ala Pro Ser Asn Pro Arg Leu Leu
1               5                   10                  15

Arg Val Ala Leu Leu Leu Leu Leu Val Ala Ala Gly Arg Arg Ala
                20                  25                  30

Ala Gly Ala Ser Val Ala Thr Glu Leu Arg Cys Gln Cys Leu Gln Thr
            35                  40                  45

Leu Gln Gly Ile His Pro Lys Asn Ile Gln Ser Val Asn Val Lys Ser
        50                  55                  60

Pro Gly Pro His Cys Ala Gln Thr Glu Val Ile Ala Thr Leu Lys Asn
65                  70                  75                  80

Gly Arg Lys Ala Cys Leu Asn Pro Ala Ser Pro Ile Val Lys Lys Ile
                85                  90                  95

Ile Glu Lys Met Leu Asn Ser Asp Lys Ser Asn
            100                 105

<210> SEQ ID NO 32
<211> LENGTH: 107
<212> TYPE: PRT
<213> ORGANISM: Homo sapiens

<400> SEQUENCE: 32

Met Ala Arg Ala Thr Leu Ser Ala Ala Pro Ser Asn Pro Arg Leu Leu
1               5                   10                  15

Arg Val Ala Leu Leu Leu Leu Leu Val Ala Ala Ser Arg Arg Ala
                20                  25                  30

Ala Gly Ala Pro Leu Ala Thr Glu Leu Arg Cys Gln Cys Leu Gln Thr
            35                  40                  45

Leu Gln Gly Ile His Leu Lys Asn Ile Gln Ser Val Lys Val Lys Ser
        50                  55                  60

Pro Gly Pro His Cys Ala Gln Thr Glu Val Ile Ala Thr Leu Lys Asn
65                  70                  75                  80

Gly Gln Lys Ala Cys Leu Asn Pro Ala Ser Pro Met Val Lys Lys Ile
                85                  90                  95

Ile Glu Lys Met Leu Lys Asn Gly Lys Ser Asn
            100                 105

<210> SEQ ID NO 33
<211> LENGTH: 107
<212> TYPE: PRT
<213> ORGANISM: Homo sapiens

<400> SEQUENCE: 33

Met Ala His Ala Thr Leu Ser Ala Ala Pro Ser Asn Pro Arg Leu Leu

-continued

```
                1               5                   10                  15
Arg Val Ala Leu Leu Leu Leu Leu Val Ala Ser Arg Arg Ala
                    20                  25                  30

Ala Gly Ala Ser Val Val Thr Glu Leu Arg Cys Gln Cys Leu Gln Thr
                    35                  40                  45

Leu Gln Gly Ile His Leu Lys Asn Ile Gln Ser Val Asn Val Arg Ser
            50                  55                  60

Pro Gly Pro His Cys Ala Gln Thr Glu Val Ile Ala Thr Leu Lys Asn
65                  70                  75                  80

Gly Lys Lys Ala Cys Leu Asn Pro Ala Ser Pro Met Val Gln Lys Ile
                    85                  90                  95

Ile Glu Lys Ile Leu Asn Lys Gly Ser Thr Asn
                100                 105

<210> SEQ ID NO 34
<211> LENGTH: 101
<212> TYPE: PRT
<213> ORGANISM: Homo sapiens

<400> SEQUENCE: 34

Met Ser Ser Ala Ala Gly Phe Cys Ala Ser Arg Pro Gly Leu Leu Phe
1               5                   10                  15

Leu Gly Leu Leu Leu Leu Pro Leu Val Val Ala Phe Ala Ser Ala Glu
                    20                  25                  30

Ala Glu Glu Asp Gly Asp Leu Gln Cys Leu Cys Val Lys Thr Thr Ser
                    35                  40                  45

Gln Val Arg Pro Arg His Ile Thr Ser Leu Glu Val Ile Lys Ala Gly
            50                  55                  60

Pro His Cys Pro Thr Ala Gln Leu Ile Ala Thr Leu Lys Asn Gly Arg
65                  70                  75                  80

Lys Ile Cys Leu Asp Leu Gln Ala Pro Leu Tyr Lys Lys Ile Ile Lys
                    85                  90                  95

Lys Leu Leu Glu Ser
                100

<210> SEQ ID NO 35
<211> LENGTH: 114
<212> TYPE: PRT
<213> ORGANISM: Homo sapiens

<400> SEQUENCE: 35

Met Ser Leu Leu Ser Ser Arg Ala Ala Arg Val Pro Gly Pro Ser Ser
1               5                   10                  15

Ser Leu Cys Ala Leu Leu Val Leu Leu Leu Leu Thr Gln Pro Gly Pro
                    20                  25                  30

Pro Ile Ala Ser Ala Gly Pro Ala Ala Ala Val Leu Arg Glu Leu Arg
                    35                  40                  45

Cys Val Cys Leu Gln Thr Thr Gln Gly Val His Pro Lys Met Ile Ser
            50                  55                  60

Asn Leu Gln Val Phe Ala Ile Gly Pro Gln Cys Ser Lys Val Glu Val
65                  70                  75                  80

Val Ala Ser Leu Lys Asn Gly Lys Glu Ile Cys Leu Asp Pro Glu Ala
                    85                  90                  95

Pro Phe Leu Lys Lys Val Ile Gln Lys Ile Leu Asp Gly Gly Asn Lys
                100                 105                 110

Glu Asn
```

<210> SEQ ID NO 36
<211> LENGTH: 114
<212> TYPE: PRT
<213> ORGANISM: Homo sapiens

<400> SEQUENCE: 36

Met Ser Leu Pro Ser Ser Arg Ala Arg Val Pro Gly Pro Ser Gly
1               5                   10                  15

Ser Leu Cys Ala Leu Leu Ala Leu Leu Leu Leu Thr Pro Pro Gly
                20                  25                  30

Pro Leu Ala Ser Ala Gly Pro Val Ser Ala Val Leu Thr Glu Leu Arg
            35                  40                  45

Cys Thr Cys Leu Arg Val Thr Leu Arg Val Asn Pro Lys Thr Ile Gly
        50                  55                  60

Lys Leu Gln Val Phe Pro Ala Gly Pro Gln Cys Ser Lys Val Glu Val
65                  70                  75                  80

Val Ala Ser Leu Lys Asn Gly Lys Gln Val Cys Leu Asp Pro Glu Ala
                85                  90                  95

Pro Phe Leu Lys Lys Val Ile Gln Lys Ile Leu Asp Ser Gly Asn Lys
            100                 105                 110

Lys Asn

<210> SEQ ID NO 37
<211> LENGTH: 128
<212> TYPE: PRT
<213> ORGANISM: Homo sapiens

<400> SEQUENCE: 37

Met Ser Leu Arg Leu Asp Thr Thr Pro Ser Cys Asn Ser Ala Arg Pro
1               5                   10                  15

Leu His Ala Leu Gln Val Leu Leu Leu Ser Leu Leu Leu Thr Ala
                20                  25                  30

Leu Ala Ser Ser Thr Lys Gly Gln Thr Lys Arg Asn Leu Ala Lys Gly
            35                  40                  45

Lys Glu Glu Ser Leu Asp Ser Asp Leu Tyr Ala Glu Leu Arg Cys Met
        50                  55                  60

Cys Ile Lys Thr Thr Ser Gly Ile His Pro Lys Asn Ile Gln Ser Leu
65                  70                  75                  80

Glu Val Ile Gly Lys Gly Thr His Cys Asn Gln Val Glu Val Ile Ala
                85                  90                  95

Thr Leu Lys Asp Gly Arg Lys Ile Cys Leu Asp Pro Asp Ala Pro Arg
            100                 105                 110

Ile Lys Lys Ile Val Gln Lys Lys Leu Ala Gly Asp Glu Ser Ala Asp
        115                 120                 125

<210> SEQ ID NO 38
<211> LENGTH: 99
<212> TYPE: PRT
<213> ORGANISM: Homo sapiens

<400> SEQUENCE: 38

Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
                20                  25                  30

Arg Cys Gln Cys Ile Lys Thr Tyr Ser Lys Pro Phe His Pro Lys Phe
            35                  40                  45

```
Ile Lys Glu Leu Arg Val Ile Glu Ser Gly Pro His Cys Ala Asn Thr
 50                  55                  60

Glu Ile Ile Val Lys Leu Ser Asp Gly Arg Glu Leu Cys Leu Asp Pro
 65                  70                  75                  80

Lys Glu Asn Trp Val Gln Arg Val Val Glu Lys Phe Leu Lys Arg Ala
                 85                  90                  95

Glu Asn Ser

<210> SEQ ID NO 39
<211> LENGTH: 125
<212> TYPE: PRT
<213> ORGANISM: Homo sapiens

<400> SEQUENCE: 39

Met Lys Lys Ser Gly Val Leu Phe Leu Leu Gly Ile Ile Leu Leu Val
 1               5                  10                  15

Leu Ile Gly Val Gln Gly Thr Pro Val Val Arg Lys Gly Arg Cys Ser
                 20                  25                  30

Cys Ile Ser Thr Asn Gln Gly Thr Ile His Leu Gln Ser Leu Lys Asp
             35                  40                  45

Leu Lys Gln Phe Ala Pro Ser Pro Ser Cys Glu Lys Ile Glu Ile Ile
 50                  55                  60

Ala Thr Leu Lys Asn Gly Val Gln Thr Cys Leu Asn Pro Asp Ser Ala
 65                  70                  75                  80

Asp Val Lys Glu Leu Ile Lys Lys Trp Glu Lys Gln Val Ser Gln Lys
                 85                  90                  95

Lys Lys Gln Lys Asn Gly Lys Lys His Gln Lys Lys Lys Val Leu Lys
            100                 105                 110

Val Arg Lys Ser Gln Arg Ser Arg Gln Lys Lys Thr Thr
            115                 120                 125

<210> SEQ ID NO 40
<211> LENGTH: 98
<212> TYPE: PRT
<213> ORGANISM: Homo sapiens

<400> SEQUENCE: 40

Met Asn Gln Thr Ala Ile Leu Ile Cys Cys Leu Ile Phe Leu Thr Leu
 1               5                  10                  15

Ser Gly Ile Gln Gly Val Pro Leu Ser Arg Thr Val Arg Cys Thr Cys
                 20                  25                  30

Ile Ser Ile Ser Asn Gln Pro Val Asn Pro Arg Ser Leu Glu Lys Leu
             35                  40                  45

Glu Ile Ile Pro Ala Ser Gln Phe Cys Pro Arg Val Glu Ile Ile Ala
 50                  55                  60

Thr Met Lys Lys Lys Gly Glu Lys Arg Cys Leu Asn Pro Glu Ser Lys
 65                  70                  75                  80

Ala Ile Lys Asn Leu Leu Lys Ala Val Ser Lys Glu Arg Ser Lys Arg
                 85                  90                  95

Ser Pro

<210> SEQ ID NO 41
<211> LENGTH: 94
<212> TYPE: PRT
<213> ORGANISM: Homo sapiens

<400> SEQUENCE: 41

Met Ser Val Lys Gly Met Ala Ile Ala Leu Ala Val Ile Leu Cys Ala
 1               5                  10                  15
```

```
                1               5                  10                 15
Thr Val Val Gln Gly Phe Pro Met Phe Lys Arg Gly Arg Cys Leu Cys
                   20                  25                 30

Ile Gly Pro Gly Val Lys Ala Val Lys Val Ala Asp Ile Glu Lys Ala
                   35                  40                 45

Ser Ile Met Tyr Pro Ser Asn Asn Cys Asp Lys Ile Glu Val Ile Ile
            50                  55                 60

Thr Leu Lys Glu Asn Lys Gly Gln Arg Cys Leu Asn Pro Lys Ser Lys
65                      70                 75                 80

Gln Ala Arg Leu Ile Ile Lys Lys Val Glu Arg Lys Asn Phe
                85                  90
```

<210> SEQ ID NO 42
<211> LENGTH: 93
<212> TYPE: PRT
<213> ORGANISM: Homo sapiens

<400> SEQUENCE: 42

```
Met Asn Ala Lys Val Val Val Leu Val Val Leu Thr Ala Leu
1               5                  10                 15

Cys Leu Ser Asp Gly Lys Pro Val Ser Leu Ser Tyr Arg Cys Pro Cys
                   20                  25                 30

Arg Phe Phe Glu Ser His Val Ala Arg Ala Asn Val Lys His Leu Lys
                   35                  40                 45

Ile Leu Asn Thr Pro Asn Cys Ala Leu Gln Ile Val Ala Arg Leu Lys
            50                  55                 60

Asn Asn Asn Arg Gln Val Cys Ile Asp Pro Lys Leu Lys Trp Ile Gln
65                      70                 75                 80

Glu Tyr Leu Glu Lys Ala Leu Asn Lys Arg Phe Lys Met
                85                  90
```

<210> SEQ ID NO 43
<211> LENGTH: 109
<212> TYPE: PRT
<213> ORGANISM: Homo sapiens

<400> SEQUENCE: 43

```
Met Lys Phe Ile Ser Thr Ser Leu Leu Leu Met Leu Leu Val Ser Ser
1               5                  10                 15

Leu Ser Pro Val Gln Gly Val Leu Glu Val Tyr Tyr Thr Ser Leu Arg
                   20                  25                 30

Cys Arg Cys Val Gln Glu Ser Ser Val Phe Ile Pro Arg Arg Phe Ile
                   35                  40                 45

Asp Arg Ile Gln Ile Leu Pro Arg Gly Asn Gly Cys Pro Arg Lys Glu
            50                  55                 60

Ile Ile Val Trp Lys Lys Asn Lys Ser Ile Val Cys Val Asp Pro Gln
65                      70                 75                 80

Ala Glu Trp Ile Gln Arg Met Met Glu Val Leu Arg Lys Arg Ser Ser
                85                  90                      95

Ser Thr Leu Pro Val Pro Val Phe Lys Arg Lys Ile Pro
                100                 105
```

<210> SEQ ID NO 44
<211> LENGTH: 273
<212> TYPE: PRT
<213> ORGANISM: Homo sapiens

<400> SEQUENCE: 44

```
Met Ser Gly Ser Gln Ser Glu Val Ala Pro Ser Pro Gln Ser Pro Arg
1               5                   10                  15

Ser Pro Glu Met Gly Arg Asp Leu Arg Pro Gly Ser Arg Val Leu Leu
                20                  25                  30

Leu Leu Leu Leu Leu Leu Leu Val Tyr Leu Thr Gln Pro Gly Asn Gly
            35                  40                  45

Asn Glu Gly Ser Val Thr Gly Ser Cys Tyr Cys Gly Lys Arg Ile Ser
    50                  55                  60

Ser Asp Ser Pro Pro Ser Val Gln Phe Met Asn Arg Leu Arg Lys His
65                  70                  75                  80

Leu Arg Ala Tyr His Arg Cys Leu Tyr Tyr Thr Arg Phe Gln Leu Leu
                85                  90                  95

Ser Trp Ser Val Cys Gly Gly Asn Lys Asp Pro Trp Val Gln Glu Leu
                100                 105                 110

Met Ser Cys Leu Asp Leu Lys Glu Cys Gly His Ala Tyr Ser Gly Ile
            115                 120                 125

Val Ala His Gln Lys His Leu Leu Pro Thr Ser Pro Pro Ile Ser Gln
        130                 135                 140

Ala Ser Glu Gly Ala Ser Ser Asp Ile His Thr Pro Ala Gln Met Leu
145                 150                 155                 160

Leu Ser Thr Leu Gln Ser Thr Gln Arg Pro Thr Leu Pro Val Gly Ser
                165                 170                 175

Leu Ser Ser Asp Lys Glu Leu Thr Arg Pro Asn Glu Thr Thr Ile His
            180                 185                 190

Thr Ala Gly His Ser Leu Ala Ala Gly Pro Glu Ala Gly Glu Asn Gln
        195                 200                 205

Lys Gln Pro Glu Lys Asn Ala Gly Pro Thr Ala Arg Thr Ser Ala Thr
210                 215                 220

Val Pro Val Leu Cys Leu Leu Ala Ile Ile Phe Ile Leu Thr Ala Ala
225                 230                 235                 240

Leu Ser Tyr Val Leu Cys Lys Arg Arg Gly Gln Ser Pro Gln Ser
                245                 250                 255

Ser Pro Asp Leu Pro Val His Tyr Ile Pro Val Ala Pro Asp Ser Asn
            260                 265                 270

Thr

<210> SEQ ID NO 45
<211> LENGTH: 114
<212> TYPE: PRT
<213> ORGANISM: Homo sapiens

<400> SEQUENCE: 45

Met Arg Leu Leu Ile Leu Ala Leu Leu Gly Ile Cys Ser Leu Thr Ala
1               5                   10                  15

Tyr Ile Val Glu Gly Val Gly Ser Glu Val Ser Asp Lys Arg Thr Cys
                20                  25                  30

Val Ser Leu Thr Thr Gln Arg Leu Pro Val Ser Arg Ile Lys Thr Tyr
            35                  40                  45

Thr Ile Thr Glu Gly Ser Leu Arg Ala Val Ile Phe Ile Thr Lys Arg
    50                  55                  60

Gly Leu Lys Val Cys Ala Asp Pro Gln Ala Thr Trp Val Arg Asp Val
65                  70                  75                  80

Val Arg Ser Met Asp Arg Lys Ser Asn Thr Arg Asn Asn Met Ile Gln
                85                  90                  95

Thr Lys Pro Thr Gly Thr Gln Gln Ser Thr Asn Thr Ala Val Thr Leu
```

```
                    100                 105                 110

Thr Gly

<210> SEQ ID NO 46
<211> LENGTH: 114
<212> TYPE: PRT
<213> ORGANISM: Homo sapiens

<400> SEQUENCE: 46

Met Arg Leu Leu Ile Leu Ala Leu Leu Gly Ile Cys Ser Leu Thr Ala
1               5                   10                  15

Tyr Ile Val Glu Gly Val Gly Ser Glu Val Ser His Arg Arg Thr Cys
            20                  25                  30

Val Ser Leu Thr Thr Gln Arg Leu Pro Val Ser Arg Ile Lys Thr Tyr
        35                  40                  45

Thr Ile Thr Glu Gly Ser Leu Arg Ala Val Ile Phe Ile Thr Lys Arg
    50                  55                  60

Gly Leu Lys Val Cys Ala Asp Pro Gln Ala Thr Trp Val Arg Asp Val
65                  70                  75                  80

Val Arg Ser Met Asp Arg Lys Ser Asn Thr Arg Asn Asn Met Ile Gln
                85                  90                  95

Thr Lys Pro Thr Gly Thr Gln Gln Ser Thr Asn Thr Ala Val Thr Leu
            100                 105                 110

Thr Gly

<210> SEQ ID NO 47
<211> LENGTH: 397
<212> TYPE: PRT
<213> ORGANISM: Homo sapiens

<400> SEQUENCE: 47

Met Ala Pro Ile Ser Leu Ser Trp Leu Leu Arg Leu Ala Thr Phe Cys
1               5                   10                  15

His Leu Thr Val Leu Leu Ala Gly Gln His His Gly Val Thr Lys Cys
            20                  25                  30

Asn Ile Thr Cys Ser Lys Met Thr Ser Lys Ile Pro Val Ala Leu Leu
        35                  40                  45

Ile His Tyr Gln Gln Asn Gln Ala Ser Cys Gly Lys Arg Ala Ile Ile
    50                  55                  60

Leu Glu Thr Arg Gln His Arg Leu Phe Cys Ala Asp Pro Lys Glu Gln
65                  70                  75                  80

Trp Val Lys Asp Ala Met Gln His Leu Asp Arg Gln Ala Ala Ala Leu
                85                  90                  95

Thr Arg Asn Gly Gly Thr Phe Glu Lys Gln Ile Gly Glu Val Lys Pro
            100                 105                 110

Arg Thr Thr Pro Ala Ala Gly Gly Met Asp Glu Ser Val Val Leu Glu
        115                 120                 125

Pro Glu Ala Thr Gly Glu Ser Ser Ser Leu Glu Pro Thr Pro Ser Ser
    130                 135                 140

Gln Glu Ala Gln Arg Ala Leu Gly Thr Ser Pro Glu Leu Pro Thr Gly
145                 150                 155                 160

Val Thr Gly Ser Ser Gly Thr Arg Leu Pro Pro Thr Pro Lys Ala Gln
                165                 170                 175

Asp Gly Gly Pro Val Gly Thr Glu Leu Phe Arg Val Pro Pro Val Ser
            180                 185                 190

Thr Ala Ala Thr Trp Gln Ser Ser Ala Pro His Gln Pro Gly Pro Ser
```

```
            195                 200                 205
Leu Trp Ala Glu Ala Lys Thr Ser Glu Ala Pro Ser Thr Gln Asp Pro
210                 215                 220

Ser Thr Gln Ala Ser Thr Ala Ser Ser Pro Ala Pro Glu Glu Asn Ala
225                 230                 235                 240

Pro Ser Glu Gly Gln Arg Val Trp Gly Gln Gly Gln Ser Pro Arg Pro
            245                 250                 255

Glu Asn Ser Leu Glu Arg Glu Glu Met Gly Pro Val Pro Ala His Thr
        260                 265                 270

Asp Ala Phe Gln Asp Trp Gly Pro Gly Ser Met Ala His Val Ser Val
    275                 280                 285

Val Pro Val Ser Ser Glu Gly Thr Pro Ser Arg Glu Pro Val Ala Ser
290                 295                 300

Gly Ser Trp Thr Pro Lys Ala Glu Glu Pro Ile His Ala Thr Met Asp
305                 310                 315                 320

Pro Gln Arg Leu Gly Val Leu Ile Thr Pro Val Pro Asp Ala Gln Ala
            325                 330                 335

Ala Thr Arg Arg Gln Ala Val Gly Leu Leu Ala Phe Leu Gly Leu Leu
        340                 345                 350

Phe Cys Leu Gly Val Ala Met Phe Thr Tyr Gln Ser Leu Gln Gly Cys
    355                 360                 365

Pro Arg Lys Met Ala Gly Glu Met Ala Glu Gly Leu Arg Tyr Ile Pro
370                 375                 380

Arg Ser Cys Gly Ser Asn Ser Tyr Val Leu Val Pro Val
385                 390                 395

<210> SEQ ID NO 48
<211> LENGTH: 233
<212> TYPE: PRT
<213> ORGANISM: Homo sapiens

<400> SEQUENCE: 48

Ser Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
            85                  90                  95

Gln Asp Trp Leu Asn Gly Lys Glu Tyr Lys Cys Lys Val Ser Asn Lys
        100                 105                 110

Ala Leu Pro Ala Pro Ile Glu Lys Thr Ile Ser Lys Ala Lys Gly Gln
    115                 120                 125

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
            165                 170                 175

Tyr Lys Thr Thr Pro Pro Val Leu Asp Ser Asp Gly Ser Phe Phe Leu
```

```
                    180                 185                 190
Tyr Ser Lys Leu Thr Val Asp Lys Ser Arg Trp Gln Gln Gly Asn Val
            195                 200                 205

Phe Ser Cys Ser Val Met His Glu Ala Leu His Asn His Tyr Thr Gln
        210                 215                 220

Lys Ser Leu Ser Leu Ser Pro Gly Lys
225                 230

<210> SEQ ID NO 49
<211> LENGTH: 228
<212> TYPE: PRT
<213> ORGANISM: Homo sapiens

<400> SEQUENCE: 49

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 50
<211> LENGTH: 279
<212> TYPE: PRT
<213> ORGANISM: Homo sapiens

<400> SEQUENCE: 50

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
            20                  25                  30

Glu Pro Lys Ser Cys Asp Thr Pro Pro Pro Cys Pro Arg Cys Pro Glu
        35                  40                  45
```

```
Pro Lys Ser Cys Asp Thr Pro Pro Cys Arg Cys Pro Ala Pro
    50                  55                  60

Glu Leu Leu Gly Gly Pro Ser Val Phe Leu Phe Pro Pro Lys Pro Lys
65                      70                  75                  80

Asp Thr Leu Met Ile Ser Arg Thr Pro Glu Val Thr Cys Val Val Val
                    85                  90                  95

Asp Val Ser His Glu Asp Pro Glu Val Gln Phe Lys Trp Tyr Val Asp
                100                 105                 110

Gly Val Glu Val His Asn Ala Lys Thr Lys Pro Arg Glu Glu Gln Phe
            115                 120                 125

Asn Ser Thr Phe Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Ser Gly Gln Pro Glu Asn Asn Tyr Asn
    210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys
            275

<210> SEQ ID NO 51
<211> LENGTH: 229
<212> TYPE: PRT
<213> ORGANISM: Homo sapiens

<400> SEQUENCE: 51

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140
```

```
Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
                195                 200                 205

Val Met His Glu Ala Leu His Asn His Tyr Thr Gln Lys Ser Leu Ser
        210                 215                 220

Leu Ser Leu Gly Lys
225

<210> SEQ ID NO 52
<211> LENGTH: 303
<212> TYPE: PRT
<213> ORGANISM: Artificial Sequence
<220> FEATURE:
<223> OTHER INFORMATION: CCL2-IgG1Fc

<400> SEQUENCE: 52

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr Asp Lys Thr His
65                  70                  75                  80

Thr Cys Pro Pro Cys Pro Ala Pro Glu Leu Leu Gly Gly Pro Ser Val
                85                  90                  95

Phe Leu Phe Pro Pro Lys Pro Lys Asp Thr Leu Met Ile Ser Arg Thr
            100                 105                 110

Pro Glu Val Thr Cys Val Val Val Asp Val Ser His Glu Asp Pro Glu
        115                 120                 125

Val Lys Phe Asn Trp Tyr Val Asp Gly Val Glu Val His Asn Ala Lys
    130                 135                 140

Thr Lys Pro Arg Glu Glu Gln Tyr Asn Ser Thr Tyr Arg Val Val Ser
145                 150                 155                 160

Val Leu Thr Val Leu His Gln Asp Trp Leu Asn Gly Lys Glu Tyr Lys
                165                 170                 175

Cys Lys Val Ser Asn Lys Ala Leu Pro Ala Pro Ile Glu Lys Thr Ile
            180                 185                 190

Ser Lys Ala Lys Gly Gln Pro Arg Glu Pro Gln Val Tyr Thr Leu Pro
        195                 200                 205

Pro Ser Arg Glu Glu Met Thr Lys Asn Gln Val Ser Leu Thr Cys Leu
    210                 215                 220

Val Lys Gly Phe Tyr Pro Ser Asp Ile Ala Val Glu Trp Glu Ser Asn
225                 230                 235                 240

Gly Gln Pro Glu Asn Asn Tyr Lys Thr Thr Pro Pro Val Leu Asp Ser
                245                 250                 255

Asp Gly Ser Phe Phe Leu Tyr Ser Lys Leu Thr Val Asp Lys Ser Arg
            260                 265                 270
```

```
Trp Gln Gln Gly Asn Val Phe Ser Cys Ser Val Met His Glu Ala Leu
        275                 280                 285
His Asn His Tyr Thr Gln Lys Ser Leu Ser Leu Ser Pro Gly Lys
        290                 295                 300

<210> SEQ ID NO 53
<211> LENGTH: 309
<212> TYPE: PRT
<213> ORGANISM: Artificial Sequence
<220> FEATURE:
<223> OTHER INFORMATION: CCL2(5-76)-IgG1Fc

<400> SEQUENCE: 53

Ala Leu Ser Leu Ala Leu Val Thr Asn Ser Ile Asn Ala Pro Val Thr
1               5                   10                  15

Cys Cys Tyr Asn Phe Thr Asn Arg Lys Ile Ser Val Gln Arg Leu Ala
            20                  25                  30

Ser Tyr Arg Arg Ile Thr Ser Ser Lys Cys Pro Lys Glu Ala Val Ile
        35                  40                  45

Phe Lys Thr Ile Val Ala Lys Glu Ile Cys Ala Asp Pro Lys Gln Lys
    50                  55                  60

Trp Val Gln Asp Ser Met Asp His Leu Asp Lys Gln Thr Gln Thr Pro
65                  70                  75                  80

Lys Thr Asp Lys Thr His Thr Cys Pro Pro Cys Pro Ala Pro Glu Leu
                85                  90                  95

Leu Gly Gly Pro Ser Val Phe Leu Phe Pro Pro Lys Pro Lys Asp Thr
            100                 105                 110

Leu Met Ile Ser Arg Thr Pro Glu Val Thr Cys Val Val Val Asp Val
        115                 120                 125

Ser His Glu Asp Pro Glu Val Lys Phe Asn Trp Tyr Val Asp Gly Val
    130                 135                 140

Glu Val His Asn Ala Lys Thr Lys Pro Arg Glu Glu Gln Tyr Asn Ser
145                 150                 155                 160

Thr Tyr Arg Val Val Ser Val Leu Thr Val Leu His Gln Asp Trp Leu
                165                 170                 175

Asn Gly Lys Glu Tyr Lys Cys Lys Val Ser Asn Lys Ala Leu Pro Ala
            180                 185                 190

Pro Ile Glu Lys Thr Ile Ser Lys Ala Lys Gly Gln Pro Arg Glu Pro
        195                 200                 205

Gln Val Tyr Thr Leu Pro Pro Ser Arg Glu Glu Met Thr Lys Asn Gln
    210                 215                 220

Val Ser Leu Thr Cys Leu Val Lys Gly Phe Tyr Pro Ser Asp Ile Ala
225                 230                 235                 240

Val Glu Trp Glu Ser Asn Gly Gln Pro Glu Asn Asn Tyr Lys Thr Thr
                245                 250                 255

Pro Pro Val Leu Asp Ser Asp Gly Ser Phe Phe Leu Tyr Ser Lys Leu
            260                 265                 270

Thr Val Asp Lys Ser Arg Trp Gln Gln Gly Asn Val Phe Ser Cys Ser
        275                 280                 285

Val Met His Glu Ala Leu His Asn His Tyr Thr Gln Lys Ser Leu Ser
    290                 295                 300

Leu Ser Pro Gly Lys
305

<210> SEQ ID NO 54
<211> LENGTH: 299
<212> TYPE: PRT
```

<213> ORGANISM: Artificial Sequence
<220> FEATURE:
<223> OTHER INFORMATION: CCL2(5-76K/H-A)-IgG1Fc

<400> SEQUENCE: 54

```
Ile Asn Ala Pro Val Thr Cys Cys Tyr Asn Phe Thr Asn Arg Lys Ile
 1               5                  10                  15
Ser Val Gln Arg Leu Ala Ser Tyr Arg Arg Ile Thr Ser Ser Lys Cys
            20                  25                  30
Pro Lys Glu Ala Val Ile Phe Lys Thr Ile Val Ala Ala Glu Ile Cys
        35                  40                  45
Ala Asp Pro Ala Gln Ala Trp Val Gln Asp Ser Met Asp Ala Leu Asp
    50                  55                  60
Ala Gln Thr Gln Thr Pro Ala Thr Asp Lys Thr His Thr Cys Pro Pro
65                  70                  75                  80
Cys Pro Ala Pro Glu Leu Leu Gly Gly Pro Ser Val Phe Leu Phe Pro
                85                  90                  95
Pro Lys Pro Lys Asp Thr Leu Met Ile Ser Arg Thr Pro Glu Val Thr
           100                 105                 110
Cys Val Val Val Asp Val Ser His Glu Asp Pro Glu Val Lys Phe Asn
       115                 120                 125
Trp Tyr Val Asp Gly Val Glu Val His Asn Ala Lys Thr Lys Pro Arg
   130                 135                 140
Glu Glu Gln Tyr Asn Ser Thr Tyr Arg Val Val Ser Val Leu Thr Val
145                 150                 155                 160
Leu His Gln Asp Trp Leu Asn Gly Lys Glu Tyr Lys Cys Lys Val Ser
                165                 170                 175
Asn Lys Ala Leu Pro Ala Pro Ile Glu Lys Thr Ile Ser Lys Ala Lys
            180                 185                 190
Gly Gln Pro Arg Glu Pro Gln Val Tyr Thr Leu Pro Pro Ser Arg Glu
        195                 200                 205
Glu Met Thr Lys Asn Gln Val Ser Leu Thr Cys Leu Val Lys Gly Phe
    210                 215                 220
Tyr Pro Ser Asp Ile Ala Val Glu Trp Glu Ser Asn Gly Gln Pro Glu
225                 230                 235                 240
Asn Asn Tyr Lys Thr Thr Pro Pro Val Leu Asp Ser Asp Gly Ser Phe
                245                 250                 255
Phe Leu Tyr Ser Lys Leu Thr Val Asp Lys Ser Arg Trp Gln Gln Gly
            260                 265                 270
Asn Val Phe Ser Cys Ser Val Met His Glu Ala Leu His Asn His Tyr
        275                 280                 285
Thr Gln Lys Ser Leu Ser Leu Ser Pro Gly Lys
    290                 295
```

<210> SEQ ID NO 55
<211> LENGTH: 289
<212> TYPE: PRT
<213> ORGANISM: Artificial Sequence
<220> FEATURE:
<223> OTHER INFORMATION: CCL7-IgG1Fc

<400> SEQUENCE: 55

```
Phe Ile Asn Lys Lys Ile Pro Lys Gln Arg Leu Glu Ser Tyr Arg Arg
 1               5                  10                  15
Thr Thr Ser Ser His Cys Pro Arg Glu Ala Val Ile Phe Lys Thr Lys
            20                  25                  30
Leu Asp Lys Glu Ile Cys Ala Asp Pro Thr Gln Lys Trp Val Gln Asp
```

```
                35                  40                  45
Phe Met Lys His Leu Asp Lys Lys Thr Gln Thr Pro Lys Leu Asp Lys
 50                  55                  60

Thr His Thr Cys Pro Pro Cys Pro Ala Pro Glu Leu Leu Gly Gly Pro
 65                  70                  75                  80

Ser Val Phe Leu Phe Pro Pro Lys Pro Lys Asp Thr Leu Met Ile Ser
                 85                  90                  95

Arg Thr Pro Glu Val Thr Cys Val Val Val Asp Val Ser His Glu Asp
            100                 105                 110

Pro Glu Val Lys Phe Asn Trp Tyr Val Asp Gly Val Glu Val His Asn
        115                 120                 125

Ala Lys Thr Lys Pro Arg Glu Glu Gln Tyr Asn Ser Thr Tyr Arg Val
    130                 135                 140

Val Ser Val Leu Thr Val Leu His Gln Asp Trp Leu Asn Gly Lys Glu
145                 150                 155                 160

Tyr Lys Cys Lys Val Ser Asn Lys Ala Leu Pro Ala Pro Ile Glu Lys
                165                 170                 175

Thr Ile Ser Lys Ala Lys Gly Gln Pro Arg Glu Pro Gln Val Tyr Thr
            180                 185                 190

Leu Pro Pro Ser Arg Glu Glu Met Thr Lys Asn Gln Val Ser Leu Thr
        195                 200                 205

Cys Leu Val Lys Gly Phe Tyr Pro Ser Asp Ile Ala Val Glu Trp Glu
    210                 215                 220

Ser Asn Gly Gln Pro Glu Asn Asn Tyr Lys Thr Thr Pro Pro Val Leu
225                 230                 235                 240

Asp Ser Asp Gly Ser Phe Phe Leu Tyr Ser Lys Leu Thr Val Asp Lys
                245                 250                 255

Ser Arg Trp Gln Gln Gly Asn Val Phe Ser Cys Ser Val Met His Glu
            260                 265                 270

Ala Leu His Asn His Tyr Thr Gln Lys Ser Leu Ser Leu Ser Pro Gly
        275                 280                 285

Lys

<210> SEQ ID NO 56
<211> LENGTH: 293
<212> TYPE: PRT
<213> ORGANISM: Artificial Sequence
<220> FEATURE:
<223> OTHER INFORMATION: CCL7(5-76)-IgGFc

<400> SEQUENCE: 56

Cys Cys Tyr Arg Phe Ile Asn Lys Lys Ile Pro Lys Gln Arg Leu Glu
 1               5                  10                  15

Ser Tyr Arg Arg Thr Thr Ser Ser His Cys Pro Arg Glu Ala Val Ile
                20                  25                  30

Phe Lys Thr Lys Leu Asp Lys Glu Ile Cys Ala Asp Pro Thr Gln Lys
            35                  40                  45

Trp Val Gln Asp Phe Met Lys His Leu Asp Lys Lys Thr Gln Thr Pro
 50                  55                  60

Lys Leu Asp Lys Thr His Thr Cys Pro Pro Cys Pro Ala Pro Glu Leu
 65                  70                  75                  80

Leu Gly Gly Pro Ser Val Phe Leu Phe Pro Pro Lys Pro Lys Asp Thr
                 85                  90                  95

Leu Met Ile Ser Arg Thr Pro Glu Val Thr Cys Val Val Val Asp Val
            100                 105                 110
```

```
Ser His Glu Asp Pro Glu Val Lys Phe Asn Trp Tyr Val Asp Gly Val
        115                 120                 125

Glu Val His Asn Ala Lys Thr Lys Pro Arg Glu Glu Gln Tyr Asn Ser
130                 135                 140

Thr Tyr Arg Val Val Ser Val Leu Thr Val Leu His Gln Asp Trp Leu
145                 150                 155                 160

Asn Gly Lys Glu Tyr Lys Cys Lys Val Ser Asn Lys Ala Leu Pro Ala
                165                 170                 175

Pro Ile Glu Lys Thr Ile Ser Lys Ala Lys Gly Gln Pro Arg Glu Pro
            180                 185                 190

Gln Val Tyr Thr Leu Pro Pro Ser Arg Glu Glu Met Thr Lys Asn Gln
        195                 200                 205

Val Ser Leu Thr Cys Leu Val Lys Gly Phe Tyr Pro Ser Asp Ile Ala
    210                 215                 220

Val Glu Trp Glu Ser Asn Gly Gln Pro Glu Asn Asn Tyr Lys Thr Thr
225                 230                 235                 240

Pro Pro Val Leu Asp Ser Asp Gly Ser Phe Phe Leu Tyr Ser Lys Leu
                245                 250                 255

Thr Val Asp Lys Ser Arg Trp Gln Gln Gly Asn Val Phe Ser Cys Ser
            260                 265                 270

Val Met His Glu Ala Leu His Asn His Tyr Thr Gln Lys Ser Leu Ser
        275                 280                 285

Leu Ser Pro Gly Lys
        290

<210> SEQ ID NO 57
<211> LENGTH: 289
<212> TYPE: PRT
<213> ORGANISM: Artificial Sequence
<220> FEATURE:
<223> OTHER INFORMATION: CCL7(5-76K/H-A)-IgGFc

<400> SEQUENCE: 57

Phe Ile Asn Lys Lys Ile Pro Lys Gln Arg Leu Glu Ser Tyr Arg Arg
1               5                   10                  15

Thr Thr Ser Ser His Cys Pro Arg Glu Ala Val Ile Phe Ala Thr Ala
            20                  25                  30

Leu Asp Ala Glu Ile Cys Ala Asp Pro Thr Gln Ala Trp Val Gln Asp
        35                  40                  45

Phe Met Ala Ala Leu Asp Ala Ala Thr Gln Thr Pro Ala Leu Asp Lys
    50                  55                  60

Thr His Thr Cys Pro Pro Cys Pro Ala Pro Glu Leu Leu Gly Gly Pro
65                  70                  75                  80

Ser Val Phe Leu Phe Pro Pro Lys Pro Lys Asp Thr Leu Met Ile Ser
                85                  90                  95

Arg Thr Pro Glu Val Thr Cys Val Val Val Asp Val Ser His Glu Asp
            100                 105                 110

Pro Glu Val Lys Phe Asn Trp Tyr Val Asp Gly Val Glu Val His Asn
        115                 120                 125

Ala Lys Thr Lys Pro Arg Glu Glu Gln Tyr Asn Ser Thr Tyr Arg Val
    130                 135                 140

Val Ser Val Leu Thr Val Leu His Gln Asp Trp Leu Asn Gly Lys Glu
145                 150                 155                 160

Tyr Lys Cys Lys Val Ser Asn Lys Ala Leu Pro Ala Pro Ile Glu Lys
                165                 170                 175

Thr Ile Ser Lys Ala Lys Gly Gln Pro Arg Glu Pro Gln Val Tyr Thr
```

```
                    180                 185                 190
Leu Pro Pro Ser Arg Glu Glu Met Thr Lys Asn Gln Val Ser Leu Thr
            195                 200                 205

Cys Leu Val Lys Gly Phe Tyr Pro Ser Asp Ile Ala Val Glu Trp Glu
        210                 215                 220

Ser Asn Gly Gln Pro Glu Asn Asn Tyr Lys Thr Thr Pro Pro Val Leu
225                 230                 235                 240

Asp Ser Asp Gly Ser Phe Phe Leu Tyr Ser Lys Leu Thr Val Asp Lys
                245                 250                 255

Ser Arg Trp Gln Gln Gly Asn Val Phe Ser Cys Ser Val Met His Glu
            260                 265                 270

Ala Leu His Asn His Tyr Thr Gln Lys Ser Leu Ser Leu Ser Pro Gly
        275                 280                 285

Lys

<210> SEQ ID NO 58
<211> LENGTH: 303
<212> TYPE: PRT
<213> ORGANISM: Artificial Sequence
<220> FEATURE:
<223> OTHER INFORMATION: CCL8-IgG1Fc

<400> SEQUENCE: 58

Gln Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Lys Pro Asp Lys Thr His
65                  70                  75                  80

Thr Cys Pro Pro Cys Pro Ala Pro Glu Leu Leu Gly Gly Pro Ser Val
                85                  90                  95

Phe Leu Phe Pro Pro Lys Pro Lys Asp Thr Leu Met Ile Ser Arg Thr
            100                 105                 110

Pro Glu Val Thr Cys Val Val Val Asp Val Ser His Glu Asp Pro Glu
        115                 120                 125

Val Lys Phe Asn Trp Tyr Val Asp Gly Val Glu Val His Asn Ala Lys
    130                 135                 140

Thr Lys Pro Arg Glu Glu Gln Tyr Asn Ser Thr Tyr Arg Val Val Ser
145                 150                 155                 160

Val Leu Thr Val Leu His Gln Asp Trp Leu Asn Gly Lys Glu Tyr Lys
                165                 170                 175

Cys Lys Val Ser Asn Lys Ala Leu Pro Ala Pro Ile Glu Lys Thr Ile
            180                 185                 190

Ser Lys Ala Lys Gly Gln Pro Arg Glu Pro Gln Val Tyr Thr Leu Pro
        195                 200                 205

Pro Ser Arg Glu Glu Met Thr Lys Asn Gln Val Ser Leu Thr Cys Leu
    210                 215                 220

Val Lys Gly Phe Tyr Pro Ser Asp Ile Ala Val Glu Trp Glu Ser Asn
225                 230                 235                 240

Gly Gln Pro Glu Asn Asn Tyr Lys Thr Thr Pro Pro Val Leu Asp Ser
                245                 250                 255
```

```
Asp Gly Ser Phe Phe Leu Tyr Ser Lys Leu Thr Val Asp Lys Ser Arg
            260                 265                 270

Trp Gln Gln Gly Asn Val Phe Ser Cys Ser Val Met His Glu Ala Leu
        275                 280                 285

His Asn His Tyr Thr Gln Lys Ser Leu Ser Leu Ser Pro Gly Lys
    290                 295                 300

<210> SEQ ID NO 59
<211> LENGTH: 299
<212> TYPE: PRT
<213> ORGANISM: Artificial Sequence
<220> FEATURE:
<223> OTHER INFORMATION: CCL8(5-76)-IgG1Fc

<400> SEQUENCE: 59

Val Ser Ile Pro Ile Thr Cys Cys Phe Asn Val Ile Asn Arg Lys Ile
1               5                   10                  15

Pro Ile Gln Arg Leu Glu Ser Tyr Thr Arg Ile Thr Asn Ile Gln Cys
            20                  25                  30

Pro Lys Glu Ala Val Ile Phe Lys Thr Lys Arg Gly Lys Glu Val Cys
        35                  40                  45

Ala Asp Pro Lys Glu Arg Trp Val Arg Asp Ser Met Lys His Leu Asp
    50                  55                  60

Gln Ile Phe Gln Asn Leu Lys Pro Asp Lys Thr His Thr Cys Pro Pro
65                  70                  75                  80

Cys Pro Ala Pro Glu Leu Leu Gly Gly Pro Ser Val Phe Leu Phe Pro
                85                  90                  95

Pro Lys Pro Lys Asp Thr Leu Met Ile Ser Arg Thr Pro Glu Val Thr
            100                 105                 110

Cys Val Val Val Asp Val Ser His Glu Asp Pro Glu Val Lys Phe Asn
        115                 120                 125

Trp Tyr Val Asp Gly Val Glu Val His Asn Ala Lys Thr Lys Pro Arg
    130                 135                 140

Glu Glu Gln Tyr Asn Ser Thr Tyr Arg Val Val Ser Val Leu Thr Val
145                 150                 155                 160

Leu His Gln Asp Trp Leu Asn Gly Lys Glu Tyr Lys Cys Lys Val Ser
                165                 170                 175

Asn Lys Ala Leu Pro Ala Pro Ile Glu Lys Thr Ile Ser Lys Ala Lys
            180                 185                 190

Gly Gln Pro Arg Glu Pro Gln Val Tyr Thr Leu Pro Pro Ser Arg Glu
        195                 200                 205

Glu Met Thr Lys Asn Gln Val Ser Leu Thr Cys Leu Val Lys Gly Phe
    210                 215                 220

Tyr Pro Ser Asp Ile Ala Val Glu Trp Glu Ser Asn Gly Gln Pro Glu
225                 230                 235                 240

Asn Asn Tyr Lys Thr Thr Pro Pro Val Leu Asp Ser Asp Gly Ser Phe
                245                 250                 255

Phe Leu Tyr Ser Lys Leu Thr Val Asp Lys Ser Arg Trp Gln Gln Gly
            260                 265                 270

Asn Val Phe Ser Cys Ser Val Met His Glu Ala Leu His Asn His Tyr
        275                 280                 285

Thr Gln Lys Ser Leu Ser Leu Ser Pro Gly Lys
    290                 295

<210> SEQ ID NO 60
<211> LENGTH: 265
<212> TYPE: PRT
```

-continued

```
<213> ORGANISM: Artificial Sequence
<220> FEATURE:
<223> OTHER INFORMATION: CCL8(5-76K/H-A)-IgG1Fc

<400> SEQUENCE: 60

Val Ser Ile Pro Ile Thr Cys Cys Phe Asn Val Ile Asn Arg Lys Ile
1               5                   10                  15

Pro Ile Gln Arg Leu Glu Ser Tyr Thr Arg Ile Thr Asn Ile Gln Cys
            20                  25                  30

Pro Lys Glu Ala Val Ile Phe Lys Thr Ala Ala Gly Ala Glu Val Cys
        35                  40                  45

Ala Asp Pro Ala Glu Ala Trp Val Ala Asp Ser Met Ala Ala Leu Asp
50                  55                  60

Gln Ile Phe Gln Asn Leu Ala Pro Asp Lys Thr His Thr Cys Pro Pro
65                  70                  75                  80

Cys Pro Ala Pro Glu Leu Leu Gly Gly Pro Ser Val Phe Leu Phe Pro
                85                  90                  95

Pro Lys Pro Lys Asp Thr Leu Met Ile Ser Arg Thr Pro Glu Val Thr
            100                 105                 110

Cys Val Val Val Asp Val Ser His Glu Asp Pro Glu Val Lys Phe Asn
        115                 120                 125

Trp Tyr Val Asp Gly Val Glu Val His Asn Ala Lys Thr Lys Pro Arg
    130                 135                 140

Glu Glu Gln Tyr Asn Ser Thr Tyr Arg Val Val Ser Val Leu Thr Val
145                 150                 155                 160

Leu His Gln Asp Trp Leu Asn Gly Lys Glu Tyr Lys Cys Lys Val Ser
                165                 170                 175

Asn Lys Ala Leu Pro Ala Pro Ile Glu Lys Thr Ile Ser Lys Ala Lys
            180                 185                 190

Gly Gln Pro Arg Glu Pro Gln Val Tyr Thr Leu Pro Pro Ser Arg Glu
        195                 200                 205

Glu Met Thr Lys Asn Gln Val Ser Leu Thr Cys Leu Val Lys Gly Phe
    210                 215                 220

Tyr Pro Ser Asp Ile Ala Val Glu Trp Glu Ser Asn Gly Gln Pro Glu
225                 230                 235                 240

Asn Asn Tyr Lys Thr Thr Pro Pro Val Leu Asp Ser Asp Gly Ser Phe
                245                 250                 255

Lys Ser Leu Ser Leu Ser Pro Gly Lys
            260                 265

<210> SEQ ID NO 61
<211> LENGTH: 302
<212> TYPE: PRT
<213> ORGANISM: Artificial Sequence
<220> FEATURE:
<223> OTHER INFORMATION: CCL13-IgG1Fc

<400> SEQUENCE: 61

Gln Pro Asp Ala Leu Asn Val Pro Ser Thr Cys Cys Phe Thr Phe Ser
1               5                   10                  15

Ser Lys Lys Ile Ser Leu Gln Arg Leu Lys Ser Tyr Val Ile Thr Thr
            20                  25                  30

Ser Arg Cys Pro Gln Lys Ala Val Ile Phe Arg Thr Lys Leu Gly Lys
        35                  40                  45

Glu Ile Cys Ala Asp Pro Lys Glu Lys Trp Val Gln Asn Tyr Met Lys
    50                  55                  60

His Leu Gly Arg Lys Ala His Thr Leu Lys Thr Asp Lys Thr His Thr
```

```
                65                  70                  75                  80
Cys Pro Pro Cys Pro Ala Pro Glu Leu Leu Gly Gly Pro Ser Val Phe
                    85                  90                  95

Leu Phe Pro Pro Lys Pro Lys Asp Thr Leu Met Ile Ser Arg Thr Pro
                100                 105                 110

Glu Val Thr Cys Val Val Val Asp Val Ser His Glu Asp Pro Glu Val
                115                 120                 125

Lys Phe Asn Trp Tyr Val Asp Gly Val Glu Val His Asn Ala Lys Thr
        130                 135                 140

Lys Pro Arg Glu Glu Gln Tyr Asn Ser Thr Tyr Arg Val Val Ser Val
145                 150                 155                 160

Leu Thr Val Leu His Gln Asp Trp Leu Asn Gly Lys Glu Tyr Lys Cys
                165                 170                 175

Lys Val Ser Asn Lys Ala Leu Pro Ala Pro Ile Glu Lys Thr Ile Ser
                180                 185                 190

Lys Ala Lys Gly Gln Pro Arg Glu Pro Gln Val Tyr Thr Leu Pro Pro
                195                 200                 205

Ser Arg Glu Glu Met Thr Lys Asn Gln Val Ser Leu Thr Cys Leu Val
        210                 215                 220

Lys Gly Phe Tyr Pro Ser Asp Ile Ala Val Glu Trp Glu Ser Asn Gly
225                 230                 235                 240

Gln Pro Glu Asn Asn Tyr Lys Thr Thr Pro Pro Val Leu Asp Ser Asp
                245                 250                 255

Gly Ser Phe Phe Leu Tyr Ser Lys Leu Thr Val Asp Lys Ser Arg Trp
                260                 265                 270

Gln Gln Gly Asn Val Phe Ser Cys Ser Val Met His Glu Ala Leu His
        275                 280                 285

Asn His Tyr Thr Gln Lys Ser Leu Ser Leu Ser Pro Gly Lys
                290                 295                 300

<210> SEQ ID NO 62
<211> LENGTH: 298
<212> TYPE: PRT
<213> ORGANISM: Artificial Sequence
<220> FEATURE:
<223> OTHER INFORMATION: CCL13(5-75)-IgG1Fc

<400> SEQUENCE: 62

Leu Asn Val Pro Ser Thr Cys Cys Phe Thr Phe Ser Ser Lys Lys Ile
1               5                   10                  15

Ser Leu Gln Arg Leu Lys Ser Tyr Val Ile Thr Thr Ser Arg Cys Pro
                20                  25                  30

Gln Lys Ala Val Ile Phe Arg Thr Lys Leu Gly Lys Glu Ile Cys Ala
            35                  40                  45

Asp Pro Lys Glu Lys Trp Val Gln Asn Tyr Met Lys His Leu Gly Arg
    50                  55                  60

Lys Ala His Thr Leu Lys Thr Asp Lys Thr His Thr Cys Pro Pro Cys
65                  70                  75                  80

Pro Ala Pro Glu Leu Leu Gly Gly Pro Ser Val Phe Leu Phe Pro Pro
                85                  90                  95

Lys Pro Lys Asp Thr Leu Met Ile Ser Arg Thr Pro Glu Val Thr Cys
                100                 105                 110

Val Val Val Asp Val Ser His Glu Asp Pro Glu Val Lys Phe Asn Trp
            115                 120                 125

Tyr Val Asp Gly Val Glu Val His Asn Ala Lys Thr Lys Pro Arg Glu
    130                 135                 140
```

```
Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
            165                 170                 175

Lys Ala Leu Pro Ala Pro Ile Glu Lys Thr Ile Ser Lys Ala Lys Gly
                180                 185                 190

Gln Pro Arg Glu Pro Gln Val Tyr Thr Leu Pro Pro Ser Arg Glu Glu
            195                 200                 205

Met Thr Lys Asn Gln Val Ser Leu Thr Cys Leu Val Lys Gly Phe Tyr
            210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
                245                 250                 255

Leu Tyr Ser Lys Leu Thr Val Asp Lys Ser Arg Trp Gln Gln Gly Asn
            260                 265                 270

Val Phe Ser Cys Ser Val Met His Glu Ala Leu His Asn His Tyr Thr
            275                 280                 285

Gln Lys Ser Leu Ser Leu Ser Pro Gly Lys
            290                 295

<210> SEQ ID NO 63
<211> LENGTH: 298
<212> TYPE: PRT
<213> ORGANISM: Artificial Sequence
<220> FEATURE:
<223> OTHER INFORMATION: CCL13(5-75K/H-A)-IgG1Fc

<400> SEQUENCE: 63

Leu Asn Val Pro Ser Thr Cys Cys Phe Thr Phe Ser Ser Lys Lys Ile
1               5                   10                  15

Ser Leu Gln Arg Leu Lys Ser Tyr Val Ile Thr Thr Ser Arg Cys Pro
            20                  25                  30

Gln Lys Ala Val Ile Phe Arg Thr Ala Leu Gly Ala Glu Ile Cys Ala
        35                  40                  45

Asp Pro Ala Glu Ala Trp Val Gln Asn Tyr Met Ala Ala Leu Gly Arg
    50                  55                  60

Lys Ala Ala Thr Leu Ala Thr Asp Lys Thr His Thr Cys Pro Pro Cys
65                  70                  75                  80

Pro Ala Pro Glu Leu Leu Gly Gly Pro Ser Val Phe Leu Phe Pro Pro
                85                  90                  95

Lys Pro Lys Asp Thr Leu Met Ile Ser Arg Thr Pro Glu Val Thr Cys
            100                 105                 110

Val Val Val Asp Val Ser His Glu Asp Pro Glu Val Lys Phe Asn Trp
        115                 120                 125

Tyr Val Asp Gly Val Glu Val His Asn Ala Lys Thr Lys Pro Arg Glu
    130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
            165                 170                 175

Lys Ala Leu Pro Ala Pro Ile Glu Lys Thr Ile Ser Lys Ala Lys Gly
                180                 185                 190

Gln Pro Arg Glu Pro Gln Val Tyr Thr Leu Pro Pro Ser Arg Glu Glu
            195                 200                 205
```

```
Met Thr Lys Asn Gln Val Ser Leu Thr Cys Leu Val Lys Gly Phe Tyr
    210                 215                 220
Pro Ser Asp Ile Ala Val Glu Trp Glu Ser Asn Gly Gln Pro Glu Asn
225                 230                 235                 240
Asn Tyr Lys Thr Thr Pro Pro Val Leu Asp Ser Asp Gly Ser Phe Phe
                245                 250                 255
Leu Tyr Ser Lys Leu Thr Val Asp Lys Ser Arg Trp Gln Gln Gly Asn
            260                 265                 270
Val Phe Ser Cys Ser Val Met His Glu Ala Leu His Asn His Tyr Thr
        275                 280                 285
Gln Lys Ser Leu Ser Leu Ser Pro Gly Lys
    290                 295

<210> SEQ ID NO 64
<211> LENGTH: 345
<212> TYPE: PRT
<213> ORGANISM: Artificial Sequence
<220> FEATURE:
<223> OTHER INFORMATION: CCL25-IgG1Fc

<400> SEQUENCE: 64

Thr Gln Gly Val Phe Glu Asp Cys Cys Leu Ala Tyr His Tyr Pro Ile
1               5                   10                  15
Gly Trp Ala Val Leu Arg His Ala Trp Thr Tyr Arg Ile Gln Glu Val
            20                  25                  30
Ser Gly Ser Cys Asn Leu Pro Ala Ala Ile Phe Tyr Leu Pro Lys Arg
        35                  40                  45
His Arg Lys Val Cys Gly Asn Pro Lys Ser Arg Glu Val Gln Arg Ala
    50                  55                  60
Met Lys Leu Leu Asp Ala Arg Asn Lys Val Phe Ala Lys Leu Arg His
65                  70                  75                  80
Asn Thr Gln Thr Phe Gln Gly Pro His Ala Val Lys Lys Leu Ser Ser
                85                  90                  95
Gly Asn Ser Lys Leu Ser Ser Ser Lys Phe Ser Asn Pro Ile Ser Ser
            100                 105                 110
Ser Lys Arg Asn Val Ser Asp Lys Thr His Thr Cys Pro Pro Cys Pro
        115                 120                 125
Ala Pro Glu Leu Leu Gly Gly Pro Ser Val Phe Leu Phe Pro Pro Lys
    130                 135                 140
Pro Lys Asp Thr Leu Met Ile Ser Arg Thr Pro Glu Val Thr Cys Val
145                 150                 155                 160
Val Val Asp Val Ser His Glu Asp Pro Glu Val Lys Phe Asn Trp Tyr
                165                 170                 175
Val Asp Gly Val Glu Val His Asn Ala Lys Thr Lys Pro Arg Glu Glu
            180                 185                 190
Gln Tyr Asn Ser Thr Tyr Arg Val Val Ser Val Leu Thr Val Leu His
        195                 200                 205
Gln Asp Trp Leu Asn Gly Lys Glu Tyr Lys Cys Lys Val Ser Asn Lys
    210                 215                 220
Ala Leu Pro Ala Pro Ile Glu Lys Thr Ile Ser Lys Ala Lys Gly Gln
225                 230                 235                 240
Pro Arg Glu Pro Gln Val Tyr Thr Leu Pro Pro Ser Arg Glu Glu Met
                245                 250                 255
Thr Lys Asn Gln Val Ser Leu Thr Cys Leu Val Lys Gly Phe Tyr Pro
            260                 265                 270
Ser Asp Ile Ala Val Glu Trp Glu Ser Asn Gly Gln Pro Glu Asn Asn
```

```
                275                 280                 285
Tyr Lys Thr Thr Pro Val Leu Asp Ser Asp Gly Ser Phe Phe Leu
290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
                340                 345

<210> SEQ ID NO 65
<211> LENGTH: 342
<212> TYPE: PRT
<213> ORGANISM: Artificial Sequence
<220> FEATURE:
<223> OTHER INFORMATION: CCL25(4-127)-IgG1Fc

<400> SEQUENCE: 65

Val Phe Glu Asp Cys Cys Leu Ala Tyr His Tyr Pro Ile Gly Trp Ala
1               5                   10                  15

Val Leu Arg His Ala Trp Thr Tyr Arg Ile Gln Glu Val Ser Gly Ser
                20                  25                  30

Cys Asn Leu Pro Ala Ala Ile Phe Tyr Leu Pro Lys Arg His Arg Lys
            35                  40                  45

Val Cys Gly Asn Pro Lys Ser Arg Glu Val Gln Arg Ala Met Lys Leu
        50                  55                  60

Leu Asp Ala Arg Asn Lys Val Phe Ala Lys Leu Arg His Asn Thr Gln
65                  70                  75                  80

Thr Phe Gln Gly Pro His Ala Val Lys Lys Leu Ser Ser Gly Asn Ser
                85                  90                  95

Lys Leu Ser Ser Ser Lys Phe Ser Asn Pro Ile Ser Ser Ser Lys Arg
            100                 105                 110

Asn Val Ser Asp Lys Thr His Thr Cys Pro Pro Cys Pro Ala Pro Glu
        115                 120                 125

Leu Leu Gly Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
    210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Val Leu Asp Ser Asp Gly Ser Phe Phe Leu Tyr Ser Lys
    290                 295                 300
```

```
Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
            325                 330                 335

Ser Leu Ser Pro Gly Lys
            340

<210> SEQ ID NO 66
<211> LENGTH: 342
<212> TYPE: PRT
<213> ORGANISM: Artificial Sequence
<220> FEATURE:
<223> OTHER INFORMATION: CCL25(4-127K/H-A)-IgG1Fc

<400> SEQUENCE: 66

Val Phe Glu Asp Cys Cys Leu Ala Tyr His Tyr Pro Ile Gly Trp Ala
1               5                   10                  15

Val Leu Arg His Ala Trp Thr Tyr Arg Ile Gln Glu Val Ser Gly Ser
            20                  25                  30

Cys Asn Leu Pro Ala Ala Ile Phe Tyr Leu Pro Ala Ala Ala Ala Ala
        35                  40                  45

Val Cys Gly Asn Pro Ala Ser Ala Glu Val Gln Ala Ala Met Ala Leu
    50                  55                  60

Leu Asp Ala Ala Asn Ala Val Phe Ala Ala Leu Ala Ala Asn Thr Gln
65                  70                  75                  80

Thr Phe Gln Gly Pro Ala Ala Val Ala Ala Leu Ser Ser Gly Asn Ser
                85                  90                  95

Ala Leu Ser Ser Ser Ala Phe Ser Asn Pro Ile Ser Ser Ser Ala Ala
            100                 105                 110

Asn Val Ser Asp Lys Thr His Thr Cys Pro Pro Cys Pro Ala Pro Glu
        115                 120                 125

Leu Leu Gly Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
    210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Val Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320
```

```
Ser Val Met His Glu Ala Leu His Asn His Tyr Thr Gln Lys Ser Leu
            325                 330                 335

Ser Leu Ser Pro Gly Lys
            340

<210> SEQ ID NO 67
<211> LENGTH: 300
<212> TYPE: PRT
<213> ORGANISM: Artificial Sequence
<220> FEATURE:
<223> OTHER INFORMATION: CXCL11-IgG1Fc

<400> SEQUENCE: 67

Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe Asp Lys Thr His Thr Cys Pro
65                  70                  75                  80

Pro Cys Pro Ala Pro Glu Leu Leu Gly Gly Pro Ser Val Phe Leu Phe
                85                  90                  95

Pro Pro Lys Pro Lys Asp Thr Leu Met Ile Ser Arg Thr Pro Glu Val
            100                 105                 110

Thr Cys Val Val Val Asp Val Ser His Glu Asp Pro Glu Val Lys Phe
        115                 120                 125

Asn Trp Tyr Val Asp Gly Val Glu Val His Asn Ala Lys Thr Lys Pro
    130                 135                 140

Arg Glu Glu Gln Tyr Asn Ser Thr Tyr Arg Val Val Ser Val Leu Thr
145                 150                 155                 160

Val Leu His Gln Asp Trp Leu Asn Gly Lys Glu Tyr Lys Cys Lys Val
                165                 170                 175

Ser Asn Lys Ala Leu Pro Ala Pro Ile Glu Lys Thr Ile Ser Lys Ala
            180                 185                 190

Lys Gly Gln Pro Arg Glu Pro Gln Val Tyr Thr Leu Pro Pro Ser Arg
        195                 200                 205

Glu Glu Met Thr Lys Asn Gln Val Ser Leu Thr Cys Leu Val Lys Gly
    210                 215                 220

Phe Tyr Pro Ser Asp Ile Ala Val Glu Trp Glu Ser Asn Gly Gln Pro
225                 230                 235                 240

Glu Asn Asn Tyr Lys Thr Thr Pro Pro Val Leu Asp Ser Asp Gly Ser
                245                 250                 255

Phe Phe Leu Tyr Ser Lys Leu Thr Val Asp Lys Ser Arg Trp Gln Gln
            260                 265                 270

Gly Asn Val Phe Ser Cys Ser Val Met His Glu Ala Leu His Asn His
        275                 280                 285

Tyr Thr Gln Lys Ser Leu Ser Leu Ser Pro Gly Lys
    290                 295                 300

<210> SEQ ID NO 68
<211> LENGTH: 297
<212> TYPE: PRT
<213> ORGANISM: Artificial Sequence
<220> FEATURE:
<223> OTHER INFORMATION: CXCL11(4-73)-IgG1Fc
```

<400> SEQUENCE: 68

```
Phe Lys Arg Gly Arg Cys Leu Cys Ile Gly Pro Gly Val Lys Ala Val
1               5                   10                  15

Lys Val Ala Asp Ile Glu Lys Ala Ser Ile Met Tyr Pro Ser Asn Asn
            20                  25                  30

Cys Asp Lys Ile Glu Val Ile Ile Thr Leu Lys Glu Asn Lys Gly Gln
        35                  40                  45

Arg Cys Leu Asn Pro Lys Ser Lys Gln Ala Arg Leu Ile Ile Lys Lys
    50                  55                  60

Val Glu Arg Lys Asn Phe Asp Lys Thr His Thr Cys Pro Pro Cys Pro
65                  70                  75                  80

Ala Pro Glu Leu Leu Gly Gly Pro Ser Val Phe Leu Phe Pro Pro Lys
                85                  90                  95

Pro Lys Asp Thr Leu Met Ile Ser Arg Thr Pro Glu Val Thr Cys Val
            100                 105                 110

Val Val Asp Val Ser His Glu Asp Pro Glu Val Lys Phe Asn Trp Tyr
        115                 120                 125

Val Asp Gly Val Glu Val His Asn Ala Lys Thr Lys Pro Arg Glu Glu
    130                 135                 140

Gln Tyr Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
            180                 185                 190

Pro Arg Glu Pro Gln Val Tyr Thr Leu Pro Pro Ser Arg Glu Glu Met
        195                 200                 205

Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Lys Leu Thr Val Asp Lys Ser Arg Trp Gln Gln Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly Lys
    290                 295
```

<210> SEQ ID NO 69
<211> LENGTH: 297
<212> TYPE: PRT
<213> ORGANISM: Artificial Sequence
<220> FEATURE:
<223> OTHER INFORMATION: CXCL11(4-73K/H-A)-IgG1Fc

<400> SEQUENCE: 69

```
Phe Lys Arg Gly Arg Cys Leu Cys Ile Gly Pro Gly Val Lys Ala Val
1               5                   10                  15

Lys Val Ala Asp Ile Glu Ala Ala Ser Ile Met Tyr Pro Ser Asn Asn
            20                  25                  30

Cys Asp Lys Ile Glu Val Ile Ile Thr Leu Ala Glu Asn Ala Gly Gln
        35                  40                  45

Ala Cys Leu Asn Pro Ala Ser Ala Gln Ala Ala Leu Ile Ile Ala Ala
```

-continued

```
                 50                  55                  60
Val Glu Ala Ala Asn Phe Asp Lys Thr His Thr Cys Pro Pro Cys Pro
 65                  70                  75                  80

Ala Pro Glu Leu Leu Gly Gly Pro Ser Val Phe Leu Phe Pro Pro Lys
                 85                  90                  95

Pro Lys Asp Thr Leu Met Ile Ser Arg Thr Pro Glu Val Thr Cys Val
                100                 105                 110

Val Val Asp Val Ser His Glu Asp Pro Glu Val Lys Phe Asn Trp Tyr
                115                 120                 125

Val Asp Gly Val Glu Val His Asn Ala Lys Thr Lys Pro Arg Glu Glu
                130                 135                 140

Gln Tyr Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
                180                 185                 190

Pro Arg Glu Pro Gln Val Tyr Thr Leu Pro Pro Ser Arg Glu Glu Met
                195                 200                 205

Thr Lys Asn Gln Val Ser Leu Thr Cys Leu Val Lys Gly Phe Tyr Pro
                210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Lys Leu Thr Val Asp Lys Ser Arg Trp Gln Gln Gly Asn Val
                260                 265                 270

Phe Ser Cys Ser Val Met His Glu Ala Leu His Asn His Tyr Thr Gln
                275                 280                 285

Lys Ser Leu Ser Leu Ser Pro Gly Lys
                290                 295

<210> SEQ ID NO 70
<211> LENGTH: 297
<212> TYPE: PRT
<213> ORGANISM: Artificial Sequence
<220> FEATURE:
<223> OTHER INFORMATION: CXCL11-IgG4Fc

<400> SEQUENCE: 70

Phe Pro Met Phe Lys Arg Gly Arg Cys Leu Cys Ile Gly Pro Gly Val
  1               5                  10                  15

Lys Ala Val Lys Val Ala Asp Ile Glu Lys Ala Ser Ile Met Tyr Pro
                 20                  25                  30

Ser Asn Asn Cys Asp Lys Ile Glu Val Ile Ile Thr Leu Lys Glu Asn
                 35                  40                  45

Lys Gly Gln Arg Cys Leu Asn Pro Lys Ser Lys Gln Ala Arg Leu Ile
 50                  55                  60

Ile Lys Lys Val Glu Arg Lys Asn Phe Pro Pro Cys Pro Ser Cys Pro
 65                  70                  75                  80

Ala Pro Glu Phe Leu Gly Gly Pro Ser Val Phe Leu Phe Pro Pro Lys
                 85                  90                  95

Pro Lys Asp Thr Leu Met Ile Ser Arg Thr Pro Glu Val Thr Cys Val
                100                 105                 110

Val Val Asp Val Ser Gln Glu Asp Pro Glu Val Gln Phe Asn Trp Tyr
                115                 120                 125
```

Val Asp Gly Val Glu Val His Asn Ala Lys Thr Lys Pro Arg Glu Glu
    130                 135                 140

Gln Phe Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Gly Leu Pro Ser Ser Ile Glu Lys Thr Ile Ser Lys Ala Lys Gly Gln
            180                 185                 190

Pro Arg Glu Pro Gln Val Tyr Thr Leu Pro Pro Ser Gln Glu Glu Met
        195                 200                 205

Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Arg Leu Thr Val Asp Lys Ser Arg Trp Gln Glu Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly Lys
    290                 295

<210> SEQ ID NO 71
<211> LENGTH: 294
<212> TYPE: PRT
<213> ORGANISM: Artificial Sequence
<220> FEATURE:
<223> OTHER INFORMATION: CXCL11(4-73)-IgG4Fc

<400> SEQUENCE: 71

Phe Lys Arg Gly Arg Cys Leu Cys Ile Gly Pro Gly Val Lys Ala Val
1               5                   10                  15

Lys Val Ala Asp Ile Glu Lys Ala Ser Ile Met Tyr Pro Ser Asn Asn
            20                  25                  30

Cys Asp Lys Ile Glu Val Ile Ile Thr Leu Lys Glu Asn Lys Gly Gln
        35                  40                  45

Arg Cys Leu Asn Pro Lys Ser Lys Gln Ala Arg Leu Ile Ile Lys Lys
    50                  55                  60

Val Glu Arg Lys Asn Phe Pro Pro Cys Pro Ser Cys Pro Ala Pro Glu
65                  70                  75                  80

Phe Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
            100                 105                 110

Val Ser Gln Glu Asp Pro Glu Val Gln Phe Asn Trp Tyr Val Asp Gly
        115                 120                 125

Val Glu Val His Asn Ala Lys Thr Lys Pro Arg Glu Glu Gln Phe Asn
    130                 135                 140

Ser Thr Tyr Arg Val Val Ser Val Leu Thr Val Leu His Gln Asp Trp
145                 150                 155                 160

Leu Asn Gly Lys Glu Tyr Lys Cys Lys Val Ser Asn Lys Gly Leu Pro
                165                 170                 175

Ser Ser Ile Glu Lys Thr Ile Ser Lys Ala Lys Gly Gln Pro Arg Glu
            180                 185                 190

```
Pro Gln Val Tyr Thr Leu Pro Pro Ser Gln Glu Glu Met Thr Lys Asn
        195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Arg
                245                 250                 255

Leu Thr Val Asp Lys Ser Arg Trp Gln Glu Gly Asn Val Phe Ser Cys
            260                 265                 270

Ser Val Met His Glu Ala Leu His Asn His Tyr Thr Gln Lys Ser Leu
        275                 280                 285

Ser Leu Ser Pro Gly Lys
        290

<210> SEQ ID NO 72
<211> LENGTH: 294
<212> TYPE: PRT
<213> ORGANISM: Artificial Sequence
<220> FEATURE:
<223> OTHER INFORMATION: CXCL11(4-73K/H-A)-IgG4Fc

<400> SEQUENCE: 72

Phe Lys Arg Gly Arg Cys Leu Cys Ile Gly Pro Gly Val Lys Ala Val
1               5                   10                  15

Lys Val Ala Asp Ile Glu Ala Ala Ser Ile Met Tyr Pro Ser Asn Asn
            20                  25                  30

Cys Asp Lys Ile Glu Val Ile Ile Thr Leu Ala Glu Asn Ala Gly Gln
        35                  40                  45

Ala Cys Leu Asn Pro Ala Ser Gln Ala Ala Leu Ile Ile Ala Ala
    50                  55                  60

Val Glu Ala Ala Asn Phe Pro Pro Cys Pro Ser Cys Pro Ala Pro Glu
65                  70                  75                  80

Phe Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
            100                 105                 110

Val Ser Gln Glu Asp Pro Glu Val Gln Phe Asn Trp Tyr Val Asp Gly
        115                 120                 125

Val Glu Val His Asn Ala Lys Thr Lys Pro Arg Glu Glu Gln Phe Asn
    130                 135                 140

Ser Thr Tyr Arg Val Val Ser Val Leu Thr Val Leu His Gln Asp Trp
145                 150                 155                 160

Leu Asn Gly Lys Glu Tyr Lys Cys Lys Val Ser Asn Lys Gly Leu Pro
                165                 170                 175

Ser Ser Ile Glu Lys Thr Ile Ser Lys Ala Lys Gly Gln Pro Arg Glu
            180                 185                 190

Pro Gln Val Tyr Thr Leu Pro Pro Ser Gln Glu Glu Met Thr Lys Asn
        195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Arg
                245                 250                 255

Leu Thr Val Asp Lys Ser Arg Trp Gln Glu Gly Asn Val Phe Ser Cys
```

260                 265                 270
Ser Val Met His Glu Ala Leu His Asn His Tyr Thr Gln Lys Ser Leu
        275                 280                 285

Ser Leu Ser Pro Gly Lys
    290

<210> SEQ ID NO 73
<211> LENGTH: 314
<212> TYPE: PRT
<213> ORGANISM: Artificial Sequence
<220> FEATURE:
<223> OTHER INFORMATION: CXCL13-IgG1Fc

<400> SEQUENCE: 73

Val Leu Glu Val Tyr Tyr Thr Ser Leu Arg Cys Arg Cys Val Gln Glu
1               5                   10                  15

Ser Ser Val Phe Ile Pro Arg Arg Phe Ile Asp Arg Ile Gln Ile Leu
            20                  25                  30

Pro Arg Gly Asn Gly Cys Pro Arg Lys Glu Ile Ile Val Trp Lys Lys
        35                  40                  45

Asn Lys Ser Ile Val Cys Val Asp Pro Gln Ala Glu Trp Ile Gln Arg
    50                  55                  60

Met Met Glu Val Leu Arg Lys Arg Ser Ser Thr Leu Pro Val Pro
65                  70                  75                  80

Val Phe Lys Arg Lys Ile Pro Asp Lys Thr His Thr Cys Pro Pro Cys
                85                  90                  95

Pro Ala Pro Glu Leu Leu Gly Gly Pro Ser Val Phe Leu Phe Pro Pro
            100                 105                 110

Lys Pro Lys Asp Thr Leu Met Ile Ser Arg Thr Pro Glu Val Thr Cys
        115                 120                 125

Val Val Val Asp Val Ser His Glu Asp Pro Glu Val Lys Phe Asn Trp
    130                 135                 140

Tyr Val Asp Gly Val Glu Val His Asn Ala Lys Thr Lys Pro Arg Glu
145                 150                 155                 160

Glu Gln Tyr Asn Ser Thr Tyr Arg Val Val Ser Val Leu Thr Val Leu
                165                 170                 175

His Gln Asp Trp Leu Asn Gly Lys Glu Tyr Lys Cys Lys Val Ser Asn
            180                 185                 190

Lys Ala Leu Pro Ala Pro Ile Glu Lys Thr Ile Ser Lys Ala Lys Gly
        195                 200                 205

Gln Pro Arg Glu Pro Gln Val Tyr Thr Leu Pro Pro Ser Arg Glu Glu
    210                 215                 220

Met Thr Lys Asn Gln Val Ser Leu Thr Cys Leu Val Lys Gly Phe Tyr
225                 230                 235                 240

Pro Ser Asp Ile Ala Val Glu Trp Glu Ser Asn Gly Gln Pro Glu Asn
                245                 250                 255

Asn Tyr Lys Thr Thr Pro Pro Val Leu Asp Ser Asp Gly Ser Phe Phe
            260                 265                 270

Leu Tyr Ser Lys Leu Thr Val Asp Lys Ser Arg Trp Gln Gln Gly Asn
        275                 280                 285

Val Phe Ser Cys Ser Val Met His Glu Ala Leu His Asn His Tyr Thr
    290                 295                 300

Gln Lys Ser Leu Ser Leu Ser Pro Gly Lys
305                 310

<210> SEQ ID NO 74

<211> LENGTH: 312
<212> TYPE: PRT
<213> ORGANISM: Artificial Sequence
<220> FEATURE:
<223> OTHER INFORMATION: CXCL13(3-87)-IgG1Fc

<400> SEQUENCE: 74

```
Glu Val Tyr Tyr Thr Ser Leu Arg Cys Arg Cys Val Gln Glu Ser Ser
1               5                   10                  15

Val Phe Ile Pro Arg Arg Phe Ile Asp Arg Ile Gln Ile Leu Pro Arg
            20                  25                  30

Gly Asn Gly Cys Pro Arg Lys Glu Ile Ile Val Trp Lys Lys Asn Lys
        35                  40                  45

Ser Ile Val Cys Val Asp Pro Gln Ala Glu Trp Ile Gln Arg Met Met
    50                  55                  60

Glu Val Leu Arg Lys Arg Ser Ser Thr Leu Pro Val Pro Val Phe
65                  70                  75                  80

Lys Arg Lys Ile Pro Asp Lys Thr His Thr Cys Pro Pro Cys Pro Ala
                85                  90                  95

Pro Glu Leu Leu Gly Gly Pro Ser Val Phe Leu Phe Pro Pro Lys Pro
            100                 105                 110

Lys Asp Thr Leu Met Ile Ser Arg Thr Pro Glu Val Thr Cys Val Val
        115                 120                 125

Val Asp Val Ser His Glu Asp Pro Glu Val Lys Phe Asn Trp Tyr Val
    130                 135                 140

Asp Gly Val Glu Val His Asn Ala Lys Thr Lys Pro Arg Glu Glu Gln
145                 150                 155                 160

Tyr Asn Ser Thr Tyr Arg Val Val Ser Val Leu Thr Val Leu His Gln
                165                 170                 175

Asp Trp Leu Asn Gly Lys Glu Tyr Lys Cys Lys Val Ser Asn Lys Ala
            180                 185                 190

Leu Pro Ala Pro Ile Glu Lys Thr Ile Ser Lys Ala Lys Gly Gln Pro
        195                 200                 205

Arg Glu Pro Gln Val Tyr Thr Leu Pro Pro Ser Arg Glu Glu Met Thr
    210                 215                 220

Lys Asn Gln Val Ser Leu Thr Cys Leu Val Lys Gly Phe Tyr Pro Ser
225                 230                 235                 240

Asp Ile Ala Val Glu Trp Glu Ser Asn Gly Gln Pro Glu Asn Asn Tyr
                245                 250                 255

Lys Thr Thr Pro Pro Val Leu Asp Ser Asp Gly Ser Phe Phe Leu Tyr
            260                 265                 270

Ser Lys Leu Thr Val Asp Lys Ser Arg Trp Gln Gln Gly Asn Val Phe
        275                 280                 285

Ser Cys Ser Val Met His Glu Ala Leu His Asn His Tyr Thr Gln Lys
    290                 295                 300

Ser Leu Ser Leu Ser Pro Gly Lys
305                 310
```

<210> SEQ ID NO 75
<211> LENGTH: 312
<212> TYPE: PRT
<213> ORGANISM: Artificial Sequence
<220> FEATURE:
<223> OTHER INFORMATION: CXCL13(3-87K/H-A)-IgG1Fc

<400> SEQUENCE: 75

```
Glu Val Tyr Tyr Thr Ser Leu Arg Cys Arg Cys Val Gln Glu Ser Ser
1               5                   10                  15
```

```
Val Phe Ile Pro Arg Arg Phe Ile Asp Ala Ile Gln Ile Leu Pro Arg
             20                  25                  30

Gly Asn Gly Cys Pro Arg Lys Glu Ile Ile Val Trp Ala Ala Asn Ala
         35                  40                  45

Ser Ile Val Cys Val Asp Pro Gln Ala Glu Trp Ile Gln Ala Met Met
 50                  55                  60

Glu Val Leu Ala Ala Ser Ser Ser Thr Leu Pro Val Pro Val Phe
65                  70                  75                  80

Ala Ala Ala Ile Pro Asp Lys Thr His Thr Cys Pro Pro Cys Pro Ala
                 85                  90                  95

Pro Glu Leu Leu Gly Gly Pro Ser Val Phe Leu Phe Pro Pro Lys Pro
             100                 105                 110

Lys Asp Thr Leu Met Ile Ser Arg Thr Pro Glu Val Thr Cys Val Val
             115                 120                 125

Val Asp Val Ser His Glu Asp Pro Glu Val Lys Phe Asn Trp Tyr Val
130                 135                 140

Asp Gly Val Glu Val His Asn Ala Lys Thr Lys Pro Arg Glu Glu Gln
145                 150                 155                 160

Tyr Asn Ser Thr Tyr Arg Val Val Ser Val Leu Thr Val Leu His Gln
                 165                 170                 175

Asp Trp Leu Asn Gly Lys Glu Tyr Lys Cys Lys Val Ser Asn Lys Ala
             180                 185                 190

Leu Pro Ala Pro Ile Glu Lys Thr Ile Ser Lys Ala Lys Gly Gln Pro
             195                 200                 205

Arg Glu Pro Gln Val Tyr Thr Leu Pro Pro Ser Arg Glu Glu Met Thr
             210                 215                 220

Lys Asn Gln Val Ser Leu Thr Cys Leu Val Lys Gly Phe Tyr Pro Ser
225                 230                 235                 240

Asp Ile Ala Val Glu Trp Glu Ser Asn Gly Gln Pro Glu Asn Asn Tyr
                 245                 250                 255

Lys Thr Thr Pro Pro Val Leu Asp Ser Asp Gly Ser Phe Phe Leu Tyr
             260                 265                 270

Ser Lys Leu Thr Val Asp Lys Ser Arg Trp Gln Gln Gly Asn Val Phe
             275                 280                 285

Ser Cys Ser Val Met His Glu Ala Leu His Asn His Tyr Thr Gln Lys
             290                 295                 300

Ser Leu Ser Leu Ser Pro Gly Lys
305                 310

<210> SEQ ID NO 76
<211> LENGTH: 311
<212> TYPE: PRT
<213> ORGANISM: Artificial Sequence
<220> FEATURE:
<223> OTHER INFORMATION: CXCL13-IgG4Fc

<400> SEQUENCE: 76

Val Leu Glu Val Tyr Tyr Thr Ser Leu Arg Cys Arg Cys Val Gln Glu
1               5                   10                  15

Ser Ser Val Phe Ile Pro Arg Arg Phe Ile Asp Arg Ile Gln Ile Leu
             20                  25                  30

Pro Arg Gly Asn Gly Cys Pro Arg Lys Glu Ile Ile Val Trp Lys Lys
         35                  40                  45

Asn Lys Ser Ile Val Cys Val Asp Pro Gln Ala Glu Trp Ile Gln Arg
 50                  55                  60
```

```
Met Met Glu Val Leu Arg Lys Arg Ser Ser Ser Thr Leu Pro Val Pro
 65                  70                  75                  80

Val Phe Lys Arg Lys Ile Pro Pro Cys Pro Ser Cys Pro Ala Pro
                 85                  90                  95

Glu Phe Leu Gly Gly Pro Ser Val Phe Leu Phe Pro Pro Lys Pro Lys
                100                 105                 110

Asp Thr Leu Met Ile Ser Arg Thr Pro Glu Val Thr Cys Val Val Val
                115                 120                 125

Asp Val Ser Gln Glu Asp Pro Glu Val Gln Phe Asn Trp Tyr Val Asp
            130                 135                 140

Gly Val Glu Val His Asn Ala Lys Thr Lys Pro Arg Glu Glu Gln Phe
145                 150                 155                 160

Asn Ser Thr Tyr Arg Val Val Ser Val Leu Thr Val Leu His Gln Asp
                165                 170                 175

Trp Leu Asn Gly Lys Glu Tyr Lys Cys Lys Val Ser Asn Lys Gly Leu
                180                 185                 190

Pro Ser Ser Ile Glu Lys Thr Ile Ser Lys Ala Lys Gly Gln Pro Arg
                195                 200                 205

Glu Pro Gln Val Tyr Thr Leu Pro Pro Ser Gln Glu Glu Met Thr Lys
    210                 215                 220

Asn Gln Val Ser Leu Thr Cys Leu Val Lys Gly Phe Tyr Pro Ser Asp
225                 230                 235                 240

Ile Ala Val Glu Trp Glu Ser Asn Gly Gln Pro Glu Asn Asn Tyr Lys
                245                 250                 255

Thr Thr Pro Pro Val Leu Asp Ser Asp Gly Ser Phe Phe Leu Tyr Ser
                260                 265                 270

Arg Leu Thr Val Asp Lys Ser Arg Trp Gln Glu Gly Asn Val Phe Ser
    275                 280                 285

Cys Ser Val Met His Glu Ala Leu His Asn His Tyr Thr Gln Lys Ser
    290                 295                 300

Leu Ser Leu Ser Pro Gly Lys
305                 310

<210> SEQ ID NO 77
<211> LENGTH: 309
<212> TYPE: PRT
<213> ORGANISM: Artificial Sequence
<220> FEATURE:
<223> OTHER INFORMATION: CXCL13(3-87)-IgG4Fc

<400> SEQUENCE: 77

Glu Val Tyr Tyr Thr Ser Leu Arg Cys Arg Cys Val Gln Glu Ser Ser
1               5                   10                  15

Val Phe Ile Pro Arg Arg Phe Ile Asp Arg Ile Gln Ile Leu Pro Arg
                20                  25                  30

Gly Asn Gly Cys Pro Arg Lys Glu Ile Ile Val Trp Lys Lys Asn Lys
            35                  40                  45

Ser Ile Val Cys Val Asp Pro Gln Ala Glu Trp Ile Gln Arg Met Met
 50                 55                  60

Glu Val Leu Arg Lys Arg Ser Ser Ser Thr Leu Pro Val Pro Val Phe
 65                 70                  75                  80

Lys Arg Lys Ile Pro Pro Cys Pro Ser Cys Pro Ala Pro Glu Phe
                85                  90                  95

Leu Gly Gly Pro Ser Val Phe Leu Phe Pro Pro Lys Pro Lys Asp Thr
                100                 105                 110

Leu Met Ile Ser Arg Thr Pro Glu Val Thr Cys Val Val Val Asp Val
```

```
                    115                 120                 125
Ser Gln Glu Asp Pro Glu Val Gln Phe Asn Trp Tyr Val Asp Gly Val
130                 135                 140

Glu Val His Asn Ala Lys Thr Lys Pro Arg Glu Glu Gln Phe Asn Ser
145                 150                 155                 160

Thr Tyr Arg Val Val Ser Val Leu Thr Val Leu His Gln Asp Trp Leu
                    165                 170                 175

Asn Gly Lys Glu Tyr Lys Cys Lys Val Ser Asn Lys Gly Leu Pro Ser
                180                 185                 190

Ser Ile Glu Lys Thr Ile Ser Lys Ala Lys Gly Gln Pro Arg Glu Pro
            195                 200                 205

Gln Val Tyr Thr Leu Pro Pro Ser Gln Glu Glu Met Thr Lys Asn Gln
210                 215                 220

Val Ser Leu Thr Cys Leu Val Lys Gly Phe Tyr Pro Ser Asp Ile Ala
225                 230                 235                 240

Val Glu Trp Glu Ser Asn Gly Gln Pro Glu Asn Asn Tyr Lys Thr Thr
                    245                 250                 255

Pro Pro Val Leu Asp Ser Asp Gly Ser Phe Phe Leu Tyr Ser Arg Leu
                260                 265                 270

Thr Val Asp Lys Ser Arg Trp Gln Glu Gly Asn Val Phe Ser Cys Ser
            275                 280                 285

Val Met His Glu Ala Leu His Asn His Tyr Thr Gln Lys Ser Leu Ser
290                 295                 300

Leu Ser Pro Gly Lys
305

<210> SEQ ID NO 78
<211> LENGTH: 309
<212> TYPE: PRT
<213> ORGANISM: Artificial Sequence
<220> FEATURE:
<223> OTHER INFORMATION: CXCL13(3-87K/H-A)-IgG4Fc

<400> SEQUENCE: 78

Glu Val Tyr Tyr Thr Ser Leu Arg Cys Arg Cys Val Gln Glu Ser Ser
1               5                   10                  15

Val Phe Ile Pro Arg Arg Phe Ile Asp Ala Ile Gln Ile Leu Pro Arg
                20                  25                  30

Gly Asn Gly Cys Pro Arg Lys Glu Ile Ile Val Trp Ala Ala Asn Ala
            35                  40                  45

Ser Ile Val Cys Val Asp Pro Gln Ala Glu Trp Ile Gln Ala Met Met
50                  55                  60

Glu Val Leu Ala Ala Ala Ser Ser Ser Thr Leu Pro Val Pro Val Phe
65                  70                  75                  80

Ala Ala Ala Ile Pro Pro Pro Cys Pro Ser Cys Pro Ala Pro Glu Phe
                85                  90                  95

Leu Gly Gly Pro Ser Val Phe Leu Phe Pro Pro Lys Pro Lys Asp Thr
            100                 105                 110

Leu Met Ile Ser Arg Thr Pro Glu Val Thr Cys Val Val Val Asp Val
        115                 120                 125

Ser Gln Glu Asp Pro Glu Val Gln Phe Asn Trp Tyr Val Asp Gly Val
130                 135                 140

Glu Val His Asn Ala Lys Thr Lys Pro Arg Glu Glu Gln Phe Asn Ser
145                 150                 155                 160

Thr Tyr Arg Val Val Ser Val Leu Thr Val Leu His Gln Asp Trp Leu
                    165                 170                 175
```

Asn Gly Lys Glu Tyr Lys Cys Lys Val Ser Asn Lys Gly Leu Pro Ser
            180                 185                 190

Ser Ile Glu Lys Thr Ile Ser Lys Ala Lys Gly Gln Pro Arg Glu Pro
        195                 200                 205

Gln Val Tyr Thr Leu Pro Pro Ser Gln Glu Glu Met Thr Lys Asn Gln
    210                 215                 220

Val Ser Leu Thr Cys Leu Val Lys Gly Phe Tyr Pro Ser Asp Ile Ala
225                 230                 235                 240

Val Glu Trp Glu Ser Asn Gly Gln Pro Glu Asn Asn Tyr Lys Thr Thr
                245                 250                 255

Pro Pro Val Leu Asp Ser Asp Gly Ser Phe Phe Leu Tyr Ser Arg Leu
            260                 265                 270

Thr Val Asp Lys Ser Arg Trp Gln Glu Gly Asn Val Phe Ser Cys Ser
        275                 280                 285

Val Met His Glu Ala Leu His Asn His Tyr Thr Gln Lys Ser Leu Ser
    290                 295                 300

Leu Ser Pro Gly Lys
305

<210> SEQ ID NO 79
<211> LENGTH: 4401
<212> TYPE: DNA
<213> ORGANISM: Artificial Sequence
<220> FEATURE:
<223> OTHER INFORMATION: pCCL2-IgG1Fc

<400> SEQUENCE: 79

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttttcc cgagggtggg ggagaaccgt    180
atataagtgc agtagtcgcc gtgaacgttc tttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc tgtggtgcc tcctgaactg      360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cgcagccaga tgcaatcaat gccccagtca     660
cctgctgtta taacttcacc aataggaaga tctcagtgca gaggctcgcg agctatagaa     720
gaatcaccag cagcaagtgt cccaaagaag ctgtgatctt caagaccatt gtggccaagg     780
agatctgtgc tgaccccaag cagaagtggg ttcaggattc catggaccac ctggacaagc     840
aaacccaaac tccgaagact gacaaaactc acacatgccc accgtgccca gcacctgaac     900
tcctgggggg accgtcagtc ttcctcttcc cccaaaaacc caaggacacc ctcatgatct     960
cccggacccc tgaggtcaca tgcgtggtgg tggacgtgag ccacgaagac cctgaggtca    1020
agttcaactg gtacgtggac ggcgtggagg tgcataatgc caagacaaag ccgcgggagg    1080
agcagtacaa cagcacgtac cgtgtggtca gcgtcctcac cgtcctgcac caggactggc    1140
tgaatggcaa ggagtacaag tgcaaggtct ccaacaaagc cctcccagcc cccatcgaga    1200
aaaccatctc caaagccaaa gggcagcccc gagaaccaca ggtgtacacc ctgcccccat    1260
```

```
cccgggagga gatgaccaag aaccaggtca gcctgacctg cctggtcaaa ggcttctatc   1320
ccagcgacat cgccgtggag tgggagagca atgggcagcc ggagaacaac tacaagacca   1380
cgcctcccgt gctggactcc gacggctcct tcttcctcta cagcaagctc accgtggaca   1440
agagcaggtg gcagcagggg aacgtcttct catgctccgt gatgcacgag gctctgcaca   1500
accactacac gcagaagagc ctctccctgt ctccgggtaa atgagtgcta gctggccaga   1560
catgataaga tacattgatg agtttggaca aaccacaact agaatgcagt gaaaaaaatg   1620
ctttatttgt gaaatttgtg atgctattgc tttatttgta accattataa gctgcaataa   1680
acaagttaac aacaacaatt gcattcattt tatgtttcag gttcaggggg aggtgtggga   1740
ggttttttaa agcaagtaaa acctctacaa atgtggtatg gaattaattc taaaatacag   1800
catagcaaaa ctttaacctc caaatcaagc ctctacttga atccttttct gagggatgaa   1860
taaggcatag gcatcagggg ctgttgccaa tgtgcattag ctgtttgcag cctcaccttc   1920
tttcatggag tttaagatat agtgtatttt cccaaggttt gaactagctc ttcatttctt   1980
tatgttttaa atgcactgac ctcccacatt cccttttag taaaatattc agaaataatt   2040
taaatacatc attgcaatga aaataaatgt tttttattag gcagaatcca gatgctcaag   2100
gcccttcata atatccccca gtttagtagt tggacttagg gaacaaagga acctttaata   2160
gaaattggac agcaagaaag cgagcttcta gcttatcctc agtcctgctc ctctgccaca   2220
aagtgcacgc agttgccggc cgggtcgcgc agggcgaact cccgccccca cggctgctcg   2280
ccgatctcgg tcatggccgg cccggaggcg tccggaagt tcgtggacac gacctccgac   2340
cactcggcgt acagctcgtc caggccgcgc acccacaccc aggccagggt gttgtccggc   2400
accacctggt cctggaccgc gctgatgaac agggtcacgt cgtcccggac cacaccggcg   2460
aagtcgtcct ccacgaagtc ccgggagaac ccgagccggt cggtccagaa ctcgaccgct   2520
ccggcgacgt cgcgcgcggt gagcaccgga acggcactgg tcaacttggc catgatggct   2580
cctcctgtca ggagaggaaa gagaagaagg ttagtacaat tgctatagtg agttgtatta   2640
tactatgcag atatactatg ccaatgatta attgtcaaac tagggctgca gggttcatag   2700
tgccactttt cctgcactgc cccatctcct gcccacccct tcccaggcat agacagtcag   2760
tgacttacca aactcacagg agggagaagg cagaagcttg agacagaccc gcgggaccgc   2820
cgaactgcga gggacgtgg ctagggcggc ttctttatg gtgcgccggc cctcggaggc   2880
agggcgctcg gggaggccta gcggccaatc tgcggtggca ggaggcgggg ccgaaggccg   2940
tgcctgacca atccggagca cataggagtc tcagcccccc gccccaaagc aaggggaagt   3000
cacgcgcctg tagcgccagc gtgttgtgaa atgggggctt ggggggttg gggccctgac   3060 tagtcaaaac aaactcccat tgacgtcaat ggggtggaga cttggaaatc cccgtgagtc   3120
aaaccgctat ccacgcccat tgatgtactg ccaaaaccgc atcatcatgg taatagcgat   3180
gactaatacg tagatgtact gccaagtagg aaagtcccat aaggtcatgt actgggcata   3240
atgccaggcg ggccatttac cgtcattgac gtcaataggg ggcgtacttg gcatatgata   3300
cacttgatgt actgccaagt gggcagttta ccgtaaatac tccacccatt gacgtcaatg   3360
gaaagtccct attggcgtta ctatgggaac atacgtcatt attgacgtca atgggcgggg   3420
gtcgttgggc ggtcagccag gcgggccatt taccgtaagt tatgtaacgc ctgcaggtta   3480
attaagaaca tgtgagcaaa aggccagcaa aaggccagga accgtaaaaa ggccgcgttg   3540
ctggcgtttt tccataggct ccgcccccct gacgagcatc acaaaaatcg acgctcaagt   3600
cagaggtggc gaaacccgac aggactataa agataccagg cgtttccccc tggaagctcc   3660
```

-continued

```
ctcgtgcgct ctcctgttcc gaccctgccg cttaccggat acctgtccgc ctttctccct    3720
tcgggaagcg tggcgctttc tcatagctca cgctgtaggt atctcagttc ggtgtaggtc    3780
gttcgctcca agctgggctg tgtgcacgaa ccccccgttc agcccgaccg ctgcgcctta    3840
tccggtaact atcgtcttga gtccaacccg gtaagacacg acttatcgcc actggcagca    3900
gccactggta acaggattag cagagcgagg tatgtaggcg gtgctacaga gttcttgaag    3960
tggtggccta actacggcta cactagaaga acagtatttg gtatctgcgc tctgctgaag    4020
ccagttacct tcggaaaaag agttggtagc tcttgatccg gcaaacaaac caccgctggt    4080
agcggtggtt ttttgtttg caagcagcag attacgcgca gaaaaaaagg atctcaagaa    4140
gatcctttga tcttttctac ggggtctgac gctcagtgga acgaaaactc acgttaaggg    4200
attttggtca tggctagtta attaacattt aaatcagcgg ccgcaataaa atatctttat    4260
tttcattaca tctgtgtgtt ggttttttgt gtgaatcgta actaacatac gctctccatc    4320
aaaacaaaac gaaacaaaac aaactagcaa ataggctgt ccccagtgca agtgcaggtg    4380
ccagaacatt tctctatcga a                                              4401
```

<210> SEQ ID NO 80
<211> LENGTH: 4389
<212> TYPE: DNA
<213> ORGANISM: Artificial Sequence
<220> FEATURE:
<223> OTHER INFORMATION: pCCL2(5-76)-IgG1Fc

<400> SEQUENCE: 80

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa    120
actgggaaag tgatgtcgtg tactggctcc gcctttttcc cgagggtggg ggagaaccgt    180
atataagtgc agtagtcgcc gtgaacgttc ttttcgcaa cgggtttgcc gccagaacac    240
agctgaagct cgaggggct cgcatctctc cttcacgcgc ccgccgccct acctgaggcc    300
gccatccacg ccggttgagt cgcgttctgc cgcctcccgc tgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cgatcaatgc cccagtcacc tgctgttata    660
acttcaccaa taggaagatc tcagtgcaga ggctcgcgag ctatagaaga atcaccagca    720
gcaagtgtcc caaagaagct gtgatcttca agaccattgt ggccaaggag atctgtgctg    780
accccaagca gaagtgggtt caggattcca tggaccacct ggacaagcaa acccaaactc    840
cgaagactga caaaactcac acatgcccac cgtgcccagc acctgaactc ctggggggac    900
cgtcagtctt cctcttcccc ccaaaaccca aggacaccct catgatctcc cggacccctg    960
aggtcacatg cgtggtggtg gacgtgagcc acgaagaccc tgaggtcaag ttcaactggt   1020
acgtggacgg cgtggaggtg cataatgcca agacaaagcc gcgggaggag cagtacaaca   1080
gcacgtaccg tgtggtcagc gtcctcaccg tcctgcacca ggactggctg aatggcaagg   1140
agtacaagtg caaggtctcc aacaaagccc tcccagcccc catcgagaaa accatctcca   1200
aagccaaagg gcagccccga gaaccacagg tgtacaccct gcccccatcc cgggaggaga   1260
tgaccaagaa ccaggtcagc ctgacctgcc tggtcaaagg cttctatccc agcgacatcg   1320
```

-continued

```
ccgtggagtg ggagagcaat gggcagccgg agaacaacta caagaccacg cctcccgtgc   1380
tggactccga cggctccttc ttcctctaca gcaagctcac cgtggacaag agcaggtggc   1440
agcaggggaa cgtcttctca tgctccgtga tgcacgaggc tctgcacaac cactacacgc   1500
agaagagcct ctccctgtct ccgggtaaat gagtgctagc tggccagaca tgataagata   1560
cattgatgag tttggacaaa ccacaactag aatgcagtga aaaaaatgct ttatttgtga   1620
aatttgtgat gctattgctt tatttgtaac cattataagc tgcaataaac aagttaacaa   1680
caacaattgc attcatttta tgtttcaggt tcaggggag gtgtgggagg ttttttaaag    1740
caagtaaaac ctctacaaat gtggtatgga attaattcta aaatacagca tagcaaaact   1800
ttaacctcca aatcaagcct ctacttgaat ccttttctga gggatgaata aggcataggc   1860
atcaggggct gttgccaatg tgcattagct gtttgcagcc tcaccttctt tcatggagtt   1920
taagatatag tgtattttcc caaggtttga actagctctt catttcttta tgttttaaat   1980
gcactgacct cccacattcc ctttttagta aatattcag aaataattta aatacatcat    2040
tgcaatgaaa ataaatgttt tttattaggc agaatccaga tgctcaaggc ccttcataat   2100
atcccccagt ttagtagttg gacttaggga acaaaggaac ctttaataga aattggacag   2160
caagaaagcg agcttctagc ttatcctcag tcctgctcct ctgccacaaa gtgcacgcag   2220
ttgccggccg gtcgcgcag ggcgaactcc cgccccacg gctgctcgcc gatctcggtc     2280
atggccggcc cggaggcgtc ccggaagttc gtggacacga cctccgacca ctcggcgtac   2340
agctcgtcca ggccgcgcac ccacacccag gccagggtgt tgtccggcac cacctggtcc   2400
tggaccgcgc tgatgaacag ggtcacgtcg tcccggacca caccggcgaa gtcgtcctcc   2460
acgaagtccc gggagaaccc gagccggtcg gtccagaact cgaccgctcc ggcgacgtcg   2520
cgcgcggtga gcaccggaac ggcactggtc aacttggcca tgatggctcc tcctgtcagg   2580
agaggaaaga gaagaaggtt agtacaattg ctatagtgag ttgtattata ctatgcagat   2640
atactatgcc aatgattaat tgtcaaacta gggctgcagg gttcatagtg ccacttttcc   2700
tgcactgccc catctcctgc ccacccttt ccaggcatag acagtcagtg acttaccaaa    2760
ctcacaggag ggagaaggca gaagcttgag acagacccgc gggaccgccg aactgcgagg   2820
ggacgtggct agggcggctt cttttatggt gcgccggccc tcggaggcag ggcgctcggg   2880
gaggcctagc ggccaatctg cggtggcagg aggcggggcc gaaggccgtg cctgaccaat   2940
ccggagcaca taggagtctc agccccccgc cccaaagcaa ggggaagtca cgcgcctgta   3000
gcgccagcgt gttgtgaaat gggggcttgg ggggttggg gccctgacta gtcaaaacaa    3060
actcccattg acgtcaatgg ggtggagact tggaaatccc cgtgagtcaa accgctatcc   3120
acgcccattg atgtactgcc aaaaccgcat catcatggta atagcgatga ctaatacgta   3180
gatgtactgc caagtaggaa agtcccataa ggtcatgtac tgggcataat gccaggcggg   3240
ccatttaccg tcattgacgt caatagggg cgtacttggc atatgataca cttgatgtac    3300
tgccaagtgg gcagtttacc gtaaatactc cacccattga cgtcaatgga aagtccctat   3360
tggcgttact atgggaacat acgtcattat tgacgtcaat gggcggggt cgttgggcgg    3420 tcagccaggc gggccatttt ccgtaagtta tgtaacgcct gcaggttaat taagaacatg   3480
tgagcaaaag gccagcaaaa ggccaggaac cgtaaaaagg ccgcgttgct ggcgtttttc   3540
cataggctcc gcccccctga cgagcatcac aaaaatcgac gctcaagtca gaggtggcga   3600
aacccgacag gactataaag ataccaggcg tttccccctg gaagctccct cgtgcgctct   3660
cctgttccga ccctgccgct taccggatac ctgtccgcct ttctcccttc gggaagcgtg   3720
```

-continued

| | |
|---|---|
| gcgctttctc atagctcacg ctgtaggtat ctcagttcgg tgtaggtcgt tcgctccaag | 3780 |
| ctgggctgtg tgcacgaacc ccccgttcag cccgaccgct gcgccttatc cggtaactat | 3840 |
| cgtcttgagt ccaacccggt aagacacgac ttatcgccac tggcagcagc cactggtaac | 3900 |
| aggattagca gagcgaggta tgtaggcggt gctacagagt tcttgaagtg gtggcctaac | 3960 |
| tacggctaca ctagaagaac agtatttggt atctgcgctc tgctgaagcc agttaccttc | 4020 |
| ggaaaaagag ttggtagctc ttgatccggc aaacaaacca ccgctggtag cggtggtttt | 4080 |
| tttgtttgca agcagcagat tacgcgcaga aaaaaggat ctcaagaaga tcctttgatc | 4140 |
| ttttctacgg ggtctgacgc tcagtggaac gaaaactcac gttaagggat tttggtcatg | 4200 |
| gctagttaat taacatttaa atcagcggcc gcaataaaat atctttattt tcattacatc | 4260 |
| tgtgtgttgg ttttttgtgt gaatcgtaac taacatacgc tctccatcaa acaaaacga | 4320 |
| aacaaaacaa actagcaaaa taggctgtcc ccagtgcaag tgcaggtgcc agaacatttc | 4380 |
| tctatcgaa | 4389 |

<210> SEQ ID NO 81
<211> LENGTH: 4389
<212> TYPE: DNA
<213> ORGANISM: Artificial Sequence
<220> FEATURE:
<223> OTHER INFORMATION: pCCL2(5-76K/H-A)-IgG1Fc

<400> SEQUENCE: 81

| | |
|---|---|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gccttttttcc cgagggtggg ggagaaccgt | 180 |
| atataagtgc agtagtcgcc gtgaacgttc tttttcgcaa cgggtttgcc gccagaacac | 240 |
| agctgaagct tcgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggcga aggagggcca ccatgtacag gatgcaactc ctgtcttgca | 600 |
| ttgcactaag tcttgcactt gtcacgaatt cgatcaatgc cccagtcacc tgctgttata | 660 |
| acttcaccaa taggaagatc tcagtgcaga ggctcgcgag ctatagaaga atcaccagca | 720 |
| gcaagtgtcc caaagaagct gtgatcttca agaccattgt ggccgcggag atctgtgctg | 780 |
| accccgctca ggcctgggtt caggattcca tggacgctct ggacgcccaa acccaaactc | 840 |
| cggcgactga caaaactcac acatgcccac cgtgcccagc acctgaactc ctggggggac | 900 |
| cgtcagtctt cctcttcccc ccaaaaccca aggacaccct catgatctcc cggacccctg | 960 |
| aggtcacatg cgtggtggtg gacgtgagcc acgaagaccc tgaggtcaag ttcaactggt | 1020 |
| acgtggacgg cgtggaggtg cataatgcca agacaaagcc gcgggaggag cagtacaaca | 1080 |
| gcacgtaccg tgtggtcagc gtcctcaccg tcctgcacca ggactggctg aatggcaagg | 1140 |
| agtacaagtg caaggtctcc aacaaagccc tcccagcccc catcgagaaa accatctcca | 1200 |
| aagccaaagg gcagccccga gaaccacagg tgtacaccct gcccccatcc cgggaggaga | 1260 |
| tgaccaagaa ccaggtcagc ctgacctgcc tggtcaaagg cttctatccc agcgacatcg | 1320 |
| ccgtggagtg ggagagcaat gggcagccgg agaacaacta caagaccacg cctcccgtgc | 1380 |

```
                                      -continued
tggactccga cggctccttc ttcctctaca gcaagctcac cgtggacaag agcaggtggc    1440 agcagggaa cgtcttctca tgctccgtga tgcacgaggc tctgcacaac cactacacgc     1500
agaagagcct ctccctgtct ccgggtaaat gagtgctagc tggccagaca tgataagata    1560
cattgatgag tttggacaaa ccacaactag aatgcagtga aaaaaatgct ttatttgtga    1620
aatttgtgat gctattgctt tatttgtaac cattataagc tgcaataaac aagttaacaa    1680
caacaattgc attcatttta tgtttcaggt tcaggggag gtgtgggagg tttttttaaag    1740 caagtaaaac ctctacaaat gtggtatgga attaattcta aaatacagca tagcaaaact    1800
ttaacctcca aatcaagcct ctacttgaat cctttctga gggatgaata aggcataggc      1860
atcaggggct gttgccaatg tgcattagct gtttgcagcc tcaccttctt tcatggagtt    1920
taagatatag tgtattttcc caaggtttga actagctctt catttcttta tgttttaaat     1980
gcactgacct cccacattcc cttttagta aatattcag aataatttta aatacatcat       2040
tgcaatgaaa ataaatgttt tttattaggc agaatccaga tgctcaaggc ccttcataat    2100
atcccccagt ttagtagttg gacttaggga acaaaggaac ctttaataga aattggacag    2160
caagaaagcg agcttctagc ttatcctcag tcctgctcct ctgccacaaa gtgcacgcag    2220
ttgccggccg ggtcgcgcag ggcgaactcc cgccccacg gctgctcgcc gatctcggtc     2280
atggccggcc cggaggcgtc ccggaagttc gtggacacga cctccgacca ctcggcgtac    2340
agctcgtcca ggccgcgcac ccacacccag gccagggtgt tgtccggcac cacctggtcc    2400
tggaccgcgc tgatgaacag ggtcacgtcg tcccggacca caccggcgaa gtcgtcctcc    2460
acgaagtccc gggagaaccc gagccggtcg gtccagaact cgaccgctcc ggcgacgtcg    2520
cgcgcggtga gcaccggaac ggcactggtc aacttggcca tgatggctcc tcctgtcagg    2580
agaggaaaga gaagaaggtt agtacaattg ctatagtgag ttgtattata ctatgcagat    2640
atactatgcc aatgattaat tgtcaaacta gggctgcagg gttcatagtg ccactttttcc   2700 tgcactgccc catctcctgc ccaccctttc ccaggcatag acagtcagtg acttaccaaa    2760
ctcacaggag ggagaaggca gaagcttgag acagacccgc gggaccgccg aactgcgagg    2820
ggacgtggct agggcggctt cttttatggt gcgccggccc tcggaggcag ggcgctcggg    2880
gaggcctagc ggccaatctg cggtggcagg aggcggggcc gaaggccgtg cctgaccaat    2940
ccggagcaca taggagtctc agccccccgc cccaaagcaa ggggaagtca cgcgcctgta    3000
gcgccagcgt gttgtgaaat gggggcttgg gggggttggg gccctgacta gtcaaaacaa    3060
actcccattg acgtcaatgg ggtggagact tggaaatccc cgtgagtcaa accgctatcc    3120
acgcccattg atgtactgcc aaaaccgcat catcatggta atagcgatga ctaatacgta    3180
gatgtactgc caagtaggaa agtcccataa ggtcatgtac tgggcataat gccaggcggg    3240
ccatttaccg tcattgacgt caatagggg gtacttggc atatgataca cttgatgtac       3300
tgccaagtgg gcagtttacc gtaaatactc cacccattga cgtcaatgga aagtccctat    3360
tggcgttact atgggaacat acgtcattat tgacgtcaat gggcggggt cgttgggcgg     3420 tcagccaggc gggccattta ccgtaagtta tgtaacgcct gcaggttaat taagaacatg    3480
tgagcaaaag gccagcaaaa ggccaggaac cgtaaaaagg ccgcgttgct ggcgtttttc    3540
cataggctcc gcccccctga cgagcatcac aaaaatcgac gctcaagtca gaggtggcga    3600
aacccgacag gactataaag ataccaggcg tttccccctg gaagctccct cgtgcgctct    3660
cctgttccga ccctgccgct taccggatac ctgtccgcct ttctcccttc gggaagcgtg    3720
gcgctttctc atagctcacg ctgtaggtat ctcagttcgg tgtaggtcgt tcgctccaag    3780
```

-continued

```
ctgggctgtg tgcacgaacc ccccgttcag cccgaccgct gcgccttatc cggtaactat    3840
cgtcttgagt ccaacccggt aagacacgac ttatcgccac tggcagcagc cactggtaac    3900
aggattagca gagcgaggta tgtaggcggt gctacagagt tcttgaagtg gtggcctaac    3960
tacggctaca ctagaagaac agtatttggt atctgcgctc tgctgaagcc agttaccttc    4020 ggaaaagag ttggtagctc ttgatccggc aaacaaacca ccgctggtag cggtggtttt    4080
tttgtttgca agcagcagat tacgcgcaga aaaaaggat ctcaagaaga tcctttgatc    4140
ttttctacgg ggtctgacgc tcagtggaac gaaaactcac gttaagggat tttggtcatg    4200
gctagttaat taacatttaa atcagcggcc gcaataaaat atctttattt tcattacatc    4260
tgtgtgttgg ttttttgtgt gaatcgtaac taacatacgc tctccatcaa acaaaacga    4320 aacaaaacaa actagcaaaa taggctgtcc ccagtgcaag tgcaggtgcc agaacatttc    4380
tctatcgaa                                                             4389
```

<210> SEQ ID NO 82
<211> LENGTH: 4371
<212> TYPE: DNA
<213> ORGANISM: Artificial Sequence
<220> FEATURE:
<223> OTHER INFORMATION: pCCL7-IgG1Fc

<400> SEQUENCE: 82

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gcctttttcc cgagggtggg ggagaaccgt     180
atataagtgc agtagtcgcc gtgaacgttc ttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc tgtggtgcc tcctgaactg      360 cgtccgccgt ctaggtaagt ttaaagctca ggtcgagacc gggcctttgt ccggcgctcc     420
cttggagcct acctagactc agccggtctc ccacgctttg cctgaccctg cttgctcaac     480
tctacgtctt tgtttcgttt tctgttctgc gccgttacga atccaagctg tgaccggcgc    540
ctacctgaga tcaccggcga aggagggcca ccatgtacag gatgcaactc ctgtcttgca    600
ttgcactaag tcttgcactt gtcacgaatt cgtgctgcta cagatttatc aataagaaaa    660
tccctaagca gaggctggag agctacagaa ggaccaccag tagccactgt ccccgggaag   720
ctgtaatctt caagaccaaa ctggacaagg agatctgtgc tgaccccaca cagaagtggg   780
tccaggactt tatgaagcac ctggacaaga aaacccaaac tccaaagctt gacaaaactc   840
acacatgccc accgtgccca gcacctgaac tcctgggggg accgtcagtc ttcctcttcc   900
ccccaaaacc caaggacacc ctcatgatct cccggacccc tgaggtcaca tgcgtggtgg   960
tggacgtgag ccacgaagac cctgaggtca agttcaactg gtacgtggac ggcgtggagg  1020
tgcataatgc caagacaaag ccgcgggagg agcagtacaa cagcacgtac cgtgtggtca  1080
gcgtcctcac cgtcctgcac caggactggc tgaatggcaa ggagtacaag tgcaaggtct  1140
ccaacaaagc cctcccagcc cccatcgaga aaccatctc caaagccaaa gggcagcccc  1200
gagaaccaca ggtgtacacc ctgccccat cccgggagga gatgaccaag aaccaggtca  1260
gcctgacctg cctggtcaaa ggcttctatc ccagcgacat cgccgtggag tgggagagca  1320
atgggcagcc ggagaacaac tacaagacca cgcctcccgt gctggactcc gacggctcct  1380
tcttcctcta cagcaagctc accgtggaca agagcaggtg gcagcagggg aacgtcttct  1440
```

```
catgctccgt gatgcacgag gctctgcaca accactacac gcagaagagc ctctccctgt    1500
ctccgggtaa atgagtgcta gctggccaga catgataaga tacattgatg agtttggaca    1560
aaccacaact agaatgcagt gaaaaaaatg ctttatttgt gaaatttgtg atgctattgc    1620
tttatttgta accattataa gctgcaataa acaagttaac aacaacaatt gcattcattt    1680
tatgtttcag gttcaggggg aggtgtggga ggttttttaa agcaagtaaa acctctacaa    1740
atgtggtatg gaattaattc taaaatacag catagcaaaa ctttaacctc caaatcaagc    1800
ctctacttga atccttttct gagggatgaa taaggcatag gcatcagggg ctgttgccaa    1860
tgtgcattag ctgtttgcag cctcaccttc tttcatggag tttaagatat agtgtatttt    1920
cccaaggttt gaactagctc ttcatttctt tatgttttaa atgcactgac ctcccacatt    1980
ccctttttag taaatattc agaaataatt taaatacatc attgcaatga aaataaatgt    2040
tttttattag gcagaatcca gatgctcaag gcccttcata atatccccca gtttagtagt    2100
tggacttagg gaacaaagga acctttaata gaaattggac agcaagaaag cgagcttcta    2160
gcttatcctc agtcctgctc ctctgccaca aagtgcacgc agttgccggc cgggtcgcgc    2220
agggcgaact cccgccccca cggctgctcg ccgatctcgg tcatggccgg cccggaggcg    2280
tcccggaagt tcgtggacac gacctccgac cactcggcgt acagctcgtc caggccgcgc    2340
acccacaccc aggccagggt gttgtccggc accacctggt cctggaccgc gctgatgaac    2400
agggtcacgt cgtcccggac cacaccggcg aagtcgtcct ccacgaagtc ccgggagaac    2460
ccgagccggt cggtccagaa ctcgaccgct ccggcgacgt cgcgcgcggt gagcaccgga    2520
acggcactgg tcaacttggc catgatggct cctcctgtca ggagaggaaa gagaagaagg    2580
ttagtacaat tgctatagtg agttgtatta tactatgcag atatactatg ccaatgatta    2640
attgtcaaac tagggctgca gggttcatag tgccacttt cctgcactgc cccatctcct    2700
gcccacccTT tcccaggcat agacagtcag tgacttacca aactcacagg agggagaagg    2760
cagaagcttg agacagaccc gcgggaccgc cgaactgcga ggggacgtgg ctagggcggc    2820
ttcttttatg gtgcgccggc cctcggaggc agggcgctcg gggaggccta gcggccaatc    2880
tgcggtggca ggaggcgggg ccgaaggccg tgcctgacca atccggagca cataggagtc    2940
tcagcccccc gccccaaagc aaggggaagt cacgcgcctg tagcgccagc gtgttgtgaa    3000
atgggggctt gggggggttg gggccctgac tagtcaaaac aaactcccat tgacgtcaat    3060
ggggtggaga cttggaaatc cccgtgagtc aaaccgctat ccacgcccat tgatgtactg    3120
ccaaaaccgc atcatcatgg taatagcgat gactaatacg tagatgtact gccaagtagg    3180
aaagtcccat aaggtcatgt actgggcata atgccaggcg ggccatttac cgtcattgac    3240
gtcaataggg ggcgtacttg gcatatgata cacttgatgt actgccaagt gggcagttta    3300
ccgtaaatac tccacccatt gacgtcaatg gaaagtccct attggcgtta ctatgggaac    3360
atacgtcatt attgacgtca atgggcgggg tcgttgggc ggtcagccag gcgggccatt    3420
taccgtaagt tatgtaacgc ctgcaggtta attaagaaca tgtgagcaaa aggccagcaa    3480
aaggccagga accgtaaaaa ggccgcgttg ctggcgtttt tccataggct ccgcccccct    3540
gacgagcatc acaaaaatcg acgctcaagt cagaggtggc gaaacccgac aggactataa    3600
agataccagg cgtttccccc tggaagctcc ctcgtgcgct ctcctgttcc gaccctgccg    3660
cttaccggat acctgtccgc ctttctccct tcgggaagcg tggcgctttc tcatagctca    3720
cgctgtaggt atctcagttc ggtgtaggtc gttcgctcca agctgggctg tgtgcacgaa    3780
ccccccgttc agcccgaccg ctgcgcctta tccggtaact atcgtcttga gtccaacccg    3840
```

-continued

| | |
|---|---|
| gtaagacacg acttatcgcc actggcagca gccactggta acaggattag cagagcgagg | 3900 |
| tatgtaggcg gtgctacaga gttcttgaag tggtggccta actacggcta cactagaaga | 3960 |
| acagtatttg gtatctgcgc tctgctgaag ccagttacct tcggaaaaag agttggtagc | 4020 |
| tcttgatccg gcaaacaaac caccgctggt agcggtggtt ttttttgtttg caagcagcag | 4080 |
| attacgcgca gaaaaaaagg atctcaagaa gatcctttga tcttttctac ggggtctgac | 4140 |
| gctcagtgga acgaaaactc acgttaaggg attttggtca tggctagtta attaacattt | 4200 |
| aaatcagcgg ccgcaataaa atatctttat tttcattaca tctgtgtgtt ggttttttgt | 4260 |
| gtgaatcgta actaacatac gctctccatc aaaacaaaac gaaacaaaac aaactagcaa | 4320 |
| aataggctgt ccccagtgca agtgcaggtg ccagaacatt tctctatcga a | 4371 |

<210> SEQ ID NO 83
<211> LENGTH: 4359
<212> TYPE: DNA
<213> ORGANISM: Artificial Sequence
<220> FEATURE:
<223> OTHER INFORMATION: pCCL7(5-76)-IgG1Fc

<400> SEQUENCE: 83

| | |
|---|---|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gcctttttcc cgagggtggg ggagaaccgt | 180 |
| atataagtgc agtagtcgcc gtgaacgttc tttttcgcaa cgggtttgcc gccagaacac | 240 |
| agctgaagct tcgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggcga aggagggcca ccatgtacag gatgcaactc ctgtcttgca | 600 |
| ttgcactaag tcttgcactt gtcacgaatt cgtttatcaa taagaaaatc cctaagcaga | 660 |
| ggctggagag ctacagaagg accaccagta gccactgtcc ccgggaagct gtaatcttca | 720 |
| agaccaaact ggacaaggag atctgtgctg accccacaca gaagtgggtc caggacttta | 780 |
| tgaagcacct ggacaagaaa acccaaactc aaagcttga caaaactcac acatgcccac | 840 |
| cgtgcccagc acctgaactc ctgggggac cgtcagtctt cctcttcccc ccaaaaccca | 900 |
| aggacaccct catgatctcc cggacccctg aggtcacatg cgtggtggtg gacgtgagcc | 960 |
| acgaagaccc tgaggtcaag ttcaactggt acgtggacgg cgtggaggtg cataatgcca | 1020 |
| agacaaagcc gcgggaggag cagtacaaca gcacgtaccg tgtggtcagc gtcctcaccg | 1080 |
| tcctgcacca ggactggctg aatggcaagg agtacaagtg caaggtctcc aacaaagccc | 1140 |
| tcccagcccc catcgagaaa accatctcca aagccaaagg gcagccccga gaaccacagg | 1200 |
| tgtacaccct gcccccatcc cgggaggaga tgaccaagaa ccaggtcagc ctgacctgcc | 1260 |
| tggtcaaagg cttctatccc agcgacatcg ccgtggagtg ggagagcaat gggcagccgg | 1320 |
| agaacaacta caagaccacg cctcccgtgc tggactccga cggctccttc ttcctctaca | 1380 |
| gcaagctcac cgtggacaag agcaggtggc agcagggaa cgtcttctca tgctccgtga | 1440 |
| tgcacgaggc tctgcacaac cactacacgc agaagagcct ctccctgtct ccgggtaaat | 1500 |
| gagtgctagc tggccagaca tgataagata cattgatgag tttggacaaa ccacaactag | 1560 |

```
aatgcagtga aaaaaatgct ttatttgtga aatttgtgat gctattgctt tatttgtaac   1620
cattataagc tgcaataaac aagttaacaa caacaattgc attcatttta tgtttcaggt   1680
tcagggggag gtgtgggagg ttttttaaag caagtaaaac ctctacaaat gtggtatgga   1740
attaattcta aaatacagca tagcaaaact ttaacctcca aatcaagcct ctacttgaat   1800 cctttctga gggatgaata aggcataggc atcaggggct gttgccaatg tgcattagct    1860
gtttgcagcc tcaccttctt tcatggagtt taagatatag tgtattttcc caaggtttga   1920
actagctctt catttcttta tgttttaaat gcactgacct cccacattcc cttttagta    1980 aaatattcag aaataattta aatacatcat tgcaatgaaa ataaatgttt tttattaggc   2040
agaatccaga tgctcaaggc ccttcataat atccccagt ttagtagttg gacttaggga    2100
acaaaggaac cttaataga aattggacag caagaaagcg agcttctagc ttatcctcag    2160
tcctgctcct ctgccacaaa gtgcacgcag ttgccggccg ggtcgcgcag ggcgaactcc   2220
cgcccccacg gctgctcgcc gatctcggtc atggccggcc cggaggcgtc ccggaagttc   2280
gtggacacga cctccgacca ctcggcgtac agctcgtcca ggccgcgcac ccacacccag   2340
gccagggtgt tgtccggcac cacctggtcc tggaccgcgc tgatgaacag ggtcacgtcg   2400
tcccggacca caccggcgaa gtcgtcctcc acgaagtccc gggagaaccc gagccggtcg   2460
gtccagaact cgaccgctcc ggcgacgtcg cgcgcggtga gcaccggaac ggcactggtc   2520
aacttggcca tgatggctcc tcctgtcagg agaggaaaga gaagaaggtt agtacaattg   2580
ctatagtgag ttgtattata ctatgcagat atactatgcc aatgattaat tgtcaaacta   2640
gggctgcagg gttcatagtg ccactttttcc tgcactgccc catctcctgc ccaccctttc   2700
ccaggcatag acagtcagtg acttaccaaa ctcacaggag ggagaaggca gaagcttgag   2760
acagacccgc gggaccgccg aactgcgagg ggacgtggct agggcggctt cttttatggt   2820
gcgccggccc tcggaggcag ggcgctcggg gaggcctagc ggccaatctg cggtggcagg   2880
aggcggggcc gaaggccgtg cctgaccaat ccggagcaca taggagtctc agccccccgc   2940
cccaaagcaa ggggaagtca cgcgcctgta gcgccagcgt gttgtgaaat ggggcttgg    3000 gggggttggg gccctgacta gtcaaaacaa actcccattg acgtcaatgg ggtggagact   3060
tggaaatccc cgtgagtcaa accgctatcc acgcccattg atgtactgcc aaaaccgcat   3120
catcatggta atagcgatga ctaatacgta gatgtactgc caagtaggaa agtcccataa   3180
ggtcatgtac tgggcataat gccaggcggg ccatttaccg tcattgacgt caatagggg    3240 cgtacttggc atatgataca cttgatgtac tgccaagtgg gcagtttacc gtaaatactc   3300
cacccattga cgtcaatgga aagtccctat tggcgttact atgggaacat acgtcattat   3360
tgacgtcaat gggcggggt cgttgggcgg tcagccaggc gggccattta ccgtaagtta    3420
tgtaacgcct gcaggttaat taagaacatg tgagcaaaag gccagcaaaa ggccaggaac   3480
cgtaaaaagg ccgcgttgct ggcgtttttc cataggctcc gcccccctga cgagcatcac   3540
aaaaatcgac gctcaagtca gaggtggcga aacccgacag gactataaag ataccaggcg   3600
tttccccctg gaagctccct cgtgcgctct cctgttccga ccctgccgct taccggatac   3660
ctgtccgcct ttctcccttc gggaagcgtg gcgctttctc atagctcacg ctgtaggtat   3720
ctcagttcgg tgtaggtcgt tcgctccaag ctgggctgtg tgcacgaacc ccccgttcag   3780
cccgaccgct gcgccttatc cggtaactat cgtcttgagt ccaacccggt aagacacgac   3840
ttatcgccac tggcagcagc cactggtaac aggattagca gagcgaggta tgtaggcggt   3900
gctacagagt tcttgaagtg gtggcctaac tacggctaca ctagaagaac agtatttggt   3960
```

| | |
|---|---|
| atctgcgctc tgctgaagcc agttaccttc ggaaaaagag ttggtagctc ttgatccggc | 4020 |
| aaacaaacca ccgctggtag cggtggtttt tttgtttgca agcagcagat tacgcgcaga | 4080 |
| aaaaaaggat ctcaagaaga tcctttgatc ttttctacgg ggtctgacgc tcagtggaac | 4140 |
| gaaaactcac gttaagggat tttggtcatg ctagttaat taacatttaa atcagcggcc | 4200 |
| gcaataaaat atctttattt tcattacatc tgtgtgttgg ttttttgtgt gaatcgtaac | 4260 |
| taacatacgc tctccatcaa aacaaaacga aacaaaacaa actagcaaaa taggctgtcc | 4320 |
| ccagtgcaag tgcaggtgcc agaacatttc tctatcgaa | 4359 |

<210> SEQ ID NO 84
<211> LENGTH: 4359
<212> TYPE: DNA
<213> ORGANISM: Artificial Sequence
<220> FEATURE:
<223> OTHER INFORMATION: pCCL7(5-76K/H-A)-IgG1Fc

<400> SEQUENCE: 84

| | |
|---|---|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gcctttttcc cgagggtggg ggagaaccgt | 180 |
| atataagtgc agtagtcgcc gtgaacgttc ttttctcgcaa cgggtttgcc gccagaacac | 240 |
| agctgaagct tcgaggggct cgcatctctc cttcacgcgc ccgccgccct acctgaggcc | 300 |
| gccatccacg ccggttgagt cgcgttctgc cgcctcccgc tgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggcga aggagggcca ccatgtacag gatgcaactc ctgtcttgca | 600 |
| ttgcactaag tcttgcactt gtcacgaatt cgtttatcaa taagaaaatc cctaagcaga | 660 |
| ggctggagag ctacagaagg accaccagta gccactgtcc ccgggaagct gtaatcttcg | 720 |
| ccaccgcgct ggacgctgag atctgtgctg accccacaca ggcctgggtc caggactta | 780 |
| tggctgccct ggacgcggct acccaaaactc cagcccttga caaaactcac acatgcccac | 840 |
| cgtgcccagc acctgaactc ctgggggac cgtcagtctt cctcttcccc ccaaaaccca | 900 |
| aggacaccct catgatctcc cggacccctg aggtcacatg cgtggtggtg gacgtgagcc | 960 |
| acgaagaccc tgaggtcaag ttcaactggt acgtggacgg cgtggaggtg cataatgcca | 1020 |
| agacaaagcc gcgggaggag cagtacaaca gcacgtaccg tgtggtcagc gtcctcaccg | 1080 |
| tcctgcacca ggactggctg aatggcaagg agtacaagtg caaggtctcc aacaaagccc | 1140 |
| tcccagcccc catcgagaaa accatctcca agccaaagg gcagcccga gaaccacagg | 1200 |
| tgtacaccct gcccccatcc cgggaggaga tgaccaagaa ccaggtcagc ctgacctgcc | 1260 |
| tggtcaaagg cttctatccc agcgacatcg ccgtggagtg ggagagcaat gggcagccgg | 1320 |
| agaacaacta caagaccacg cctcccgtgc tggactccga cggctccttc ttcctctaca | 1380 |
| gcaagctcac cgtggacaag agcaggtggc agcaggggaa cgtcttctca tgctccgtga | 1440 |
| tgcacgaggc tctgcacaac cactacacgc agaagagcct ctccctgtct ccgggtaaat | 1500 |
| gagtgctagc tggccagaca tgataagata cattgatgag tttggacaaa ccacaactag | 1560 |
| aatgcagtga aaaaaatgct ttatttgtga aatttgtgat gctattgctt tatttgtaac | 1620 |
| cattataagc tgcaataaac aagttaacaa caacaattgc attcatttta tgtttcaggt | 1680 |

```
tcaggggag  gtgtgggagg  ttttttaaag  caagtaaaac  ctctacaaat  gtggtatgga    1740
attaattcta  aaatacagca  tagcaaaact  ttaacctcca  aatcaagcct  ctacttgaat    1800 cctttctga  gggatgaata  aggcatagc   atcaggggct  gttgccaatg  tgcattagct    1860
gtttgcagcc  tcaccttctt  tcatggagtt  taagatatag  tgtatttcc   caaggtttga    1920 actagctctt  catttcttta  tgttttaaat  gcactgacct  cccacattcc  cttttagta    1980 aaatattcag  aaataattta  aatacatcat  tgcaatgaaa  ataaatgttt  tttattaggc    2040
agaatccaga  tgctcaaggc  ccttcataat  atccccagt   ttagtagttg  gacttaggga    2100
acaaaggaac  ctttaataga  aattggacag  caagaaagcg  agcttctagc  ttatcctcag    2160
tcctgctcct  ctgccacaaa  gtgcacgcag  ttgccggccg  ggtcgcgcag  ggcgaactcc    2220 cgccccacg   gctgctcgcc  gatctcggtc  atggccggcc  cggaggcgtc  ccggaagttc    2280
gtggacacga  cctccgacca  ctcggcgtac  agctcgtcca  ggccgcgcac  ccacacccag    2340
gccagggtgt  tgtccggcac  cacctggtcc  tggaccgcgc  tgatgaacag  ggtcacgtcg    2400
tcccggacca  caccggcgaa  gtcgtcctcc  acgaagtccc  gggagaaccc  gagccggtcg    2460
gtccagaact  cgaccgctcc  ggcgacgtcg  cgcgcggtga  gcaccggaac  ggcactggtc    2520
aacttggcca  tgatggctcc  tcctgtcagg  agaggaaaga  gaagaaggtt  agtacaattg    2580
ctatagtgag  ttgtattata  ctatgcagat  atactatgcc  aatgattaat  tgtcaaacta    2640
gggctgcagg  gttcatagtg  ccacttttcc  tgcactgccc  catctcctgc  ccacccttc    2700 ccaggcatag  acagtcagtg  acttaccaaa  ctcacaggag  ggagaaggca  gaagcttgag    2760
acagacccgc  gggaccgccg  aactgcgagg  ggacgtggct  agggcggctt  cttttatggt    2820
gcgccggccc  tcggaggcag  ggcgctcggg  gaggcctagc  ggccaatctg  cggtggcagg    2880
aggcggggcc  gaaggccgtg  cctgaccaat  ccggagcaca  taggagtctc  agcccccgc    2940 cccaaagcaa  ggggaagtca  cgcgcctgta  gcgccagcgt  gttgtgaaat  ggggcttgg    3000 ggggttggg   gccctgacta  gtcaaaacaa  actcccattg  acgtcaatgg  ggtggagact    3060
tggaaatccc  cgtgagtcaa  accgctatcc  acgcccattg  atgtactgcc  aaaaccgcat    3120
catcatggta  atagcgatga  ctaatacgta  gatgtactgc  caagtaggaa  agtcccataa    3180
ggtcatgtac  tgggcataat  gccaggcggg  ccatttaccg  tcattgacgt  caatagggg    3240 cgtacttggc  atatgataca  cttgatgtac  tgccaagtgg  gcagtttacc  gtaaatactc    3300
cacccattga  cgtcaatgga  aagtccctat  tggcgttact  atgggaacat  acgtcattat    3360
tgacgtcaat  gggcggggt   cgttgggcgg  tcagccaggc  gggccattta  ccgtaagtta    3420
tgtaacgcct  gcaggttaat  taagaacatg  tgagcaaaag  gccagcaaaa  ggccaggaac    3480
cgtaaaaagg  ccgcgttgct  ggcgttttc   cataggctcc  gcccccctga  cgagcatcac    3540
aaaaatcgac  gctcaagtca  gaggtggcga  aacccgacag  gactataaag  ataccaggcg    3600 tttcccctg   gaagctccct  cgtgcgctct  cctgttccga  ccctgccgct  taccggatac    3660
ctgtccgcct  ttctcccttc  gggaagcgtg  gcgctttctc  atagctcacg  ctgtaggtat    3720
ctcagttcgg  tgtaggtcgt  tcgctccaag  ctgggctgtg  tgcacgaacc  ccccgttcag    3780
cccgaccgct  gcgccttatc  cggtaactat  cgtcttgagt  ccaacccggt  aagacacgac    3840
ttatcgccac  tggcagcagc  cactggtaac  aggattagca  gagcgaggta  tgtaggcggt    3900
gctacagagt  tcttgaagtg  gtggcctaac  tacggctaca  ctagaagaac  agtatttggt    3960
atctgcgctc  tgctgaagcc  agttaccttc  ggaaaaagag  ttggtagctc  ttgatccggc    4020
aaacaaacca  ccgctggtag  cggtggtttt  tttgtttgca  agcagcagat  tacgcgcaga    4080
```

-continued

| | |
|---|---|
| aaaaaaggat ctcaagaaga tcctttgatc ttttctacgg ggtctgacgc tcagtggaac | 4140 |
| gaaaactcac gttaagggat tttggtcatg gctagttaat taacatttaa atcagcggcc | 4200 |
| gcaataaaat atctttattt tcattacatc tgtgtgttgg ttttttgtgt gaatcgtaac | 4260 |
| taacatacgc tctccatcaa aacaaaacga aacaaaacaa actagcaaaa taggctgtcc | 4320 |
| ccagtgcaag tgcaggtgcc agaacatttc tctatcgaa | 4359 |

<210> SEQ ID NO 85
<211> LENGTH: 4401
<212> TYPE: DNA
<213> ORGANISM: Artificial Sequence
<220> FEATURE:
<223> OTHER INFORMATION: pCCL8-IgG1Fc

<400> SEQUENCE: 85

| | |
|---|---|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gcctttttcc cgagggtggg ggagaaccgt | 180 |
| atataagtgc agtagtcgcc gtgaacgttc tttttcgcaa cgggtttgcc gccagaacac | 240 |
| agctgaagct tcgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggcga aggagggcca ccatgtacag gatgcaactc ctgtcttgca | 600 |
| ttgcactaag tcttgcactt gtcacgaatt cgcagccaga ttcagtttcc attccaatca | 660 |
| cctgctgctt taacgtgatc aataggaaaa ttcctatcca gaggctggag agctacacaa | 720 |
| gaatcaccaa catccaatgt cccaaggaag ctgtgatctt caagaccaaa cggggcaagg | 780 |
| aggtctgtgc tgaccccaag gagagatggg tcagggattc catgaagcat ctggaccaaa | 840 |
| tatttcaaaa tctgaagcca gacaaaactc acacatgccc accgtgccca gcacctgaac | 900 |
| tcctgggggg accgtcagtc ttcctcttcc cccaaaaacc caaggacacc ctcatgatct | 960 |
| cccggacccc tgaggtcaca tgcgtggtgg tggacgtgag ccacgaagac cctgaggtca | 1020 |
| agttcaactg gtacgtggac ggcgtggagg tgcataatgc caagacaaag ccgcgggagg | 1080 |
| agcagtacaa cagcacgtac cgtgtggtca gcgtcctcac cgtcctgcac caggactggc | 1140 |
| tgaatggcaa ggagtacaag tgcaaggtct ccaacaaagc cctcccagcc cccatcgaga | 1200 |
| aaaccatctc caaagccaaa gggcagcccc gagaaccaca ggtgtacacc ctgcccccat | 1260 |
| cccgggagga gatgaccaag aaccaggtca gcctgacctg cctggtcaaa ggcttctatc | 1320 |
| ccagcgacat cgccgtggag tgggagagca atgggcagcc ggagaacaac tacaagacca | 1380 |
| cgcctcccgt gctggactcc gacggctcct tcttcctcta cagcaagctc accgtggaca | 1440 |
| agagcaggtg gcagcagggg aacgtcttct catgctccgt gatgcacgag gctctgcaca | 1500 |
| accactacac gcagaagagc ctctccctgt ctccgggtaa atgagtgcta gctggccaga | 1560 |
| catgataaga tacattgatg agtttggaca accacaact agaatgcagt gaaaaaaatg | 1620 |
| ctttatttgt gaaatttgtg atgctattgc tttatttgta accattataa gctgcaataa | 1680 |
| acaagttaac aacaacaatt gcattcattt tatgtttcag gttcagggg aggtgtggga | 1740 |
| ggttttttaa agcaagtaaa acctctacaa atgtggtatg gaattaattc taaaatacag | 1800 |

```
catagcaaaa ctttaacctc caaatcaagc ctctacttga atcctttct gagggatgaa    1860 taaggcatag gcatcagggg ctgttgccaa tgtgcattag ctgtttgcag cctcaccttc    1920
tttcatggag tttaagatat agtgtatttt cccaaggttt gaactagctc ttcatttctt    1980
tatgttttaa atgcactgac ctcccacatt ccctttttag taaaatattc agaaataatt    2040
taaatacatc attgcaatga aaataaatgt ttttttattag gcagaatcca gatgctcaag    2100
gcccttcata atatccccca gtttagtagt tggacttagg gaacaaagga acctttaata    2160
gaaattggac agcaagaaag cgagcttcta gcttatcctc agtcctgctc ctctgccaca    2220
aagtgcacgc agttgccggc cgggtcgcgc agggcgaact cccgccccca cggctgctcg    2280
ccgatctcgg tcatggccgg cccggaggcg tcccggaagt tcgtggacac gacctccgac    2340
cactcggcgt acagctcgtc caggccgcgc acccacaccc aggccagggt gttgtccggc    2400
accacctggt cctggaccgc gctgatgaac agggtcacgt cgtcccggac cacaccggcg    2460
aagtcgtcct ccacgaagtc ccgggagaac ccgagccggt cggtccagaa ctcgaccgct    2520
ccggcgacgt cgcgcgcggt gagcaccgga acggcactgg tcaacttggc catgatggct    2580
cctcctgtca ggagaggaaa gagaagaagg ttagtacaat tgctatagtg agttgtatta    2640
tactatgcag atatactatg ccaatgatta attgtcaaac tagggctgca gggttcatag    2700
tgccactttt cctgcactgc cccatctcct gcccacccctt tcccaggcat agacagtcag    2760
tgacttacca aactcacagg agggagaagg cagaagcttg agacagaccc gcgggaccgc    2820
cgaactgcga ggggacgtgg ctagggcggc ttctttatg gtgcgccggc cctcggaggc    2880
agggcgctcg gggaggccta gcggccaatc tgcggtggca ggaggcgggg ccgaaggccg    2940
tgcctgacca atccggagca cataggagtc tcagcccccc gccccaaagc aaggggaagt    3000
cacgcgcctg tagcgccagc gtgttgtgaa atgggggctt gggggggttg gggccctgac    3060
tagtcaaaac aaactcccat tgacgtcaat ggggtggaga cttggaaatc cccgtgagtc    3120
aaaccgctat ccacgcccat tgatgtactg ccaaaaccgc atcatcatgg taatagcgat    3180
gactaatacg tagatgtact gccaagtagg aaagtcccat aaggtcatgt actgggcata    3240
atgccaggcg ggccatttac cgtcattgac gtcaataggg ggcgtacttg gcatatgata    3300
cacttgatgt actgccaagt gggcagttta ccgtaaatac tccacccatt gacgtcaatg    3360
gaaagtccct attggcgtta ctatgggaac atacgtcatt attgacgtca atgggcgggg    3420
gtcgttgggc ggtcagccag gcgggccatt taccgtaagt tatgtaacgc ctgcaggtta    3480
attaagaaca tgtgagcaaa aggccagcaa aggccagga accgtaaaaa ggccgcgttg    3540
ctggcgtttt tccataggct ccgcccccct gacgagcatc acaaaaatcg acgctcaagt    3600
cagaggtggc gaaacccgac aggactataa agataccagg cgtttccccc tggaagctcc    3660
ctcgtgcgct ctcctgttcc gaccctgccg cttaccggat acctgtccgc ctttctccct    3720
tcgggaagcg tggcgctttc tcatagctca cgctgtaggt atctcagttc ggtgtaggtc    3780
gttcgctcca agctgggctg tgtgcacgaa ccccccgttc agcccgaccg ctgcgcctta    3840
tccggtaact atcgtcttga gtccaacccg gtaagacacg acttatcgcc actggcagca    3900
gccactggta acaggattag cagagcgagg tatgtaggcg gtgctacaga gttcttgaag    3960
tggtggccta actacggcta cactagaaga acagtatttg gtatctgcgc tctgctgaag    4020
ccagttacct tcggaaaaag agttggtagc tcttgatccg gcaaacaaac caccgctggt    4080
agcggtggtt tttttgtttg caagcagcag attacgcgca gaaaaaaagg atctcaagaa    4140
gatcctttga tcttttctac ggggtctgac gctcagtgga acgaaaactc acgttaaggg    4200
```

| | |
|---|---|
| attttggtca tggctagtta attaacattt aaatcagcgg ccgcaataaa atatctttat | 4260 |
| tttcattaca tctgtgtgtt ggttttttgt gtgaatcgta actaacatac gctctccatc | 4320 |
| aaaacaaaac gaaacaaaac aaactagcaa aataggctgt ccccagtgca agtgcaggtg | 4380 |
| ccagaacatt tctctatcga a | 4401 |

<210> SEQ ID NO 86
<211> LENGTH: 4389
<212> TYPE: DNA
<213> ORGANISM: Artificial Sequence
<220> FEATURE:
<223> OTHER INFORMATION: pCCL8(5-76)-IgG1Fc

<400> SEQUENCE: 86

| | |
|---|---|
| ggatctgcga tcgctccggt gcccgtcagt gggcagagcg cacatcgccc acagtccccg | 60 |
| agaagttggg gggagggtc ggcaattgaa cgggtgccta gagaaggtgg cgcggggtaa | 120 |
| actgggaaag tgatgtcgtg tactggctcc gccttttcc cgagggtggg ggagaaccgt | 180 |
| atataagtgc agtagtcgcc gtgaacgttc tttttcgcaa cgggtttgcc gccagaacac | 240 |
| agctgaagct cgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg taccggcgc | 540 |
| ctacctgaga tcaccggcga aggagggcca ccatgtacag gatgcaactc ctgtcttgca | 600 |
| ttgcactaag tcttgcactt gtcacgaatt cggtttccat tccaatcacc tgctgcttta | 660 |
| acgtgatcaa taggaaaatt cctatccaga ggctggagag ctacacaaga atcaccaaca | 720 |
| tccaatgtcc caaggaagct gtgatcttca agaccaaacg gggcaaggag gtctgtgctg | 780 |
| accccaagga gagatgggtc agggattcca tgaagcatct ggaccaaata tttcaaaatc | 840 |
| tgaagccaga caaaactcac acatgcccac cgtgcccagc acctgaactc ctggggggac | 900 |
| cgtcagtctt cctcttcccc ccaaaaccca aggacaccct catgatctcc cggacccctg | 960 |
| aggtcacatg cgtggtggtg gacgtgagcc acgaagaccc tgaggtcaag ttcaactggt | 1020 |
| acgtggacgg cgtggaggtg cataatgcca agacaaagcc gcgggaggag cagtacaaca | 1080 |
| gcacgtaccg tgtggtcagc gtcctcaccg tcctgcacca ggactggctg aatggcaagg | 1140 |
| agtacaagtg caaggtctcc aacaaagccc tcccagcccc catcgagaaa accatctcca | 1200 |
| aagccaaagg gcagccccga gaaccacagg tgtacaccct gcccccatcc cgggaggaga | 1260 |
| tgaccaagaa ccaggtcagc ctgacctgcc tggtcaaagg cttctatccc agcgacatcg | 1320 |
| ccgtggagtg ggagagcaat gggcagccgg agaacaacta caagaccacg cctcccgtgc | 1380 |
| tggactccga cggctccttc ttcctctaca gcaagctcac cgtggacaag agcaggtggc | 1440 |
| agcaggggaa cgtcttctca tgctccgtga tgcacgaggc tctgcacaac cactacacgc | 1500 |
| agaagagcct ctccctgtct ccgggtaaat gagtgctagc tggccagaca tgataagata | 1560 |
| cattgatgag tttggacaaa ccacaactag aatgcagtga aaaaaatgct ttatttgtga | 1620 |
| aatttgtgat gctattgctt tatttgtaac cattataagc tgcaataaac aagttaacaa | 1680 |
| caacaattgc attcatttta tgtttcaggt tcaggggag gtgtgggagg ttttttaaag | 1740 |
| caagtaaaac ctctacaaat gtggtatgga attaattcta aaatacagca tagcaaaact | 1800 |
| ttaacctcca aatcagcct ctacttgaat ccttttctga gggatgaata aggcataggc | 1860 |

```
atcagggget gttgccaatg tgcattagct gtttgcagcc tcaccttctt tcatggagtt    1920
taagatatag tgtattttcc caaggtttga actagctctt catttcttta tgttttaaat    1980
gcactgacct cccacattcc cttttagta aaatattcag aaataattta aatacatcat    2040
tgcaatgaaa ataaatgttt tttattaggc agaatccaga tgctcaaggc ccttcataat    2100 atccccagt ttagtagttg acttaggga acaaggaac ctttaataga aattggacag      2160
caagaaagcg agcttctagc ttatcctcag tcctgctcct ctgccacaaa gtgcacgcag    2220
ttgccggccg ggtcgcgcag ggcgaactcc cgccccacg gctgctcgcc gatctcggtc    2280
atggccggcc cggaggcgtc ccggaagttc gtggacacga cctccgacca ctcggcgtac    2340
agctcgtcca ggccgcgcac ccacacccag gccagggtgt tgtccggcac cacctggtcc    2400 tggaccgcg tgatgaacag ggtcacgtcg tcccggacca caccggcgaa gtcgtcctcc    2460
acgaagtccc gggagaaccc gagccggtcg gtccagaact cgaccgctcc ggcgacgtcg    2520
cgcgcggtga gcaccggaac ggcactggtc aacttggcca tgatggctcc tcctgtcagg    2580
agaggaaaga gaagaaggtt agtacaattg ctatagtgag ttgtattata ctatgcagat    2640
atactatgcc aatgattaat tgtcaaacta gggctgcagg gttcatagtg ccacttttcc    2700
tgcactgccc catctcctgc ccacccttc ccaggcatag acagtcagtg acttaccaaa    2760
ctcacaggag ggagaaggca gaagcttgag acagacccgc gggaccgccg aactgcgagg    2820
ggacgtggct agggcggctt cttttatggt gcgccggccc tcggaggcag ggcgctcggg    2880
gaggcctagc ggccaatctg cggtggcagg aggcggggcc gaaggccgtg cctgaccaat    2940
ccggagcaca taggagtctc agcccccgc cccaaagcaa ggggaagtca cgcgcctgta    3000
gcgccagcgt gttgtgaaat gggggcttgg ggggttggg gccctgacta gtcaaaacaa    3060
actcccattg acgtcaatgg ggtggagact tggaaatccc cgtgagtcaa accgctatcc    3120
acgcccattg atgtactgcc aaaaccgcat catcatggta atagcgatga ctaatacgta    3180
gatgtactgc caagtaggaa agtccctaa ggtcatgtac tgggcataat gccaggcggg    3240
ccatttaccg tcattgacgt caatagggg cgtacttggc atatgataca cttgatgtac    3300
tgccaagtgg gcagtttacc gtaaatactc cacccattga cgtcaatgga aagtccctat    3360
tggcgttact atgggaacat acgtcattat tgacgtcaat gggcggggt cgttgggcgg    3420 tcagccaggc gggccattta ccgtaagtta tgtaacgcct gcaggttaat taagaacatg    3480
tgagcaaaag gccagcaaaa ggccaggaac cgtaaaaagg ccgcgttgct ggcgtttttc    3540
cataggctcc gcccccctga cgagcatcac aaaaatcgac gctcaagtca gaggtggcga    3600
aacccgacag gactataaag ataccaggcg tttccccctg gaagctccct cgtgcgctct    3660
cctgttccga ccctgccgct taccggatac ctgtccgcct ttctcccttc gggaagcgtg    3720
gcgctttctc atagctcacg ctgtaggtat ctcagttcgg tgtaggtcgt tcgctccaag    3780
ctgggctgtg tgcacgaacc ccccgttcag cccgaccgct cgccttatc cggtaactat    3840 cgtcttgagt ccaacccggt aagacacgac ttatcgccac tggcagcagc cactggtaac    3900
aggattagca gagcgaggta tgtaggcggt gctacagagt tcttgaagtg gtggcctaac    3960
tacggctaca ctagaagaac agtatttggt atctgcgctc tgctgaagcc agttaccttc    4020
ggaaaaagag ttggtagctc ttgatccggc aaacaaacca ccgctggtag cggtggtttt    4080
tttgtttgca agcagcagat tacgcgcaga aaaaaggat ctcaagaaga tcctttgatc    4140
ttttctacgg ggtctgacgc tcagtggaac gaaaactcac gttaagggat tttggtcatg    4200
gctagttaat taacatttaa atcagcggcc gcaataaaat atctttattt tcattacatc    4260
```

-continued

```
tgtgtgttgg tttttgtgt gaatcgtaac taacatacgc tctccatcaa acaaaacga      4320 aacaaaacaa actagcaaaa taggctgtcc ccagtgcaag tgcaggtgcc agaacatttc     4380
tctatcgaa                                                             4389
```

<210> SEQ ID NO 87
<211> LENGTH: 4389
<212> TYPE: DNA
<213> ORGANISM: Artificial Sequence
<220> FEATURE:
<223> OTHER INFORMATION: pCCL8(5-76K/H-A)-IgG1Fc

<400> SEQUENCE: 87

```
ggatctgcga tcgctccggt gcccgtcagt gggcagagcg cacatcgccc acagtccccg       60
agaagttggg gggaggggtc ggcaattgaa cgggtgccta gagaaggtgg cgcggggtaa      120
actgggaaag tgatgtcgtg tactggctcc gccttttttcc cgagggtggg ggagaaccgt      180
atataagtgc agtagtcgcc gtgaacgttc ttttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc tgtggtgcc tcctgaactg      360 cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc      540
ctacctgaga tcaccggcga aggagggcca ccatgtacag gatgcaactc ctgtcttgca     600
ttgcactaag tcttgcactt gtcacgaatt cggtttccat tccaatcacc tgctgcttta     660
acgtgatcaa taggaaaatt cctatccaga ggctggagag ctacacaaga atcaccaaca     720
tccaatgtcc caaggaagct gtgatcttca agaccgccgc gggcgctgag gtctgtgctg     780
accccgccga ggcgtgggtc gctgattcca tggccgcgct ggaccaaata tttcaaaatc     840
tggctccaga caaaactcac acatgcccac cgtgcccagc acctgaactc ctggggggac     900
cgtcagtctt cctcttcccc ccaaaaccca aggacaccct catgatctcc cggacccctg     960
aggtcacatg cgtggtggtg gacgtgagcc acgaagaccc tgaggtcaag ttcaactggt     1020
acgtggacgg cgtggaggtg cataatgcca agacaaagcc gcgggaggag cagtacaaca     1080
gcacgtaccg tgtggtcagc gtcctcaccg tcctgcacca ggactggctg aatggcaagg     1140
agtacaagtg caaggtctcc aacaaagccc tcccagcccc catcgagaaa accatctcca     1200
aagccaaagg gcagccccga gaaccacagg tgtacaccct gcccccatcc cgggaggaga     1260
tgaccaagaa ccaggtcagc ctgacctgcc tggtcaaagg cttctatccc agcgacatcg     1320
ccgtggagtg ggagagcaat gggcagccgg agaacaacta caagaccacg cctcccgtgc     1380
tggactccga cggctccttc ttcctctaca gcaagctcac cgtggacaag agcaggtggc     1440
agcaggggaa cgtcttctca tgctccgtga tgcacgaggc tctgcacaac cactacacgc     1500
agaagagcct ctccctgtct ccgggtaaat gagtgctagc tggccagaca tgataagata     1560
cattgatgag tttggacaaa ccacaactag aatgcagtga aaaaaatgct ttatttgtga     1620
aatttgtgat gctattgctt tatttgtaac cattataagc tgcaataaac aagttaacaa     1680
caacaattgc attcatttta tgtttcaggt tcaggggag gtgtgggagg ttttttaaag     1740
caagtaaaac ctctacaaat gtggtatgga attaattcta aaatacagca tagcaaaact     1800
ttaacctcca atcaagcct ctacttgaat ccttttctga gggatgaata aggcataggc     1860 atcagggct gttgccaatg tgcattagct gtttgcagcc tcaccttctt tcatggagtt     1920
```

```
taagatatag tgtattttcc caaggtttga actagctctt catttcttta tgttttaaat   1980
gcactgacct cccacattcc cttttagta aatattcag aataattta aatacatcat     2040
tgcaatgaaa ataaatgttt tttattaggc agaatccaga tgctcaaggc ccttcataat   2100
atcccccagt ttagtagttg gacttaggga acaaaggaac ctttaataga aattggacag   2160
caagaaagcg agcttctagc ttatcctcag tcctgctcct ctgccacaaa gtgcacgcag   2220
ttgccggccg ggtcgcgcag ggcgaactcc cgccccacg gctgctcgcc gatctcggtc    2280
atggccggcc cggaggcgtc ccggaagttc gtggacacga cctccgacca ctcggcgtac   2340
agctcgtcca ggccgcgcac ccacacccag gccagggtgt tgtccggcac cacctggtcc   2400
tggaccgcgc tgatgaacag ggtcacgtcg tcccggacca caccggcgaa gtcgtcctcc   2460
acgaagtccc gggagaaccc gagccggtcg gtccagaact cgaccgctcc ggcgacgtcg   2520
cgcgcggtga gcaccggaac ggcactggtc aacttggcca tgatggctcc tcctgtcagg   2580
agaggaaaga gaagaaggtt agtacaattg ctatagtgag ttgtattata ctatgcagat   2640
atactatgcc aatgattaat tgtcaaacta gggctgcagg gttcatagtg ccacttttcc   2700
tgcactgccc catctcctgc ccacccttc ccaggcatag acagtcagtg acttaccaaa    2760
ctcacaggag ggagaaggca gaagcttgag acagacccgc gggaccgccg aactgcgagg   2820
ggacgtggct agggcggctt cttttatggt gcgccggccc tcggaggcag ggcgctcggg   2880
gaggcctagc ggccaatctg cggtggcagg aggcggggcc gaaggccgtg cctgaccaat   2940
ccggagcaca taggagtctc agccccccgc cccaaagcaa ggggaagtca cgcgcctgta   3000
gcgccagcgt gttgtgaaat ggggggcttgg gggggttggg gccctgacta gtcaaaacaa   3060
actcccattg acgtcaatgg ggtggagact tggaaatccc cgtgagtcaa accgctatcc   3120
acgcccattg atgtactgcc aaaaccgcat catcatggta atagcgatga ctaatacgta   3180
gatgtactgc caagtaggaa agtcccataa ggtcatgtac tgggcataat gccaggcggg   3240
ccatttaccg tcattgacgt caataggggg cgtacttggc atatgataca cttgatgtac   3300
tgccaagtgg gcagtttacc gtaaatactc cacccattga cgtcaatgga aagtccctat   3360
tggcgttact atgggaacat acgtcattat tgacgtcaat gggcggggt cgttgggcgg    3420
tcagccaggc gggccattta ccgtaagtta tgtaacgcct gcaggttaat taagaacatg   3480
tgagcaaaag gccagcaaaa ggccaggaac cgtaaaaagg ccgcgttgct ggcgttttc    3540
cataggctcc gcccccctga cgagcatcac aaaaatcgac gctcaagtca gaggtggcga   3600
aacccgacag gactataaag ataccaggcg tttccccctg gaagctccct cgtgcgctct   3660
cctgttccga ccctgccgct taccggatac ctgtccgcct ttctcccttc gggaagcgtg   3720
gcgctttctc atagctcacg ctgtaggtat ctcagttcgg tgtaggtcgt tcgctccaag   3780
ctgggctgtg tgcacgaacc ccccgttcag cccgaccgct gcgccttatc cggtaactat   3840
cgtcttgagt ccaacccggt aagacacgac ttatcgccac tggcagcagc cactggtaac   3900
aggattagca gagcgaggta tgtaggcggt gctacagagt tcttgaagtg gtggcctaac   3960
tacggctaca ctagaagaac agtatttggt atctgcgctc tgctgaagcc agttaccttc   4020
ggaaaaagag ttggtagctc ttgatccggc aaacaaacca ccgctggtag cggtggtttt   4080
tttgtttgca agcagcagat tacgcgcaga aaaaaaggat ctcaagaaga tcctttgatc   4140
ttttctacgg ggtctgacgc tcagtggaac gaaaactcac gttaagggat tttggtcatg   4200
gctagttaat taacatttaa atcagcggcc gcaataaaat atctttattt tcattacatc   4260
tgtgtgttgg ttttttgtgt gaatcgtaac taacatacgc tctccatcaa aacaaaacga   4320
```

| | |
|---|---:|
| aacaaaacaa actagcaaaa taggctgtcc ccagtgcaag tgcaggtgcc agaacatttc | 4380 |
| tctatcgaa | 4389 |

<210> SEQ ID NO 88
<211> LENGTH: 4398
<212> TYPE: DNA
<213> ORGANISM: Artificial Sequence
<220> FEATURE:
<223> OTHER INFORMATION: pCCL13-IgG1Fc

<400> SEQUENCE: 88

| | |
|---|---:|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gccttttttcc cgagggtggg ggagaaccgt | 180 |
| atataagtgc agtagtcgcc gtgaacgttc tttttcgcaa cgggtttgcc gccagaacac | 240 |
| agctgaagct cgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggcga aggagggcca ccatgtacag gatgcaactc ctgtcttgca | 600 |
| ttgcactaag tcttgcactt gtcacgaatt cgcagccaga tgcactcaac gtcccatcta | 660 |
| cttgctgctt cacatttagc agtaagaaga tctccttgca gaggctgaag agctatgtga | 720 |
| tcaccaccag caggtgtccc cagaaggctg tcatcttcag aaccaaactg ggcaaggaga | 780 |
| tctgtgctga cccaaaggag aagtgggtcc agaattatat gaaacacctg gccggaaag | 840 |
| ctcacaccct gaagactgac aaaactcaca catgcccacc gtgcccagca cctgaactcc | 900 |
| tggggggacc gtcagtcttc ctcttccccc caaaacccaa ggacaccctc atgatctccc | 960 |
| ggacccctga ggtcacatgc gtggtggtgg acgtgagcca cgaagaccct gaggtcaagt | 1020 |
| tcaactggta cgtggacggc gtggaggtgc ataatgccaa gacaaagccg cgggaggagc | 1080 |
| agtacaacag cacgtaccgt gtggtcagcg tcctcaccgt cctgcaccag gactggctga | 1140 |
| atggcaagga gtacaagtgc aaggtctcca acaaagccct cccagccccc atcgagaaaa | 1200 |
| ccatctccaa agccaagggg cagccccgag aaccacaggt gtacaccctg cccccatccc | 1260 |
| gggaggagat gaccaagaac caggtcagcc tgacctgcct ggtcaaaggc ttctatccca | 1320 |
| gcgacatcgc cgtggagtgg gagagcaatg ggcagccgga gaacaactac aagaccacgc | 1380 |
| ctcccgtgct ggactccgac ggctccttct tcctctacag caagctcacc gtggacaaga | 1440 |
| gcaggtggca gcaggggaac gtcttctcat gctccgtgat gcacgaggct ctgcacaacc | 1500 |
| actacacgca gaagagcctc tccctgtctc cgggtaaatg agtgctagct ggccagacat | 1560 |
| gataagatac attgatgagt ttggacaaac cacaactaga atgcagtgaa aaaaatgctt | 1620 |
| tatttgtgaa atttgtgatg ctattgcttt atttgtaacc attataagct gcaataaaca | 1680 |
| agttaacaac aacaattgca ttcatttat gtttcaggtt caggggagg tgtgggaggt | 1740 |
| tttttaaagc aagtaaaacc tctacaaatg tggtatggaa ttaattctaa aatacagcat | 1800 |
| agcaaaactt taacctccaa atcaagcctc tacttgaatc cttttctgag ggatgaataa | 1860 |
| ggcataggca tcaggggctg ttgccaatgt gcattagctg tttgcagcct caccttcttt | 1920 |
| catggagttt aagatatagt gtattttccc aaggtttgaa ctagctcttc atttctttat | 1980 |

-continued

```
gttttaaatg cactgacctc ccacattccc tttttagtaa atattcaga aataatttaa    2040 atacatcatt gcaatgaaaa taaatgtttt ttattaggca gaatccagat gctcaaggcc    2100
cttcataata tcccccagtt tagtagttgg acttagggaa caaaggaacc tttaatagaa    2160
attggacagc aagaaagcga gcttctagct tatcctcagt cctgctcctc tgccacaaag    2220
tgcacgcagt tgccggccgg gtcgcgcagg gcgaactccc gcccccacgg ctgctcgccg    2280
atctcggtca tggccggccc ggaggcgtcc cggaagttcg tggacacgac ctccgaccac    2340
tcggcgtaca gctcgtccag gccgcgcacc cacacccagg ccagggtgtt gtccggcacc    2400
acctggtcct ggaccgcgct gatgaacagg gtcacgtcgt cccggaccac accggcgaag    2460
tcgtcctcca cgaagtcccg ggagaacccg agccggtcgg tccagaactc gaccgctccg    2520
gcgacgtcgc gcgcggtgag caccggaacg gcactggtca acttggccat gatggctcct    2580
cctgtcagga gaggaaagag aagaaggtta gtacaattgc tatagtgagt tgtattatac    2640
tatgcagata tactatgcca atgattaatt gtcaaactag gctgcaggg ttcatagtgc     2700 cacttttcct gcactgcccc atctcctgcc caccctttcc caggcataga cagtcagtga    2760
cttaccaaac tcacaggagg gagaaggcag aagcttgaga cagacccgcg ggaccgccga    2820
actgcgaggg gacgtggcta gggcggcttc ttttatggtg cgccggccct cggaggcagg    2880
gcgctcgggg aggcctagcg gccaatctgc ggtggcagga ggcggggccg aaggccgtgc    2940
ctgaccaatc cggagcacat aggagtctca gccccccgcc ccaaagcaag gggaagtcac    3000
gcgcctgtag cgccagcgtg ttgtgaaatg ggggcttggg ggggttgggg ccctgactag    3060
tcaaaacaaa ctcccattga cgtcaatggg gtggagactt ggaaatcccc gtgagtcaaa    3120
ccgctatcca cgcccattga tgtactgcca aaaccgcatc atcatggtaa tagcgatgac    3180
taatacgtag atgtactgcc aagtaggaaa gtcccataag gtcatgtact gggcataatg    3240
ccaggcgggc catttaccgt cattgacgtc aatagggggc gtacttggca tatgatacac    3300
ttgatgtact gccaagtggg cagtttaccg taaatactcc acccattgac gtcaatggaa    3360
agtccctatt ggcgttacta tgggaacata cgtcattatt gacgtcaatg ggcgggggtc    3420
gttgggcggt cagccaggcg ggccatttac cgtaagttat gtaacgcctg caggttaatt    3480
aagaacatgt gagcaaaagg ccagcaaaag gccaggaacc gtaaaaaggc cgcgttgctg    3540 gcgttttttcc ataggctccg ccccctgac gagcatcaca aaaatcgacg ctcaagtcag    3600
aggtggcgaa acccgacagg actataaaga taccaggcgt ttccccctgg aagctccctc    3660
gtgcgctctc ctgttccgac cctgccgctt accggatacc tgtccgcctt tctcccttcg    3720
ggaagcgtgg cgctttctca tagctcacgc tgtaggtatc tcagttcggt gtaggtcgtt    3780
cgctccaagc tgggctgtgt gcacgaaccc cccgttcagc ccgaccgctg cgccttatcc    3840
ggtaactatc gtcttgagtc aacccggta agacacgact tatcgccact ggcagcagcc    3900
actggtaaca ggattagcag agcgaggtat gtaggcggtg ctacagagtt cttgaagtgg    3960
tggcctaact acggctacac tagaagaaca gtatttggta tctgcgctct gctgaagcca    4020
gttaccttcg gaaaaagagt tggtagctct tgatccggca acaaaccac cgctggtagc     4080 ggtggttttt ttgtttgcaa gcagcagatt acgcgcagaa aaaaggatc tcaagaagat     4140 cctttgatct tttctacggg gtctgacgct cagtggaacg aaaactcacg ttaagggatt    4200
ttggtcatgg ctagttaatt aacatttaaa tcagcggccg caataaaata tctttatttt    4260
cattacatct gtgtgttggt ttttgtgtg aatcgtaact aacatacgct ctccatcaaa     4320
acaaaacgaa acaaaacaaa ctagcaaaat aggctgtccc cagtgcaagt gcaggtgcca    4380
```

| | |
|---|---:|
| gaacatttct ctatcgaa | 4398 |

<210> SEQ ID NO 89
<211> LENGTH: 4386
<212> TYPE: DNA
<213> ORGANISM: Artificial Sequence
<220> FEATURE:
<223> OTHER INFORMATION: pCCL13(5-75)-IgG1Fc

<400> SEQUENCE: 89

| | |
|---|---:|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gcctttttcc cgagggtggg ggagaaccgt | 180 |
| atataagtgc agtagtcgcc gtgaacgttc tttttcgcaa cgggtttgcc gccagaacac | 240 |
| agctgaagct tcgaggggct cgcatctctc cttcacgcgc ccgccgccct acctgaggcc | 300 |
| gccatccacg ccggttgagt cgcgttctgc cgcctcccgc tgtggtgcc tcctgaactg | 360 |
| cgtccgccgt ctaggtaagt ttaaagctca ggtcgagacc gggcctttgt ccggcgctcc | 420 |
| cttggagcct acctagactc agccggtctc cacgctttg cctgaccctg cttgctcaac | 480 |
| tctacgtctt tgtttcgttt tctgttctgc gccgttacag atccaagctg tgaccggcgc | 540 |
| ctacctgaga tcaccggcga aggagggcca ccatgtacag gatgcaactc ctgtcttgca | 600 |
| ttgcactaag tcttgcactt gtcacgaatt cgctcaacgt cccatctact tgctgcttca | 660 |
| catttagcag taagaagatc tccttgcaga ggctgaagag ctatgtgatc accaccagca | 720 |
| ggtgtcccca gaaggctgtc atcttcagaa ccaaactggg caaggagatc tgtgctgacc | 780 |
| caaaggagaa gtgggtccag aattatatga acacctgggc cggaaagct cacaccctga | 840 |
| agactgacaa aactcacaca tgcccaccgt gcccagcacc tgaactcctg ggggaccgt | 900 |
| cagtcttcct cttccccca aaacccaagg acaccctcat gatctcccgg acccctgagg | 960 |
| tcacatgcgt ggtggtggac gtgagccacg aagaccctga ggtcaagttc aactggtacg | 1020 |
| tggacggcgt ggaggtgcat aatgccaaga caaagccgcg ggaggagcag tacaacagca | 1080 |
| cgtaccgtgt ggtcagcgtc ctcaccgtcc tgcaccagga ctggctgaat ggcaaggagt | 1140 |
| acaagtgcaa ggtctccaac aaagccctcc cagcccccat cgagaaaacc atctccaaag | 1200 |
| ccaaagggca gccccgagaa ccacaggtgt acaccctgcc cccatcccgg gaggagatga | 1260 |
| ccaagaacca ggtcagcctg acctgcctgg tcaaaggctt ctatcccagc gacatcgccg | 1320 |
| tggagtggga gagcaatggg cagccggaga caactacaa gaccacgcct cccgtgctgg | 1380 |
| actccgacgg ctccttcttc ctctacagca agctcaccgt ggacaagagc aggtggcagc | 1440 |
| aggggaacgt cttctcatgc tccgtgatgc acgaggctct gcacaaccac tacacgcaga | 1500 |
| agagcctctc cctgtctccg ggtaaatgag tgctagctgg ccagacatga taagatacat | 1560 |
| tgatgagttt ggacaaacca aactagaat gcagtgaaaa aaatgcttta tttgtgaaat | 1620 |
| ttgtgatgct attgctttat tgtaaccat tataagctgc aataaacaag ttaacaacaa | 1680 |
| caattgcatt cattttatgt ttcaggttca ggggaggtg tggaggttt tttaaagcaa | 1740 |
| gtaaaacctc tacaaatgtg gtatggaatt aattctaaaa tacagcatag caaaacttta | 1800 |
| acctccaaat caagcctcta cttgaatcct tttctgaggg atgaataagg cataggcatc | 1860 |
| aggggctgtt gccaatgtgc attagctgtt tgcagcctca ccttctttca tggagtttaa | 1920 |
| gatatagtgt attttcccaa ggtttgaact agctcttcat ttcttatgt tttaaatgca | 1980 |
| ctgacctccc acattccctt tttagtaaaa tattcagaaa taatttaaat acatcattgc | 2040 |

-continued

```
aatgaaaata aatgttttt attaggcaga atccagatgc tcaaggccct tcataatatc    2100
ccccagttta gtagttggac ttagggaaca aaggaacctt taatagaaat tggacagcaa    2160
gaaagcgagc ttctagctta tcctcagtcc tgctcctctg ccacaaagtg cacgcagttg    2220
ccggccgggt cgcgcagggc gaactcccgc ccccacggct gctcgccgat ctcggtcatg    2280
gccggcccgg aggcgtcccg gaagttcgtg gacacgacct ccgaccactc ggcgtacagc    2340
tcgtccaggc cgcgcaccca cacccaggcc agggtgttgt ccggcaccac ctggtcctgg    2400
accgcgctga tgaacagggt cacgtcgtcc cggaccacac cggcgaagtc gtcctccacg    2460
aagtcccggg agaacccgag ccggtcggtc cagaactcga ccgctccggc gacgtcgcgc    2520
gcggtgagca ccggaacggc actggtcaac ttggccatga tggctcctcc tgtcaggaga    2580
ggaaagagaa gaaggttagt acaattgcta tagtgagttg tattatacta tgcagatata    2640
ctatgccaat gattaattgt caaactaggg ctgcagggtt catagtgcca cttttcctgc    2700
actgccccat ctcctgccca ccctttccca ggcatagaca gtcagtgact taccaaactc    2760
acaggaggga gaaggcagaa gcttgagaca gacccgcggg accgccgaac tgcgagggga    2820
cgtggctagg gcggcttctt ttatggtgcg ccggccctcg gaggcagggc gctcggggag    2880
gcctagcggc caatctgcgg tggcaggagg cggggccgaa ggccgtgcct gaccaatccg    2940
gagcacatag gagtctcagc cccccgcccc aaagcaaggg gaagtcacgc gcctgtagcg    3000
ccagcgtgtt gtgaaatggg ggcttggggg ggttggggcc ctgactagtc aaaacaaact    3060
cccattgacg tcaatggggt ggagacttgg aaatccccgt gagtcaaacc gctatccacg    3120
cccattgatg tactgccaaa accgcatcat catggtaata gcgatgacta atacgtagat    3180
gtactgccaa gtaggaaagt cccataaggt catgtactgg gcataatgcc aggcgggcca    3240
tttaccgtca ttgacgtcaa tagggggcgt acttggcata tgatacactt gatgtactgc    3300
caagtgggca gtttaccgta aatactccac ccattgacgt caatggaaag tccctattgg    3360
cgttactatg ggaacatacg tcattattga cgtcaatggg cggggtcgt tggcggtca    3420 gccaggcggg ccatttaccg taagttatgt aacgcctgca ggttaattaa gaacatgtga    3480
gcaaaaggcc agcaaaaggc caggaaccgt aaaaaggccg cgttgctggc gttttccat    3540 aggctccgcc cccctgacga gcatcacaaa aatcgacgct caagtcagag gtggcgaaac    3600
ccgacaggac tataaagata ccaggcgttt ccccctggaa gctccctcgt gcgctctcct    3660
gttccgaccc tgccgcttac cggatacctg tccgcctttc tcccttcggg aagcgtggcg    3720
ctttctcata gctcacgctg taggtatctc agttcggtgt aggtcgttcg ctccaagctg    3780
ggctgtgtgc acgaaccccc cgttcagccc gaccgctgcg ccttatccgg taactatcgt    3840
cttgagtcca acccggtaag acacgactta tcgccactgg cagcagccac tggtaacagg    3900
attagcagag cgaggtatgt aggcggtgct acagagttct tgaagtggtg gcctaactac    3960
ggctacacta gaagaacagt atttggtatc tgcgctctgc tgaagccagt taccttcgga    4020
aaaagagttg gtagctcttg atccggcaaa caaaccaccg ctggtagcgg tggtttttt    4080 gtttgcaagc agcagattac gcgcagaaaa aaaggatctc aagaagatcc tttgatcttt    4140
tctacggggt ctgacgctca gtggaacgaa aactcacgtt aagggatttt ggtcatggct    4200
agttaattaa catttaaatc agcggccgca ataaatatc tttatttca ttacatctgt    4260 gtgttggttt tttgtgtgaa tcgtaactaa catacgctct ccatcaaaac aaaacgaaac    4320
aaaacaaact agcaaaatag gctgtcccca gtgcaagtgc aggtgccaga acatttctct    4380
atcgaa                                                                4386
```

<210> SEQ ID NO 90
<211> LENGTH: 4386
<212> TYPE: DNA
<213> ORGANISM: Artificial Sequence
<220> FEATURE:
<223> OTHER INFORMATION: pCCL13(5-75K/H-A)-IgG1Fc

<400> SEQUENCE: 90

| | | | | | |
|---|---|---|---|---|---|
| ggatctgcga | tcgctccggt | gcccgtcagt | gggcagagcg | cacatcgccc | acagtccccg | 60 |
| agaagttggg | gggaggggtc | ggcaattgaa | cgggtgccta | gagaaggtgg | cgcggggtaa | 120 |
| actgggaaag | tgatgtcgtg | tactggctcc | gccttttcc | cgagggtggg | ggagaaccgt | 180 |
| atataagtgc | agtagtcgcc | gtgaacgttc | tttttcgcaa | cgggtttgcc | gccagaacac | 240 |
| agctgaagct | tcgaggggct | cgcatctctc | cttcacgcgc | ccgccgccct | acctgaggcc | 300 |
| gccatccacg | ccggttgagt | cgcgttctgc | cgcctcccgc | ctgtggtgcc | tcctgaactg | 360 |
| cgtccgccgt | ctaggtaagt | ttaaagctca | ggtcgagacc | gggcctttgt | ccggcgctcc | 420 |
| cttggagcct | acctagactc | agccggctct | ccacgctttg | cctgaccctg | cttgctcaac | 480 |
| tctacgtctt | tgtttcgttt | tctgttctgc | gccgttacag | atccaagctg | tgaccggcgc | 540 |
| ctacctgaga | tcaccggcga | aggagggcca | ccatgtacag | gatgcaactc | ctgtcttgca | 600 |
| ttgcactaag | tcttgcactt | gtcacgaatt | cgctcaacgt | cccatctact | tgctgcttca | 660 |
| catttagcag | taagaagatc | tccttgcaga | ggctgaagag | ctatgtgatc | accaccagca | 720 |
| ggtgtcccca | gaaggctgtc | atcttcagaa | ccgccctggg | cgcggagatc | tgtgctgacc | 780 |
| cagccgaggc | ctgggtccag | aattatatgg | cggctctggg | ccggaaagct | gccaccctgg | 840 |
| ctactgacaa | aactcacaca | tgcccaccgt | gcccagcacc | tgaactcctg | ggggaccgt | 900 |
| cagtcttcct | cttccccca | aaacccaagg | acaccctcat | gatctcccgg | acccctgagg | 960 |
| tcacatgcgt | ggtggtggac | gtgagccacg | aagaccctga | ggtcaagttc | aactggtacg | 1020 |
| tggacggcgt | ggaggtgcat | aatgccaaga | caaagccgcg | ggaggagcag | tacaacagca | 1080 |
| cgtaccgtgt | ggtcagcgtc | ctcaccgtcc | tgcaccagga | ctggctgaat | ggcaaggagt | 1140 |
| acaagtgcaa | ggtctccaac | aaagccctcc | cagcccccat | cgagaaaacc | atctccaaag | 1200 |
| ccaaagggca | gccccgagaa | ccacaggtgt | acaccctgcc | cccatcccgg | gaggagatga | 1260 |
| ccaagaacca | ggtcagcctg | acctgcctgg | tcaaaggctt | ctatcccagc | gacatcgccg | 1320 |
| tggagtggga | gagcaatggg | cagccggaga | acaactacaa | gaccacgcct | cccgtgctgg | 1380 |
| actccgacgg | ctccttcttc | ctctacagca | agctcaccgt | ggacaagagc | aggtggcagc | 1440 |
| aggggaacgt | cttctcatgc | tccgtgatgc | acgaggctct | gcacaaccac | tacacgcaga | 1500 |
| agagcctctc | cctgtctccg | ggtaaatgag | tgctagctgg | ccagacatga | taagatacat | 1560 |
| tgatgagttt | ggacaaacca | caactagaat | gcagtgaaaa | aaatgcttta | tttgtgaaat | 1620 |
| ttgtgatgct | attgctttat | ttgtaaccat | tataagctgc | aataaacaag | ttaacaacaa | 1680 |
| caattgcatt | cattttatgt | ttcaggttca | ggggaggtg | tgggaggttt | tttaaagcaa | 1740 |
| gtaaaacctc | tacaaatgtg | gtatggaatt | aattctaaaa | tacagcatag | caaaacttta | 1800 |
| acctccaaat | caagcctcta | cttgaatcct | tttctgaggg | atgaataagg | cataggcatc | 1860 |
| aggggctgtt | gccaatgtgc | attagctgtt | tgcagcctca | ccttctttca | tggagtttaa | 1920 |
| gatatagtgt | attttcccaa | ggtttgaact | agctcttcat | ttctttatgt | tttaaatgca | 1980 |
| ctgacctccc | acattccctt | tttagtaaaa | tattcagaaa | taatttaaat | acatcattgc | 2040 |
| aatgaaaata | aatgttttt | attaggcaga | atccagatgc | tcaaggccct | tcataatatc | 2100 |

```
ccccagttta gtagttggac ttagggaaca aggaaccctt taatagaaat tggacagcaa    2160
gaaagcgagc ttctagctta tcctcagtcc tgctcctctg ccacaaagtg cacgcagttg    2220
ccggccgggt cgcgcagggc gaactcccgc cccacggct gctcgccgat ctcggtcatg     2280
gccggcccgg aggcgtcccg gaagttcgtg gacacgacct ccgaccactc ggcgtacagc    2340
tcgtccaggc cgcgcaccca cacccaggcc agggtgttgt ccggcaccac ctggtcctgg    2400
accgcgctga tgaacagggt cacgtcgtcc cggaccacac cggcgaagtc gtcctccacg    2460
aagtcccggg agaacccgag ccggtcggtc cagaactcga ccgctccggc gacgtcgcgc    2520
gcggtgagca ccggaacggc actggtcaac ttggccatga tggctcctcc tgtcaggaga    2580
ggaaagagaa gaaggttagt acaattgcta tagtgagttg tattatacta tgcagatata    2640
ctatgccaat gattaattgt caaactaggg ctgcagggtt catagtgcca ctttcctgc     2700 actgccccat ctcctgccca ccctttccca ggcatagaca gtcagtgact taccaaactc    2760
acaggaggga gaaggcagaa gcttgagaca gacccgcggg accgccgaac tgcgagggga    2820
cgtggctagg gcggcttctt ttatggtgcg ccggccctcg gaggcagggc gctcggggag    2880
gcctagcggc caatctgcgg tgcaggagg cgggccgaa ggccgtgcct gaccaatccg      2940
gagcacatag gagtctcagc ccccgcccc aaagcaaggg gaagtcacgc gcctgtagcg     3000
ccagcgtgtt gtgaaatggg ggcttggggg ggttggggcc ctgactagtc aaaacaaact    3060
cccattgacg tcaatggggt ggagacttgg aaatcccgt gagtcaaacc gctatccacg     3120
cccattgatg tactgccaaa accgcatcat catggtaata gcgatgacta atacgtagat    3180
gtactgccaa gtaggaaagt cccataaggt catgtactgg gcataatgcc aggcgggcca    3240
tttaccgtca ttgacgtcaa taggggggcgt acttggcata tgatacactt gatgtactgc    3300
caagtgggca gtttaccgta atactccac ccattgacgt caatggaaag tccctattgg     3360
cgttactatg ggaacatacg tcattattga cgtcaatggg cggggtcgt tgggcggtca     3420 gccaggcggg ccatttaccg taagttatgt aacgcctgca ggttaattaa gaacatgtga    3480
gcaaaaggcc agcaaaaggc caggaaccgt aaaaaggccg cgttgctggc gtttttccat    3540
aggctccgcc cccctgacga gcatcacaaa aatcgacgct caagtcagag gtggcgaaac    3600
ccgacaggac tataaagata ccaggcgttt ccccctggaa gctccctcgt gcgctctcct    3660
gttccgaccc tgccgcttac cggatacctg tccgcctttc tccttcggg aagcgtggcg     3720 ctttctcata gctcacgctg taggtatctc agttcggtgt aggtcgttcg ctccaagctg    3780
ggctgtgtgc acgaaccccc cgttcagccc gaccgctgcg ccttatccgg taactatcgt    3840
cttgagtcca acccggtaag acacgactta tcgccactgg cagcagccac tggtaacagg    3900
attagcagag cgaggtatgt aggcggtgct acagagttct tgaagtggtg gcctaactac    3960
ggctacacta gaagaacagt atttggtatc tgcgctctgc tgaagccagt taccttcgga    4020
aaaagagttg gtagctcttg atccggcaaa caaaccaccg ctggtagcgg tggtttttt     4080 gtttgcaagc agcagattac gcgcagaaaa aaggatctc aagaagatcc tttgatcttt     4140
tctacggggt ctgacgctca gtggaacgaa aactcacgtt aagggatttt ggtcatggct    4200
agttaattaa catttaaatc agcggccgca ataaatatc tttattttca ttacatctgt     4260
gtgttggttt tttgtgtgaa tcgtaactaa catacgctct ccatcaaaac aaaacgaaac    4320
aaaacaaact agcaaaatag gctgtcccca gtgcaagtgc aggtgccaga acatttctct    4380
atcgaa                                                              4386
```

<210> SEQ ID NO 91

<211> LENGTH: 4527
<212> TYPE: DNA
<213> ORGANISM: Artificial Sequence
<220> FEATURE:
<223> OTHER INFORMATION: pCCL25-IgG1Fc

<400> SEQUENCE: 91

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gcctttttcc cgagggtggg ggagaaccgt     180
atataagtgc agtagtcgcc gtgaacgttc tttttcgcaa cgggtttgcc gccagaacac     240
agctgaagct cgaggggct cgcatctctc cttcacgcgc ccgccgccct acctgaggcc      300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cgacccaagg tgtctttgag gactgctgcc     660
tggcctacca ctaccccatt gggtgggctg tgctccggca cgcctggact taccggatcc     720
aggaggtgag cgggagctgc aatctgcctg ctgcgatatt ctacctcccc aagagacaca     780
ggaaggtgtg tgggaacccc aaaagcaggg aggtgcagag agccatgaag ctcctggatg     840
ctcgaaataa ggttttttgca aagctccgcc acaacacgca gaccttccaa ggccctcatg     900
ctgtaaagaa gttgagttct ggaaactcca agttatcatc gtccaagttt agcaatccca     960
tcagcagcag caagaggaat gtctccgaca aaactcacac atgcccaccg tgcccagcac    1020
ctgaactcct gggggaccg tcagtcttcc tcttcccccc aaaacccaag gacaccctca    1080
tgatctcccg gacccctgag gtcacatgcg tggtggtgga cgtgagccac gaagaccctg    1140
aggtcaagtt caactggtac gtggacggcg tggaggtgca taatgccaag acaaagccgc    1200
gggaggagca gtacaacagc acgtaccgtg tggtcagcgt cctcaccgtc ctgcaccagg    1260
actggctgaa tggcaaggag tacaagtgca aggtctccaa caaagccctc ccagccccca    1320
tcgagaaaac catctccaaa gccaagggc agccccgaga accacaggtg tacaccctgc    1380
ccccatcccg ggaggagatg accaagaacc aggtcagcct gacctgcctg gtcaaaggct    1440
tctatcccag cgacatcgcc gtggagtggg agagcaatgg gcagccggag aacaactaca    1500
agaccacgcc tcccgtgctg gactccgacg gctccttctt cctctacagc aagctcaccg    1560
tggacaagag caggtggcag caggggaacg tcttctcatg ctccgtgatg cacgaggctc    1620
tgcacaacca ctacacgcag aagagcctct ccctgtctcc gggtaaatga gtgctagctg    1680
gccagacatg ataagataca ttgatgagtt tggacaaacc acaactagaa tgcagtgaaa    1740
aaaatgcttt atttgtgaaa tttgtgatgc tattgcttta tttgtaacca ttataagctg    1800
caataaacaa gttaacaaca caattgcat tcattttatg tttcaggttc agggggaggt    1860
gtgggaggtt ttttaaagca agtaaaacct ctacaaatgt ggtatggaat aattctaaa    1920
atacagcata gcaaacttt aacctccaaa tcaagcctct acttgaatcc ttttctgagg    1980
gatgaataag gcataggcat caggggctgt tgccaatgtg cattagctgt tgcagcctc    2040
accttctttc atggagttta agatatagtg tattttccca aggtttgaac tagctcttca    2100
tttctttatg ttttaaatgc actgacctcc cacattccct tttagtaaa atattcagaa    2160
```

-continued

```
ataatttaaa tacatcattg caatgaaaat aaatgttttt tattaggcag aatccagatg    2220
ctcaaggccc ttcataatat cccccagttt agtagttgga cttagggaac aaaggaacct    2280
ttaatagaaa ttggacagca agaaagcgag cttctagctt atcctcagtc ctgctcctct    2340
gccacaaagt gcacgcagtt gccggccggg tcgcgcaggg cgaactcccg cccccacggc    2400
tgctcgccga tctcggtcat ggccggcccg gaggcgtccc ggaagttcgt ggacacgacc    2460
tccgaccact cggcgtacag ctcgtccagg ccgcgcaccc acaccaggc cagggtgttg    2520 tccggcacca cctggtcctg gaccgcgctg atgaacaggg tcacgtcgtc ccggaccaca    2580
ccggcgaagt cgtcctccac gaagtccggg agaacccga gccggtcggt ccagaactcg    2640
accgctccgg cgacgtcgcg cgcggtgagc accggaacgg cactggtcaa cttggccatg    2700
atggctcctc ctgtcaggag aggaaagaga agaaggttag tacaattgct atagtgagtt    2760
gtattatact atgcagatat actatgccaa tgattaattg tcaaactagg gctgcagggt    2820
tcatagtgcc acttttcctg cactgcccca tctcctgccc acccttccc aggcatagac    2880 agtcagtgac ttaccaaact cacaggaggg agaaggcaga agcttgagac agacccgcgg    2940
gaccgccgaa ctgcgagggg acgtggctag ggcggcttct tttatggtgc gccggccctc    3000
ggaggcaggg cgctcgggga ggcctagcgg ccaatctgcg gtggcaggag gcggggccga    3060
aggccgtgcc tgaccaatcc ggagcacata ggagtctcag ccccccgccc caaagcaagg    3120
ggaagtcacg cgcctgtagc gccagcgtgt tgtgaaatgg gggcttgggg gggttgggc    3180 cctgactagt caaaacaaac tcccattgac gtcaatgggg tggagacttg gaatccccg    3240 tgagtcaaac cgctatccac gcccattgat gtactgccaa aaccgcatca tcatggtaat    3300
agcgatgact aatacgtaga tgtactgcca agtaggaaag tcccataagg tcatgtactg    3360
ggcataatgc caggcgggcc atttaccgtc attgacgtca ataggggggcg tacttggcat    3420 atgatacact tgatgtactg ccaagtgggc agtttaccgt aaatactcca cccattgacg    3480
tcaatggaaa gtccctattg gcgttactat gggaacatac gtcattattg acgtcaatgg    3540 gcggggggtcg ttgggcggtc agccaggcgg gccatttacc gtaagttatg taacgcctgc    3600
aggttaatta agaacatgtg agcaaaaggc cagcaaaagg ccaggaaccg taaaaaggcc    3660
gcgttgctgg cgttttttcca taggctccgc ccccctgacg agcatcacaa aaatcgacgc    3720
tcaagtcaga ggtggcgaaa cccgacagga ctataaagat accaggcgtt tccccctgga    3780
agctccctcg tgcgctctcc tgttccgacc ctgccgctta ccggatacct gtccgccttt    3840
ctcccttcgg gaagcgtggc gctttctcat agctcacgct gtaggtatct cagttcggtg    3900
taggtcgttc gctccaagct gggctgtgtg cacgaacccc ccgttcagcc cgaccgctgc    3960
gccttatccg gtaactatcg tcttgagtcc aacccggtaa gacacgactt atcgccactg    4020
gcagcagcca ctggtaacag gattagcaga gcgaggtatg taggcggtgc tacagagttc    4080
ttgaagtggt ggcctaacta cggctacact agaagaacag tatttggtat ctgcgctctg    4140
ctgaagccag ttaccttcgg aaaaagagtt ggtagctctt gatccggcaa acaaaccacc    4200
gctggtagcg gtggtttttt tgtttgcaag cagcagatta cgcgcagaaa aaaggatct    4260 caagaagatc ctttgatctt ttctacgggg tctgacgctc agtggaacga aaactcacgt    4320
taagggattt tggtcatggc tagttaatta acatttaaat cagcggccgc aataaaatat    4380
ctttattttc attacatctg tgtgttggtt ttttgtgtga atcgtaacta acatacgctc    4440
tccatcaaaa caaaacgaaa caaaacaaac tagcaaaata ggctgtcccc agtgcaagtg    4500
caggtgccag aacatttctc tatcgaa                                       4527
```

<210> SEQ ID NO 92
<211> LENGTH: 4518
<212> TYPE: DNA
<213> ORGANISM: Artificial Sequence
<220> FEATURE:
<223> OTHER INFORMATION: pCCL25(4-127)-IgG1Fc

<400> SEQUENCE: 92

| | | | | | |
|---|---|---|---|---|---|
| ggatctgcga | tcgctccggt | gcccgtcagt | gggcagagcg | cacatcgccc | acagtccccg | 60 |
| agaagttggg | gggaggggtc | ggcaattgaa | cgggtgccta | gagaaggtgg | cgcggggtaa | 120 |
| actgggaaag | tgatgtcgtg | tactggctcc | gccttttttcc | cgagggtggg | ggagaaccgt | 180 |
| atataagtgc | agtagtcgcc | gtgaacgttc | tttttcgcaa | cgggtttgcc | gccagaacac | 240 |
| agctgaagct | cgaggggct | cgcatctctc | cttcacgcgc | ccgccgccct | acctgaggcc | 300 |
| gccatccacg | ccggttgagt | cgcgttctgc | cgcctcccgc | ctgtggtgcc | tcctgaactg | 360 |
| cgtccgccgt | ctaggtaagt | ttaaagctca | ggtcgagacc | gggcctttgt | ccggcgctcc | 420 |
| cttggagcct | acctagactc | agccggctct | ccacgctttg | cctgaccctg | cttgctcaac | 480 |
| tctacgtctt | tgtttcgttt | tctgttctgc | gccgttacag | atccaagctg | tgaccggcgc | 540 |
| ctacctgaga | tcaccggcga | aggagggcca | ccatgtacag | gatgcaactc | ctgtcttgca | 600 |
| ttgcactaag | tcttgcactt | gtcacgaatt | cggtctttga | ggactgctgc | ctggcctacc | 660 |
| actacccccat | tgggtgggct | gtgctccggc | acgcctggac | ttaccggatc | caggaggtga | 720 |
| gcggagctg | caatctgcct | gctgcgatat | tctacctccc | caagagacac | aggaaggtgt | 780 |
| gtgggaaccc | caaaagcagg | gaggtgcaga | gagccatgaa | gctcctggat | gctcgaaata | 840 |
| aggttttttgc | aaagctccgc | cacaacacg | agaccttcca | aggccctcat | gctgtaaaga | 900 |
| agttgagttc | tggaaactcc | aagttatcat | cgtccaagtt | tagcaatccc | atcagcagca | 960 |
| gcaagaggaa | tgtctccgac | aaaactcaca | catgcccacc | gtgcccagca | cctgaactcc | 1020 |
| tgggggggacc | gtcagtcttc | ctcttccccc | caaaacccaa | ggacaccctc | atgatctccc | 1080 |
| ggacccctga | ggtcacatgc | gtggtggtgg | acgtgagcca | cgaagaccct | gaggtcaagt | 1140 |
| tcaactggta | cgtggacggc | gtggaggtgc | ataatgccaa | gacaaagccg | cgggaggagc | 1200 |
| agtacaacag | cacgtaccgt | gtggtcagcg | tcctcaccgt | cctgcaccag | gactggctga | 1260 |
| atggcaagga | gtacaagtgc | aaggtctcca | acaaagccct | cccagccccc | atcgagaaaa | 1320 |
| ccatctccaa | agccaaaggg | cagccccgag | aaccacaggt | gtacaccctg | cccccatccc | 1380 |
| gggaggagat | gaccaagaac | caggtcagcc | tgacctgcct | ggtcaaaggc | ttctatccca | 1440 |
| gcgacatcgc | cgtggagtgg | gagagcaatg | ggcagccgga | gaacaactac | aagaccacgc | 1500 |
| ctcccgtgct | ggactccgac | ggctccttct | tcctctacag | caagctcacc | gtggacaaga | 1560 |
| gcaggtggca | gcaggggaac | gtcttctcat | gctccgtgat | gcacgaggct | ctgcacaacc | 1620 |
| actacacgca | gaagagcctc | tccctgtctc | cgggtaaatg | agtgctagct | ggccagacat | 1680 |
| gataagatac | attgatgagt | ttggacaaac | cacaactaga | atgcagtgaa | aaaaatgctt | 1740 |
| tatttgtgaa | atttgtgatg | ctattgcttt | atttgtaacc | attataagct | gcaataaaca | 1800 |
| agttaacaac | aacaattgca | ttcattttat | gtttcaggtt | caggggagg | tgtgggaggt | 1860 |
| tttttaaagc | aagtaaaacc | tctacaaatg | tggtatggaa | ttaattctaa | aatacagcat | 1920 |
| agcaaaactt | taacctccaa | atcaagcctc | tacttgaatc | cttttctgag | ggatgaataa | 1980 |
| ggcataggca | tcaggggctg | ttgccaatgt | gcattagctg | tttgcagcct | caccttcttt | 2040 |
| catggagttt | aagatatagt | gtattttccc | aaggtttgaa | ctagctcttc | atttctttat | 2100 |

```
gttttaaatg cactgacctc ccacattccc tttttagtaa atatattcaga aataatttaa    2160 atacatcatt gcaatgaaaa taaatgtttt ttattaggca gaatccagat gctcaaggcc    2220
cttcataata tcccccagtt tagtagttgg acttagggaa caaaggaacc tttaatagaa    2280
attggacagc aagaaagcga gcttctagct tatcctcagt cctgctcctc tgccacaaag    2340
tgcacgcagt tgccggccgg gtcgcgcagg gcgaactccc gcccccacgg ctgctcgccg    2400
atctcggtca tggccggccc ggaggcgtcc cggaagttcg tggacacgac ctccgaccac    2460
tcggcgtaca gctcgtccag gccgcgcacc cacacccagg ccagggtgtt gtccggcacc    2520
acctggtcct ggaccgcgct gatgaacagg gtcacgtcgt cccggaccac accggcgaag    2580
tcgtcctcca cgaagtcccg ggagaacccg agccggtcgg tccagaactc gaccgctccg    2640
gcgacgtcgc gcgcggtgag caccggaacg gcactggtca acttggccat gatggctcct    2700
cctgtcagga gaggaaagag aagaaggtta gtacaattgc tatagtgagt tgtattatac    2760
tatgcagata tactatgcca atgattaatt gtcaaactag gctgcaggg ttcatagtgc    2820 cactttcct gcactgcccc atctcctgcc cacccttcc caggcataga cagtcagtga    2880
cttaccaaac tcacaggagg gagaaggcag aagcttgaga cagacccgcg ggaccgccga    2940
actgcgaggg gacgtggcta gggcggcttc ttttatggtg cgccggccct cggaggcagg    3000
gcgctcgggg aggcctagcg gccaatctgc ggtggcagga ggcggggccg aaggccgtgc    3060
ctgaccaatc cggagcacat aggagtctca gccccccgcc ccaaagcaag gggaagtcac    3120
gcgcctgtag cgccagcgtg ttgtgaaatg ggggcttggg ggggttgggg ccctgactag    3180
tcaaaacaaa ctcccattga cgtcaatggg gtggagactt ggaaatcccc gtgagtcaaa    3240
ccgctatcca cgcccattga tgtactgcca aaccgcatc atcatggtaa tagcgatgac    3300
taatacgtag atgtactgcc aagtaggaaa gtcccataag gtcatgtact gggcataatg    3360
ccaggcgggc catttaccgt cattgacgtc aatagggggc gtacttggca tatgatacac    3420
ttgatgtact gccaagtggg cagtttaccg taaatactcc acccattgac gtcaatggaa    3480
agtccctatt ggcgttacta tgggaacata cgtcattatt gacgtcaatg ggcgggggtc    3540
gttgggcggt cagccaggcg ggccatttac cgtaagttat gtaacgcctg caggttaatt    3600
aagaacatgt gagcaaaagg ccagcaaaag gccaggaacc gtaaaaaggc cgcgttgctg    3660 gcgttttcc ataggctccg ccccctgac gagcatcaca aaaatcgacg ctcaagtcag    3720
aggtggcgaa acccgacagg actataaaga taccaggcgt ttccccctgg aagctccctc    3780
gtgcgctctc ctgttccgac cctgccgctt accggatacc tgtccgcctt tctcccttcg    3840
ggaagcgtgg cgctttctca tagctcacgc tgtaggtatc tcagttcggt gtaggtcgtt    3900
cgctccaagc tgggctgtgt gcacgaaccc cccgttcagc ccgaccgctg cgccttatcc    3960
ggtaactatc gtcttgagtc caacccggta agacacgact tatcgccact ggcagcagcc    4020
actggtaaca ggattagcag agcgaggtat gtaggcggtg ctacagagtt cttgaagtgg    4080
tggcctaact acggctacac tagaagaaca gtatttggta tctgcgctct gctgaagcca    4140
gttaccttcg gaaaaagagt tggtagctct tgatccggca acaaaccac cgctggtagc    4200 ggtggttttt ttgtttgcaa gcagcagatt acgcgcagaa aaaaggatc tcaagaagat    4260 cctttgatct tttctacggg gtctgacgct cagtggaacg aaaactcacg ttaagggatt    4320
ttggtcatgg ctagttaatt aacatttaaa tcagcggccg caataaaata tctttatttt    4380
cattacatct gtgtgttggt ttttgtgtg aatcgtaact aacatacgct ctccatcaaa    4440
acaaaacgaa acaaaacaaa ctagcaaaat aggctgtccc cagtgcaagt gcaggtgcca    4500
```

-continued gaacatttct ctatcgaa    4518

<210> SEQ ID NO 93
<211> LENGTH: 4518
<212> TYPE: DNA
<213> ORGANISM: Artificial Sequence
<220> FEATURE:
<223> OTHER INFORMATION: pCCL25(4-127K/H-A)-IgG1Fc

<400> SEQUENCE: 93

| | | | | | |
|---|---|---|---|---|---|
| ggatctgcga | tcgctccggt | gcccgtcagt | gggcagagcg | cacatcgccc | acagtccccg | 60 |
| agaagttggg | gggaggggtc | ggcaattgaa | cgggtgccta | gagaaggtgg | cgcggggtaa | 120 |
| actgggaaag | tgatgtcgtg | tactggctcc | gccttttttcc | cgagggtggg | ggagaaccgt | 180 |
| atataagtgc | agtagtcgcc | gtgaacgttc | tttttcgcaa | cgggtttgcc | gccagaacac | 240 |
| agctgaagct | tcgaggggct | cgcatctctc | cttcacgcgc | ccgccgccct | acctgaggcc | 300 |
| gccatccacg | ccggttgagt | cgcgttctgc | cgcctcccgc | ctgtggtgcc | tcctgaactg | 360 |
| cgtccgccgt | ctaggtaagt | ttaaagctca | ggtcgagacc | gggcctttgt | ccggcgctcc | 420 |
| cttggagcct | acctagactc | agccggctct | ccacgctttg | cctgaccctg | cttgctcaac | 480 |
| tctacgtctt | tgtttcgttt | tctgttctgc | gccgttacag | atccaagctg | tgaccggcgc | 540 |
| ctacctgaga | tcaccggcga | aggagggcca | ccatgtacag | gatgcaactc | ctgtcttgca | 600 |
| ttgcactaag | tcttgcactt | gtcacgaatt | cggtctttga | ggactgctgc | ctggcctacc | 660 |
| actacccccat | tgggtgggct | gtgctccggc | acgcctggac | ttaccggatc | caggaggtga | 720 |
| gcgggagctg | caatctgcct | gctgcgatat | tctacctccc | cgctgccgct | gccgcggtgt | 780 |
| gtgggaaccc | cgctagcgcc | gaggtgcagg | ctgccatggc | cctcctggat | gctgctaatg | 840 |
| ccgttttttgc | agcgctcgct | gccaacacgc | agaccttcca | aggccctgcg | gctgtagccg | 900 |
| ctttgagttc | tggaaactcc | gccttatcat | cgtccgcgtt | tagcaatccc | atcagcagca | 960 |
| gcgctgccaa | tgtctccgac | aaaactcaca | catgcccacc | gtgcccagca | cctgaactcc | 1020 |
| tggggggacc | gtcagtcttc | ctcttccccc | caaaacccaa | ggacaccctc | atgatctccc | 1080 |
| ggaccccctga | ggtcacatgc | gtggtggtgg | acgtgagcca | cgaagaccct | gaggtcaagt | 1140 |
| tcaactggta | cgtggacggc | gtggaggtgc | ataatgccaa | gacaaagccg | cgggaggagc | 1200 |
| agtacaacag | cacgtaccgt | gtggtcagcg | tcctcaccgt | cctgcaccag | gactggctga | 1260 |
| atggcaagga | gtacaagtgc | aaggtctcca | acaaagccct | cccagccccc | atcgagaaaa | 1320 |
| ccatctccaa | agccaaaggg | cagccccgag | aaccacaggt | gtacaccctg | cccccatccc | 1380 |
| gggaggagat | gaccaagaac | caggtcagcc | tgacctgcct | ggtcaaaggc | ttctatccca | 1440 |
| gcgacatcgc | cgtggagtgg | gagagcaatg | ggcagccgga | gaacaactac | aagaccacgc | 1500 |
| ctcccgtgct | ggactccgac | ggctccttct | tcctctacag | caagctcacc | gtggacaaga | 1560 |
| gcaggtggca | gcaggggaac | gtcttctcat | gctccgtgat | gcacgaggct | ctgcacaacc | 1620 |
| actacacgca | gaagagcctc | tccctgtctc | cgggtaaatg | agtgctagct | ggccagacat | 1680 |
| gataagatac | attgatgagt | ttggacaaac | cacaactaga | atgcagtgaa | aaaaatgctt | 1740 |
| tatttgtgaa | atttgtgatg | ctattgcttt | atttgtaacc | attataagct | gcaataaaca | 1800 |
| agttaacaac | aacaattgca | ttcattttat | gtttcaggtt | cagggggagg | tgtgggaggt | 1860 |
| tttttaaagc | aagtaaaacc | tctacaaatg | tggtatggaa | ttaattctaa | aatacagcat | 1920 |
| agcaaaactt | taacctccaa | atcaagcctc | tacttgaatc | cttttctgag | ggatgaataa | 1980 |
| ggcataggca | tcaggggctg | ttgccaatgt | gcattagctg | tttgcagcct | caccttcttt | 2040 |

```
catggagttt aagatatagt gtattttccc aaggtttgaa ctagctcttc atttctttat   2100
gttttaaatg cactgacctc ccacattccc tttttagtaa atattcaga ataatttaa    2160 atacatcatt gcaatgaaaa taaatgtttt ttattaggca gaatccagat gctcaaggcc  2220
cttcataata tcccccagtt tagtagttgg acttagggaa caaaggaacc tttaatagaa  2280
attggacagc aagaaagcga gcttctagct tatcctcagt cctgctcctc tgccacaaag  2340
tgcacgcagt tgccggccgg gtcgcgcagg gcgaactccc gcccccacgg ctgctcgccg  2400
atctcggtca tggccggccc ggaggcgtcc cggaagttcg tggacacgac ctccgaccac  2460
tcggcgtaca gctcgtccag gccgcgcacc cacacccagg ccagggtgtt gtccggcacc  2520
acctggtcct ggaccgcgct gatgaacagg gtcacgtcgt cccggaccac accggcgaag  2580
tcgtcctcca cgaagtcccg ggagaacccg agccggtcgg tccagaactc gaccgctccg  2640
gcgacgtcgc gcgcggtgag caccggaacg gcactggtca acttggccat gatggctcct  2700
cctgtcagga gaggaaagag aagaaggtta gtacaattgc tatagtgagt tgtattatac  2760
tatgcagata tactatgcca atgattaatt gtcaaactag ggctgcaggg ttcatagtgc  2820
cacttttcct gcactgcccc atctcctgcc cacccttttcc caggcataga cagtcagtga  2880
cttaccaaac tcacaggagg gagaaggcag aagcttgaga cagacccgcg ggaccgccga  2940
actgcgaggg gacgtggcta gggcggcttc ttttatggtg cgccggccct cggaggcagg  3000
gcgctcgggg aggcctagcg gccaatctgc ggtggcagga ggcggggccg aaggccgtgc  3060
ctgaccaatc cggagcacat aggagtctca gccccccgcc ccaaagcaag gggaagtcac  3120
gcgcctgtag cgccagcgtg ttgtgaaatg ggggcttggg ggggttgggg ccctgactag  3180
tcaaaacaaa ctcccattga cgtcaatggg gtggagactt ggaaatcccc gtgagtcaaa  3240
ccgctatcca cgcccattga tgtactgcca aaaccgcatc atcatggtaa tagcgatgac  3300
taatacgtag atgtactgcc aagtaggaaa gtcccataag gtcatgtact gggcataatg  3360
ccaggcgggc catttaccgt cattgacgtc aataggggc gtacttggca tatgatacac  3420
ttgatgtact gccaagtggg cagtttaccg taaatactcc acccattgac gtcaatggaa  3480
agtccctatt ggcgttacta tgggaacata cgtcattatt gacgtcaatg ggcggggtc   3540 gttgggcggt cagccaggcg ggccatttac cgtaagttat gtaacgcctg caggttaatt  3600
aagaacatgt gagcaaaagg ccagcaaaag gccaggaacc gtaaaaaggc cgcgttgctg  3660 gcgttttttcc ataggctccg cccccctgac gagcatcaca aaaatcgacg ctcaagtcag  3720
aggtggcgaa acccgacagg actataaaga taccaggcgt ttccccctgg aagctccctc  3780
gtgcgctctc ctgttccgac cctgccgctt accggatacc tgtccgcctt tctcccttcg  3840
ggaagcgtgg cgctttctca tagctcacgc tgtaggtatc tcagttcggt gtaggtcgtt  3900
cgctccaagc tgggctgtgt gcacgaaccc cccgttcagc ccgaccgctg cgccttatcc  3960
ggtaactatc gtcttgagtc aacccggta agacacgact tatcgccact ggcagcagcc  4020
actggtaaca ggattagcag agcgaggtat gtaggcggtg ctacagagtt cttgaagtgg  4080
tggcctaact acggctacac tagaagaaca gtatttggta tctgcgctct gctgaagcca  4140
gttaccttcg gaaaaagagt tggtagctct tgatccggca acaaaccac cgctggtagc    4200 ggtggttttt tgtttgcaa gcagcagatt acgcgcagaa aaaaggatc tcaagaagat  4260 cctttgatct tttctacggg gtctgacgct cagtggaacg aaaactcacg ttaagggatt  4320
ttggtcatgg ctagttaatt aacatttaaa tcagcggccg caataaaata tctttatttt  4380
cattacatct gtgtgttggt tttttgtgtg aatcgtaact aacatacgct ctccatcaaa  4440
```

<210> SEQ ID NO 94
<211> LENGTH: 4392
<212> TYPE: DNA
<213> ORGANISM: Artificial Sequence
<220> FEATURE:
<223> OTHER INFORMATION: pCXCL11-IgG1Fc

<400> SEQUENCE: 94

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttcc cgagggtggg ggagaaccgt      180
atataagtgc agtagtcgcc gtgaacgttc tttttcgcaa cgggtttgcc gccagaacac     240
agctgaagct cgaggggct cgcatctctc cttcacgcgc ccgccgccct acctgaggcc      300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cgttccccat gttcaaaaga ggacgctgtc     660
tttgcatagg ccctggggta aaagcagtga agtggcaga tattgagaaa gcctccataa       720
tgtacccaag taacaactgt gacaaaatag aagtgattat taccctgaaa gaaaataaag     780
gacaacgatg cctaaatccc aaatcgaagc aagcaaggct tataatcaaa aagttgaaa      840
gaaagaattt tgacaaaact cacacatgcc caccgtgccc agcacctgaa ctcctggggg     900
gaccgtcagt cttcctcttc cccccaaaac ccaaggacac cctcatgatc tcccggaccc     960
ctgaggtcac atgcgtggtg gtggacgtga gccacgaaga ccctgaggtc aagttcaact    1020
ggtacgtgga cggcgtggag gtgcataatg ccaagacaaa gccgcgggag gagcagtaca    1080
acagcacgta ccgtgtggtc agcgtcctca ccgtcctgca ccaggactgg ctgaatggca    1140
aggagtacaa gtgcaaggtc tccaacaaag ccctcccagc ccccatcgag aaaaccatct    1200
ccaaagccaa agggcagccc cgagaaccac aggtgtacac cctgccccca tcccgggagg    1260
agatgaccaa gaaccaggtc agcctgacct gcctggtcaa aggcttctat cccagcgaca    1320
tcgccgtgga gtgggagagc aatgggcagc cggagaacaa ctacaagacc acgcctcccg    1380
tgctggactc cgacggctcc ttcttcctct acagcaagct caccgtggac aagagcaggt    1440
ggcagcaggg gaacgtcttc tcatgctccg tgatgcacga ggctctgcac aaccactaca    1500
cgcagaagag cctctccctg tctccgggta aatgagtgct agctggccag acatgataag    1560
atacattgat gagtttggac aaaccacaac tagaatgcag tgaaaaaaat gctttatttg    1620
tgaaatttgt gatgctattg ctttatttgt aaccattata agctgcaata acaagttaa     1680
caacaacaat tgcattcatt ttatgtttca ggttcagggg gaggtgtggg aggttttta     1740
aagcaagtaa aacctctaca aatgtggtat ggaattaatt ctaaaataca gcatagcaaa    1800
actttaacct ccaaatcaag cctctacttg aatcctttc tgagggatga ataaggcata     1860
ggcatcaggg gctgttgcca atgtgcatta gctgtttgca gcctcacctt ctttcatgga    1920
gtttaagata tagtgtattt tcccaaggtt tgaactagct cttcatttct ttatgtttta    1980
```

```
aatgcactga cctcccacat tccctttta gtaaaatatt cagaaataat ttaaatacat    2040
cattgcaatg aaaataaatg ttttttatta ggcagaatcc agatgctcaa ggcccttcat    2100
aatatccccc agtttagtag ttggacttag ggaacaaagg aacctttaat agaaattgga    2160
cagcaagaaa gcgagcttct agcttatcct cagtcctgct cctctgccac aaagtgcacg    2220
cagttgccgg ccgggtcgcg cagggcgaac tcccgccccc acggctgctc gccgatctcg    2280
gtcatggccg gccggaggc gtcccggaag ttcgtggaca cgacctccga ccactcggcg    2340
tacagctcgt ccaggccgcg cacccacacc caggccaggg tgttgtccgg caccacctgg    2400
tcctggaccg cgctgatgaa cagggtcacg tcgtcccgga ccacccggc gaagtcgtcc     2460
tccacgaagt cccgggagaa cccgagccgg tcggtccaga actcgaccgc tccggcgacg    2520
tcgcgcgcgg tgagcaccgg aacggcactg gtcaacttgg ccatgatggc tcctcctgtc    2580
aggagaggaa agagaagaag gttagtacaa ttgctatagt gagttgtatt atactatgca    2640
gatatactat gccaatgatt aattgtcaaa ctagggctgc agggttcata gtgccacttt    2700
tcctgcactg ccccatctcc tgcccaccct ttcccaggca tagacagtca gtgacttacc    2760
aaactcacag gagggagaag gcagaagctt gagacagacc cgcgggaccg ccgaactgcg    2820
aggggacgtg gctagggcgg cttctttat ggtgcgccgg ccctcggagg cagggcgctc    2880
ggggaggcct agcggccaat ctgcggtggc aggaggcggg gccgaaggcc gtgcctgacc    2940
aatccggagc acataggagt ctcagccccc cgccccaaag caaggggaag tcacgcgcct    3000
gtagcgccag cgtgttgtga atgggggct tgggggggtt gggcccctga ctagtcaaaa    3060
caaactccca ttgacgtcaa tggggtggag acttggaaat ccccgtgagt caaaccgcta    3120
tccacgccca ttgatgtact gccaaaaccg catcatcatg gtaatagcga tgactaatac    3180
gtagatgtac tgccaagtag gaaagtccca taaggtcatg tactgggcat aatgccaggc    3240
gggccattta ccgtcattga cgtcaatagg gggcgtactt ggcatatgat acacttgatg    3300
tactgccaag tgggcagttt accgtaaata ctccacccat tgacgtcaat ggaaagtccc    3360
tattggcgtt actatgggaa catacgtcat tattgacgtc aatgggcggg ggtcgttggg    3420
cggtcagcca ggcgggccat ttaccgtaag ttatgtaacg cctgcaggtt aattaagaac    3480
atgtgagcaa aaggccagca aaaggccagg aaccgtaaaa aggccgcgtt gctggcgttt    3540
ttccataggc tccgccccc tgacgagcat cacaaaaatc gacgctcaag tcagaggtgg    3600
cgaaacccga caggactata agataccag gcgtttcccc ctggaagctc cctcgtgcgc    3660
tctcctgttc cgaccctgcc gcttaccgga tacctgtccg cctttctccc ttcgggaagc    3720
gtggcgcttt ctcatagctc acgctgtagg tatctcagtt cggtgtaggt cgttcgctcc    3780
aagctgggct gtgtgcacga accccccgtt cagcccgacc gctgcgcctt atccggtaac    3840
tatcgtcttg agtccaaccc ggtaagacac gacttatcgc cactggcagc agccactggt    3900
aacaggatta gcagagcgag gtatgtaggc ggtgctacag agttcttgaa gtggtggcct    3960
aactacggct acactagaag aacagtattt ggtatctgcg ctctgctgaa gccagttacc    4020
ttcggaaaaa gagttggtag ctcttgatcc ggcaaacaaa ccaccgctgg tagcggtggt    4080
ttttttgttt gcaagcagca gattacgcgc agaaaaaaag gatctcaaga agatcctttg    4140
atcttttcta cggggtctga cgctcagtgg aacgaaaact cacgttaagg attttggtc     4200
atggctagtt aattaacatt taaatcagcg gccgcaataa aatatcttta ttttcattac    4260
atctgtgtgt tggtttttg tgtgaatcgt aactaacata cgctctccat caaaacaaaa    4320
cgaaacaaaa caaactagca aaataggctg tccccagtgc aagtgcaggt gccagaacat    4380
```
ttctctatcg aa                                                                  4392

<210> SEQ ID NO 95
<211> LENGTH: 4383
<212> TYPE: DNA
<213> ORGANISM: Artificial Sequence
<220> FEATURE:
<223> OTHER INFORMATION: pCXCL11(4-73)-IgG1Fc

<400> SEQUENCE: 95

| | | | | | |
|---|---|---|---|---|---|
| ggatctgcga | tcgctccggt | gcccgtcagt | gggcagagcg | cacatcgccc | acagtccccg | 60 |
| agaagttggg | gggaggggtc | ggcaattgaa | cgggtgccta | gagaaggtgg | cgcggggtaa | 120 |
| actgggaaag | tgatgtcgtg | tactggctcc | gccttttttcc | cgagggtggg | ggagaaccgt | 180 |
| atataagtgc | agtagtcgcc | gtgaacgttc | tttttcgcaa | cgggtttgcc | gccagaacac | 240 |
| agctgaagct | cgaggggct | cgcatctctc | cttcacgcgc | ccgccgccct | acctgaggcc | 300 |
| gccatccacg | ccggttgagt | cgcgttctgc | cgcctcccgc | ctgtggtgcc | tcctgaactg | 360 |
| cgtccgccgt | ctaggtaagt | ttaaagctca | ggtcgagacc | gggcctttgt | ccggcgctcc | 420 |
| cttggagcct | acctagactc | agccggctct | ccacgctttg | cctgaccctg | cttgctcaac | 480 |
| tctacgtctt | tgtttcgttt | tctgttctgc | gccgttacag | atccaagctg | tgaccggcgc | 540 |
| ctacctgaga | tcaccggcga | aggagggcca | ccatgtacag | gatgcaactc | ctgtcttgca | 600 |
| ttgcactaag | tcttgcactt | gtcacgaatt | cgttcaaaag | aggacgctgt | ctttgcatag | 660 |
| gccctggggg | aaaagcagtg | aaagtggcag | atattgagaa | agcctccata | atgtacccaa | 720 |
| gtaacaactg | tgacaaaata | gaagtgatta | ttaccctgaa | agaaaataaa | ggacaacgat | 780 |
| gcctaaatcc | caaatcgaag | caagcaaggc | ttataatcaa | aaaagttgaa | agaaagaatt | 840 |
| ttgacaaaac | tcacacatgc | ccaccgtgcc | cagcacctga | actcctgggg | ggaccgtcag | 900 |
| tcttcctctt | ccccccaaaa | cccaaggaca | ccctcatgat | ctcccggacc | cctgaggtca | 960 |
| catgcgtggt | ggtggacgtg | agccacgaag | accctgaggt | caagttcaac | tggtacgtgg | 1020 |
| acggcgtgga | ggtgcataat | gccaagacaa | agccgcggga | ggagcagtac | aacagcacgt | 1080 |
| accgtgtggt | cagcgtcctc | accgtcctgc | accaggactg | gctgaatggc | aaggagtaca | 1140 |
| agtgcaaggt | ctccaacaaa | gccctcccag | cccccatcga | gaaaaccatc | tccaaagcca | 1200 |
| aagggcagcc | ccgagaacca | caggtgtaca | ccctgccccc | atcccgggag | gagatgacca | 1260 |
| agaaccaggt | cagcctgacc | tgcctggtca | aaggcttcta | tcccagcgac | atcgccgtgg | 1320 |
| agtgggagag | caatgggcag | ccggagaaca | actacaagac | cacgcctccc | gtgctggact | 1380 |
| ccgacggctc | cttcttcctc | tacagcaagc | tcaccgtgga | caagagcagg | tggcagcagg | 1440 |
| ggaacgtctt | ctcatgctcc | gtgatgcacg | aggctctgca | caaccactac | acgcagaaga | 1500 |
| gcctctccct | gtctccgggt | aaatgagtgc | tagctggcca | gacatgataa | gatacattga | 1560 |
| tgagtttgga | caaaccacaa | ctagaatgca | gtgaaaaaaa | tgctttattt | gtgaaatttg | 1620 |
| tgatgctatt | gctttatttg | taaccattat | aagctgcaat | aaacaagtta | acaacaacaa | 1680 |
| ttgcattcat | tttatgtttc | aggttcaggg | ggaggtgtgg | gaggtttttt | aaagcaagta | 1740 |
| aaacctctac | aaatgtggta | tggaattaat | tctaaaatac | agcatagcaa | aactttaacc | 1800 |
| tccaaatcaa | gcctctactt | gaatcctttt | ctgagggatg | aataaggcat | aggcatcagg | 1860 |
| ggctgttgcc | aatgtgcatt | agctgtttgc | agcctcacct | tctttcatgg | agtttaagat | 1920 |
| atagtgtatt | tcccaaggt | ttgaactagc | tcttcatttc | tttatgtttt | aaatgcactg | 1980 |
| acctcccaca | ttcccttttt | agtaaaatat | tcagaaataa | tttaaataca | tcattgcaat | 2040 |

-continued

```
gaaaataaat gtttttatt aggcagaatc cagatgctca aggcccttca taatatcccc    2100
cagtttagta gttggactta gggaacaaag gaacctttaa tagaaattgg acagcaagaa    2160
agcgagcttc tagcttatcc tcagtcctgc tcctctgcca caaagtgcac gcagttgccg    2220
gccgggtcgc gcagggcgaa ctcccgcccc cacggctgct cgccgatctc ggtcatggcc    2280
ggcccggagg cgtcccggaa gttcgtggac acgacctccg accactcggc gtacagctcg    2340
tccaggccgc gcacccacac ccaggccagg gtgttgtccg gcaccacctg gtcctggacc    2400
gcgctgatga acagggtcac gtcgtcccgg accacaccgg cgaagtcgtc ctccacgaag    2460
tcccgggaga acccgagccg gtcggtccag aactcgaccg ctccggcgac gtcgcgcgcg    2520
gtgagcaccg gaacggcact ggtcaacttg gccatgatgg ctcctcctgt caggagagga    2580
aagagaagaa ggttagtaca attgctatag tgagttgtat tatactatgc agatatacta    2640
tgccaatgat taattgtcaa actagggctg cagggttcat agtgccactt ttcctgcact    2700
gccccatctc ctgcccaccc tttcccaggc atagacagtc agtgacttac caaactcaca    2760
ggagggagaa ggcagaagct tgagacagac ccgcgggacc gccgaactgc gagggacgt    2820 ggctagggcg gcttctttta tggtgcgccg gccctcggag gcagggcgct cggggaggcc    2880
tagcggccaa tctgcggtgg caggaggcgg ggccgaaggc cgtgcctgac caatccggag    2940
cacataggag tctcagcccc ccgccccaaa gcaaggggaa gtcacgcgcc tgtagcgcca    3000
gcgtgttgtg aaatggggc ttgggggggt tggggccctg actagtcaaa caaactccc    3060 attgacgtca atggggtgga gacttggaaa tccccgtgag tcaaaccgct atccacgccc    3120
attgatgtac tgccaaaacc gcatcatcat ggtaatagcg atgactaata cgtagatgta    3180
ctgccaagta ggaaagtccc ataaggtcat gtactgggca taatgccagg cgggccattt    3240
accgtcattg acgtcaatag ggggcgtact tggcatatga tacacttgat gtactgccaa    3300
gtgggcagtt taccgtaaat actccaccca ttgacgtcaa tggaaagtcc ctattggcgt    3360
tactatggga acatacgtca ttattgacgt caatgggcgg gggtcgttgg gcggtcagcc    3420
aggcgggcca tttaccgtaa gttatgtaac gcctgcaggt taattaagaa catgtgagca    3480
aaaggccagc aaaaggccag gaaccgtaaa aaggccgcgt tgctggcgtt tttccatagg    3540
ctccgccccc ctgacgagca tcacaaaaat cgacgctcaa gtcagaggtg gcgaaacccg    3600
acaggactat aaagatacca ggcgtttccc cctggaagct ccctcgtgcg ctctcctgtt    3660
ccgaccctgc cgcttaccgg atacctgtcc gcctttctcc cttcgggaag cgtggcgctt    3720
tctcatagct cacgctgtag gtatctcagt tcggtgtagg tcgttcgctc caagctgggc    3780
tgtgtgcacg aacccccgt tcagcccgac cgctgcgcct tatccggtaa ctatcgtctt    3840
gagtccaacc cggtaagaca cgacttatcg ccactggcag cagccactgg taacaggatt    3900
agcagagcga ggtatgtagg cggtgctaca gagttcttga agtggtggcc taactacggc    3960
tacactagaa gaacagtatt tggtatctgc gctctgctga agccagttac cttcggaaaa    4020
agagttggta gctcttgatc cggcaaacaa accaccgctg gtagcggtgg tttttttgtt    4080
tgcaagcagc agattacgcg cagaaaaaaa ggatctcaag aagatccttt gatcttttct    4140
acggggtctg acgctcagtg aacgaaaac tcacgttaag ggattttggt catggctagt    4200
taattaacat ttaaatcagc ggccgcaata aaatatcttt attttcatta catctgtgtg    4260
ttggtttttt gtgtgaatcg taactaacat acgctctcca tcaaaacaaa acgaaacaaa    4320
acaaactagc aaaataggct gtccccagtg caagtgcagg tgccagaaca tttctctatc    4380
gaa                                                                 4383
```

<210> SEQ ID NO 96
<211> LENGTH: 4383
<212> TYPE: DNA
<213> ORGANISM: Artificial Sequence
<220> FEATURE:
<223> OTHER INFORMATION: pCXCL11(4-73K/H-A)-IgG1Fc

<400> SEQUENCE: 96

| | | | | | |
|---|---|---|---|---|---|
| ggatctgcga | tcgctccggt | gcccgtcagt | gggcagagcg | cacatcgccc | acagtccccg | 60 |
| agaagttggg | gggaggggtc | ggcaattgaa | cgggtgccta | gagaaggtgg | cgcggggtaa | 120 |
| actgggaaag | tgatgtcgtg | tactggctcc | gccttttcc | cgagggtggg | ggagaaccgt | 180 |
| atataagtgc | agtagtcgcc | gtgaacgttc | tttttcgcaa | cgggtttgcc | gccagaacac | 240 |
| agctgaagct | cgaggggct | cgcatctctc | cttcacgcgc | ccgccgccct | acctgaggcc | 300 |
| gccatccacg | ccggttgagt | cgcgttctgc | cgcctcccgc | ctgtggtgcc | tcctgaactg | 360 |
| cgtccgccgt | ctaggtaagt | ttaaagctca | ggtcgagacc | gggcctttgt | ccggcgctcc | 420 |
| cttggagcct | acctagactc | agccggctct | ccacgctttg | cctgaccctg | cttgctcaac | 480 |
| tctacgtctt | tgtttcgttt | tctgttctgc | gccgttacag | atccaagctg | tgaccggcgc | 540 |
| ctacctgaga | tcaccggcga | aggagggcca | ccatgtacag | gatgcaactc | ctgtcttgca | 600 |
| ttgcactaag | tcttgcactt | gtcacgaatt | cgttcaaaag | aggacgctgt | ctttgcatag | 660 |
| gccctggggt | aaaagcagtg | aaagtggcag | atattgaggc | cgcctccata | atgtacccaa | 720 |
| gtaacaactg | tgacaaaata | gaagtgatta | ttaccctggc | agaaaatgcc | ggacaagcat | 780 |
| gcctaaatcc | cgcctcggca | caagcagccc | ttataatcgc | agccgttgaa | gcagccaatt | 840 |
| ttgacaaaac | tcacacatgc | ccaccgtgcc | cagcacctga | actcctgggg | ggaccgtcag | 900 |
| tcttcctctt | cccccaaaa | cccaaggaca | ccctcatgat | ctcccggacc | cctgaggtca | 960 |
| catgcgtggt | ggtggacgtg | agccacgaag | accctgaggt | caagttcaac | tggtacgtgg | 1020 |
| acggcgtgga | ggtgcataat | gccaagacaa | agccgcggga | ggagcagtac | aacagcacgt | 1080 |
| accgtgtggt | cagcgtcctc | accgtcctgc | accaggactg | gctgaatggc | aaggagtaca | 1140 |
| agtgcaaggt | ctccaacaaa | gccctcccag | cccccatcga | gaaaaccatc | tccaaagcca | 1200 |
| aagggcagcc | ccgagaacca | caggtgtaca | ccctgccccc | atcccgggag | gagatgacca | 1260 |
| agaaccaggt | cagcctgacc | tgcctggtca | aaggcttcta | tcccagcgac | atcgccgtgg | 1320 |
| agtgggagag | caatgggcag | ccggagaaca | actacaagac | cacgcctccc | gtgctggact | 1380 |
| ccgacggctc | cttcttcctc | tacagcaagc | tcaccgtgga | caagagcagg | tggcagcagg | 1440 |
| ggaacgtctt | ctcatgctcc | gtgatgcacg | aggctctgca | caaccactac | acgcagaaga | 1500 |
| gcctctccct | gtctccgggt | aaatgagtgc | tagctggcca | gacatgataa | gatacattga | 1560 |
| tgagtttgga | caaaccacaa | ctagaatgca | gtgaaaaaaa | tgctttattt | gtgaaatttg | 1620 |
| tgatgctatt | gctttatttg | taaccattat | aagctgcaat | aaacaagtta | acaacaacaa | 1680 |
| ttgcattcat | tttatgtttc | aggttcaggg | ggaggtgtgg | gaggtttttt | aaagcaagta | 1740 |
| aaacctctac | aaatgtggta | tggaattaat | tctaaaatac | agcatagcaa | aactttaacc | 1800 |
| tccaaatcaa | gcctctactt | gaatccttt | ctgagggatg | aataaggcat | aggcatcagg | 1860 |
| ggctgttgcc | aatgtgcatt | agctgtttgc | agcctcacct | tctttcatgg | agtttaagat | 1920 |
| atagtgtatt | ttcccaaggt | ttgaactagc | tcttcatttc | tttatgtttt | aaatgcactg | 1980 |
| acctcccaca | ttcccttttt | agtaaaatat | tcagaaataa | tttaaataca | tcattgcaat | 2040 |
| gaaaataaat | gttttttatt | aggcagaatc | cagatgctca | aggcccttca | taatatcccc | 2100 |

```
cagtttagta gttggactta gggaacaaag gaacctttaa tagaaattgg acagcaagaa      2160
agcgagcttc tagcttatcc tcagtcctgc tcctctgcca caaagtgcac gcagttgccg      2220
gccgggtcgc gcagggcgaa ctcccgcccc cacggctgct cgccgatctc ggtcatggcc      2280
ggcccggagg cgtcccggaa gttcgtggac acgacctccg accactcggc gtacagctcg      2340
tccaggccgc gcacccacac ccaggccagg gtgttgtccg gcaccacctg gtcctggacc      2400
gcgctgatga acagggtcac gtcgtcccgg accacaccgg cgaagtcgtc ctccacgaag      2460
tcccgggaga acccgagccg gtcggtccag aactcgaccg ctccggcgac gtcgcgcgcg      2520
gtgagcaccg gaacggcact ggtcaacttg gccatgatgg ctcctcctgt caggagagga      2580
aagagaagaa ggttagtaca attgctatag tgagttgtat tatactatgc agatatacta      2640
tgccaatgat taattgtcaa actagggctg cagggttcat agtgccactt ttcctgcact      2700
gccccatctc ctgcccaccc tttcccaggc atagacagtc agtgacttac caaactcaca      2760
ggagggagaa ggcagaagct tgagacagac ccgcgggacc gccgaactgc gaggggacgt      2820
ggctagggcg gcttctttta tggtgcgccg gccctcggag gcagggcgct cggggaggcc      2880
tagcggccaa tctgcggtgg caggaggcgg ggccgaaggc cgtgcctgac caatccggag      2940
cacataggag tctcagcccc ccgccccaaa gcaagggaa gtcacgcgcc tgtagcgcca      3000
gcgtgttgtg aaatggggc ttgggggggt tggggccctg actagtcaaa acaaactccc      3060
attgacgtca atggggtgga gacttggaaa tccccgtgag tcaaaccgct atccacgccc      3120
attgatgtac tgccaaaacc gcatcatcat ggtaatagcg atgactaata cgtagatgta      3180
ctgccaagta ggaaagtccc ataaggtcat gtactgggca taatgccagg cgggccattt      3240
accgtcattg acgtcaatag ggggcgtact tggcatatga tacacttgat gtactgccaa      3300
gtgggcagtt taccgtaaat actccaccca ttgacgtcaa tggaaagtcc ctattggcgt      3360
tactatggga acatacgtca ttattgacgt caatgggcgg gggtcgttgg gcggtcagcc      3420
aggcgggcca tttaccgtaa gttatgtaac gcctgcaggt taattaagaa catgtgagca      3480
aaaggccagc aaaaggccag gaaccgtaaa aaggccgcgt tgctggcgtt tttccatagg      3540
ctccgccccc ctgacgagca tcacaaaaat cgacgctcaa gtcagaggtg gcgaaacccg      3600
acaggactat aaagatacca ggcgtttccc cctggaagct ccctcgtgcg ctctcctgtt      3660
ccgaccctgc cgcttaccgg atacctgtcc gcctttctcc cttcgggaag cgtggcgctt      3720
tctcatagct cacgctgtag gtatctcagt tcggtgtagg tcgttcgctc caagctgggc      3780
tgtgtgcacg aaccccccgt tcagcccgac cgctgcgcct tatccggtaa ctatcgtctt      3840
gagtccaacc cggtaagaca cgacttatcg ccactggcag cagccactgg taacaggatt      3900
agcagagcga ggtatgtagg cggtgctaca gagttcttga agtggtggcc taactacggc      3960
tacactagaa gaacagtatt tggtatctgc gctctgctga agccagttac cttcggaaaa      4020
agagttggta gctcttgatc cggcaaacaa accaccgctg gtagcggtgg tttttttgtt      4080
tgcaagcagc agattacgcg cagaaaaaaa ggatctcaag aagatccttt gatcttttct      4140
acggggtctg acgctcagtg gaacgaaaac tcacgttaag ggattttggt catggctagt      4200
taattaacat ttaaatcagc ggccgcaata aaatatcttt atttcatta catctgtgtg      4260 ttggtttttt gtgtgaatcg taactaacat acgctctcca tcaaaacaaa acgaaacaaa      4320
acaaactagc aaaataggct gtccccagtg caagtgcagg tgccagaaca tttctctatc      4380
gaa                                                                   4383
```

<210> SEQ ID NO 97

<211> LENGTH: 4383
<212> TYPE: DNA
<213> ORGANISM: Artificial Sequence
<220> FEATURE:
<223> OTHER INFORMATION: pCXCL11-IgG4Fc

<400> SEQUENCE: 97

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttttcc cgagggtggg ggagaaccgt    180
atataagtgc agtagtcgcc gtgaacgttc ttttcgcaa cgggtttgcc gccagaacac      240
agctgaagct tcgaggggct cgcatctctc cttcacgcgc ccgccgccct acctgaggcc     300
gccatccacg ccgttgagt cgcgttctgc cgcctcccgc ctgtggtgcc tcctgaactg      360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cgttccccat gttcaaaaga ggacgctgtc    660
tttgcatagg ccctggggta aaagcagtga agtggcaga tattgagaaa gcctccataa     720
tgtacccaag taacaactgt gacaaaatag aagtgattat taccctgaaa gaaaataaag    780
gacaacgatg cctaaatccc aaatcgaagc aagcaaggct tataatcaaa aagttgaaa    840
gaaagaattt tcccccatgc ccatcatgcc cagcacctga gttcctgggg ggaccatcag    900
tcttcctgtt ccccccaaaa cccaaggaca ctctcatgat ctcccggacc cctgaggtca    960
cgtgcgtggt ggtggacgtg agccaggaag accccgaggt ccagttcaac tggtacgtgg   1020
atggcgtgga ggtgcataat gccaagacaa agccgcggga ggagcagttc aacagcacgt   1080
accgtgtggt cagcgtcctc accgtcctgc accaggactg gctgaacggc aaggagtaca   1140
agtgcaaggt ctccaacaaa ggcctcccgt cctccatcga aaaaccatc tccaaagcca   1200
aagggcagcc ccgagagcca caggtgtaca cccctgcccc atcccaggag gagatgacca   1260
agaaccaggt cagcctgacc tgcctggtca aaggcttcta ccccagcgac atcgccgtgg   1320
agtgggagag caatgggcag ccggagaaca actacaagac cacgcctccc gtgctggact   1380
ccgacggctc cttcttcctc tacagcaggc taaccgtgga caagagcagg tggcaggagg   1440
ggaatgtctt ctcatgctcc gtgatgcatg aggctctgca caaccactac acacagaaga   1500
gcctctccct gtctccgggt aaatgagtgc tagctggcca gacatgataa gatacattga   1560
tgagtttgga caaaccacaa ctagaatgca gtgaaaaaaa tgctttattt gtgaaatttg   1620
tgatgctatt gctttatttg taaccattat aagctgcaat aaacaagtta acaacaacaa   1680
ttgcattcat tttatgtttc aggttcaggg ggaggtgtgg gaggtttttt aaagcaagta   1740
aaacctctac aaatgtggta tggaattaat tctaaaatac agcatagcaa aactttaacc   1800
tccaaatcaa gcctctactt gaatccttttt ccgaggcatg aataaggcat aggcatcagg   1860
ggctgttgcc aatgtgcatt agctgtttgc agcctcacct tctttcatgg agtttaagat   1920
atagtgtatt ttcccaaggt ttgaactagc tcttcatttc tttatgtttt aaatgcactg   1980
acctcccaca ttcccttttt agtaaaatat tcagaaataa tttaaataca tcattgcaat   2040
gaaaataaat gttttttatt aggcagaatc cagatgctca aggcccttca taatatcccc   2100
cagtttagta gttggactta gggaacaaag gaacctttaa tagaaattgg acagcaagaa   2160
```

| | |
|---|---|
| agcgagcttc tagcttatcc tcagtcctgc tcctctgcca caaagtgcac gcagttgccg | 2220 |
| gccgggtcgc gcagggcgaa ctcccgcccc cacggctgct cgccgatctc ggtcatggcc | 2280 |
| ggcccggagg cgtcccggaa gttcgtggac acgacctccg accactcggc gtacagctcg | 2340 |
| tccaggccgc gcacccacac ccaggccagg gtgttgtccg gcaccacctg gtcctggacc | 2400 |
| gcgctgatga acagggtcac gtcgtcccgg accacaccgg cgaagtcgtc ctccacgaag | 2460 |
| tcccgggaga cccgagccg gtcggtccag aactcgaccg ctccggcgac gtcgcgcgcg | 2520 |
| gtgagcaccg gaacggcact ggtcaacttg gccatgatgg ctcctcctgt caggagagga | 2580 |
| aagagaagaa ggttagtaca attgctatag tgagttgtat tatactatgc agatatacta | 2640 |
| tgccaatgat taattgtcaa actagggctg cagggttcat agtgccactt ttcctgcact | 2700 |
| gccccatctc ctgcccaccc tttcccaggc atagacagtc agtgacttac caaactcaca | 2760 |
| ggagggagaa ggcagaagct tgagacagac ccgcgggacc gccgaactgc gaggggacgt | 2820 |
| ggctagggcg gcttcttta tggtgcgccg gccctcggag gcagggcgct cggggaggcc | 2880 |
| tagcggccaa tctgcggtgg caggaggcgg ggccgaaggc cgtgcctgac caatccggag | 2940 |
| cacataggag tctcagcccc ccgcccaaa gcaaggggaa gtcacgcgcc tgtagcgcca | 3000 |
| gcgtgttgtg aaatggggc ttgggggggt tgggccctg actagtcaaa acaaactccc | 3060 |
| attgacgtca atggggtgga gacttggaaa tccccgtgag tcaaaccgct atccacgccc | 3120 |
| attgatgtac tgccaaaacc gcatcatcat ggtaatagcg atgactaata cgtagatgta | 3180 |
| ctgccaagta ggaaagtccc ataaggtcat gtactgggca taatgccagg cgggccattt | 3240 |
| accgtcattg acgtcaatag ggggcgtact tggcatatga tacacttgat gtactgccaa | 3300 |
| gtgggcagtt taccgtaaat actccaccca ttgacgtcaa tggaaagtcc ctattggcgt | 3360 |
| tactatggga acatacgtca ttattgacgt caatgggcgg gggtcgttgg gcggtcagcc | 3420 |
| aggcgggcca tttaccgtaa gttatgtaac gcctgcaggt taattaagaa catgtgagca | 3480 |
| aaaggccagc aaaaggccag gaaccgtaaa aaggccgcgt tgctggcgtt tttccatagg | 3540 |
| ctccgccccc ctgacgagca tcacaaaaat cgacgctcaa gtcagaggtg gcgaaacccg | 3600 |
| acaggactat aaagatacca ggcgtttccc cctggaagct ccctcgtgcg ctctcctgtt | 3660 |
| ccgaccctgc cgcttaccgg atacctgtcc gcctttctcc cttcgggaag cgtggcgctt | 3720 |
| tctcatagct cacgctgtag gtatctcagt tcggtgtagg tcgttcgctc caagctgggc | 3780 |
| tgtgtgcacg aaccccccgt tcagcccgac cgctgcgcct tatccggtaa ctatcgtctt | 3840 |
| gagtccaacc cggtaagaca cgacttatcg ccactggcag cagccactgg taacaggatt | 3900 |
| agcagagcga ggtatgtagg cggtgctaca gagttcttga agtggtggcc taactacggc | 3960 |
| tacactagaa gaacagtatt tggtatctgc gctctgctga agccagttac cttcggaaaa | 4020 |
| agagttggta gctcttgatc cggcaaacaa accaccgctg gtagcggtgg ttttttttgtt | 4080 |
| tgcaagcagc agattacgcg cagaaaaaaa ggatctcaag aagatccttt gatcttttct | 4140 |
| acggggtctg acgctcagtg gaacgaaaac tcacgttaag ggattttggt catggctagt | 4200 |
| taattaacat ttaaatcagc ggccgcaata aaatatcttt attttcatta catctgtgtg | 4260 |
| ttggtttttt gtgtgaatcg taactaacat acgctctcca tcaaaacaaa acgaaacaaa | 4320 |
| acaaactagc aaaataggct gtccccagtg caagtgcagg tgccagaaca tttctctatc | 4380 |
| gaa | 4383 |

<210> SEQ ID NO 98
<211> LENGTH: 4374
<212> TYPE: DNA

<213> ORGANISM: Artificial Sequence
<220> FEATURE:
<223> OTHER INFORMATION: pCXCL11(4-73)-IgG4Fc

<400> SEQUENCE: 98

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttttcc cgagggtggg ggagaaccgt    180
atataagtgc agtagtcgcc gtgaacgttc tttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cgttcaaaag aggacgctgt ctttgcatag     660
gccctggggt aaaagcagtg aaagtggcag atattgagaa agcctccata atgtacccaa     720
gtaacaactg tgcaaaaata gaagtgatta ttaccctgaa agaaaataaa ggacaacgat     780
gcctaaatcc caaatcgaag caagcaaggc ttataatcaa aaaagttgaa agaaagaatt     840
ttccccatg cccatcatgc ccagcacctg agttcctggg gggaccatca gtcttcctgt     900
tccccccaaa acccaaggac actctcatga tctcccggac ccctgaggtc acgtgcgtgg     960
tggtggacgt gagccaggaa gaccccgagg tccagttcaa ctggtacgtg gatggcgtgg    1020
aggtgcataa tgccaagaca aagccgcggg aggagcagtt caacagcacg taccgtgtgg    1080
tcagcgtcct caccgtcctg caccaggact ggctgaacgg caaggagtac aagtgcaagg    1140
tctccaacaa aggcctcccg tcctccatcg agaaaaccat ctccaaagcc aaagggcagc    1200
cccgagagcc acaggtgtac accctgcccc catcccagga ggagatgacc aagaaccagg    1260
tcagcctgac ctgcctggtc aaaggcttct accccagcga catcgccgtg gagtgggaga    1320
gcaatgggca gccggagaac aactacaaga ccacgcctcc cgtgctggac tccgacggct    1380
ccttcttcct ctacagcagg ctaaccgtgg acaagagcag gtggcaggag gggaatgtct    1440
tctcatgctc cgtgatgcat gaggctctgc acaaccacta cacacagaag agcctctccc    1500
tgtctccggg taaatgagtg ctagctggcc agacatgata agatacattg atgagtttgg    1560
acaaaccaca actagaatgc agtgaaaaaa atgctttatt tgtgaaattt gtgatgctat    1620
tgctttattt gtaaccatta taagctgcaa taaacaagtt aacaacaaca attgcattca    1680
ttttatgttt caggttcagg gggaggtgtg ggaggttttt taaagcaagt aaaacctcta    1740
caaatgtggt atggaattaa ttctaaaata cagcatagca aactttaac ctccaaatca     1800
agcctctact tgaatccttt tctgagggat gaataaggca taggcatcag ggctgttgc     1860
caatgtgcat tagctgtttg cagcctcacc ttctttcatg gagtttaaga tatagtgtat    1920
tttcccaagg tttgaactag ctcttcattt ctttatgttt taaatgcact gacctcccac    1980
attccctttt tagtaaaata ttcagaaata atttaaatac atcattgcaa tgaaaataaa    2040
tgttttttat taggcagaat ccagatgctc aaggcccttc ataatatccc ccagtttagt    2100
agttggactt agggaacaaa ggaacctttta atagaaattg acagcaaga aagcgagctt     2160
ctagcttatc ctcagtcctg ctcctctgcc acaaagtgca cgcagttgcc ggccgggtcg    2220
```

```
cgcagggcga actcccgccc ccacggctgc tcgccgatct cggtcatggc cggcccggag    2280
gcgtcccgga agttcgtgga cacgacctcc gaccactcgg cgtacagctc gtccaggccg    2340
cgcacccaca cccaggccag ggtgttgtcc ggcaccacct ggtcctggac cgcgctgatg    2400
aacagggtca cgtcgtcccg gaccacaccg gcgaagtcgt cctccacgaa gtcccgggag    2460
aacccgagcc ggtcggtcca gaactcgacc gctccggcga cgtcgcgcgc ggtgagcacc    2520
ggaacggcac tggtcaactt ggccatgatg gctcctcctg tcaggagagg aaagagaaga    2580
aggttagtac aattgctata gtgagttgta ttatactatg cagatatact atgccaatga    2640
ttaattgtca aactagggct gcaggggttca tagtgccact tttcctgcac tgccccatct    2700
cctgcccacc ctttcccagg catagacagt cagtgactta ccaaactcac aggagggaga    2760
aggcagaagc ttgagacaga cccgcgggac cgccgaactg cgaggggacg tggctagggc    2820
ggcttctttt atggtgcgcc ggccctcgga ggcagggcgc tcggggaggc ctagcggcca    2880
atctgcggtg gcaggaggcg gggccgaagg ccgtgcctga ccaatccgga gcacatagga    2940
gtctcagccc cccgccccaa agcaagggga agtcacgcgc ctgtagcgcc agcgtgttgt    3000
gaaatggggg cttgggggggg ttggggcccct gactagtcaa aacaaactcc cattgacgtc    3060
aatggggtgg agacttggaa atccccgtga gtcaaaccgc tatccacgcc cattgatgta    3120
ctgccaaaac cgcatcatca tggtaatagc gatgactaat acgtagatgt actgccaagt    3180
aggaaagtcc cataaggtca tgtactgggc ataatgccag gcgggccatt taccgtcatt    3240
gacgtcaata gggggcgtac ttggcatatg atacacttga tgtactgcca agtgggcagt    3300
ttaccgtaaa tactccaccc attgacgtca atggaaagtc cctattggcg ttactatggg    3360
aacatacgtc attattgacg tcaatgggcg gggtcgttg ggcggtcagc caggcgggcc    3420
atttaccgta agttatgtaa cgcctgcagg ttaattaaga acatgtgagc aaaaggccag    3480
caaaaggcca ggaaccgtaa aaaggccgcg ttgctggcgt ttttccatag gctccgcccc    3540
cctgacgagc atcacaaaaa tcgacgctca agtcagaggt ggcgaaaccc gacaggacta    3600
taaagatacc aggcgtttcc ccctggaagc tccctcgtgc gctctcctgt tccgaccctg    3660
ccgcttaccg gatacctgtc cgcctttctc ccttcgggaa gcgtggcgct ttctcatagc    3720
tcacgctgta ggtatctcag ttcggtgtag tcgttcgct ccaagctggg ctgtgtgcac    3780
gaaccccccg ttcagcccga ccgctgcgcc ttatccggta actatcgtct tgagtccaac    3840
ccggtaagac acgacttatc gccactggca gcagccactg gtaacaggat tagcagagcg    3900
aggtatgtag gcggtgctac agagttcttg aagtggtggc ctaactacgg ctacactaga    3960
agaacagtat ttggtatctg cgctctgctg aagccagtta ccttcggaaa aagagttggt    4020
agctcttgat ccggcaaaca aaccaccgct ggtagcggtg gtttttttgt ttgcaagcag    4080
cagattacgc gcagaaaaaa aggatctcaa gaagatcctt tgatcttttc tacggggtct    4140
gacgctcagt ggaacgaaaa ctcacgttaa gggattttgg tcatggctag ttaattaaca    4200
tttaaatcag cggccgcaat aaaatatctt tattttcatt acatctgtgt gttggttttt    4260
tgtgtgaatc gtaactaaca tacgctctcc atcaaaacaa aacgaaacaa aacaaactag    4320
caaaataggc tgtccccagt gcaagtgcag gtgccagaac atttctctat cgaa          4374
```

<210> SEQ ID NO 99
<211> LENGTH: 4374
<212> TYPE: DNA
<213> ORGANISM: Artificial Sequence
<220> FEATURE:
<223> OTHER INFORMATION: pCXCL11(4-73K/H-A)-IgG4Fc

<400> SEQUENCE: 99

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttttcc cgagggtggg ggagaaccgt    180
atataagtgc agtagtcgcc gtgaacgttc tttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cgttcaaaag aggacgctgt ctttgcatag     660
gccctggggt aaaagcagtg aaagtggcag atattgaggc cgcctccata atgtacccaa     720
gtaacaactg tgacaaaata gaagtgatta ttaccctggc agaaaatgcc ggacaagcat     780
gcctaaatcc cgcctcggca caagcagccc ttataatcgc agccgttgaa gcagccaatt     840
ttcccccatg cccatcatgc ccagcacctg agttcctggg gggaccatca gtcttcctgt     900
tcccccaaa acccaaggac actctcatga tctcccggac ccctgaggtc acgtgcgtgg     960
tggtggacgt gagccaggaa gaccccgagg tccagttcaa ctggtacgtg gatggcgtgg    1020
aggtgcataa tgccaagaca aagccgcggg aggagcagtt caacagcacg taccgtgtgg    1080
tcagcgtcct caccgtcctg caccaggact ggctgaacgg caaggagtac aagtgcaagg    1140
tctccaacaa aggcctcccg tcctccatcg agaaaaccat ctccaaagcc aaagggcagc    1200
cccgagagcc acaggtgtac accctgcccc catcccagga ggagatgacc aagaaccagg    1260
tcagcctgac ctgcctggtc aaaggcttct accccagcga catcgccgtg gagtgggaga    1320
gcaatgggca gccggagaac aactacaaga ccacgcctcc cgtgctggac tccgacggct    1380
ccttcttcct ctacagcagg ctaaccgtgg acaagagcag gtggcaggag gggaatgtct    1440
tctcatgctc cgtgatgcat gaggctctgc acaaccacta cacacagaag agcctctccc    1500
tgtctccggg taaatgagtg ctagctggcc agacatgata agatacattg atgagtttgg    1560
acaaaccaca actagaatgc agtgaaaaaa atgctttatt tgtgaaattt gtgatgctat    1620
tgctttattt gtaaccatta taagctgcaa taaacaagtt aacaacaaca attgcattca    1680
ttttatgttt caggttcagg gggaggtgtg ggaggttttt taaagcaagt aaaacctcta    1740
caaatgtggt atggaattaa ttctaaaata cagcatagca aactttaac ctccaaatca     1800
agcctctact tgaatccttt tctgagggat gaataaggca taggcatcag gggctgttgc    1860
caatgtgcat tagctgtttg cagcctcacc ttctttcatg gagtttaaga tatagtgtat    1920
tttcccaagg tttgaactag ctcttcattt ctttatgttt taaatgcact gacctcccac    1980
attcccttt tagtaaaata ttcagaaata atttaaatac atcattgcaa tgaaaataaa     2040
tgttttttat taggcagaat ccagatgctc aaggcccttc ataatatccc ccagtttagt    2100
agttggactt agggaacaaa ggaaccttta atagaaattg gacagcaaga aagcgagctt    2160
ctagcttatc ctcagtcctg ctcctctgcc acaaagtgca cgcagttgcc ggccgggtcg    2220
cgcagggcga actcccgccc ccacggctgc tcgccgatct cggtcatggc cggcccggag    2280
gcgtcccgga agttcgtgga cacgacctcc gaccactcgg cgtacagctc gtccaggccg    2340
```

```
cgcacccaca cccaggccag ggtgttgtcc ggcaccacct ggtcctggac cgcgctgatg      2400
aacagggtca cgtcgtcccg gaccacaccg gcgaagtcgt cctccacgaa gtcccgggag      2460
aacccgagcc ggtcggtcca gaactcgacc gctccggcga cgtcgcgcgc ggtgagcacc      2520
ggaacggcac tggtcaactt ggccatgatg gctcctcctg tcaggagagg aaagagaaga      2580
aggttagtac aattgctata gtgagttgta ttatactatg cagatatact atgccaatga      2640
ttaattgtca aactagggct gcaggggttca tagtgccact tttcctgcac tgccccatct      2700
cctgcccacc ctttcccagg catagacagt cagtgactta ccaaactcac aggagggaga      2760
aggcagaagc ttgagacaga cccgcgggac cgccgaactg cgaggggacg tggctagggc      2820
ggcttctttt atggtgcgcc ggccctcgga ggcagggcgc tcggggaggc ctagcggcca      2880
atctgcggtg gcaggaggcg gggccgaagg ccgtgcctga ccaatccgga gcacatagga      2940
gtctcagccc cccgccccaa agcaagggga agtcacgcgc ctgtagcgcc agcgtgttgt      3000
gaaatggggg cttgggggg ttggggccct gactagtcaa aacaaactcc cattgacgtc      3060
aatggggtgg agacttggaa atccccgtga gtcaaaccgc tatccacgcc cattgatgta      3120
ctgccaaaac cgcatcatca tggtaatagc gatgactaat acgtagatgt actgccaagt      3180
aggaaagtcc cataaggtca tgtactgggc ataatgccag gcgggccatt taccgtcatt      3240
gacgtcaata gggggcgtac ttggcatatg atacacttga tgtactgcca agtgggcagt      3300
ttaccgtaaa tactccaccc attgacgtca atggaaagtc cctattggcg ttactatggg      3360
aacatacgtc attattgacg tcaatgggcg gggtcgttg gcggtcagc caggcgggcc      3420 atttaccgta agttatgtaa cgcctgcagg ttaattaaga acatgtgagc aaaaggccag      3480
caaaaggcca ggaaccgtaa aaaggccgcg ttgctggcgt ttttccatag gctccgcccc      3540
cctgacgagc atcacaaaaa tcgacgctca agtcagaggt ggcgaaaccc gacaggacta      3600
taaagatacc aggcgtttcc ccctggaagc tccctcgtgc gctctcctgt tccgaccctg      3660
ccgcttaccg gatacctgtc cgcctttctc ccttcgggaa gcgtggcgct ttctcatagc      3720
tcacgctgta ggtatctcag ttcggtgtag tcgttcgct ccaagctggg ctgtgtgcac      3780
gaaccccccg ttcagcccga ccgctgcgcc ttatccggta actatcgtct tgagtccaac      3840
ccggtaagac acgacttatc gccactggca gcagccactg gtaacaggat tagcagagcg      3900
aggtatgtag gcggtgctac agagttcttg aagtggtggc ctaactacgg ctacactaga      3960
agaacagtat ttggtatctg cgctctgctg aagccagtta ccttcggaaa aagagttggt      4020
agctcttgat ccggcaaaca aaccaccgct ggtagcggtg gtttttttgt ttgcaagcag      4080
cagattacgc gcagaaaaaa aggatctcaa gaagatcctt tgatcttttc tacggggtct      4140
gacgctcagt ggaacgaaaa ctcacgttaa gggattttgg tcatggctag ttaattaaca      4200
tttaaatcag cggccgcaat aaaatatctt tattttcatt acatctgtgt gttggttttt      4260
tgtgtgaatc gtaactaaca tacgctctcc atcaaaacaa aacgaaacaa aacaaactag      4320
caaaataggc tgtccccagt gcaagtgcag gtgccagaac atttctctat cgaa           4374

<210> SEQ ID NO 100
<211> LENGTH: 4434
<212> TYPE: DNA
<213> ORGANISM: Artificial Sequence
<220> FEATURE:
<223> OTHER INFORMATION: pCXCL13-IgG1Fc

<400> SEQUENCE: 100
ggatctgcga tcgctccggt gcccgtcagt gggcagagcg cacatcgccc acagtccccg       60
```

```
agaagttggg gggaggggtc ggcaattgaa cgggtgccta gagaaggtgg cgcggggtaa    120
actgggaaag tgatgtcgtg tactggctcc gccttttcc  cgagggtggg ggagaaccgt    180
atataagtgc agtagtcgcc gtgaacgttc tttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cggttctgga ggtctattac acaagcttga    660
ggtgtagatg tgtccaagag agctcagtct ttatccctag acgcttcatt gatcgaattc    720
aaatcttgcc ccgtgggaat ggttgtccaa gaaagaaat  catagtctgg aagaagaaca    780
agtcaattgt gtgtgtggac cctcaagctg aatggataca agaatgatg  gaagtattga    840 gaaaagaag  ttcttcaact ctaccagttc cagtgtttaa gagaaagatt cccgacaaaa    900
ctcacacatg cccaccgtgc ccagcacctg aactcctggg gggaccgtca gtcttcctct    960 tcccccaaa  acccaaggac accctcatga tctcccggac ccctgaggtc acatgcgtgg   1020
tggtggacgt gagccacgaa gaccctgagg tcaagttcaa ctggtacgtg gacggcgtgg   1080
aggtgcataa tgccaagaca aagccgcggg aggagcagta caacagcacg taccgtgtgg   1140
tcagcgtcct caccgtcctg caccaggact ggctgaatgg caaggagtac aagtgcaagg   1200
tctccaacaa agccctccca gcccccatcg agaaaaccat ctccaaagcc aaagggcagc   1260
cccgagaacc acaggtgtac accctgcccc catcccggga ggagatgacc aagaaccagg   1320
tcagcctgac ctgcctggtc aaaggcttct atcccagcga catcgccgtg gagtgggaga   1380
gcaatgggca gccggagaac aactacaaga ccacgcctcc cgtgctggac tccgacggct   1440
ccttcttcct ctacagcaag ctcaccgtgg acaagagcag gtggcagcag gggaacgtct   1500
tctcatgctc cgtgatgcac gaggctctgc acaaccacta cacgcagaag agcctctccc   1560
tgtctccggg taaatgagtg ctagctggcc agacatgata agatacattg atgagtttgg   1620
acaaaccaca actagaatgc agtgaaaaaa atgctttatt tgtgaaattt gtgatgctat   1680
tgctttattt gtaaccatta taagctgcaa taaacaagtt aacaacaaca attgcattca   1740
ttttatgttt caggttcagg gggaggtgtg ggaggttttt taaagcaagt aaaacctcta   1800
caaatgtggt atggaattaa ttctaaaata cagcatagca aactttaac  ctccaaatca   1860 agcctctact tgaatccttt tctgagggat gaataaggca taggcatcag gggctgttgc   1920
caatgtgcat tagctgtttg cagcctcacc ttctttcatg gagtttaaga tatagtgtat   1980
tttcccaagg tttgaactag ctcttcattt ctttatgttt taaatgcact gacctcccac   2040
attccctttt tagtaaaata ttcagaaata atttaaatac atcattgcaa tgaaaataaa   2100
tgttttttat taggcagaat ccagatgctc aaggcccttc ataatatccc ccagtttagt   2160
agttggactt agggaacaaa ggaaccttta atagaaattg acagcaaga  aagcgagctt   2220 ctagcttatc ctcagtcctg ctcctctgcc acaaagtgca cgcagttgcc ggccgggtcg   2280
cgcagggcga actcccgccc ccacggctgc tcgccgatct cggtcatggc cggccggag   2340 gcgtccggga agttcgtgga cacgacctcc gaccactcgg cgtacagctc gtccaggccg   2400
cgcacccaca cccaggccag ggtgttgtcc ggcaccacct ggtcctggac cgcgctgatg   2460
```

```
aacagggtca cgtcgtcccg gaccacaccg gcgaagtcgt cctccacgaa gtcccgggag   2520
aacccgagcc ggtcggtcca gaactcgacc gctccggcga cgtcgcgcgc ggtgagcacc   2580
ggaacggcac tggtcaactt ggccatgatg gctcctcctg tcaggagagg aaagagaaga   2640
aggttagtac aattgctata gtgagttgta ttatactatg cagatatact atgccaatga   2700
ttaattgtca aactagggct gcagggttca tagtgccact tttcctgcac tgccccatct   2760
cctgcccacc ctttcccagg catagacagt cagtgactta ccaaactcac aggagggaga   2820
aggcagaagc ttgagacaga cccgcgggac cgccgaactg cgaggggacg tggctagggc   2880
ggcttctttt atggtgcgcc ggcctcgga ggcagggcgc tcggggaggc ctagcggcca    2940
atctgcggtg gcaggaggcg gggccgaagg ccgtgcctga ccaatccgga gcacatagga   3000
gtctcagccc cccgccccaa agcaagggga agtcacgcgc ctgtagcgcc agcgtgttgt   3060
gaaatggggg cttgggggg ttggggccct gactagtcaa acaaactcc cattgacgtc     3120 aatgggtgg agacttggaa atccccgtga gtcaaaccgc tatccacgcc cattgatgta    3180
ctgccaaaac cgcatcatca tggtaatagc gatgactaat acgtagatgt actgccaagt   3240
aggaaagtcc cataaggtca tgtactgggc ataatgccag gcgggccatt taccgtcatt   3300
gacgtcaata gggggcgtac ttggcatatg atacacttga tgtactgcca agtgggcagt   3360
ttaccgtaaa tactccaccc attgacgtca atggaaagtc cctattggcg ttactatggg   3420
aacatacgtc attattgacg tcaatgggcg ggggtcgttg ggcggtcagc caggcgggcc   3480
atttaccgta agttatgtaa cgcctgcagg ttaattaaga acatgtgagc aaaaggccag   3540
caaaaggcca ggaaccgtaa aaaggccgcg ttgctggcgt ttttccatag gctccgcccc   3600
cctgacgagc atcacaaaaa tcgacgctca agtcagaggt ggcgaaaccc gacaggacta   3660
taaagatacc aggcgtttcc ccctggaagc tccctcgtgc gctctcctgt tccgaccctg   3720
ccgcttaccg gatacctgtc cgcctttctc ccttcgggaa gcgtggcgct ttctcatagc   3780
tcacgctgta ggtatctcag ttcggtgtag gtcgttcgct ccaagctggg ctgtgtgcac   3840 gaacccccg ttcagcccga ccgctgcgcc ttatccggta actatcgtct tgagtccaac    3900
ccggtaagac acgacttatc gccactggca gcagccactg gtaacaggat tagcagagcg   3960
aggtatgtag gcggtgctac agagttcttg aagtggtggc ctaactacgg ctacactaga   4020
agaacagtat ttggtatctg cgctctgctg aagccagtta ccttcggaaa aagagttggt   4080
agctcttgat ccggcaaaca aaccaccgct ggtagcggtg gtttttttgt ttgcaagcag   4140
cagattacgc gcagaaaaaa aggatctcaa gaagatcctt tgatcttttc tacgggtct    4200 gacgctcagt ggaacgaaaa ctcacgttaa gggattttgg tcatggctag ttaattaaca   4260
tttaaatcag cggccgcaat aaaatatctt tattttcatt acatctgtgt gttggttttt   4320
tgtgtgaatc gtaactaaca tacgctctcc atcaaaacaa aacgaaacaa aacaaactag   4380
caaaataggc tgtccccagt gcaagtgcag gtgccagaac atttctctat cgaa          4434
```

<210> SEQ ID NO 101
<211> LENGTH: 4428
<212> TYPE: DNA
<213> ORGANISM: Artificial Sequence
<220> FEATURE:
<223> OTHER INFORMATION: pCXCL13(3-87)-IgG1Fc

<400> SEQUENCE: 101

```
ggatctgcga tcgctccggt gcccgtcagt gggcagagcg cacatcgccc acagtccccg     60
agaagttggg gggaggggtc ggcaattgaa cgggtgccta gagaaggtgg cgcggggtaa   120
```

```
actgggaaag tgatgtcgtg tactggctcc gccttttttcc cgagggtggg ggagaaccgt    180
atataagtgc agtagtcgcc gtgaacgttc tttttcgcaa cgggtttgcc gccagaacac    240
agctgaagct tcgaggggct cgcatctctc cttcacgcgc ccgccgccct acctgaggcc    300
gccatccacg ccgttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cggaggtcta ttacacaagc ttgaggtgta    660
gatgtgtcca agagagctca gtctttatcc ctagacgctt cattgatcga attcaaatct    720
tgccccgtgg gaatggttgt ccaagaaaag aaatcatagt ctggaagaag aacaagtcaa    780
ttgtgtgtgt ggaccctcaa gctgaatgga tacaaagaat gatggaagta ttgagaaaaa    840
gaagttcttc aactctacca gttccagtgt ttaagagaaa gattcccgac aaaactcaca    900
catgcccacc gtgcccagca cctgaactcc tggggggacc gtcagtcttc ctcttccccc    960
caaaacccaa ggacaccctc atgatctccc ggacccctga ggtcacatgc gtggtggtgg   1020
acgtgagcca cgaagaccct gaggtcaagt tcaactggta cgtggacggc gtggaggtgc   1080
ataatgccaa gacaaagccg cgggaggagc agtacaacag cacgtaccgt gtggtcagcg   1140
tcctcaccgt cctgcaccag gactggctga atggcaagga gtacaagtgc aaggtctcca   1200
acaaagccct cccagccccc atcgagaaaa ccatctccaa agccaaaggg cagccccgag   1260
aaccacaggt gtacaccctg cccccatccc gggaggagat gaccaagaac caggtcagcc   1320
tgacctgcct ggtcaaaggc ttctatccca gcgacatcgc cgtggagtgg gagagcaatg   1380
ggcagccgga gaacaactac aagaccacgc ctcccgtgct ggactccgac ggctccttct   1440
tcctctacag caagctcacc gtggacaaga gcaggtggca gcaggggaac gtcttctcat   1500
gctccgtgat gcacgaggct ctgcacaacc actacacgca gaagagcctc tccctgtctc   1560
cgggtaaatg agtgctagct ggccagacat gataagatac attgatgagt ttggacaaac   1620
cacaactaga atgcagtgaa aaaaatgctt tatttgtgaa atttgtgatg ctattgcttt   1680
atttgtaacc attataagct gcaataaaca agttaacaac aacaattgca ttcattttat   1740
gtttcaggtt cagggggagg tgtgggaggt tttttaaagc aagtaaaacc tctacaaatg   1800
tggtatggaa ttaattctaa aatacagcat agcaaaactt taacctccaa atcaagcctc   1860
tacttgaatc cttttctgag ggatgaataa ggcataggca tcagggctg ttgccaatgt   1920
gcattagctg tttgcagcct caccttcttt catggagttt aagatatagt gtattttccc   1980
aaggtttgaa ctagctcttc atttctttat gttttaaatg cactgacctc ccacattccc   2040
tttttagtaa atattcaga aataatttaa atacatcatt gcaatgaaaa taatgttttt   2100
ttattaggca gaatccagat gctcaaggcc cttcataata tcccccagtt tagtagttgg   2160
acttagggaa caaaggaacc tttaatagaa attggacagc aagaaagcga gcttctagct   2220
tatcctcagt cctgctcctc tgccacaaag tgcacgcagt tgccggccgg tcgcgcagg   2280
gcgaactccc gcccccacgg ctgctcgccg atctcggtca tggccggccc ggaggcgtcc   2340
cggaagttcg tggacacgac ctccgaccac tcggcgtaca gctcgtccag gccgcgcacc   2400
cacacccagg ccagggtgtt gtccggcacc acctggtcct ggaccgcgct gatgaacagg   2460
gtcacgtcgt cccggaccac accggcgaag tcgtcctcca cgaagtcccg ggagaacccg   2520
```

```
agccggtcgg tccagaactc gaccgctccg gcgacgtcgc gcgcggtgag caccggaacg    2580
gcactggtca acttggccat gatggctcct cctgtcagga gaggaaagag aagaaggtta    2640
gtacaattgc tatagtgagt tgtattatac tatgcagata tactatgcca atgattaatt    2700
gtcaaactag ggctgcaggg ttcatagtgc cacttttcct gcactgcccc atctcctgcc    2760 cacccttctcc caggcataga cagtcagtga cttaccaaac tcacaggagg gagaaggcag    2820
aagcttgaga cagacccgcg ggaccgccga actgcgaggg gacgtggcta gggcggcttc    2880 tttttatggtg cgccggccct cggaggcagg gcgctcgggg aggcctagcg gccaatctgc    2940
ggtggcagga ggcggggccg aaggccgtgc ctgaccaatc cggagcacat aggagtctca    3000
gccccccgcc ccaaagcaag gggaagtcac gcgcctgtag cgccagcgtg ttgtgaaatg    3060
ggggcttggg ggggttgggg ccctgactag tcaaaacaaa ctcccattga cgtcaatggg    3120
gtggagactt ggaaatcccc gtgagtcaaa ccgctatcca cgcccattga tgtactgcca    3180
aaaccgcatc atcatggtaa tagcgatgac taatacgtag atgtactgcc aagtaggaaa    3240
gtcccataag gtcatgtact gggcataatg ccaggcgggc catttaccgt cattgacgtc    3300 aataggggc gtacttggca tatgatacac ttgatgtact gccaagtggg cagtttaccg    3360
taaatactcc acccattgac gtcaatggaa agtccctatt ggcgttacta tgggaacata    3420
cgtcattatt gacgtcaatg gcgggggtc gttgggcggt cagccaggcg ggccatttac    3480
cgtaagttat gtaacgcctg caggttaatt aagaacatgt gagcaaaagg ccagcaaaag    3540
gccaggaacc gtaaaaaggc cgcgttgctg gcgtttttcc ataggctccg ccccctgac    3600 gagcatcaca aaaatcgacg ctcaagtcag aggtggcgaa acccgacagg actataaaga    3660
taccaggcgt ttccccctgg aagctccctc gtgcgctctc ctgttccgac cctgccgctt    3720
accggatacc tgtccgcctt tctcccttcg ggaagcgtgg cgctttctca tagctcacgc    3780
tgtaggtatc tcagttcggt gtaggtcgtt cgctccaagc tgggctgtgt gcacgaaccc    3840
cccgttcagc ccgaccgctg cgccttatcc ggtaactatc gtcttgagtc caacccggta    3900
agacacgact tatcgccact ggcagcagcc actggtaaca ggattagcag agcgaggtat    3960
gtaggcggtg ctacagagtt cttgaagtgg tggcctaact acggctacac tagaagaaca    4020
gtatttggta tctgcgctct gctgaagcca gttaccttcg gaaaaagagt tggtagctct    4080
tgatccggca aacaaaccac cgctggtagc ggtggttttt ttgtttgcaa gcagcagatt    4140
acgcgcagaa aaaaggatc tcaagaagat cctttgatct tttctacggg gtctgacgct    4200
cagtggaacg aaaactcacg ttaagggatt ttggtcatgg ctagttaatt aacatttaaa    4260
tcagcggccg caataaaata tctttatttt cattacatct gtgtgttggt ttttgtgtg    4320 aatcgtaact aacatacgct ctccatcaaa acaaaacgaa acaaaacaaa ctagcaaaat    4380
aggctgtccc cagtgcaagt gcaggtgcca gaacatttct ctatcgaa                4428
```

<210> SEQ ID NO 102
<211> LENGTH: 4428
<212> TYPE: DNA
<213> ORGANISM: Artificial Sequence
<220> FEATURE:
<223> OTHER INFORMATION: pCXCL13(3-87K/H-A)-IgG1Fc

<400> SEQUENCE: 102

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gcctttttcc cgagggtggg ggagaaccgt     180
```

```
atataagtgc agtagtcgcc gtgaacgttc ttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cggaggtcta ttacacaagc ttgaggtgta    660
gatgtgtcca agagagctca gtctttatcc ctagacgctt cattgatgcc attcaaatct    720
tgccccgtgg gaatggttgt ccaagaaaag aaatcatagt ctgggctgcg aacgcttcaa    780
ttgtgtgtgt ggaccctcaa gctgaatgga tacaagccat gatggaagta ttggctgcgg    840
ctagttcttc aactctacca gttccagtgt ttgccgctgc gattcccgac aaaactcaca    900
catgcccacc gtgcccagca cctgaactcc tgggggggacc gtcagtcttc ctcttccccc    960
caaaacccaa ggacaccctc atgatctccc ggacccctga ggtcacatgc gtggtggtgg   1020
acgtgagcca cgaagaccct gaggtcaagt tcaactggta cgtggacggc gtggaggtgc   1080
ataatgccaa gacaaagccg cgggaggagc agtacaacag cacgtaccgt gtggtcagcg   1140
tcctcaccgt cctgcaccag gactggctga atggcaagga gtacaagtgc aaggtctcca   1200
acaaagccct cccagccccc atcgagaaaa ccatctccaa agccaaaggg cagccccgag   1260
aaccacaggt gtacaccctg cccccatccc gggaggagat gaccaagaac caggtcagcc   1320
tgacctgcct ggtcaaaggc ttctatccca gcgacatcgc cgtggagtgg gagagcaatg   1380
ggcagccgga gaacaactac aagaccacgc ctcccgtgct ggactccgac ggctccttct   1440
tcctctacag caagctcacc gtggacaaga gcaggtggca gcaggggaac gtcttctcat   1500
gctccgtgat gcacgaggct ctgcacaacc actacacgca gaagagcctc tccctgtctc   1560
cgggtaaatg agtgctagct ggccagacat gataagatac attgatgagt ttggacaaac   1620
cacaactaga atgcagtgaa aaaaatgctt tatttgtgaa atttgtgatg ctattgcttt   1680
atttgtaacc attataagct gcaataaaca agttaacaac aacaattgca ttcattttat   1740
gtttcaggtt cagggggagg tgtgggaggt tttttaaagc aagtaaaacc tctacaaatg   1800
tggtatggaa ttaattctaa aatacagcat agcaaaactt taacctccaa atcaagcctc   1860
tacttgaatc ctttttctgag ggatgaataa ggcataggca tcaggggctg ttgccaatgt   1920
gcattagctg tttgcagcct caccttcttt catggagttt aagatatagt gtattttccc   1980
aaggtttgaa ctagctcttc atttctttat gttttaaatg cactgacctc ccacattccc   2040
tttttagtaa atattcaga ataatttaa atacatcatt gcaatgaaaa taaatgtttt   2100
ttattaggca gaatccagat gctcaaggcc cttcataata tcccccagtt tagtagttgg   2160
acttagggaa caaaggaacc tttaatagaa attggacagc aagaaagcga gcttctagct   2220
tatcctcagt cctgctcctc tgccacaaag tgcacgcagt gccggccgg tcgcgcagg    2280 gcgaactccc gcccccacgg ctgctcgccg atctcggtca tggccggccc ggaggcgtcc   2340
cggaagttcg tggacacgac ctccgaccac tcggcgtaca gctcgtccag gccgcgcacc   2400
cacacccagg ccagggtgtt gtccggcacc acctggtcct ggaccgcgct gatgaacagg   2460
gtcacgtcgt cccggaccac accggcgaag tcgtcctcca cgaagtcccg ggagaacccg   2520
agccggtcgg tccagaactc gaccgctccg gcgacgtcgc gcgcggtgag caccggaacg   2580
```

| | |
|---|---|
| gcactggtca acttggccat gatggctcct cctgtcagga gaggaaagag aagaaggtta | 2640 |
| gtacaattgc tatagtgagt tgtattatac tatgcagata tactatgcca atgattaatt | 2700 |
| gtcaaactag gctgcaggg ttcatagtgc cacttttcct gcactgcccc atctcctgcc | 2760 |
| cacccttttcc caggcataga cagtcagtga cttaccaaac tcacaggagg gagaaggcag | 2820 |
| aagcttgaga cagacccgcg ggaccgccga actgcgaggg gacgtggcta gggcggcttc | 2880 |
| tttttatggtg cgccggccct cggaggcagg gcgctcgggg aggcctagcg gccaatctgc | 2940 |
| ggtggcagga ggcggggccg aaggccgtgc ctgaccaatc cggagcacat aggagtctca | 3000 |
| gcccccccgcc ccaaagcaag gggaagtcac gcgcctgtag cgccagcgtg ttgtgaaatg | 3060 |
| ggggcttggg ggggttgggg ccctgactag tcaaaacaaa ctcccattga cgtcaatggg | 3120 |
| gtggagactt ggaaatcccc gtgagtcaaa ccgctatcca cgcccattga tgtactgcca | 3180 |
| aaaccgcatc atcatggtaa tagcgatgac taatacgtag atgtactgcc aagtaggaaa | 3240 |
| gtcccataag gtcatgtact gggcataatg ccaggcgggc catttaccgt cattgacgtc | 3300 |
| aataggggc gtacttggca tatgatacac ttgatgtact gccaagtggg cagtttaccg | 3360 |
| taaatactcc acccattgac gtcaatggaa agtccctatt ggcgttacta tgggaacata | 3420 |
| cgtcattatt gacgtcaatg ggcggggtc gttgggcggt cagccaggcg ggccatttac | 3480 |
| cgtaagttat gtaacgcctg caggttaatt aagaacatgt gagcaaaagg ccagcaaaag | 3540 |
| gccaggaacc gtaaaaaggc cgcgttgctg gcgtttttcc ataggctccg cccccctgac | 3600 |
| gagcatcaca aaaatcgacg ctcaagtcag aggtggcgaa acccgacagg actataaaga | 3660 |
| taccaggcgt ttccccctgg aagctccctc gtgcgctctc ctgttccgac cctgccgctt | 3720 |
| accggatacc tgtccgcctt tctcccttcg ggaagcgtgg cgctttctca tagctcacgc | 3780 |
| tgtaggtatc tcagttcggt gtaggtcgtt cgctccaagc tgggctgtgt gcacgaaccc | 3840 |
| cccgttcagc ccgaccgctg cgccttatcc ggtaactatc gtcttgagtc caacccggta | 3900 |
| agacacgact tatcgccact ggcagcagcc actggtaaca ggattagcag agcgaggtat | 3960 |
| gtaggcggtg ctacagagtt cttgaagtgg tggcctaact acggctacac tagaagaaca | 4020 |
| gtatttggta tctgcgctct gctgaagcca gttaccttcg gaaaaagagt tggtagctct | 4080 |
| tgatccggca acaaaccac cgctggtagc ggtggttttt ttgtttgcaa gcagcagatt | 4140 |
| acgcgcagaa aaaaggatc tcaagaagat cctttgatct tttctacggg gtctgacgct | 4200 |
| cagtggaacg aaaactcacg ttaagggatt ttggtcatgg ctagttaatt aacatttaaa | 4260 |
| tcagcggccg caataaaata tctttatttt cattacatct gtgtgttggt tttttgtgtg | 4320 |
| aatcgtaact aacatacgct ctccatcaaa acaaaacgaa acaaaacaaa ctagcaaaat | 4380 |
| aggctgtccc cagtgcaagt gcaggtgcca gaacatttct ctatcgaa | 4428 |

<210> SEQ ID NO 103
<211> LENGTH: 4425
<212> TYPE: DNA
<213> ORGANISM: Artificial Sequence
<220> FEATURE:
<223> OTHER INFORMATION: pCXCL13-IgG4Fc

<400> SEQUENCE: 103

| | |
|---|---|
| ggatctgcga tcgctccggt gcccgtcagt gggcagagcg cacatcgccc acagtccccg | 60 |
| agaagtttggg gggaggggtc ggcaattgaa cgggtgccta gagaaggtgg cgcggggtaa | 120 |
| actgggaaag tgatgtcgtg tactggctcc gcctttttcc cgagggtggg ggagaaccgt | 180 |
| atataagtgc agtagtcgcc gtgaacgttc tttttcgcaa cgggtttgcc gccagaacac | 240 |

-continued

| | |
|---|---|
| agctgaagct tcgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggcga aggagggcca ccatgtacag gatgcaactc ctgtcttgca | 600 |
| ttgcactaag tcttgcactt gtcacgaatt cggttctgga ggtctattac acaagcttga | 660 |
| ggtgtagatg tgtccaagag agctcagtct ttatccctag acgcttcatt gatcgaattc | 720 |
| aaatcttgcc ccgtgggaat ggttgtccaa gaaagaaat catagtctgg aagaagaaca | 780 |
| agtcaattgt gtgtgtggac cctcaagctg aatggataca agaatgatg gaagtattga | 840 |
| gaaaagaag ttcttcaact ctaccagttc cagtgtttaa gagaaagatt cccccccat | 900 |
| gcccatcatg cccagcacct gagttcctgg ggggaccatc agtcttcctg ttcccccaa | 960 |
| aacccaagga cactctcatg atctcccgga cccctgaggt cacgtgcgtg gtggtggacg | 1020 |
| tgagccagga agaccccgag gtccagttca actggtacgt ggatggcgtg gaggtgcata | 1080 |
| atgccaagac aaagccgcgg gaggagcagt tcaacagcac gtaccgtgtg gtcagcgtcc | 1140 |
| tcaccgtcct gcaccaggac tggctgaacg gcaaggagta caagtgcaag gtctccaaca | 1200 |
| aaggcctccc gtcctccatc gagaaaacca tctccaaagc caagggcag ccccgagagc | 1260 |
| cacaggtgta caccctgccc ccatcccagg aggagatgac caagaaccag gtcagcctga | 1320 |
| cctgcctggt caaaggcttc taccccagcg acatcgccgt ggagtgggag agcaatgggc | 1380 |
| agccggagaa caactacaag accacgcctc ccgtgctgga ctccgacggc tccttcttcc | 1440 |
| tctacagcag gctaaccgtg gacaagagca ggtggcagga gggaatgtc ttctcatgct | 1500 |
| ccgtgatgca tgaggctctg cacaaccact acacacagaa gagcctctcc ctgtctccgg | 1560 |
| gtaaatgagt gctagctggc cagacatgat aagatacatt gatgagtttg gacaaaccac | 1620 |
| aactagaatg cagtgaaaaa aatgctttat ttgtgaaatt tgtgatgcta ttgctttatt | 1680 |
| tgtaaccatt ataagctgca ataaacaagt taacaacaac aattgcattc attttatgtt | 1740 |
| tcaggttcag ggggaggtgt gggaggtttt ttaaagcaag taaaacctct acaaatgtgg | 1800 |
| tatgaatta attctaaaat acagcatagc aaaactttaa cctccaaatc aagcctctac | 1860 |
| ttgaatcctt ttctgaggga tgaataaggc ataggcatca ggggctgttg ccaatgtgca | 1920 |
| ttagctgttt gcagcctcac cttctttcat ggagtttaag atatagtgta ttttcccaag | 1980 |
| gtttgaacta gctctcatt tctttatgtt ttaaatgcac tgacctccca cattcccttt | 2040 |
| ttagtaaaat attcagaaat aatttaaata catcattgca atgaaaataa atgtttttta | 2100 |
| ttaggcagaa tccagatgct caaggccctt cataatatcc cccagtttag tagttggact | 2160 |
| tagggaacaa aggaaccttt aatagaaatt ggacagcaag aaagcgagct tctagcttat | 2220 |
| cctcagtcct gctcctctgc cacaaagtgc acgcagttgc cggccgggtc gcgcagggcg | 2280 |
| aactcccgcc cccacggctg ctcgccgatc tcggtcatgg ccggcccgga ggcgtcccgg | 2340 |
| aagttcgtgg acacgacctc cgaccactcg gcgtacagct cgtccaggcc gcgcacccac | 2400 |
| acccaggcca gggtgttgtc cggcaccacc tggtcctgga ccgcgctgat gaacagggtc | 2460 |
| acgtcgtccc ggaccacacc ggcgaagtcg tcctccacga agtcccggga gaacccgagc | 2520 |
| cggtcggtcc agaactcgac cgctccggcg acgtcgcgcg cggtgagcac cggaacggca | 2580 |
| ctggtcaact ggccatgat ggctcctcct gtcaggagag gaaagagaag aaggttagta | 2640 |

| | |
|---|---|
| caattgctat agtgagttgt attatactat gcagatatac tatgccaatg attaattgtc | 2700 |
| aaactagggc tgcagggttc atagtgccac ttttcctgca ctgccccatc tcctgcccac | 2760 |
| cctttcccag gcatagacag tcagtgactt accaaactca caggagggag aaggcagaag | 2820 |
| cttgagacag acccgcggga ccgccgaact gcgaggggac gtggctaggg cggcttcttt | 2880 |
| tatggtgcgc cggccctcgg aggcagggcg ctcggggagg cctagcggcc aatctgcggt | 2940 |
| ggcaggaggc ggggccgaag gccgtgcctg accaatccgg agcacatagg agtctcagcc | 3000 |
| ccccgcccca agcaaggggg aagtcacgcg cctgtagcgc cagcgtgttg tgaaatgggg | 3060 |
| gcttgggggg gttggggccc tgactagtca aaacaaactc ccattgacgt caatggggtg | 3120 |
| gagacttgga atccccgtg agtcaaaccg ctatccacgc ccattgatgt actgccaaaa | 3180 |
| ccgcatcatc atggtaatag cgatgactaa tacgtagatg tactgccaag taggaaagtc | 3240 |
| ccataaggtc atgtactggg cataatgcca ggcgggccat ttaccgtcat tgacgtcaat | 3300 |
| aggggggcgta cttggcatat gatacacttg atgtactgcc aagtgggcag tttaccgtaa | 3360 |
| atactccacc cattgacgtc aatggaaagt ccctattggc gttactatgg aacatacgt | 3420 |
| cattattgac gtcaatgggc gggggtcgtt gggcggtcag ccaggcgggc catttaccgt | 3480 |
| aagttatgta acgcctgcag gttaattaag aacatgtgag caaaaggcca gcaaaaggcc | 3540 |
| aggaaccgta aaaaggccgc gttgctggcg tttttccata ggctccgccc cctgacgag | 3600 |
| catcacaaaa atcgacgctc aagtcagagg tggcgaaacc cgacaggact ataaagatac | 3660 |
| caggcgtttc ccccctggaag ctccctcgtg cgctctcctg ttccgaccct gccgcttacc | 3720 |
| ggatacctgt ccgcctttct cccttcggga agcgtggcgc tttctcatag ctcacgctgt | 3780 |
| aggtatctca gttcggtgta ggtcgttcgc tccaagctgg gctgtgtgca cgaaccccc | 3840 |
| gttcagcccg accgctgcgc cttatccggt aactatcgtc ttgagtccaa cccggtaaga | 3900 |
| cacgacttat cgccactggc agcagccact ggtaacagga ttagcagagc gaggtatgta | 3960 |
| ggcggtgcta cagagttctt gaagtggtgg cctaactacg gctacactag aagaacagta | 4020 |
| tttggtatct gcgctctgct gaagccagtt accttcggaa aaagagttgg tagctcttga | 4080 |
| tccggcaaac aaaccaccgc tggtagcggt ggttttttttg tttgcaagca gcagattacg | 4140 |
| cgcagaaaaa aaggatctca agaagatcct ttgatctttt ctacgggtc tgacgctcag | 4200 |
| tggaacgaaa actcacgtta agggattttg gtcatggcta gttaattaac atttaaatca | 4260 |
| gcggccgcaa taaatatct ttatttttcat tacatctgtg tgttggtttt ttgtgtgaat | 4320 |
| cgtaactaac atacgctctc catcaaaaca aaacgaaaca aaacaaacta gcaaaatagg | 4380 |
| ctgtccccag tgcaagtgca ggtgccagaa catttctcta tcgaa | 4425 |

<210> SEQ ID NO 104
<211> LENGTH: 4419
<212> TYPE: DNA
<213> ORGANISM: Artificial Sequence
<220> FEATURE:
<223> OTHER INFORMATION: pCXCL13(3-87)-IgG4Fc

<400> SEQUENCE: 104

| | |
|---|---|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gcctttttcc cgagggtggg ggagaaccgt | 180 |
| atataagtgc agtagtcgcc gtgaacgttc ttttttcgcaa cgggtttgcc gccagaacac | 240 |
| agctgaagct tcgaggggct cgcatctctc cttcacgcgc ccgccgccct acctgaggcc | 300 |

| | |
|---|---|
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggcga aggagggcca ccatgtacag gatgcaactc ctgtcttgca | 600 |
| ttgcactaag tcttgcactt gtcacgaatt cggaggtcta ttacacaagc ttgaggtgta | 660 |
| gatgtgtcca agagagctca gtctttatcc ctagacgctt cattgatcga attcaaatct | 720 |
| tgccccgtgg gaatggttgt ccaagaaaag aaatcatagt ctggaagaag aacaagtcaa | 780 |
| ttgtgtgtgt ggaccctcaa gctgaatgga tacaaagaat gatggaagta ttgagaaaaa | 840 |
| gaagttcttc aactctacca gttccagtgt ttaagagaaa gattccccccc ccatgcccat | 900 |
| catgcccagc acctgagttc ctgggggggac catcagtctt cctgttcccc ccaaaaccca | 960 |
| aggacactct catgatctcc cggacccctg aggtcacgtg cgtggtggtg gacgtgagcc | 1020 |
| aggaagaccc cgaggtccag ttcaactggt acgtggatgg cgtggaggtg cataatgcca | 1080 |
| agacaaagcc gcgggaggag cagttcaaca gcacgtaccg tgtggtcagc gtcctcaccg | 1140 |
| tcctgcacca ggactggctg aacggcaagg agtacaagtg caaggtctcc aacaaaggcc | 1200 |
| tcccgtcctc catcgagaaa accatctcca aagccaaagg gcagcccga gagccacagg | 1260 |
| tgtacaccct gcccccatcc caggaggaga tgaccaagaa ccaggtcagc ctgacctgcc | 1320 |
| tggtcaaagg cttctacccc agcgacatcg ccgtggagtg ggagagcaat gggcagccgg | 1380 |
| agaacaacta caagaccacg cctcccgtgc tggactccga cggctccttc ttcctctaca | 1440 |
| gcaggctaac cgtggacaag agcaggtggc aggaggggaa tgtcttctca tgctccgtga | 1500 |
| tgcatgaggc tctgcacaac cactacacac agaagagcct ctccctgtct ccgggtaaat | 1560 |
| gagtgctagc tggccagaca tgataagata cattgatgag tttggacaaa ccacaactag | 1620 |
| aatgcagtga aaaaaatgct ttatttgtga aatttgtgat gctattgctt tatttgtaac | 1680 |
| cattataagc tgcaataaac aagttaacaa caacaattgc attcatttta tgtttcaggt | 1740 |
| tcaggggggag gtgtgggagg ttttttaaag caagtaaaac ctctacaaat gtggtatgga | 1800 |
| attaattcta aaatacagca tagcaaaact ttaacctcca aatcaagcct ctacttgaat | 1860 |
| ccttttctga gggatgaata aggcataggc atcaggggct gttgccaatg tgcattagct | 1920 |
| gtttgcagcc tcaccttctt tcatggagtt taagatatag tgtattttcc caaggtttga | 1980 |
| actagctctt catttcttta tgttttaaat gcactgacct cccacattcc cttttagta | 2040 |
| aaatattcag aaataattta aatacatcat tgcaatgaaa ataaatgttt tttattaggc | 2100 |
| agaatccaga tgctcaaggc ccttcataat atccccccagt ttagtagttg gacttaggga | 2160 |
| acaaaggaac ctttaataga aattggacag caagaaagcg agcttctagc ttatcctcag | 2220 |
| tcctgctcct ctgccacaaa gtgcacgcag ttgccggccg gtcgcgcag ggcgaactcc | 2280 |
| cgccccccacg gctgctcgcc gatctcggtc atggccggcc cggaggcgtc ccggaagttc | 2340 |
| gtggacacga cctccgacca ctcggcgtac agctcgtcca ggccgcgcac ccacacccag | 2400 |
| gccagggtgt tgtccggcac cacctggtcc tggaccgcgc tgatgaacag ggtcacgtcg | 2460 |
| tcccggacca caccggcgaa gtcgtcctcc acgaagtccc gggagaaccc gagccggtcg | 2520 |
| gtccagaact cgaccgctcc ggcgacgtcg cgcgcggtga gcaccggaac ggcactggtc | 2580 |
| aacttggcca tgatggctcc tcctgtcagg agaggaaaga gaagaaggtt agtacaattg | 2640 |
| ctatagtgag ttgtattata ctatgcagat atactatgcc aatgattaat tgtcaaacta | 2700 |

-continued

| | |
|---|---|
| gggctgcagg gttcatagtg ccacttttcc tgcactgccc catctcctgc ccacccttt | 2760 |
| ccaggcatag acagtcagtg acttaccaaa ctcacaggag ggagaaggca gaagcttgag | 2820 |
| acagacccgc gggaccgccg aactgcgagg ggacgtggct agggcggctt cttttatggt | 2880 |
| gcgccggccc tcggaggcag ggcgctcggg gaggcctagc ggccaatctg cggtggcagg | 2940 |
| aggcggggcc gaaggccgtg cctgaccaat ccggagcaca taggagtctc agccccccgc | 3000 |
| cccaaagcaa ggggaagtca cgcgcctgta gcgccagcgt gttgtgaaat ggggcttgg | 3060 |
| gggggttggg gccctgacta gtcaaaacaa actcccattg acgtcaatgg ggtggagact | 3120 |
| tggaaatccc cgtgagtcaa accgctatcc acgcccattg atgtactgcc aaaaccgcat | 3180 |
| catcatggta atagcgatga ctaatacgta gatgtactgc caagtaggaa agtcccataa | 3240 |
| ggtcatgtac tgggcataat gccaggcggg ccatttaccg tcattgacgt caataggggg | 3300 |
| cgtacttggc atatgataca cttgatgtac tgccaagtgg gcagtttacc gtaaatactc | 3360 |
| cacccattga cgtcaatgga aagtccctat tggcgttact atgggaacat acgtcattat | 3420 |
| tgacgtcaat gggcgggggt cgttgggcgg tcagccaggc gggccattta ccgtaagtta | 3480 |
| tgtaacgcct gcaggttaat taagaacatg tgagcaaaag gccagcaaaa ggccaggaac | 3540 |
| cgtaaaaagg ccgcgttgct ggcgtttttc cataggctcc gcccccctga cgagcatcac | 3600 |
| aaaaatcgac gctcaagtca gaggtggcga acccgacag gactataaag ataccaggcg | 3660 |
| tttccccctg gaagctccct cgtgcgctct cctgttccga ccctgccgct taccggatac | 3720 |
| ctgtccgcct ttctcccttc gggaagcgtg gcgctttctc atagctcacg ctgtaggtat | 3780 |
| ctcagttcgg tgtaggtcgt tcgctccaag ctgggctgtg tgcacgaacc ccccgttcag | 3840 |
| cccgaccgct gcgccttatc cggtaactat cgtcttgagt ccaacccggt aagcacgac | 3900 |
| ttatcgccac tggcagcagc cactggtaac aggattagca gagcgaggta tgtaggcggt | 3960 |
| gctacagagt tcttgaagtg gtggcctaac tacggctaca ctagaagaac agtatttggt | 4020 |
| atctgcgctc tgctgaagcc agttaccttc ggaaaaagag ttggtagctc ttgatccggc | 4080 |
| aaacaaacca ccgctggtag cggtggtttt tttgtttgca agcagcagat tacgcgcaga | 4140 |
| aaaaaaggat ctcaagaaga tcctttgatc ttttctacgg ggtctgacgc tcagtggaac | 4200 |
| gaaaactcac gttaagggat tttggtcatg ctagttaat taacatttaa atcagcggcc | 4260 |
| gcaataaaat atctttattt tcattacatc tgtgtgttgg ttttttgtgt gaatcgtaac | 4320 |
| taacatacgc tctccatcaa aacaaaacga aacaaaacaa actagcaaaa taggctgtcc | 4380 |
| ccagtgcaag tgcaggtgcc agaacatttc tctatcgaa | 4419 |

<210> SEQ ID NO 105
<211> LENGTH: 4419
<212> TYPE: DNA
<213> ORGANISM: Artificial Sequence
<220> FEATURE:
<223> OTHER INFORMATION: pCXCL13(3-87K/H-A)-IgG4Fc

<400> SEQUENCE: 105

| | |
|---|---|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gcctttttcc cgagggtggg ggagaaccgt | 180 |
| atataagtgc agtagtcgcc gtgaacgttc tttttcgcaa cgggtttgcc gccagaacac | 240 |
| agctgaagct tcgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |

```
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cggaggtcta ttacacaagc ttgaggtgta    660
gatgtgtcca agagagctca gtcttatcc ctagacgctt cattgatgcc attcaaatct     720
tgccccgtgg gaatggttgt ccaagaaaag aaatcatagt ctgggctgcg aacgcttcaa    780
ttgtgtgtgt ggaccctcaa gctgaatgga tacaagccat gatggaagta ttggctgcgg    840
ctagttcttc aactctacca gttccagtgt ttgccgctgc gattccccc  ccatgcccat     900 catgcccagc acctgagttc ctgggggac  catcagtctt cctgttcccc ccaaaaccca     960
aggacactct catgatctcc cggacccctg aggtcacgtg cgtggtggtg gacgtgagcc    1020
aggaagaccc cgaggtccag ttcaactggt acgtggatgg cgtggaggtg cataatgcca    1080
agacaaagcc gcgggaggag cagttcaaca gcacgtaccg tgtggtcagc gtcctcaccg    1140
tcctgcacca ggactggctg aacggcaagg agtacaagtg caaggtctcc aacaaaggcc    1200
tcccgtcctc catcgagaaa accatctcca agccaaagg gcagcccga  gagccacagg     1260 tgtacaccct gccccatcc caggaggaga tgaccaagaa ccaggtcagc ctgacctgcc     1320
tggtcaaagg cttctacccc agcgacatcg ccgtggagtg ggagagcaat gggcagccgg    1380
agaacaacta caagaccacg cctcccgtgc tggactccga cggctccttc ttcctctaca    1440
gcaggctaac cgtggacaag agcaggtggc aggagggaa  tgtcttctca tgctccgtga     1500
tgcatgaggc tctgcacaac cactacacac agaagagcct ctccctgtct ccgggtaaat    1560
gagtgctagc tggccagaca tgataagata cattgatgag tttggacaaa ccacaactag    1620
aatgcagtga aaaaaatgct ttatttgtga aatttgtgat gctattgctt tatttgtaac    1680
cattataagc tgcaataaac aagttaacaa caacaattgc attcatttta tgtttcaggt    1740
tcagggggag gtgtgggagg ttttttaaag caagtaaaac ctctacaaat gtggtatgga    1800
attaattcta aaatacagca tagcaaaact ttaacctcca aatcaagcct ctacttgaat    1860
ccttttctga gggatgaata aggcataggc atcaggggct gttgccaatg tgcattagct    1920
gtttgcagcc tcaccttctt tcatggagtt taagatatag tgtattttcc caaggtttga    1980
actagctctt catttcttta tgttttaaat gcactgacct cccacattcc ctttttagta    2040
aaatattcag aaataattta aatacatcat tgcaatgaaa ataaatgttt tttattaggc    2100
agaatccaga tgctcaaggc ccttcataat atccccagt  ttagtagttg gacttaggga     2160
acaaaggaac ctttaataga aattggacag caagaaagcg agcttctagc ttatcctcag    2220
tcctgctcct ctgccacaaa gtgcacgcag ttgccggccg ggtcgcgcag ggcgaactcc    2280 cgccccacg  gctgctcgcc gatctcggtc atggccggcc cggaggcgtc ccggaagttc     2340
gtggacacga cctccgacca ctcggcgtac agctcgtcca ggccgcgcac ccacacccag    2400
gccagggtgt gtccggcac  cacctggtcc tggaccgcgc tgatgaacag ggtcacgtcg     2460
tcccggacca caccggcgaa gtcgtcctcc acgaagtccc gggagaaccc gagccggtcg    2520
gtccagaact cgaccgctcc ggcgacgtcg cgcgcggtga gcaccggaac ggcactggtc    2580
aacttggcca tgatggctcc tcctgtcagg agaggaaaga gaagaaggtt agtacaattg    2640
ctatagtgag ttgtattata ctatgcagat atactatgcc aatgattaat tgtcaaacta    2700
gggctgcagg gttcatagtg ccacttttcc tgcactgccc catctcctgc ccacccttc     2760
```

```
ccaggcatag acagtcagtg acttaccaaa ctcacaggag ggagaaggca gaagcttgag    2820
acagacccgc gggaccgccg aactgcgagg ggacgtggct agggcggctt cttttatggt    2880
gcgccggccc tcggaggcag ggcgctcggg gaggcctagc ggccaatctg cggtggcagg    2940
aggcggggcc gaaggccgtg cctgaccaat ccggagcaca taggagtctc agccccccgc    3000
cccaaagcaa gggaagtca cgcgcctgta gcgccagcgt gttgtgaaat gggggcttgg     3060
gggggttggg gccctgacta gtcaaaacaa actcccattg acgtcaatgg ggtggagact    3120
tggaaatccc cgtgagtcaa accgctatcc acgcccattg atgtactgcc aaaaccgcat    3180
catcatggta atagcgatga ctaatacgta gatgtactgc caagtaggaa agtcccataa    3240
ggtcatgtac tgggcataat gccaggcggg ccatttaccg tcattgacgt caataggggg    3300
cgtacttggc atatgataca cttgatgtac tgccaagtgg gcagtttacc gtaaatactc    3360
cacccattga cgtcaatgga aagtcccctat tggcgttact atgggaacat acgtcattat    3420
tgacgtcaat gggcggggt cgttgggcgg tcagccaggc gggccattta ccgtaagtta    3480
tgtaacgcct gcaggttaat taagaacatg tgagcaaaag gccagcaaaa ggccaggaac    3540
cgtaaaaagg ccgcgttgct ggcgttttc cataggctcc gccccctga cgagcatcac    3600 aaaaatcgac gctcaagtca gaggtggcga acccgacag gactataaag ataccaggcg    3660
tttccccctg gaagctccct cgtgcgctct cctgttccga ccctgccgct taccggatac    3720
ctgtccgcct ttctcccttc gggaagcgtg gcgctttctc atagctcacg ctgtaggtat    3780
ctcagttcgg tgtaggtcgt tcgctccaag ctgggctgtg tgcacgaacc ccccgttcag    3840
cccgaccgct gcgccttatc cggtaactat cgtcttgagt ccaacccggt aagacacgac    3900
ttatcgccac tggcagcagc cactggtaac aggattagca gagcgaggta tgtaggcggt    3960
gctacagagt tcttgaagtg gtggcctaac tacggctaca ctagaagaac agtatttggt    4020
atctgcgctc tgctgaagcc agttaccttc ggaaaaagag ttggtagctc ttgatccggc    4080
aaacaaacca ccgctggtag cggtggtttt tttgtttgca agcagcagat tacgcgcaga    4140
aaaaaaggat ctcaagaaga tcctttgatc ttttctacgg ggtctgacgc tcagtggaac    4200
gaaaactcac gttaagggat tttggtcatg ctagttaat taacatttaa atcagcggcc    4260
gcaataaaat atctttattt tcattacatc tgtgtgttgg ttttttgtgt gaatcgtaac    4320
taacatacgc tctccatcaa aacaaaacga aacaaaacaa actagcaaaa taggctgtcc    4380
ccagtgcaag tgcaggtgcc agaacatttc tctatcgaa                          4419
```

<210> SEQ ID NO 106
<211> LENGTH: 20
<212> TYPE: PRT
<213> ORGANISM: Artificial Sequence
<220> FEATURE:
<223> OTHER INFORMATION: IL-2 Secretion Signal

<400> SEQUENCE: 106

```
Met Tyr Arg Met Gln Leu Leu Ser Cys Ile Ala Leu Ser Leu Ala Leu
1               5                   10                  15

Val Thr Asn Ser
            20
```